(12) United States Patent
Banner et al.

(10) Patent No.: US 7,129,238 B2
(45) Date of Patent: Oct. 31, 2006

(54) MANDELIC ACID DERIVATIVES

(75) Inventors: David William Banner, Basel (CH);
Luca Claudio Gobbi, Oberwil (CH);
Katrin Groebke Zbinden, Basel (CH);
Ulrike Obst, Reinach (CH); Christoph Martin Stahl, Freiburg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 341 days.

(21) Appl. No.: 10/720,790

(22) Filed: Nov. 21, 2003

(65) Prior Publication Data

US 2004/0122057 A1 Jun. 24, 2004

(30) Foreign Application Priority Data

Nov. 25, 2002 (EP) .................. 02026365

(51) Int. Cl.
*A61K 31/538* (2006.01)
*A61K 31/4402* (2006.01)
*C07D 211/98* (2006.01)
*C07D 235/12* (2006.01)
*C07D 207/08* (2006.01)

(52) U.S. Cl. ............... 514/230.5; 514/238.5; 514/275; 514/315; 514/349; 514/351; 514/352; 514/364; 514/394; 514/415; 514/428; 514/460; 514/471; 514/619; 544/105; 544/168; 544/332; 546/242; 546/297; 546/300; 546/311; 548/131; 548/309.7; 548/494; 548/567; 549/419; 549/496; 564/163

(58) Field of Classification Search .................. None
See application file for complete search history.

(56) References Cited

U.S. PATENT DOCUMENTS 5,292,769 A 3/1994 Mohrs et al.
6,060,491 A * 5/2000 Pruitt et al. .................. 514/355
7,001,887 B1 * 2/2006 Shiraishi et al. ............... 514/19

FOREIGN PATENT DOCUMENTS

WO  WO 00 35858    12/1999
WO  WO 2004/048335  6/2004

OTHER PUBLICATIONS

Shiraishi et al, STN International, HCAPLUS Database, Columbus, OH, Accession No. 2002:615652, Reg. No. 446846-14-6 and 446846-17-9 (2006).*
Dixon, M. "The Determination of Enzyme Inhibitor Constants" Biochem J. vol. 55 (1953) pp. 170-171.
Su, et al., Science Direct-Biorganic & Medicinal Chemistry Letters, pp. 2279-2282 (2001).

* cited by examiner

*Primary Examiner*—Kamal A. Saeed
*Assistant Examiner*—Andrew B. Freistein
(74) *Attorney, Agent, or Firm*—George W. Johnston; Patricia S. Rocha-Tramaloni; David E. Wildman

(57) ABSTRACT

The invention is concerned with novel mandelic acid derivatives of formula (I)

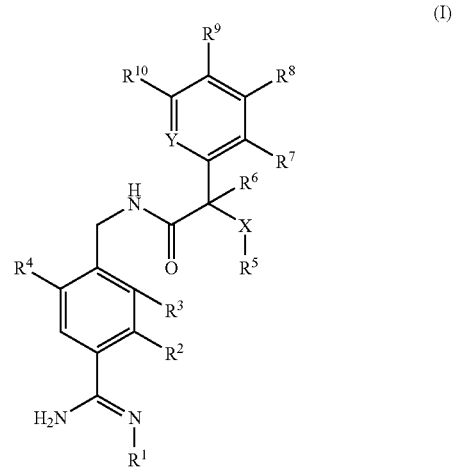

wherein $R^1$ to $R^{10}$, X and Y are as defined in the description and in the claims, as well as pharmaceutically acceptable salts thereof.

These compounds inhibit the formation of coagulation factors Xa, IXa and thrombin induced by factor VIIa and tissue factor.

64 Claims, No Drawings

MANDELIC ACID DERIVATIVES

FIELD OF THE INVENTION

This invention is related to novel mandelic acid derivatives.

SUMMARY OF THE INVENTION

The invention is concerned with novel mandelic acid derivatives of the formula (I)

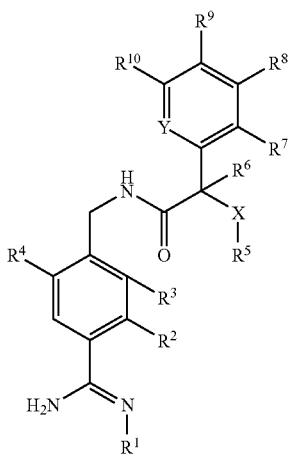

wherein
$R^1$ is hydrogen, OH, $NH_2$, lower-alkoxy-carbonyl, aryl-lower-alkoxy-carbonyl, aryloxy-carbonyl, lower-alkyl-carbonyl, aryl-carbonyl, or halogen-substituted lower-alkoxy-carbonyl;
$R^2$, $R^3$ and $R^4$ independently from each other are selected from the group consisting of hydrogen, halogen, hydroxy, carboxy-lower-alkyl-NH, carbamoyl-lower-alkyl-NH, lower-alkoxy-carbonyl-lower-alkyl-NH, hydroxy-cycloalkyl-oxy, dihydroxy-cycloalkyl-oxy, aryl, aryloxy, aryl-NH, aryl-lower-alkyl-NH, aryl-lower-alkyl-SO$_2$—NH, aryl-lower-alkoxy-carbonyl-NH, aryl-lower-alkyl-NH-carbonyl-NH, heteroaryloxy, heteroaryl-lower-alkyl-NH, lower-alkoxy, and lower-alkoxy substituted with hydroxy, carboxy, carbamoyl, carbamimidoyl, $CF_3$, aryl, heteroaryl, lower-alkyl-carbamoyl, lower-alkoxy-carbonyl, aryl-carbamoyl, lower-alkoxy-lower-alkyl-carbamoyl, heterocyclyl-lower-alkyl-carbamoyl, or N(lower-alkyl)$_2$-lower-alkyl-carbamoyl;
$R^5$ is lower-alkyl or cycloalkyl, or, if X is O or $NR^{12}$, $R^5$ is lower-alkyl, cycloalkyl or hydrogen;
$R^6$ is hydrogen, lower-alkyl, or fluoro-lower-alkyl;
Y is N or C—$R^1$;
$R^7$, $R^8$, $R^9$, $R^{10}$ and $R^{11}$ independently from each other are selected from the group consisting of hydrogen, hydroxy, halogen, amino, lower-alkyl-amino, di-lower-alkyl-amino, lower-alkyl-carbonyl-amino, $NO_2$, fluoro-lower-alkyl, lower-alkoxy, hydroxy-lower-alkoxy, fluoro-lower-alkoxy, lower-alkinyl, hydroxy-lower-alkinyl, aryl, aryl-lower-alkoxy, aryloxy, aryloxy-lower-alkoxy, heterocyclyl, heterocyclyloxy, lower-alkoxy-carbonyl-lower-alkoxy, carbamoyl-lower-alkoxy, carboxy-lower-alkoxy, cycloalkyloxy, heteroaryl, amino-lower-alkoxy, lower-alkyl-amino-lower-alkoxy, and di-lower-alkyl-amino-lower-alkoxy, lower-alkyl-carbonyl-amino-lower-alkyl, HO—N=CH, HCO, fluoro-lower-alkyl-SO$_2$—O, (lower-alkoxy)$_{2-4}$, CH(lower-alkoxy)$_2$, hydroxy-chloro-lower-alkoxy, aryl-lower-alkoxy-lower-alkoxy, aryl-NH, aryl-NH-lower-alkyl, aryl-lower-alkyl-carbonyl-NH, heterocyclyl-lower-alkyl, heterocyclyl-carbonyl, heterocyclyl-lower-alkoxy, lower-alkyl-carbamoyl, fluoro-lower-alkyl-carbamoyl, cycloalkyl-carbamoyl, cycloalkyl-lower-alkyl-carbamoyl, di-lower-alkyl-carbamoyl, lower-alkoxy-lower-alkyl-carbamoyl, di-lower-alkyl-carbamoyl-lower-alkoxy, heteroaryloxy, heteroaryl-lower-alkoxy, amino-lower-alkyl, lower-alkyl, hydroxy-lower-alkyl, cycloalkyl, cycloalkyl-lower-alkoxy, and cyclo-lower-alkoxy substituted with lower-alkyl; or
$R^8$ and $R^9$ or $R^8$ and $R^7$ are bound to each other to form a ring together with the carbon atoms to which they are attached and $R^8$ and $R^9$ together or $R^8$ and $R^7$ together are —O—CH$_2$—O—, —O—CH$_2$—CO—NH—, —O—CH$_2$—CH$_2$—CH$_2$—, —CH=CH—CH=CH—, or —CH=CH—CH=CH— substituted with lower-alkyl or lower-alkoxy, and $R^{10}$, $R^{11}$ and $R^7$ or $R^9$ respectively are as defined above;
X is O, S, $NR^{12}$, or $SO_2$;
$R^{12}$ is hydrogen, lower-alkyl, or lower-alkyl-carbonyl;
or a pharmaceutically acceptable salt thereof.

Further, the invention is related to a process for the manufacture of the above compounds, pharmaceutical preparations which contain such compounds as well as the use of these compounds for the production of pharmaceutical preparations.

The compounds of formula (I) are active compounds and inhibit the formation of coagulation factors Xa, IXa and thrombin induced by factor VIIa and tissue factor, or are derivatives which are converted under physiological conditions to such active compounds. These compounds consequently influence both platelet aggregation (which is induced by these factors) and plasmatic blood coagulation. They therefore inhibit the formation of thrombi and can be used for the treatment and/or prevention of diseases, such as arterial and venous thrombosis, deep vein thrombosis, pulmonary embolism, unstable angina pectoris, cardiac infarction, stroke due to atrial fibrillation, inflammation and arteriosclerosis. Furthermore, these compounds have an effect on tumor cells and prevent metastases. They can therefore also be used as antitumor agents.

Inhibitors of factor VIIa had previously been suggested for the inhibition of the formation of thrombi and for the treatment of related diseases (WO 00/35858). However, there is still a need for novel factor VIIa inhibitors which exhibit improved pharmacological properties.

DETAILED DESCRIPTION OF THE INVENTION

The present invention provides the novel compounds of formula (I) which are factor VIIa inhibitors. The compounds of the present invention exhibit improved pharmacological properties compared to the known compounds.

Unless otherwise indicated, the following definitions are set forth to illustrate and define the meaning and scope of the various terms used to describe the invention herein.

In this specification, the term "lower" means a group consisting of one to seven, preferably of one to four carbon atom(s).

The term "halogen" refers to fluorine, chlorine, bromine and iodine. Preferably, halogens are fluorine, chlorine and bromine.

The term "alkyl", alone or in combination with other groups, refers to a branched or straight-chain monovalent saturated aliphatic hydrocarbon radical of one to twenty carbon atoms. Preferably, alkyl refers to one to sixteen carbon atoms, more preferably one to ten carbon atoms. Lower-alkyl groups as described below also are preferred alkyl groups.

The term "lower-alkyl", alone or in combination with other groups, refers to a branched or straight-chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the like. Lower-alkyl groups may be substituted, e.g., by hydroxy. Such substituted lower-alkyl-groups are referred to as "hydroxy-lower-alkyl". Other possible optional substituents are e.g., halogen.

The term "fluoro-lower-alkyl" refers to lower-alkyl groups which are mono- or multiply substituted with fluorine. Examples of fluoro-lower-alkyl groups are e.g., $CFH_2$, $CF_2H$, $CF_3$, $CF_3CH_2$, $CF_3(CH_2)_2$, $(CF_3)_2CH$ and $CF_2H-CF_2$ The term "cycloalkyl" refers to a monovalent carbocyclic radical of 3 to 10 carbon atoms, preferably 3 to 6 carbon atoms, such as cyclopropyl, cyclobutyl, cyclopentyl, or cyclohexyl. Cycloalkyl groups can optionally be substituted, e.g., by hydroxy or lower-alkyl.

The term "cycloalkyloxy" refers to the group cycloalkyl-O—.

The term "alkoxy" refers to the group R'—O—, wherein R' is an alkyl. The term "lower-alkoxy" refers to the group R'—O—, wherein R' is a lower-alkyl.

The term "thio-alkoxy" refers to the group R'—S—, wherein R' is an alkyl. The term "thio-lower-alkoxy" refers to the group R'—S—, wherein R' is a lower-alkyl.

The term "fluoro-lower-alkoxy" refers to the group R"—O—, wherein R" is fluoro-lower-alkyl. Examples of fluoro-lower-alkoxy groups are e.g. $CFH_2$—O, $CF_2H$—O, $CF_3$—O, $CF_3CH_2$—O, $CF_3(CH_2)_2$—O, $(CF_3)_2CH$—O, and $CF_2H$—$CF_2$—O.

The term "alkenyl", alone or in combination with other groups, stands for a straight-chain or branched hydrocarbon residue comprising an olefinic bond and 2 to 20, preferably 2 to 16 carbon atoms, more preferably 2 to 10 carbon atoms. Lower-alkenyl groups as described below also are preferred alkenyl groups. The term "lower-alkenyl" refers to a straight-chain or branched hydrocarbon residue comprising an olefinic bond and 2 to 7, preferably 2 to 4 carbon atoms, such as e.g., 2-propenyl.

The term "alkinyl", alone or in combination with other groups, stands for a straight-chain or branched hydrocarbon residue comprising a tripple bond and up to 20, preferably up to 16 carbon atoms. The term "lower-alkinyl" refers to a straight-chain or branched hydrocarbon residue comprising a tripple bond and 2 to 7, preferably 2 to 4 carbon atoms, such as e.g., 2-propinyl. Lower-alkinyl groups can be substituted, e.g., by hydroxy.

The term "alkylene" refers to a straight chain or branched divalent saturated aliphatic hydrocarbon group of 1 to 20 carbon atoms, preferably 1 to 16 carbon atoms, more preferably up to 10 carbon atoms. Lower-alkylene groups as described below also are preferred alkylene groups. The term "lower-alkylene" refers to a straight chain or branched divalent saturated aliphatic hydrocarbon group of 1 to 7, preferably 1 to 6 or 3 to 6 carbon atoms. Straight chain alkylene or lower-alkylene groups are preferred.

The term "aryl" refers to a phenyl or naphthyl group, preferably the phenyl group, which can optionally be substituted by 1 to 5, preferably 1 to 3, substituents independently selected from the group consisting of lower-alkenyl, lower-alkinyl, dioxo-lower-alkylene (forming e.g., a benzodioxyl group), halogen, hydroxy, CN, $CF_3$, $NH_2$, N(H, lower-alkyl), N(lower-alkyl)$_2$, aminocarbonyl, carboxy, $NO_2$, lower-alkoxy, thio-lower-alkoxy, lower-alkylcarbonyl, lower-alkylcarbonyloxy, lower-alkoxycarbonyl, lower-alkyl-carbonyl-NH, fluoro-lower-alkyl, fluoro-lower-alkoxy, lower-alkoxy-carbonyl-lower-alkoxy, carboxy-lower-alkoxy, carbamoyl-lower-alkoxy, hydroxy-lower-alkoxy, $NH_2$-lower-alkoxy, N(H, lower-alkyl)-lower-alkoxy, N(lower-alkyl)$_2$-lower-alkoxy, benzyloxy-lower-alkoxy, HO—N=CH—, and lower alkyl which can optionally be substituted with halogen, hydroxy, $NH_2$, N(H, lower-alkyl) or N(lower-alkyl)$_2$. Preferred substituents are halogen, lower-alkoxy, lower-alkyl-carbamoyl-NH, CN, fluoro-lower-alkoxy, fluoro-lower-alkyl, lower-alkyl, thio-lower-alkoxy, lower-alkoxy-carbonyl-lower-alkoxy, carboxy-lower-alkoxy, carbamoyl-lower-alkoxy, hydroxy-lower-alkoxy, N(lower-alkyl)$_2$-lower-alkoxy, benzyloxy-lower-alkoxy, lower-alkoxy-carbonyl, carboxy, hydroxy-lower-alkyl, chloro-lower-alkyl, HO—N=CH—, amino-lower-alkyl, amino, and $NO_2$.

The term "aryloxy" refers to the group aryl-O—.

The term "heterocyclyl" as used herein denotes non-aromatic monocyclic heterocycles with 5 or 6 ring members, which comprise 1, 2 or 3 hetero atoms selected from nitrogen, oxygen and sulfur. Examples of suitable heterocycles are pyrrolidinyl, oxopyrrolidinyl, pyrrolinyl, imidazolidinyl, imidazolinyl, pyrazolidinyl, pyrazolinyl, piperidyl, piperazinyl, morpholinyl, pyranyl, tetrahydropyranyl, 4,5-dihydro-oxazolyl, 4,5-dihydro-thiazolyl. Preferred heterocycles are piperidinyl, morpholinyl, pyrrolidinyl, oxopyrrolidinyl, tetrahydrofuranyl and tetrahydropyranyl. A heterocyclyl group may have a substitution pattern as described earlier in connection with the term "aryl". Preferred substituents are lower-alkyl, lower-alkyl-sulfonyl, benzenesulfonyl, lower-alkyl-carbonyl and benzoyl.

The term "heterocyclyloxy" refers to the group heterocyclyl-O—.

As used herein, the phrase "halogen substituted compound" has the same meaning as a compound which is substituted by halogen. For example, halogen substituted lower-alkyl-carbonyl has the same meaning as lower-alkoxy-carbonyl substituted by halogen.

The term "heteroaryl" refers to an aromatic 5 to 6 membered monocyclic ring or 9 to 10 membered bicyclic ring which can comprise 1, 2 or 3 atoms selected from nitrogen, oxygen and/or sulfur, such as furyl, pyridyl, oxo-pyridinyl, pyridazinyl, pyrimidinyl, pyrazinyl, thienyl, isoxazolyl, oxazolyl, oxadiazolyl, imidazolyl, pyrrolyl, tetrazolyl, benzoimidazolyl, indolyl. Preferred heteroaryl groups are pyridinyl, oxo-pyridinyl, thienyl, furyl, oxadiazolyl, pyrimidinyl, benzoimidazolyl, indolyl. A heteroaryl group may have a substitution pattern as described earlier in connection with the term "aryl". Preferred substituents are $NO_2$, $NH_2$, lower-alkoxy.

The term "heteroaryloxy" refers to the group heteroaryl-O—.

Compounds of formula (I) can form pharmaceutically acceptable acid addition salts. Examples of such pharmaceutically acceptable salts are salts of compounds of formula (I) with physiologically compatible mineral acids, such as hydrochloric acid, sulfuric acid, sulfurous acid or phosphoric acid; or with organic acids, such as methanesulfonic acid, p-toluenesulfonic acid, acetic acid, lactic acid, trifluoroacetic acid, citric acid, fumaric acid, maleic acid, tartaric acid, succinic acid or salicylic acid. The term "pharmaceutically acceptable salts" refers to such salts. Compounds of formula (I) in which a COOH group is present can further form salts with bases. Examples of such salts are alkaline, earth-alkaline and ammonium salts such as e.g., Na—, K—, Ca— and trimethylammoniumsalt. The term "pharmaceutically acceptable salts" also refers to such salts. Acid addition salts as described above are preferred.

In detail, the present invention relates to compounds of formula (I)

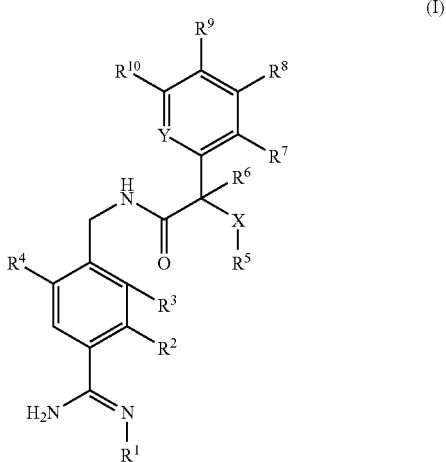

(I)

wherein
$R^1$ is hydrogen, OH, $NH_2$, lower-alkoxy-carbonyl, aryl-lower-alkoxy-carbonyl, aryloxy-carbonyl, lower-alkyl-carbonyl, aryl-carbonyl, or halogen substituted lower-alkoxy-carbonyl;
$R^2$, $R^3$ and $R^4$ independently from each other are selected from the group consisting of hydrogen, halogen, hydroxy, carboxy-lower-alkyl-NH, carbamoyl-lower-alkyl-NH, lower-alkoxy-carbonyl-lower-alkyl-NH, hydroxy-cycloalkyl-oxy, dihydroxy-cycloalkyl-oxy, aryl, aryloxy, aryl-NH, aryl-lower-alkyl-NH, aryl-lower-alkyl-$SO_2$—NH, aryl-lower-alkoxy-carbonyl-NH, aryl-lower-alkyl-NH-carbonyl-NH, heteroaryloxy, heteroaryl-lower-alkyl-NH, and lower-alkoxy, which lower-alkoxy can optionally be substituted with hydroxy, carboxy, carbamoyl, carbamimidoyl, $CF_3$, aryl, heteroaryl, lower-alkyl-carbamoyl, lower-alkoxy-carbonyl, aryl-carbamoyl, lower-alkoxy-lower-alkyl-carbamoyl, heterocyclyl-lower-alkyl-carbamoyl, or N(lower-alkyl)$_2$-lower-alkyl-carbamoyl;
$R^5$ is lower-alkyl or cycloalkyl, or, if X is O or $NR^{12}$, $R^5$ is lower alkyl, cycloalkyl or hydrogen;
$R^6$ is hydrogen, lower-alkyl, or fluoro-lower-alkyl;
Y is N or C—$R^{11}$;
$R^7$, $R^8$, $R^9$, $R^{10}$ and $R^{11}$ independently from each other are selected from the group consisting of hydrogen, hydroxy, halogen, amino, lower-alkyl-amino, di-lower-alkyl-amino, lower-alkyl-carbonyl-amino, $NO_2$, fluoro-lower-alkyl, lower-alkoxy, hydroxy-lower-alkoxy, fluoro-lower-alkoxy, lower-alkinyl, hydroxy-lower-alkinyl, aryl, aryl-lower-alkoxy, aryloxy, aryloxy-lower-alkoxy, heterocyclyl, heterocyclyloxy, lower-alkoxy-carbonyl-lower-alkoxy, carbamoyl-lower-alkoxy, carboxy-lower-alkoxy, cycloalkyloxy, heteroaryl, amino-lower-alkoxy, lower-alkyl-amino-lower-alkoxy, and di-lower-alkyl-amino-lower-alkoxy, lower-alkyl-carbonyl-amino-lower-alkyl, HO—N=CH, HCO, fluoro-lower-alkyl-$SO_2$—O, (lower-alkoxy)$_{2-4}$, CH(lower-alkoxy)$_2$, hydroxy-chloro-lower-alkoxy, aryl-lower-alkoxy-lower-alkoxy, aryl-NH, aryl-NH-lower-alkyl, aryl-lower-alkyl-carbonyl-NH, heterocyclyl-lower-alkyl, heterocyclyl-carbonyl, heterocyclyl-lower-alkoxy, lower-alkyl-carbamoyl, fluoro-lower-alkyl-carbamoyl, cycloalkyl-carbamoyl, cycloalkyl-lower-alkyl-carbamoyl, di-lower-alkyl-carbamoyl, lower-alkoxy-lower-alkyl-carbamoyl, di-lower-alkyl-carbamoyl-lower-alkoxy, heteroaryloxy, heteroaryl-lower-alkoxy, amino-lower-alkyl, lower-alkyl, hydroxy-lower-alkyl, cycloalkyl, cycloalkyl-lower-alkoxy, and cycloalkyl-lower-alkoxy substituted with lower-alkyl; or
$R^8$ and $R^9$ or $R^8$ and $R^7$ are bound to each other to form a ring together with the carbon atoms to which they are attached and $R^8$ and $R^9$ together or $R^8$ and $R^7$ together are —O—$CH_2$—O—, —O—$CH_2$—CO—NH—, —O—$CH_2$—$CH_2$—$CH_2$—, —CH=CH—CH=CH—, or —CH=CH—CH=CH— substituted with lower-alkyl or lower-alkoxy, and $R^{10}$, $R^{11}$ and $R^7$ or $R^9$ respectively are as defined above;
X is O, S, $NR^{12}$, or $SO_2$;
$R^{12}$ is hydrogen, lower-alkyl, or lower-alkyl-carbonyl;
Or a pharmaceutically acceptable salt thereof.

One preferred embodiment of the present invention relates to compounds of formula (1) as defined above, wherein
$R^1$ is hydrogen, OH, $NH_2$, lower-alkoxy-carbonyl, aryl-lower-alkoxy-carbonyl, aryloxy-carbonyl, lower-alkyl-carbonyl, aryl-carbonyl, or lower-alkoxy-carbonyl which is substituted with halogen;
$R^2$, $R^3$ and $R^4$ independently from each other are selected from the group consisting of hydrogen, halogen, hydroxy, and lower-alkoxy, and lower-alkoxy substituted with hydroxy, carboxy or carbamoyl;
$R^5$ is lower-alkyl or cycloalkyl, or, if X is O or $NR^{12}$, $R^5$ can also be hydrogen;
$R^6$ is hydrogen, lower-alkyl, or fluoro-lower-alkyl;
Y is N or C—$R^{11}$;
$R^7$, $R^8$, $R^9$, $R^{10}$ and $R^{11}$ independently from each other are selected from the group consisting of hydrogen, hydroxy, halogen, amino, lower-alkyl-amino, di-lower-alkyl-amino, lower-alkyl-carbonyl-amino, $NO_2$, fluoro-lower-alkyl, lower-alkoxy, hydroxy-lower-alkoxy, fluoro-lower-alkoxy, lower-alkinyl, hydroxy-lower-alkinyl, aryl, aryl-lower-alkoxy, aryloxy, aryloxy-lower-alkoxy, heterocyclyl, heterocyclyloxy, lower-alkoxy-carbonyl-lower-alkoxy, carbamoyl-lower-alkoxy, carboxy-lower-alkoxy, cycloalkyloxy, heteroaryl, amino-lower-alkoxy, lower-alkyl-amino-lower-alkoxy, and di-lower-alkyl-amino-lower-alkoxy, or
$R^8$ and $R^9$ or $R^8$ and $R^7$ are bound to each other to form a ring together with the carbon atoms to which they are attached and $R^8$ and $R^9$ together or $R^8$ and $R^7$ together are —O—$CH_2$—O—, —O—$CH_2$—CO—NH—, —O—$CH_2$—$CH_2$—$CH_2$—, —CH=CH—CH=CH—, or —CH=CH—CH=CH— substituted with lower-alkyl or lower-alkoxy, and $R^{10}$, $R^{11}$ and $R^7$ or $R^9$ respectively are as defined above;
X is O, S, $NR^{12}$, or $SO_2$;
$R^{12}$ is hydrogen, lower-alkyl, or lower-alkyl-carbonyl;
or a pharmaceutically acceptable salt thereof.

The compounds of formula (I) have at least one asymmetric C atom and can therefore exist as an enantiomeric mixture, diastereomeric mixture or as optically pure compounds. Compounds of formula (I) can exist in tautomeric forms and the invention encompasses all such tautomeric forms. In particular, the substituent $R^1$ can be exchanged with a hydrogen atom bound to the other nitrogen atom of the amidino (carbamimidoyl) group.

Compounds of formula (I) are individually preferred and physiologically acceptable salts thereof are individually preferred, with the compounds of formula (I) being particularly preferred.

Preferred compounds of formula (I) are those, wherein $R^1$ is hydrogen, OH, $NH_2$, or lower-alkoxy-carbonyl, preferably those, wherein $R^1$ is hydrogen, OH, or lower-alkoxy-carbonyl, more preferably those wherein $R^1$ is hydrogen, OH, or ethoxycarbonyl, and most preferably those wherein $R^1$ is hydrogen. Another preferred embodiment of the present invention relates to compounds as described above, wherein $R^2$, $R^3$ and $R^4$ independently from each other are hydrogen or halogen, with those compounds wherein $R^2$, $R^3$ and $R^4$ are hydrogen being most preferred.

In another preferred embodiment of the present invention, $R^2$ and $R^4$ are hydrogen. Compounds as defined above, wherein $R^3$ is hydrogen, halogen, hydroxy, carboxy-lower-alkyl-NH, carbamoyl-lower-alkyl-NH, lower-alkoxy-carbonyl-lower-alkyl-NH, hydroxy-cycloalkyl-oxy, dihydroxy-cycloalkyl-oxy, aryl, aryloxy, aryl-NH, aryl-lower-alkyl-NH, aryl-lower-alkyl-SO$_2$—NH, aryl-lower-alkoxy-carbonyl-NH, aryl-lower-alkyl-NH-carbonyl-NH, heteroaryloxy, heteroaryl-lower-alkyl-NH, or lower-alkoxy, which lower-alkoxy can optionally be substituted with hydroxy, carboxy, carbamoyl, carbamimidoyl, $CF_3$, aryl, heteroaryl, lower-alkyl-carbamoyl, lower-alkoxy-carbonyl, aryl-carbamoyl, lower-alkoxy-lower-alkyl-carbamoyl, heterocyclyl-lower-alkyl-carbamoyl, or N(lower-alkyl)$_2$-lower-alkyl-carbamoyl, are also preferred. More preferably, $R^3$ is hydrogen, halogen, carboxy-lower-alkyl-NH, aryl-lower-alkyl-NH, heteroaryl-lower-alkyl-NH, or lower-alkoxy, which lower-alkoxy can optionally be substituted with carbamoyl, heteroaryl, or lower-alkoxy-lower-alkyl-carbamoyl. Even more preferably, $R^3$ is hydrogen, fluorine, carbamoylmethoxy, (2-methoxy-ethylcarbamoyl)-methoxy, pyridin-2-yl-methoxy, benzylamino, carboxymethyl-amino, or pyridin-2-ylmethyl-amino.

In a further preferred embodiment, the invention relates to compounds as described above in which X is O. Compounds in which $R^5$ is lower-alkyl, or, if X is O or $NR^{12}$, $R^5$ can also be hydrogen, are preferred. Compounds in which $R^5$ is lower-alkyl are also preferred, with those compounds wherein $R^5$ is methyl or ethyl being particularly preferred.

The invention embraces especially compounds in accordance with the above definitions in which $R^6$ is hydrogen, methyl or $CF_3$, preferably hydrogen.

In one preferred embodiment, $R^8$ and $R^9$ or $R^8$ and $R^7$ are bound to each other to form a ring together with the carbon atoms to which they are attached. Moreover, the invention relates especially to compounds as defined above wherein Y is C—$R^{11}$ and $R^7$, $R^8$, $R^9$, $R^{10}$ and $R^{11}$ independently from each other are selected from the group consisting of hydrogen, hydroxy, halogen, di-lower-alkyl-amino, lower-alkyl-carbonyl-amino, $NO_2$, fluoro-lower-alkyl, lower-alkoxy, hydroxy-lower-alkoxy, fluoro-lower-alkoxy, aryl, aryl-lower-alkoxy, aryloxy, aryloxy-lower-alkoxy, heterocyclyl, heterocyclyloxy, lower-alkoxy-carbonyl-lower-alkoxy, carbamoyl-lower-alkoxy, carboxy-lower-alkoxy, cycloalkyloxy, heteroaryl, and di-lower-alkyl-amino-lower-alkoxy. More preferably, Y is C—$R^{11}$ and $R^7$, $R^8$, $R^9$, $R^{10}$ and $R^{11}$ independently from each other are selected from the group consisting of hydrogen, halogen, lower-alkoxy, and pyridyl. Even more preferably, Y is C—$R^{11}$ and $R^7$, $R^8$, $R^9$, $R^{10}$ and $R^{11}$ independently from each other are selected from the group consisting of hydrogen, fluoro, bromo, methoxy, and pyridyl.

In another preferred embodiment of the present invention, Y is C—$R^{11}$, $R^8$ and $R^9$ or $R^8$ and $R^7$ are bound to each other to form a ring together with the carbon atoms to which they are attached and $R^8$ and $R^9$ together or $R^8$ and $R^7$ together are —O—$CH_2$—O—, —O—$CH_2$—CO—NH—, —O—$CH_2$—$CH_2$—$CH_2$—, —CH=CH—CH=CH—, or —CH=CH—CH=CH— substituted with lower-alkyl or lower-alkoxy, and $R^{10}$, $R^{11}$ and $R^7$ or $R^9$ respectively are hydrogen.

Compounds as defined above, wherein Y is C—$R^{11}$ and $R^7$, $R^8$, $R^9$, $R^{10}$ and $R^{11}$ independently from each other are selected from the group consisting of hydrogen, halogen, lower-alkoxy and heteroaryl, are also preferred. Even more preferred are compounds as defined above, wherein Y is C—$R^{11}$, $R^7$ is halogen, $R^8$ is hydrogen, $R^9$ is lower-alkoxy, heteroaryl or heteroaryl-lower-alkoxy, $R^{10}$ is hydrogen and $R^{11}$ is hydrogen or halogen. Most preferred are those compounds as defined above, wherein Y is C—$R^{11}$, $R^7$ is fluorine, $R^8$ is hydrogen, $R^9$ is methoxy, pyridin-3-yl, 5-amino-pyridin-2-yl, 6-amino-pyridin-3-yl, pyridin-2-yl-methoxy, or 2-amino-pyrimidin-5-yl, $R^{10}$ is hydrogen and $R^{11}$ is hydrogen or fluorine.

In particular, preferred compounds are the compounds of formula (I) described in the examples as individual compounds as well as pharmaceutically acceptable salts thereof.

Preferred compounds of formula (I) are those selected from the group consisting of
(S)-N-(4-Carbamimidoyl-benzyl)-2-methoxy-2-phenyl-acetamide hydrochloride,
(R)-N-(4-Carbamimidoyl-benzyl)-2-methoxy-2-phenyl-acetamide hydrochloride,
(RS)-2-(4-Benzyloxy-phenyl)-N-(4-carbamimidoyl-benzyl)-2-methoxy-acetamide hydrochloride,
(RS)-N-(4-Carbamimidoyl-benzyl)-2-methoxy-2-(4-phenoxy-phenyl)-acetamide hydrochloride,
(RS)-N-(4-Carbamimidoyl-benzyl)-2-methoxy-2-(3-phenoxy-phenyl)-acetamide hydrochloride,
(RS)-N-(4-Carbamimidoyl-benzyl)-2-ethoxy-2-phenyl-acetamide hydrochloride,
(RS)-N-(4-Carbamimidoyl-benzyl)-2-(2-fluoro-phenyl)-2-methoxy-acetamide hydrochloride,
(RS)-2-(3-Benzyloxy-phenyl)-N-(4-carbamimidoyl-benzyl)-2-methoxy-acetamide hydrochloride,
(RS)-N-(4-Carbamimidoyl-benzyl)-2-(3-hydroxy-phenyl)-2-methoxy-acetamide hydrochloride,
(RS)-N-(4-Carbamimidoyl-benzyl)-2-methoxy-2-(3-nitro-phenyl)-acetamide hydrochloride,
(RS)-2-Biphenyl-4-yl-N-(4-carbamimidoyl-benzyl)-2-methoxy-acetamide hydrochloride,
(RS)-2-Benzo[1,3]dioxol-5-yl-N-(4-carbamimidoyl-benzyl)-2-methoxy-acetamide hydrochloride,
(RS)-2-Benzo[1,3]dioxol-5-yl-N-(4-carbamimidoyl-benzyl)-2-ethoxy-acetamide hydrochloride,
(RS)-N-(4-Carbamimidoyl-benzyl)-2-[5-ethoxy-2-fluoro-3-(1-methyl-piperidin-4-yloxy)-phenyl]-2-methoxy-acetamide hydrochloride,
(RS)-N-(4-Carbamimidoyl-benzyl)-2-(2-fluoro-4-methoxy-phenyl)-2-methoxy-acetamide hydrochloride,
(RS)-[Amino-(4-{[2-(2-fluoro-4-methoxy-phenyl)-2-methoxy-acetylamino]-methyl}-phenyl)-methylene]-carbamic acid ethyl ester,
(RS)-2-(2-Fluoro-4-methoxy-phenyl)-N-[4-(N-hydroxycarbamimidoyl)-benzyl]-2-methoxy-acetamide, (RS)-2-(2-Fluoro-4-methoxy-phenyl)-N-[4-(N-aminocar-bamimidoyl)-benzyl]-2-methoxy-acetamide,
(RS)-{5-[(4-Carbamimidoyl-benzylcarbamoyl)-methoxy-methyl]-2-methoxy-phenoxy}-acetic acid methyl ester hydrochloride,
(RS)-N-(4-Carbamimidoyl-benzyl)-2-(3-carbamoyl-methoxy-4-methoxy-phenyl)-2-methoxy-acetamide hydrochloride,
(RS)-{5-[(4-Carbamimidoyl-benzylcarbamoyl)-ethoxy-methyl]-2-methoxy-phenoxy}-acetic acid ethyl ester hydrochloride,
(RS)-N-(4-Carbamimidoyl-benzyl)-2-(3-carbamoyl-methoxy-4-methoxy-phenyl)-2-ethoxy-acetamide hydrochloride,
(RS)-{5-[(4-Carbamimidoyl-benzylcarbamoyl)-ethoxy-methyl]-2-methoxy-phenoxy}-acetic acid,
(RS)-N-(4-Carbamimidoyl-benzyl)-2-ethoxy-2-(4-ethoxy-phenyl)-acetamide hydrochloride,
(RS)-N-(4-Carbamimidoyl-benzyl)-2-methoxy-2-[4-(1-methyl-piperidin-4-yloxy)-phenyl]-acetamide hydrochloride,
(RS)-N-(4-Carbamimidoyl-benzyl)-3,3,3-trifluoro-2-methoxy-2-phenyl-propionamide hydrochloride,
(RS)-N-(4-Carbamimidoyl-benzyl)-2-(2-fluoro-4,5-dimethoxy-phenyl)-2-methoxy-acetamide hydrochloride,
(RS)-N-(4-Carbamimidoyl-benzyl)-2-(3-isopropoxy-phenyl)-2-methoxy-acetamide hydrochloride,
(RS)-N-(4-Carbamimidoyl-benzyl)-2-(4-cyclopentyloxy-phenyl)-2-methoxy-acetamide hydrochloride,
(RS)-N-(4-Carbamimidoyl-benzyl)-2-(4-isopropoxy-phenyl)-2-methoxy-acetamide hydrochloride,
(RS)-{4-[(4-Carbamimidoyl-benzylcarbamoyl)-methoxy-methyl]-phenoxy}-acetic acid methyl ester hydrochloride,
(RS)-{4-[(4-Carbamimidoyl-benzylcarbamoyl)-methoxy-methyl]-phenoxy}-acetic acid,
(RS)-N-(4-Carbamimidoyl-benzyl)-2-methoxy-2-[3-(tetrahydro-pyran-4-yloxy)-phenyl]-acetamide hydrochloride,
(RS)-N-(4-Carbamimidoyl-benzyl)-2-(3,5-diethoxy-2-fluoro-phenyl)-2-methoxy-acetamide hydrochloride,
(RS)-N-(4-Carbamimidoyl-benzyl)-2-[5-ethoxy-2-fluoro-4-(2-hydroxy-ethoxy)-phenyl]-2-methoxy-acetamide hydrochloride,
(RS)-N-(4-Carbamimidoyl-benzyl)-2-(3,4-diethoxy-2-fluoro-phenyl)-2-methoxy-acetamide hydrochloride,
(RS)-N-(4-Carbamimidoyl-2-fluoro-benzyl)-2-(2-fluoro-4-methoxy-phenyl)-2-methoxy-acetamide hydrochloride,
(RS)-N-(4-Carbamimidoyl-3-fluoro-benzyl)-2-(2-fluoro-4-methoxy-phenyl)-2-methoxy-acetamide hydrochloride,
(RS)-2-(2,4-Bis-trifluoromethyl-phenyl)-N-(4-carbamimidoyl-benzyl)-2-methoxy-acetamide hydrochloride,
(RS)-N-[4-(N-Hydroxycarbamimidoyl)-benzyl]-2-(2-hydroxy-4-methoxy-phenyl)-2-methoxy-acetamide,
(RS)-N-(4-Carbamimidoyl-benzyl)-2-(2-hydroxy-4-methoxy-phenyl)-2-methoxy-acetamide actetate,
(RS)-N-(4-Carbamimidoyl-benzyl)-2-(2-fluoro-5-methoxy-phenyl)-2-methoxy-acetamide hydrochloride,
(RS)-N-(4-Carbamimidoyl-benzyl)-2-(2,3-difluoro-phenyl)-2-methoxy-acetamide hydrochloride,
(RS)-N-(4-Carbamimidoyl-benzyl)-2-(2,6-difluoro-phenyl)-2-methoxy-acetamide hydrochloride,
(RS)-2-(4-Bromo-2-fluoro-phenyl)-N-(4-carbamimidoyl-benzyl)-2-methoxy-acetamide hydrochloride,
(RS)-2-(4-Bromo-2-fluoro-phenyl)-N-(4-carbamimidoyl-benzyl)-2-ethoxy-acetamide hydrochloride,
(RS)-2-(4-Bromo-2-fluoro-phenyl)-N-(4-carbamimidoyl-benzyl)-2-propoxy-acetamide hydrochloride,
(RS)-N-(4-Carbamimidoyl-benzyl)-2-(2-fluoro-4-trifluoromethyl-phenyl)-2-methoxy-acetamide hydrochloride,
(RS)-N-(4-Carbamimidoyl-benzyl)-2-[4-(2-hydroxy-ethoxy)-phenyl]-2-methoxy-acetamide hydrochloride,
(RS)-N-(4-Carbamimidoyl-benzyl)-2-(4-dimethylamino-phenyl)-2-methoxy-acetamide hxdrochloride,
(RS)-N-(4-Carbamimidoyl-benzyl)-2-methoxy-2-(3-oxo-3,4-dihydro-2H-benzo[1,4]oxazin-6-yl)-acetamide hydrochloride,
(RS)-N-(4-Carbamimidoyl-benzyl)-2-methoxy-2-(4-pyrrolidin-1-yl-phenyl)-acetamide hydrochloride,
(RS)-N-(4-Carbamimidoyl-benzyl)-2-(2-chloro-phenyl)-2-methoxy-acetamide hydrochloride,
(RS)-2-(4-Acetylamino-phenyl)-N-(4-carbamimidoyl-benzyl)-2-methoxy-acetamide hydrochloride,
(RS)-N-(4-Carbamimidoyl-benzyl)-2-methoxy-2-(4-trifluoromethoxy-phenyl)-acetamide hydrochloride,
(RS)-N-(4-Carbamimidoyl-benzyl)-2-(4-imidazol-1-yl-phenyl)-2-methoxy-acetamide hydrochloride,
(RS)-N-(4-Carbamimidoyl-benzyl)-2-methoxy-2-(6-methoxy-naphthalen-2-yl)-acetamide hydrochloride,
(RS)-N-(4-Carbamimidoyl-benzyl)-2-methoxy-2-(4-morpholin-4-yl-phenyl)-acetamide hydrochloride,
(RS)-N-(4-Carbamimidoyl-benzyl)-2-methoxy-2-(2-morpholin-4-yl-phenyl)-acetamide hydrochloride,
(RS)-N-(4-Carbamimidoyl-benzyl)-2-[4-(3-dimethylamino-propoxy)-phenyl]-2-methoxy-acetamide hydrochloride,
(RS)-N-(4-Carbamimidoyl-benzyl)-2-(4'-dimethylamino-3-fluoro-biphenyl-4-yl)-2-methoxy-acetamide hydrochloride,
(RS)-N-(4-Carbamimidoyl-benzyl)-2-(3-fluoro-4'-methoxy-biphenyl-4-yl)-2-methoxy-acetamide hydrochloride,
(RS)-N-(4-Carbamimidoyl-benzyl)-2-(3-fluoro-2'-methoxy-biphenyl-4-yl)-2-methoxy-acetamide hydrochloride,
(RS)-N-(4-Carbamimidoyl-benzyl)-2-(3-fluoro-biphenyl-4-yl)-2-methoxy-acetamide hydrochloride,
(RS)-N-(4-Carbamimidoyl-benzyl)-2-(3-fluoro-3'-methoxy-biphenyl-4-yl)-2-methoxy-acetamide hydrochloride,
(RS)-N-(4-Carbamimidoyl-benzyl)-2-(2,2-dimethyl-chroman-6-yl)-2-methoxy-acetamide hydrochloride,
(RS)-N-(4-Carbamimidoyl-benzyl)-2-ethoxy-2-(2-fluoro-4-methoxy-phenyl)-acetamide hydrochloride,
(RS)-2-Ethoxy-2-(2-fluoro-4-methoxy-phenyl)-N-[4-(N-hydroxycarbamimidoyl)-benzyl]-acetamide,
(RS)-4-[3-(3-Cyclopentyloxy-4-methoxy-phenyl)-3-methoxy-2-oxo-propylamino]-benzamidine hydrochloride,
(RS)-N-(4-Carbamimidoyl-benzyl)-2-(2-chloro-4-methoxy-phenyl)-2-methoxy-acetamide hydrochloride,
(RS)-N-(4-Carbamimidoyl-benzyl)-2-(2,6-difluoro-4-methoxy-phenyl)-2-methoxy-acetamide hydrochloride,
(RS)-N-(4-Carbamimidoyl-benzyl)-2-(2-fluoro-4-methoxy-phenyl)-2-propoxy-acetamide hydrochloride,
(RS)-N-(4-Carbamimidoyl-benzyl)-2-methoxy-2-naphthalen-1-yl-propionamide hydrochloride,
(RS)-2-(4-Bromo-2,6-difluoro-phenyl)-N-(4-carbamimidoyl-benzyl)-2-methoxy-acetamide hydrochloride,
(RS)-N-(4-Carbamimidoyl-benzyl)-2-(2-fluoro-4-isopropoxy-phenyl)-2-methoxy-acetamide hydrochloride,
(RS)-N-(4-Carbamimidoyl-benzyl)-2-(2-fluoro-4-isobutoxy-phenyl)-2-methoxy-acetamide hydrochloride,
(RS)-N-(4-Carbamimidoyl-benzyl)-2-{2-fluoro-4-[2-(4-fluoro-phenyl)-ethoxy]-phenyl}-2-methoxy-acetamide hydrochloride,
(RS)-N-(4-Carbamimidoyl-benzyl)-2-(2-fluoro-4-pyridin-3-yl-phenyl)-2-methoxy-acetamide hydrochloride, (RS)-N-(4-Carbamimidoyl-benzyl)-2-(2-fluoro-4-pyridin-4-yl-phenyl)-2-methoxy-acetamide hydrochloride,
(RS)-2-(5-Bromo-2-fluoro-phenyl)-N-(4-carbamimidoyl-benzyl)-2-methoxy-acetamide hydrochloride,
(RS)-N-(4-Carbamimidoyl-benzyl)-2-(4-fluoro-biphenyl-3-yl)-2-methoxy-acetamide hydrochloride,
(RS)-N-(4-Carbamimidoyl-benzyl)-2-(2-fluoro-5-methyl-phenyl)-2-methoxy-acetamide hydrochloride,
(RS)-N-(4-Carbamimidoyl-benzyl)-2-(2-fluoro-5-trifluoromethyl-phenyl)-2-methoxy-acetamide hydrochloride,
(RS)-N-(4-Carbamimidoyl-benzyl)-2-(2-fluoro-6-methoxy-phenyl)-2-methoxy-acetamide hydrochloride,
(RS)-N-(4-Carbamimidoyl-benzyl)-2-(2-fluoro-6-hydroxy-phenyl)-2-methoxy-acetamide hydrochloride,
(RS)-N-(4-Carbamimidoyl-benzyl)-2-dimethylamino-2-phenyl-acetamide hydrochloride,
(RS)-N-(4-Carbamimidoyl-benzyl)-2-methylamino-2-phenyl-acetamide hydrochloride,
(RS)-N-(4-Carbamimidoyl-benzyl)-2-methylsulfanyl-2-phenyl-acetamide hydrochloride,
(RS)-N-(4-Carbamimidoyl-benzyl)-2-ethylsulfanyl-2-phenyl-acetamide hydrochloride,
(RS)-N-(4-Carbamimidoyl-benzyl)-2-methanesulfonyl-2-phenyl-acetamide hydrochloride,
(RS)-2-Amino-N-(4-carbamimidoyl-benzyl)-2-phenyl-acetamide hydrochloride,
(RS)-2-Acetylamino-N-(4-carbamimidoyl-benzyl)-2-phenyl-acetamide hydrochloride,
(RS)-N-(4-Carbamimidoyl-benzyl)-2-[2-fluoro-4-(2-phenoxy-ethoxy)-phenyl]-2-methoxy-acetamide hydrochloride,
(RS)-N-(4-Carbamimidoyl-benzyl)-2-methoxy-2-pyridin-2-yl-acetamide hydrochloride,
(RS)-N-(4-Carbamimidoyl-benzyl)-2-methoxy-2-phenyl-propionamide hydrochloride,
(RS)-2-(4-Bromo-2,6-difluoro-phenyl)-N-(4-carbamimidoyl-benzyl)-2-ethoxy-acetamide hydrochloride,
N-(4-Carbamimidoyl-benzyl)-2-[2-fluoro-6-(2-hydroxy-ethoxy)-phenyl]-2-methoxy-acetamide hydrochloride, and
N-(4-Carbamimidoyl-benzyl)-2-(2-carbamoylmethoxy-6-fluoro-phenyl)-2-methoxy-acetamide hydrochloride, and pharmaceutically acceptable salts thereof.

Other preferred compounds of formula (I) are those selected from the group consisting of (RS)-2-Biphenyl-4-yl-N-(4-carbamimidoyl-benzyl)-2-ethoxy-propionamide hydrochloride,
(RS)-2-[3-(1-Benzenesulfonyl-piperidin-4-yloxy)-5-ethoxy-2-fluoro-phenyl]-N-(4-carbamimidoyl-benzyl)-2-methoxy-acetamide hydrochloride,
(RS)-N-(4-Carbamimidoyl-benzyl)-2-[5-ethoxy-2-fluoro-3-(1-methanesulfonyl-piperidin-4-yloxy)-phenyl]-2-methoxy-acetamide hydrochloride,
(RS)-2-[3-(1-Acetyl-piperidin-4-yloxy)-5-ethoxy-2-fluoro-phenyl]-N-(4-carbamimidoyl-benzyl)-2-methoxy-acetamide hydrochloride,
(RS)-2-[3-(1-Benzoyl-piperidin-4-yloxy)-5-ethoxy-2-fluoro-phenyl]-N-(4-carbamimidoyl-benzyl)-2-methoxy-acetamide hydrochloride,
(RS)-N-(4-Carbamimidoyl-2-chloro-benzyl)-2-(2-fluoro-4-methoxy-phenyl)-2-methoxy-acetamide hydrochloride,
(RS)-N-(4-Carbamimidoyl-2-chloro-benzyl)-2-ethoxy-2-(2-fluoro-4-methoxy-phenyl)-acetamide hydrochloride,
(RS)-N-(4-Carbamimidoyl-2-chloro-benzyl)-2-(2,6-difluoro-4-methoxy-phenyl)-2-ethoxy-acetamide hydrochloride,
(RS)-N-(4-Carbamimidoyl-2-chloro-benzyl)-2-(2,6-difluoro-4-methoxy-phenyl)-2-methoxy-acetamide hydrochloride,
(RS)-N-[3-Chloro-4-(N-hydroxycarbamimidoyl)-benzyl]-2-ethoxy-2-(2-fluoro-4-methoxy-phenyl)-acetamide,
(RS)-N-(4-Carbamimidoyl-3-chloro-benzyl)-2-ethoxy-2-(2-fluoro-4-methoxy-phenyl)-acetamide acetate,
(RS)-2-(4-Bromo-2,6-difluoro-phenyl)-N-(4-carbamimidoyl-2-methoxy-benzyl)-2-ethoxy-acetamide hydrochloride,
(RS)-N-(4-Carbamimidoyl-2-methoxy-benzyl)-2-ethoxy-2-(2-fluoro-4-methoxy-phenyl)-acetamide hydrochloride,
(RS)-N-(4-Carbamimidoyl-2-phenoxy-benzyl)-2-ethoxy-2-(2-fluoro-4-methoxy-phenyl)-acetamide hydrochloride,
(RS)-N-(4-Carbamimidoyl-2-o-tolyloxy-benzyl)-2-ethoxy-2-(2-fluoro-4-methoxy-phenyl)-acetamide hydrochloride,
(RS)-N-[4-Carbamimidoyl-2-(4-fluoro-phenoxy)-benzyl]-2-ethoxy-2-(2-fluoro-4-methoxy-phenyl)-acetamide hydrochloride,
(RS)-N-[4-Carbamimidoyl-2-(pyridin-3-yloxy)-benzyl]-2-ethoxy-2-(2-fluoro-4-methoxy-phenyl)-acetamide acetic acid,
(RS)-N-[4-Carbamimidoyl-2-(5-nitro-pyridin-2-yloxy)-benzyl]-2-ethoxy-2-(2-fluoro-4-methoxy-phenyl)-acetamide hydrochloride,
(RS)-N-[2-(5-Amino-pyridin-2-yloxy)-4-carbamimidoyl-benzyl]-2-ethoxy-2-(2-fluoro-4-methoxy-phenyl)-acetamide hydrochloride,
(RS)-N-(5-Carbamimidoyl-biphenyl-2-ylmethyl)-2-ethoxy-2-(2-fluoro-4-methoxy-phenyl)-acetamide hydrochloride,
(RS)-(5-Carbamimidoyl-2-{[2-ethoxy-2-(2-fluoro-4-methoxy-phenyl)-acetylamino]-methyl}-phenoxy)-acetic acid ethyl ester hydrochloride 1:1,
(RS)-N-(4-Carbamimidoyl-2-carbamoylmethoxy-benzyl)-2-ethoxy-2-(2-fluoro-4-methoxy-phenyl)-acetamide hydrochloride 1:1,
(RS)-N-(4-Carbamimidoyl-2-isopropoxy-benzyl)-2-ethoxy-2-(2-fluoro-4-methoxy-phenyl)-acetamide hydrochloride,
(RS)-N-[4-Carbamimidoyl-2-(2-hydroxy-ethoxy)-benzyl]-2-ethoxy-2-(2-fluoro-4-methoxy-phenyl)-acetamide hydrochloride,
2-(5-Carbamimidoyl-2-{[2-ethoxy-2-(2-fluoro-4-methoxy-phenyl)-acetylamino]-methyl}-phenoxy)-N-isopropyl-2-phenyl-acetamide hydrochloride,
(RS)-(5-Carbamimidoyl-2-{[2-ethoxy-2-(2-fluoro-4-methoxy-phenyl)-acetylamino]-methyl}-phenoxy)-acetic acid,
(RS)-(S)-2-(5-Carbamimidoyl-2-{[2-ethoxy-2-(2-fluoro-4-methoxy-phenyl)-acetylamino]-methyl}-phenoxy)-propionic acid ethyl ester hydrochloride,
((RS)-S)-2-(5-Carbamimidoyl-2-{[2-ethoxy-2-(2-fluoro-4-methoxy-phenyl)-acetylamino]-methyl}-phenoxy)-propionamide hydrochloride,
(RS)-(R)-2-(5-Carbamimidoyl-2-{[2-ethoxy-2-(2-fluoro-4-methoxy-phenyl)-acetylamino]-methyl}-phenoxy)-propionic acid ethyl ester hydrochloride,
(RS)-(R)-2-(5-Carbamimidoyl-2-{[2-ethoxy-2-(2-fluoro-4-methoxy-phenyl)-acetylamino]-methyl}-phenoxy)-propionamide hydrochloride,
(RS)-N-(4-Carbamimidoyl-2-carbamoylmethoxy-benzyl)-2-(2-fluoro-4-methoxy-phenyl)-2-methoxy-acetamide hydrochloride,
(RS)-N-(4-Carbamimidoyl-2-phenoxy-benzyl)-2-(2,6-difluoro-4-methoxy-phenyl)-2-ethoxy-acetamide hydrochloride,
(RS)-N-(4-Carbamimidoyl-2-methoxy-benzyl)-2-(2,6-difluoro-4-methoxy-phenyl)-2-ethoxy-acetamide hydrochloride, (RS)-N-(4-Carbamimidoyl-2-carbamoylmethoxy-benzyl)-2-(2,6-difluoro-4-methoxy-phenyl)-2-ethoxy-acetamide hydrochloride,
(RS)-N-[4-Carbamimidoyl-2-(2-fluoro-benzyloxy)-benzyl]-2-(2,6-difluoro-4-methoxy-phenyl)-2-ethoxy-acetamide hydrochloride,
(RS)-N-[4-Carbamimidoyl-2-(5-chloro-2-fluoro-benzyloxy)-benzyl]-2-(2,6-difluoro-4-methoxy-phenyl)-2-ethoxy-acetamide hydrochloride,
(RS)-N-{4-Carbamimidoyl-2-[(2-methoxy-ethylcarbamoyl)-methoxy]-benzyl}-2-(2,6-difluoro-4-methoxy-phenyl)-2-ethoxy-acetamide hydrochloride,
(RS)-N-{4-Carbamimidoyl-2-[(2-morpholin-4-yl-ethylcarbamoyl)-methoxy]-benzyl}-2-(2,6-difluoro-4-methoxy-phenyl)-2-ethoxy-acetamide hydrochloride,
(RS)-N-{4-Carbamimidoyl-2-[(2-diethylamino-ethylcarbamoyl)-methoxy]-benzyl}-2-(2,6-difluoro-4-methoxy-phenyl)-2-ethoxy-acetamide hydrochloride,
(RS)-N-[4-Carbamimidoyl-2-([1,2,4]oxadiazol-3-ylmethoxy)-benzyl]-2-(2,6-difluoro-4-methoxy-phenyl)-2-ethoxy-acetamide hydrochloride,
(RS)-N-(4-Carbamimidoyl-2-carbamimidoylmethoxy-benzyl)-2-(2,6-difluoro-4-methoxy-phenyl)-2-ethoxy-acetamide hydrochloride,
(RS)-N-[2-(1H-Benzoimidazol-2-ylmethoxy)-4-carbamimidoyl-benzyl]-2-(2,6-difluoro-4-methoxy-phenyl)-2-ethoxy-acetamide hydrochloride,
(RS)-N-[4-Carbamimidoyl-2-((1S,3R,4S)-3,4-dihydroxy-cyclopentyloxy)-benzyl]-2-(2,6-difluoro-4-methoxy-phenyl)-2-ethoxy-acetamide hydrochloride,
a mixture of (RS) and (SR)-N-[4-Carbamimidoyl-2-((1RS,2RS)-2-hydroxy-cyclopentyloxy)-benzyl]-2-(2,6-difluoro-4-methoxy-phenyl)-2-ethoxy-acetamide hydrochloride,
(RS)-N-(4-Carbamimidoyl-2-carbamoylmethoxy-benzyl)-2-(2,6-difluoro-4-methoxy-phenyl)-2-methoxy-acetamide hydrochloride,
(RS)-N-(4-Carbamimidoyl-2-methylcarbamoylmethoxy-benzyl)-2-(2,6-difluoro-4-methoxy-phenyl)-2-methoxy-acetamide hydrochloride,
(RS)-N-[4-Carbamimidoyl-2-(isopropylcarbamoyl-methoxy)-benzyl]-2-(2,6-difluoro-4-methoxy-phenyl)-2-methoxy-acetamide hydrochloride,
(RS)-N-{4-Carbamimidoyl-2-[(4-fluoro-phenylcarbamoyl)-methoxy]-benzyl}-2-(2,6-difluoro-4-methoxy-phenyl)-2-methoxy-acetamide hydrochloride,
(RS)-N-[4-Carbamimidoyl-2-(pyridin-2-ylmethoxy)-benzyl]-2-(2,6-difluoro-4-methoxy-phenyl)-2-methoxy-acetamide hydrochloride,
(RS)-N-[4-Carbamimidoyl-2-(2,2,2-trifluoro-ethoxy)-benzyl]-2-(2,6-difluoro-4-methoxy-phenyl)-2-methoxy-acetamide hydrochloride,
(RS)-N-[4-Carbamimidoyl-2-(pyridin-3-ylmethoxy)-benzyl]-2-(2,6-difluoro-4-methoxy-phenyl)-2-methoxy-acetamide hydrochloride,
(RS)-N-[4-Carbamimidoyl-2-(pyridin-4-ylmethoxy)-benzyl]-2-(2,6-difluoro-4-methoxy-phenyl)-2-methoxy-acetamide hydrochloride,
(RS)-N-(4-Carbamimidoyl-benzyl)-2-(2,6-difluoro-4-hydroxy-phenyl)-2-ethoxy-acetamide hydrochloride,
(RS)-N-(4-Carbamimidoyl-benzyl)-2-[2,6-difluoro-4-(2-morpholin-4-yl-ethoxy)-phenyl]-2-ethoxy-acetamide dihydrochloride,
(RS)-{[4-({2-[2,6-Difluoro-4-(2-morpholin-4-yl-ethoxy)-phenyl]-2-ethoxy-acetylamino}-methyl)-phenyl]-imino-methyl}-carbamic acid benzyl ester,
(RS)-N-(4-Carbamimidoyl-benzyl)-2-(2,6-difluoro-4-phenethyloxy-phenyl)-2-ethoxy-acetamide hydrochloride,
(RS)-N-(4-Carbamimidoyl-benzyl)-2-(4-cyclopropylmethoxy-2,6-difluoro-phenyl)-2-ethoxy-acetamide hydrochloride,
(RS)-N-(4-Carbamimidoyl-benzyl)-2-ethoxy-2-(4-ethoxy-2,6-difluoro-phenyl)-acetamide hydrochloride,
(RS)-N-(4-Carbamimidoyl-benzyl)-2-[2,6-difluoro-4-(4-methoxy-phenoxy)-phenyl]-2-ethoxy-acetamide,
(RS)-N-(4-Carbamimidoyl-benzyl)-2-[4-(3,4-dimethoxy-phenoxy)-2,6-difluoro-phenyl]-2-ethoxy-acetamide hydrochloride,
(RS)-N-(4-Carbamimidoyl-benzyl)-2-[2,6-difluoro-4-(3-methoxy-phenoxy)-phenyl]-2-ethoxy-acetamide hydrochloride,
(RS)-2-[4-(3-Acetylamino-phenoxy)-2,6-difluoro-phenyl]-N-(4-carbamimidoyl-benzyl)-2-ethoxy-acetamide hydrochloride,
(RS)-N-(4-Carbamimidoyl-benzyl)-2-[4-(4-cyano-phenoxy)-2,6-difluoro-phenyl]-2-ethoxy-acetamide hydrochloride,
(RS)-N-(4-Carbamimidoyl-benzyl)-2-[2,6-difluoro-4-(3-trifluoromethoxy-phenoxy)-phenyl]-2-ethoxy-acetamide hydrochloride,
(RS)-(2,6-Difluoro-4-trifluoromethanesulfonyloxy-phenyl)-ethoxy-acetic acid ethyl ester,
(RS)-4-(Ethoxy-ethoxycarbonyl-methyl)-3,5-difluoro-benzoic acid 2-trimethylsilanyl-ethyl ester,
(RS)-4-[(4-Carbamimidoyl-benzylcarbamoyl)-ethoxy-methyl]-3,5-difluoro-N-isobutyl-benzamide hydrochloride,
(RS)-4-[(4-Carbamimidoyl-benzylcarbamoyl)-ethoxy-methyl]-N-ethyl-3,5-difluoro-benzamide hydrochloride,
(RS)-4-[(4-Carbamimidoyl-benzylcarbamoyl)-ethoxy-methyl]-3,5-difluoro-N-(2-methoxy-ethyl)-benzamide hydrochloride,
(RS)-4-[(4-Carbamimidoyl-benzylcarbamoyl)-ethoxy-methyl]-N-cyclopentyl-3,5-difluoro-benzamide hydrochloride,
(RS)-4-[(4-Carbamimidoyl-benzylcarbamoyl)-ethoxy-methyl]-3,5-difluoro-N-(2,2,2-trifluoro-ethyl)-benzamide hydrochloride,
(RS)-4-[(4-Carbamimidoyl-benzylcarbamoyl)-ethoxy-methyl]-N-cyclopropylmethyl-3,5-difluoro-benzamide hydrochloride,
(RS)-[(4-{[2-(2,6-Difluoro-3-hydroxy-phenyl)-2-ethoxy-acetylamino]-methyl}-phenyl)-imino-methyl]-carbamic acid benzyl ester,
(RS)-N-(4-Carbamimidoyl-benzyl)-2-(2,6-difluoro-3-hydroxy-phenyl)-2-ethoxy-acetamide hydrochloride,
(RS)-N-(4-Carbamimidoyl-benzyl)-2-ethoxy-2-{3-[2-(2-ethoxy-ethoxy)-ethoxy]-2,6-difluoro-phenyl}-acetamide hydrochloride,
(RS)-N-(4-Carbamimidoyl-benzyl)-2-[3-(3-dimethylamino-propoxy)-2,6-difluoro-phenyl]-2-ethoxy-acetamide dihydrochloride,
(RS)-N-(4-Carbamimidoyl-benzyl)-2-(2,6-difluoro-3-{2-[2-(2-methoxy-ethoxy)-ethoxy]-ethoxy}-phenyl)-2-ethoxy-acetamide hydrochloride,
(RS)-N-(4-Carbamimidoyl-benzyl)-2-[2,6-difluoro-3-(3-pyridin-4-yl-propoxy)-phenyl]-2-ethoxy-acetamide dihydrochloride,
(RS)-N-(4-Carbamimidoyl-benzyl)-2-[2,6-difluoro-3-(2-pyrrolidin-1-yl-ethoxy)-phenyl]-2-ethoxy-acetamide dihydrochloride,
(RS)-N-(4-Carbamimidoyl-benzyl)-2-[2,6-difluoro-3-(1-methyl-cyclopropylmethoxy)-phenyl]-2-ethoxy-acetamide hydrochloride, (RS)-N-(4-Carbamimidoyl-benzyl)-2-[2,6-difluoro-3-(2-piperidin-1-yl-ethoxy)-phenyl]-2-ethoxy-acetamide dihydrochloride,
(RS,RS)-N-(4-Carbamimidoyl-benzyl)-2-[3-(3-chloro-2-hydroxymethyl-2-methyl-propoxy)-2,6-difluoro-phenyl]-2-ethoxy-acetamide hydrochloride,
(RS)-N-(4-Carbamimidoyl-benzyl)-2-ethoxy-2-[3-(2-ethoxy-ethoxy)-2,6-difluoro-phenyl]-acetamide hydrochloride,
(RS)-N-(4-Carbamimidoyl-benzyl)-2-[2,6-difluoro-3-(2-methoxy-ethoxy)-phenyl]-2-ethoxy-acetamide hydrochloride,
(RS)-N-(4-Carbamimidoyl-benzyl)-2-[3-(3-dimethylamino-2,2-dimethyl-propoxy)-2,6-difluoro-phenyl]-2-ethoxy-acetamide dihydrochloride,
(RS)-N-(4-Carbamimidoyl-benzyl)-2-[2,6-difluoro-3-(2-thiophen-2-yl-ethoxy)-phenyl]-2-ethoxy-acetamide hydrochloride,
(RS,RS)-N-(4-Carbamimidoyl-benzyl)-2-[2,6-difluoro-3-(tetrahydro-furan-2-ylmethoxy)-phenyl]-2-ethoxy-acetamide hydrochloride,
(RS)-N-(4-Carbamimidoyl-benzyl)-2-(2,6-difluoro-3-isobutoxy-phenyl)-2-ethoxy-acetamide hydrochloride,
(RS,RS,RS)-N-(4-Carbamimidoyl-benzyl)-2-[2,6-difluoro-3-(2-methyl-cyclopropylmethoxy)-phenyl]-2-ethoxy-acetamide hydrochloride,
(RS)-N-(4-Carbamimidoyl-benzyl)-2-[3-(2-cyclopropyl-ethoxy)-2,6-difluoro-phenyl]-2-ethoxy-acetamide hydrochloride,
(RS)-N-(4-Carbamimidoyl-benzyl)-2-ethoxy-2-(3-ethoxy-2,6-difluoro-phenyl)-acetamide hydrochloride,
(RS)-N-(4-Carbamimidoyl-benzyl)-2-(2,6-difluoro-3-propoxy-phenyl)-2-ethoxy-acetamide hydrochloride,
(RS)-N-(4-Carbamimidoyl-benzyl)-2-(3-cyclopropyl-methoxy-2,6-difluoro-phenyl)-2-ethoxy-acetamide hydrochloride,
(RS)-N-(4-Carbamimidoyl-benzyl)-2-[3-(2-dimethylamino-ethoxy)-2,6-difluoro-phenyl]-2-ethoxy-acetamide dihydrochloride,
(RS)-N-(4-Carbamimidoyl-benzyl)-2-(3-cyclobutyl-methoxy-2,6-difluoro-phenyl)-2-ethoxy-acetamide hydrochloride,
(RS)-N-(4-Carbamimidoyl-benzyl)-2-{2,6-difluoro-3-[2-(2-oxo-pyrrolidin-1-yl)-ethoxy]-phenyl}-2-ethoxy-acetamide hydrochloride,
(RS)-N-(4-Carbamimidoyl-benzyl)-2-[2,6-difluoro-3-(3,3,3-trifluoro-propoxy)-phenyl]-2-ethoxy-acetamide hydrochloride,
(RS)-N-(4-Carbamimidoyl-benzyl)-2-[2,6-difluoro-3-(2-pyridin-3-yl-ethoxy)-phenyl]-2-ethoxy-acetamide dihydrochloride,
(RS)-N-(4-Carbamimidoyl-benzyl)-2-(3-diethylcarbamoyl-methoxy-2,6-difluoro-phenyl)-2-ethoxy-acetamide hydrochloride,
(RS)-N-(4-Carbamimidoyl-benzyl)-2-[2,6-difluoro-3-(2-morpholin-4-yl-ethoxy)-phenyl]-2-ethoxy-acetamide dihydrochloride,
(RS,RS)-N-(4-Carbamimidoyl-benzyl)-2-[2,6-difluoro-3-(1-methyl-piperidin-3-ylmethoxy)-phenyl]-2-ethoxy-acetamide dihydrochloride,
(RS,RS)-N-(4-Carbamimidoyl-benzyl)-2-[2,6-difluoro-3-(1-methyl-piperidin-2-ylmethoxy)-phenyl]-2-ethoxy-acetamide dihydrochloride,
(RS)-N-(4-Carbamimidoyl-benzyl)-2-[2,6-difluoro-3-(2-pyridin-2-yl-ethoxy)-phenyl]-2-ethoxy-acetamide dihydrochloride,
(RS,RS)-N-(4-Carbamimidoyl-benzyl)-2-[2,6-difluoro-3-(2-piperidin-2-yl-ethoxy)-phenyl]-2-ethoxy-acetamide dihydrochloride,
(RS)-N-(4-Carbamimidoyl-benzyl)-2-(2,6-difluoro-3-methoxy-phenyl)-2-ethoxy-acetamide hydrochloride,
(RS)-N-(4-Carbamimidoyl-benzyl)-2-(3-cyclohexyloxy-2,6-difluoro-phenyl)-2-ethoxy-acetamide hydrochloride,
(RS)-N-(4-Carbamimidoyl-benzyl)-2-[2,6-difluoro-3-(piperidin-4-yloxy)-phenyl]-2-ethoxy-acetamide dihydrochloride,
(R,S)-N-(4-Carbamimidoyl-benzyl)-2-[2,6-difluoro-3-(4-fluoro-phenoxy)-phenyl]-2-ethoxy-acetamide hydrochloride,
(RS)-N-(4-Carbamimidoyl-benzyl)-2-[2,6-difluoro-3-(pyridin-3-yloxy)-phenyl]-2-ethoxy-acetamide dihydrochloride,
(RS)-N-(4-Carbamimidoyl-benzyl)-2-[2,6-difluoro-3-(3-trifluoromethyl-phenoxy)-phenyl]-2-ethoxy-acetamide hydrochloride,
(RS)-N-(4-Carbamimidoyl-benzyl)-2-(2,6-difluoro-3-m-tolyloxy-phenyl)-2-ethoxy-acetamide hydrochloride,
(RS)-N-(4-Carbamimidoyl-benzyl)-2-ethoxy-2-[3-(3-ethoxy-phenoxy)-2,6-difluoro-phenyl]-acetamide hydrochloride,
(RS)-N-(4-Carbamimidoyl-benzyl)-2-ethoxy-2-[3-(1-ethyl-propoxy)-2,6-difluoro-phenyl]-acetamide acetate,
(RS)-N-(4-Carbamimidoyl-benzyl)-2-(3-cyclopentyloxy-2,6-difluoro-phenyl)-2-ethoxy-acetamide acetate,
(RS)-N-(4-Carbamimidoyl-benzyl)-2-[2,6-difluoro-3-(tetrahydro-pyran-4-yloxy)-phenyl]-2-ethoxy-acetamide acetate,
(RS)-N-(4-Carbamimidoyl-benzyl)-2-(2,6-difluoro-3-pyridin-2-yl-phenyl)-2-ethoxy-acetamide dihydrochloride,
(RS)-N-(4-Carbamimidoyl-benzyl)-2-[2,6-difluoro-3-(6-methoxy-pyridin-3-yl)-phenyl]-2-ethoxy-acetamide dihydrochloride,
(RS)-N-(4-Carbamimidoyl-benzyl)-2-(2,6-difluoro-3-pyridin-3-yl-phenyl)-2-ethoxy-acetamide dihydrochloride,
(RS)-N-(4-Carbamimidoyl-benzyl)-2-(2,6-difluoro-3-pyrimidin-5-yl-phenyl)-2-ethoxy-acetamide dihydrochloride,
(RS)-N-(4-Carbamimidoyl-benzyl)-2-(2,6-difluoro-3-pyridin-4-yl-phenyl)-2-ethoxy-acetamide dihydrochloride,
(RS)-N-(4-Carbamimidoyl-benzyl)-2-(2,4-difluoro-3'-methyl-biphenyl-3-yl)-2-methoxy-acetamide,
(RS)-N-(4-Carbamimidoyl-benzyl)-2-(2,4-difluoro-4'-methyl-biphenyl-3-yl)-2-methoxy-acetamide hydrochloride,
(RS)-N-(4-Carbamimidoyl-benzyl)-2-methoxy-2-(2,4,4'-trifluoro-biphenyl-3-yl)-acetamide acetate,
(RS)-N-(4-Carbamimidoyl-benzyl)-2-(2,4-difluoro-4'-methylsulfanyl-biphenyl-3-yl)-2-methoxy-acetamide hydrochloride,
(RS)-N-(4-Carbamimidoyl-benzyl)-2-(2,4-difluoro-3'-trifluoromethyl-biphenyl-3-yl)-2-methoxy-acetamide acetate,
(RS)-N-(4-Carbamimidoyl-benzyl)-2-(2,4-difluoro-4'-methoxy-biphenyl-3-yl)-2-methoxy-acetamide hydrochloride,
(RS)-N-(4-Carbamimidoyl-benzyl)-2-[2,6-difluoro-3-(morpholine-4-carbonyl)-phenyl]-2-methoxy-acetamide acetate,
(RS)-2-[2,6-difluoro-3-(morpholine-4-carbonyl)-phenyl]-N-[4-(N-hydroxycarbamimidoyl)-benzyl]-2-methoxy-acetamide,
(RS)-3-[(4-Carbamimidoyl-benzylcarbamoyl)-methoxymethyl]-N-ethyl-2,4-difluoro-benzamide acetate, (RS)-3-[(4-Carbamimidoyl-benzylcarbamoyl)-methoxy-methyl]-2,4-difluoro-N-(2-methoxy-ethyl)-benzamide acetate,
(RS)-3-[(4-Carbamimidoyl-benzylcarbamoyl)-methoxy-methyl]-N,N-diethyl-2,4-difluoro-benzamide acetate,
(RS)-3-[(4-Carbamimidoyl-benzylcarbamoyl)-methoxy-methyl]-2,4-difluoro-N-(2,2,2-trifluoro-ethyl)-benzamide acetate,
(RS)-3-[(4-Carbamimidoyl-benzylcarbamoyl)-methoxy-methyl]-N-cyclopropylmethyl-2,4-difluoro-benzamide acetate,
(RS)-N-(4-Carbamimidoyl-benzyl)-2-[2,6-difluoro-3-(pyridin-2-ylmethoxy)-phenyl]-2-methoxy-acetamide dihydrochloride,
(RS)-N-(4-Carbamimidoyl-benzyl)-2-[2,6-difluoro-3-(pyridin-3-ylmethoxy)-phenyl]-2-methoxy-acetamide dihydrochloride,
(RS)-N-(4-Carbamimidoyl-benzyl)-2-[2,6-difluoro-3-(pyridin-4-ylmethoxy)-phenyl]-2-methoxy-acetamide dihydrochloride,
(RS)-N-(4-Carbamimidoyl-benzyl)-2-[2,6-difluoro-3-(4-fluoro-phenoxy)-phenyl]-2-methoxy-acetamide acetate,
(RS)-2-[2,6-difluoro-3-(4-fluoro-phenoxy)-phenyl]-N-[4-(N-hydroxycarbamimidoyl)-benzyl]-2-methoxy-acetamide,
(RS)-N-(4-Carbamimidoyl-benzyl)-2-[2,6-difluoro-3-(pyridin-3-yloxy)-phenyl]-2-methoxy-acetamide acetate,
(RS)-N-(4-Carbamimidoyl-benzyl)-2-(3,5-difluoro-biphenyl-4-yl)-2-methoxy-acetamide hydrochloride,
(RS)-N-(4-Carbamimidoyl-benzyl)-2-(3,5-difluoro-biphenyl-4-yl)-2-ethoxy-acetamide hydrochloride,
(RS)-N-(4-Carbamimidoyl-benzyl)-2-[2,6-difluoro-4-(1H-indol-5-yl)-phenyl]-2-ethoxy-acetamide acetic acid,
(RS)-2-(2,6-Difluoro-4-furan-2-yl-phenyl)-2-ethoxy-N-[4-(N-hydroxycarbamimidoyl)-benzyl]-acetamide,
(RS)-N-(4-Carbamimidoyl-benzyl)-2-(2,6-difluoro-4-furan-2-yl-phenyl)-2-ethoxy-acetamide acetate,
N-(4-Carbamimidoyl-benzyl)-2-[2,6-difluoro-4-(tetrahydro-furan-2-yl)-phenyl]-2-ethoxy-acetamide acetic acid,
(RS)-{4'-[(4-Carbamimidoyl-benzylcarbamoyl)-ethoxy-methyl]-3',5'-difluoro-biphenyl-3-yloxy}-acetic acid ethyl ester hydrochloride,
(RS)-{4'-[(4-Carbamimidoyl-benzylcarbamoyl)-ethoxy-methyl]-3',5'-difluoro-biphenyl-3-yloxy}-acetic acid,
(RS)-N-(4-Carbamimidoyl-benzyl)-2-(3'-carbamoyl-methoxy-3,5-difluoro-biphenyl-4-yl)-2-ethoxy-acetamide hydrochloride,
(RS)-N-(4-Carbamimidoyl-benzyl)-2-[3,5-difluoro-3'-(2-hydroxy-ethoxy)-biphenyl-4-yl]-2-ethoxy-acetamide hydrochloride,
(RS)-N-(4-Carbamimidoyl-benzyl)-2-[3'-(3-dimethylamino-propoxy)-3,5-difluoro-biphenyl-4-yl]-2-ethoxy-acetamide hydrochloride,
(RS)-2-[2'-(2-Benzyloxy-ethoxy)-3,5-difluoro-biphenyl-4-yl]-N-(4-carbamimidoyl-benzyl)-2-ethoxy-acetamide hydrochloride,
(RS)-N-(4-Carbamimidoyl-benzyl)-2-[2'-(2-dimethylamino-ethoxy)-3,5-difluoro-biphenyl-4-yl]-2-ethoxy-acetamide hydrochloride,
(RS)-N-(4-Carbamimidoyl-benzyl)-2-[3,5-difluoro-2'-(2-hydroxy-ethoxy)-biphenyl-4-yl]-2-ethoxy-acetamide hydrochloride,
(RS)-{4'-[(4-Carbamimidoyl-benzylcarbamoyl)-ethoxy-methyl]-3',5'-difluoro-biphenyl-2-yloxy}-acetic acid ethyl ester hydrochloride,
(RS)-{4'-[(4-Carbamimidoyl-benzylcarbamoyl)-ethoxy-methyl]-3',5'-difluoro-biphenyl-2-yloxy}-acetic acid,
(RS)-2-(2'-Carbamoylmethoxy-3,5-difluoro-biphenyl-4-yl)-2-ethoxy-N-[4-(N-hydroxycarbamimidoyl)-benzyl]-acetamide,
(RS)-N-(4-Carbamimidoyl-benzyl)-2-(2'-carbamoyl-methoxy-3,5-difluoro-biphenyl-4-yl)-2-ethoxy-acetamide acetate,
(RS)-N-(4-Carbamimidoyl-benzyl)-2-(2,6-difluoro-4-pyridin-4-yl-phenyl)-2-ethoxy-acetamide hydrochloride,
(RS)-N-(4-Carbamimidoyl-benzyl)-2-(2,6-difluoro-4-pyrimidin-5-yl-phenyl)-2-ethoxy-acetamide hydrochloride,
(RS)-N-(4-Carbamimidoyl-benzyl)-2-(2,6-difluoro-4-pyrimidin-2-yl-phenyl)-2-ethoxy-acetamide hydrochloride,
(RS)-N-(4-Carbamimidoyl-benzyl)-2-(2,6-difluoro-4-pyridin-2-yl-phenyl)-2-ethoxy-acetamide hydrochloride,
(RS)-2-[4-(2-Amino-pyrimidin-5-yl)-2,6-difluoro-phenyl]-N-(4-carbamimidoyl-benzyl)-2-ethoxy-acetamide hydrochloride,
(RS)-N-(4-Carbamimidoyl-benzyl)-2-(2,6-difluoro-4-pyridin-3-yl-phenyl)-2-ethoxy-acetamide hydrochloride,
(RS)-2-[4-(6-Amino-pyridin-2-yl)-2,6-difluoro-phenyl]-N-(4-carbamimidoyl-benzyl)-2-ethoxy-acetamide hydrochloride,
(RS)-2-[4-(5-Amino-pyridin-2-yl)-2,6-difluoro-phenyl]-N-(4-carbamimidoyl-benzyl)-2-ethoxy-acetamide hydrochloride,
(RS)-4'-[(4-Carbamimidoyl-benzylcarbamoyl)-ethoxy-methyl]-3',5'-difluoro-biphenyl-3-carboxylic acid methyl ester hydrochloride,
(RS)-(2-[4-(6-Amino-pyridin-3-yl)-2,6-difluoro-phenyl]-N-(4-carbamimidoyl-benzyl)-2-ethoxy-acetamide hydrochloride,
(RS)-4'-[(4-Carbamimidoyl-benzylcarbamoyl)-ethoxy-methyl]-3',5'-difluoro-biphenyl-3-carboxylic acid,
(RS){Amino-[4-({2-[4-(6-amino-pyridin-3-yl)-2,6-difluoro-phenyl]-2-ethoxy-acetylamino}-methyl)-phenyl]-methylene}-carbamic acid ethyl ester,
(RS)-2-[4-(6-Amino-pyridin-3-yl)-2,6-difluoro-phenyl]-2-ethoxy-N-[4-(N-hydroxycarbamimidoyl)-benzyl]-acetamide,
(RS)-N-(4-Carbamimidoyl-benzyl)-2-(3,5-difluoro-2'-hydroxymethyl-biphenyl-4-yl)-2-ethoxy-acetamide hydrochloride,
(RS)-N-(4-Carbamimidoyl-benzyl)-2-(2'-chloromethyl-3,5-difluoro-biphenyl-4-yl)-2-ethoxy-acetamide,
(RS)-2-[3,5-Difluoro-2'-(hydroxyimino-methyl)-biphenyl-4-yl]-2-ethoxy-N-[4-(N-hydroxycarbamimidoyl)-benzyl]-acetamide,
(RS)-2-(2'-Aminomethyl-3,5-difluoro-biphenyl-4-yl)-N-(4-carbamimidoyl-benzyl)-2-ethoxy-acetamide acetate,
(RS)-N-(4-Carbamimidoyl-benzyl)-2-(2-fluoro-4-methoxy-3-phenoxy-phenyl)-2-methoxy-acetamide hydrochloride,
(RS)-N-(4-carbamimidoyl-benzyl)-2-(2-ethynyl-6-fluoro-phenyl)-2-methoxy-acetamide hydrochlorideaccording,
(RS)-N-(4-Carbamimidoyl-benzyl)-2-(2-ethyl-6-fluoro-phenyl)-2-methoxy-acetamide hydrochloride,
(RS)-N-(4-Carbamimidoyl-benzyl)-2-[2-fluoro-6-(3-hydroxy-prop-1-ynyl)-phenyl]-2-methoxy-acetamide hydrochloride,
(RS)-N-(4-Carbamimidoyl-benzyl)-2-[2-fluoro-6-(3-hydroxy-propyl)-phenyl]-2-methoxy-acetamide hydrochloride,
(RS)-N-(4-Carbamimidoyl-benzyl)-2-(3-fluoro-biphenyl-2-yl)-2-methoxy-acetamide hydrochloride,
(RS)-2-(3'-Amino-3-fluoro-biphenyl-2-yl)-N-(4-carbamimidoyl-benzyl)-2-methoxy-acetamide hydrochloride,
(RS)-N-(4-Carbamimidoyl-benzyl)-2-(3-fluoro-3'-nitro-biphenyl-2-yl)-2-methoxy-acetamide hydrochloride, (RS)-2-[2-(6-Amino-pyridin-2-yl)-6-fluoro-phenyl]-N-(4-carbamimidoyl-benzyl)-2-methoxy-acetamide acetate, (RS)-{2-[(4-Carbamimidoyl-benzylcarbamoyl)-methoxy-methyl]-3-fluoro-phenoxy}-acetic acid methyl ester acetate, (RS)-{2-[(4-Carbamimidoyl-benzylcarbamoyl)-methoxy-methyl]-3-fluoro-phenoxy}-acetic acid, (RS)-N-(4-Carbamimidoyl-benzyl)-2-[2-(3-dimethylamino-propoxy)-6-fluoro-phenyl]-2-methoxy-acetamide hydrochloride, (RS)-N-(4-Carbamimidoyl-benzyl)-2-(2-fluoro-6-phenoxy-phenyl)-2-methoxy-acetamide hydrochloride, (RS)-N-(4-Carbamimidoyl-benzyl)-2-(2,6-difluoro-4-methoxy-phenyl)-2-ethoxy-acetamide hydrochloride, (RS)-2-(4-Benzyloxy-2,6-difluoro-phenyl)-N-(4-carbamimidoyl-benzyl)-2-ethoxy-acetamide hydrochloride, (RS)-N-(4-Carbamimidoyl-benzyl)-2-(2,6-difluoro-4-isopropoxy-phenyl)-2-ethoxy-acetamide hydrochloride, (RS)-N-(4-Carbamimidoyl-benzyl)-2-[2,6-difluoro-4-(pyridin-2-ylmethoxy)-phenyl]-2-ethoxy-acetamide hydrochloride, (RS)-2-[2,6-Difluoro-4-(pyridin-2-ylmethoxy)-phenyl]-2-ethoxy-N-[4-(N-hydroxycarbamimidoyl)-benzyl]-acetamide, (RS)-{Amino-[4-({2-[2,6-difluoro-4-(pyridin-2-ylmethoxy)-phenyl]-2-ethoxy-acetylamino}-methyl)-phenyl]-methylene}-carbamic acid ethyl ester, (RS)-N-(4-Carbamimidoyl-benzyl)-2-[2,6-difluoro-4-(pyridin-3-ylmethoxy)-phenyl]-2-ethoxy-acetamide hydrochloride, (RS)-N-(4-Carbamimidoyl-benzyl)-2-[2,6-difluoro-4-(pyridin-4-ylmethoxy)-phenyl]-2-ethoxy-acetamide hydrochloride, (RS)-N-(4-Carbamimidoyl-benzyl)-2-(2,6-difluoro-4-phenoxy-phenyl)-2-ethoxy-acetamide hydrochloride, (RS)-N-(4-Carbamimidoyl-benzyl)-2-[2,6-difluoro-4-(pyridin-3-yloxy)-phenyl]-2-ethoxy-acetamide hydrochloride, (RS)-N-(4-Carbamimidoyl-benzyl)-2-(2,6-difluoro-3-isopropoxy-phenyl)-2-ethoxy-acetamide hydrochloride, (RS)-N-(4-Carbamimidoyl-benzyl)-2-(3-carbamoylmethoxy-2,6-difluoro-phenyl)-2-ethoxy-acetamide hydrochloride, (RS)-2-[3-(2-Benzyloxy-ethoxy)-2,6-difluoro-phenyl]-N-(4-carbamimidoyl-benzyl)-2-ethoxy-acetamide hydrochloride, (RS)-N-(4-Carbamimidoyl-benzyl)-2-[2,6-difluoro-3-(2-hydroxy-ethoxy)-phenyl]-2-ethoxy-acetamide hydrochloride, (RS)-N-(4-Carbamimidoyl-benzyl)-2-(2,6-difluoro-3-phenoxy-phenyl)-2-ethoxy-acetamide acetate, (RS)-N-(4-Carbamimidoyl-benzyl)-2-(2,4-difluoro-biphenyl-3-yl)-2-ethoxy-acetamide hydrochloride, (RS)-2-(2,6-Difluoro-3-phenylamino-phenyl)-N-[4-(N-hydroxycarbamimidoyl)-benzyl]-2-methoxy-acetamide, (RS)-N-(4-Carbamimidoyl-benzyl)-2-(2,6-difluoro-3-phenylamino-phenyl)-2-methoxy-acetamide acetate, (RS)-N-(4-Carbamimidoyl-benzyl)-2-(2,6-difluoro-3-isopropylamino-phenyl)-2-methoxy-acetamide acetate, (RS)-2-(3-Acetylamino-2,6-difluoro-phenyl)-N-(4-carbamimidoyl-benzyl)-2-methoxy-acetamide hydrochloride, (RS)-(4-Carbamimidoyl-benzyl)-2-(2,6-difluoro-3-phenylacetylamino-phenyl)-2-methoxy-acetamide hydrochloride, (RS)-N-(4-Carbamimidoyl-benzyl)-2-(2,6-difluoro-3-hydroxymethyl-phenyl)-2-ethoxy-acetamide hydrochloride, (RS)-2-[3-(Acetylamino-methyl)-2,6-difluoro-phenyl]-N-(4-carbamimidoyl-benzyl)-2-ethoxy-acetamide hydrochloride, (RS)-2-(3-Aminomethyl-2,6-difluoro-phenyl)-N-(4-carbamimidoyl-benzyl)-2-ethoxy-acetamide acetic acid, (RS)-(4-Carbamimidoyl-benzyl)-2-(2,6-difluoro-3-phenylaminomethyl-phenyl)-2-ethoxy-acetamide hydrochloride, (RS)-(4-Carbamimidoyl-benzyl)-2-(2,6-difluoro-3-morpholin-4-ylmethyl-phenyl)-2-ethoxy-acetamide hydrochloride, (RS)-(4-Carbamimidoyl-benzyl)-2-(2,6-difluoro-3-piperidin-1-ylmethyl-phenyl)-2-ethoxy-acetamide hydrochloride, (RS)-2-(3-Diethoxymethyl-2,6-difluoro-phenyl)-2-ethoxy-N-[4-(N-hydroxycarbamimidoyl)-benzyl]-acetamide, (RS)-(4-Carbamimidoyl-benzyl)-2-(2,6-difluoro-3-formyl-phenyl)-2-ethoxy-acetamide acetic acid, (RS)-N-(4-Carbamimidoyl-2,6-difluoro-benzyl)-2-(2,6-difluoro-4-methoxy-phenyl)-2-ethoxy-acetamide; hydrochloride, (RS)-N-(4-Carbamimidoyl-2,6-difluoro-benzyl)-2-ethoxy-2-(2-fluoro-4-methoxy-phenyl)-acetamide acetate, (RS)-N-(4-Carbamimidoyl-2,6-difluoro-benzyl)-2-(2,6-difluoro-4-methoxy-phenyl)-2-methoxy-acetamide acetate, (RS)-N-(4-Carbamimidoyl-2,6-difluoro-benzyl)-2-(2-fluoro-4-methoxy-phenyl)-2-methoxy-acetamide acetate, (RS)-[4-Carbamimidoyl-2-(carbamoylmethyl-amino)-benzyl]-2-ethoxy-2-(2-fluoro-4-methoxy-phenyl)-acetamide hydrochloride, (RS)-N-(2-Benzylamino-4-carbamimidoyl-benzyl)-2-ethoxy-2-(2-fluoro-4-methoxy-phenyl)-acetamide acetate, (RS)-[4-Carbamimidoyl-2-(2-fluoro-benzylamino)-benzyl]-2-ethoxy-2-(2-fluoro-4-methoxy-phenyl)-acetamide hydrochloride, (RS)-{4-Carbamimidoyl-2-[(pyridin-2-ylmethyl)-amino]-benzyl}-2-ethoxy-2-(2-fluoro-4-methoxy-phenyl)-acetamide hydrochloride, (RS)-[4-Carbamimidoyl-2-(4-chloro-2-fluoro-benzylamino)-benzyl]-2-ethoxy-2-(2-fluoro-4-methoxy-phenyl)-acetamide hydrochloride, (RS)-(4-Carbamimidoyl-2-phenethylamino-benzyl)-2-ethoxy-2-(2-fluoro-4-methoxy-phenyl)-acetamide hydrochloride, (RS)-(5-Carbamimidoyl-2-{[2-ethoxy-2-(2-fluoro-4-methoxy-phenyl)-acetylamino]-methyl}-phenylamino)-acetic acid ethyl ester hydrochloride, (RS)-(5-Carbamimidoyl-2-[2-ethoxy-2-(2-fluoro-4-methoxy-phenyl)-acetylamino]-methyl}-phenylamino)-acetic acid acetate, (RS)-(4-Carbamimidoyl-2-phenylmethanesulfonylamino-benzyl)-2-ethoxy-2-(2-fluoro-4-methoxy-phenyl)-acetamide hydrochloride, (RS)-[2-(3-Benzyl-ureido)-4-carbamimidoyl-benzyl]-2-ethoxy-2-(2-fluoro-4-methoxy-phenyl)-acetamide acetate, (RS)-(5-Carbamimidoyl-2-{[2-ethoxy-2-(2-fluoro-4-methoxy-phenyl)-acetylamino]-methyl}-phenyl)-carbamic acid benzyl ester hydrochloride, (RS)-(4-Carbamimidoyl-2-phenylamino-benzyl)-2-ethoxy-2-(2-fluoro-4-methoxy-phenyl)-acetamide hydrochloride, (RS)-2-[4-(6-Amino-pyridin-3-yl)-2,6-difluoro-phenyl]-N-(4-carbamimidoyl-2-carbamoylmethoxy-benzyl)-2-ethoxy-acetamide hydrochloride acetic acid, (RS)-(4-Carbamimidoyl-2-carbamoylmethoxy-benzyl)-2-[2,6-difluoro-4-(pyridin-2-ylmethoxy)-phenyl]-2-ethoxy-acetamide hydrochloride,
(RS)-2-[4-(6-Amino-pyridin-3-yl)-2,6-difluoro-phenyl]-N-(4-carbamimidoyl-2,6-difluoro-benzyl)-2-ethoxy-acetamide acetate,
(RS)-[(4-{[2-(2,6-Difluoro-4-methoxy-phenyl)-2-methoxy-acetylamino]-methyl}-phenyl)-imino-methyl]-carbamic acid tert-butyl ester,
(S)-[(4-{[2-(2,6-Difluoro-4-methoxy-phenyl)-2-methoxy-acetylamino]-methyl}-phenyl)-imino-methyl]-carbamic acid tert-butyl ester,
(R)-[(4-{[2-(2,6-Difluoro-4-methoxy-phenyl)-2-methoxy-acetylamino]-methyl}-phenyl)-imino-methyl]-carbamic acid tert-butyl ester,
(S)-N-(4-Carbamimidoyl-benzyl)-2-(2,6-difluoro-4-methoxy-phenyl)-2-methoxy-acetamide formiate,
(R)-N-(4-Carbamimidoyl-benzyl)-2-(2,6-difluoro-4-methoxy-phenyl)-2-methoxy-acetamide formiate,
[1-Amino-1-(4-{[(R)-2-ethoxy-2-(2-fluoro-4-methoxy-phenyl)-acetylamino]-methyl}-phenyl)-meth-(E)-ylidene]-carbamic acid benzyl ester,
(R)-N-(4-Carbamimidoyl-benzyl)-2-ethoxy-2-(2-fluoro-4-methoxy-phenyl)-acetamide acetate,
(RS)-[Amino-(4-{[2-ethoxy-2-(2-fluoro-4-methoxy-phenyl)-acetylamino]-methyl}-phenyl)-methylene]-carbamic acid benzyl ester,
(RS)-[(4-{[2-(2,6-Difluoro-4-methoxy-phenyl)-2-methoxy-acetylamino]-methyl}-phenyl)-imino-methyl]-carbamic acid benzyl ester,
(RS)-N-(4-Carbamimidoyl-benzyl)-2-[2,6-difluoro-4-(1-oxy-pyridin-4-yl)-phenyl]-2-methoxy-acetamide hydrochloride,
(RS)-(4-Carbamimidoyl-benzyl)-2-[2,6-difluoro-4-(tetrahydro-pyran-4-yl)-phenyl]-2-ethoxy-acetamide acetate, and
(RS)-(4-Carbamimidoyl-benzyl)-2-(4-cyclohexyl-2,6-difluoro-phenyl)-2-ethoxy-acetamide acetate, and pharmaceutically acceptable salts thereof.

Particularly preferred compounds of formula (I) are those selected from the group consisting of
(S)-N-(4-Carbamimidoyl-benzyl)-2-methoxy-2-phenyl-acetamide hydrochloride,
(RS)-N-(4-Carbamimidoyl-benzyl)-2-(2-fluoro-4-methoxy-phenyl)-2-methoxy-acetamide hydrochloride,
(RS)-[Amino-(4-{[2-(2-fluoro-4-methoxy-phenyl)-2-methoxy-acetylamino]-methyl}-phenyl)-methylene]-carbamic acid ethyl ester,
(RS)-2-(2-Fluoro-4-methoxy-phenyl)-N-[4-(N-hydroxycarbamimidoyl)-benzyl]-2-methoxy-acetamide,
(RS)-N-(4-Carbamimidoyl-benzyl)-2-(3-fluoro-3'-methoxy-biphenyl-4-yl)-2-methoxy-acetamide hydrochloride,
(RS)-N-(4-Carbamimidoyl-benzyl)-2-ethoxy-2-(2-fluoro-4-methoxy-phenyl)-acetamide hydrochloride,
(RS)-N-(4-Carbamimidoyl-benzyl)-2-(2,6-difluoro-4-methoxy-phenyl)-2-methoxy-acetamide hydrochloride,
(RS)-N-(4-Carbamimidoyl-benzyl)-2-(2-fluoro-4-pyridin-3-yl-phenyl)-2-methoxy-acetamide hydrochloride, and
(RS)-2-(4-Bromo-2,6-difluoro-phenyl)-N-(4-carbamimidoyl-benzyl)-2-ethoxy-acetamide hydrochloride, and pharmaceutically acceptable salts thereof.

Other particularly preferred compounds are those selected from the group consisting of
(RS)-N-(4-Carbamimidoyl-2-carbamoylmethoxy-benzyl)-2-(2,6-difluoro-4-methoxy-phenyl)-2-ethoxy-acetamide hydrochloride,
(RS)-N-{4-Carbamimidoyl-2-[(2-methoxy-ethylcarbamoyl)-methoxy]-benzyl}-2-(2,6-difluoro-4-methoxy-phenyl)-2-ethoxy-acetamide hydrochloride,
(RS)-N-[4-Carbamimidoyl-2-(pyridin-2-ylmethoxy)-benzyl]-2-(2,6-difluoro-4-methoxy-phenyl)-2-methoxy-acetamide hydrochloride,
(RS)-2-[4-(2-Amino-pyrimidin-5-yl)-2,6-difluoro-phenyl]-N-(4-carbamimidoyl-benzyl)-2-ethoxy-acetamide hydrochloride,
(RS)-N-(4-Carbamimidoyl-benzyl)-2-(2,6-difluoro-4-pyridin-3-yl-phenyl)-2-ethoxy-acetamide hydrochloride,
(RS)-2-[4-(5-Amino-pyridin-2-yl)-2,6-difluoro-phenyl]-N-(4-carbamimidoyl-benzyl)-2-ethoxy-acetamide hydrochloride,
(RS)-(2-[4-(6-Amino-pyridin-3-yl)-2,6-difluoro-phenyl]-N-(4-carbamimidoyl-benzyl)-2-ethoxy-acetamide hydrochloride,
(RS)-N-(4-Carbamimidoyl-benzyl)-2-[2,6-difluoro-4-(pyridin-2-ylmethoxy)-phenyl]-2-ethoxy-acetamide hydrochloride,
(RS)-N-(2-Benzylamino-4-carbamimidoyl-benzyl)-2-ethoxy-2-(2-fluoro-4-methoxy-phenyl)-acetamide acetate,
(RS)-(5-Carbamimidoyl-2-{[2-ethoxy-2-(2-fluoro-4-methoxy-phenyl)-acetylamino]-methyl}-phenylamino)-acetic acid acetate,
(RS)-(4-Carbamimidoyl-2-carbamoylmethoxy-benzyl)-2-[2,6-difluoro-4-(pyridin-2-ylmethoxy)-phenyl]-2-ethoxy-acetamide hydrochloride,
(RS)-2-[4-(6-Amino-pyridin-3-yl)-2,6-difluoro-phenyl]-N-(4-carbamimidoyl-2,6-difluoro-benzyl)-2-ethoxy-acetamide acetate, and
(RS)-{4-Carbamimidoyl-2-[(pyridin-2-ylmethyl)-amino]-benzyl}-2-ethoxy-2-(2-fluoro-4-methoxy-phenyl)-acetamide hydrochloride, and pharmaceutically acceptable salts thereof.

It will be appreciated that the compounds of general formula (I) in this invention may be derived at functional groups to provide derivatives which are capable of converting back to the parent compound in vivo.

The invention further relates to a process for the manufacture of compounds of formula (I) as defined above, which process comprises converting the nitrile group in a compound of formula (II)

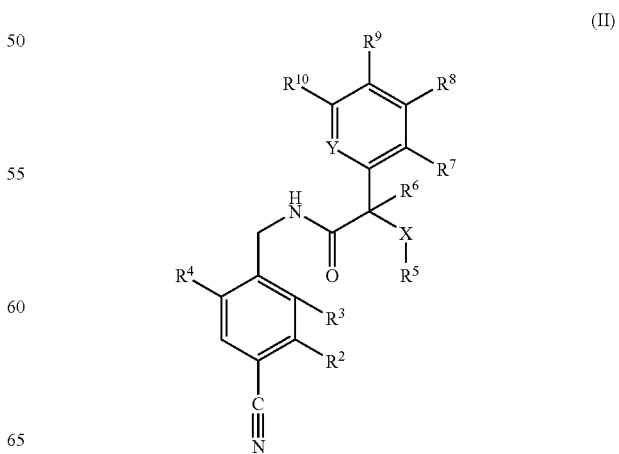

(II)

wherein $R^2$, $R^3$, $R^4$, $R^5$, $R^6$, $R^7$, $R^8$, $R^9$, $R^{10}$, X and Y are defined above, into a carbamimidoyl group, or into a N-hydroxy-carbamimidoyl group, or into a N-amino-carbamimidoyl group, and, if desired, converting the obtained compound of formula (I) into a pharmaceutically acceptable salt. A preferred process as described above comprises the conversion of the nitrile group into a carbamamidoyl group, or into a N-hydroxy-carbamimidoyl group, or into a N-amino-carbamimidoyl group.

The conversion of the nitrile group in a compound of formula II into a carbamimidoyl group —C(NH)NH$_2$ or into a N-hydroxy-carbamimidoyl group —C(NOH)NH$_2$ or into a N-amino-carbamimidoyl group —C(N—NH$_2$)NH$_2$ can be carried out according to methods known in the art. For example, the conversion into a N-hydroxy-carbamimidoyl group can be performed by dissolving a compound of formula II in a solvent, such as DMF, ethanol or methanol, treating the solution with hydroxylamine or a salt of hydroxylamine with an inorganic acid, such as hydroxylamine hydrochloride, and thereafter with a base, such as diisopropylethylamine or triethylamine, sodium hydride or sodium methanolate, conveniently at a temperature up to 80° C.

The conversion of the nitrile group into a carbamimidoyl group can be carried out e.g., by treating a compound of formula II in a solvent, such as ethanol or methanol, or a solvent mixture, such as chloroform and methanol, or chloroform and ethanol, with a dry stream of hydrogen chloride, conveniently at a temperature below 10° C. The solution containing the iminoether can be evaporated and the residue can be treated with gaseous ammonia or an ammonium salt in methanol or ethanol. In an analogous manner, the iminoether can be converted into a N-hydroxy-carbamimidoyl compound of formula I with hydroxylamine or a salt thereof in the presence of a base or into a N-amino-carbamimidoyl compound of formula I with hydrazine or a salt thereof in the presence of a base. In so doing, other reactive groups present in the compound of formula I and reactive towards the treatment wih hydrogen chloride or gaseous ammonia or ammonium chloride or hydroxylamine or hydrazine can be modified. For example, in the case of treatment with hydrogen chloride a benzyloxy group $R^2$, $R^3$, $R^4$, $R^7$, $R^8$, $R^9$, $R^{10}$ or $R^{11}$ can be converted into the hydroxy group. In the case of treatment with gaseous ammonia in methanol or ethanol a lower-alkoxy-carbonyl-lower-alkoxy group $R^2$, $R^3$, $R^4$, $R^7$, $R^8$, $R^9$, $R^{10}$ or $R^{11}$ can be converted into a carbamoyl-lower-alkoxy group.

If a carbamimidoyl compound of formula (I) is obtained from a nitrile of formula (II) by treatment with hydrogen chloride and subsequent reaction with gaseous ammonia or ammonium chloride, the carbamimidoyl product is obtained as hydrochloride salt. This salt can be converted into any other pharmaceutically acceptable salt by chromatography over an adequately charged basic ion exchange resin. Alternatively, the hydrochloride salt of a carbamimidoyl compound of formula (I) can be converted into the corresponding free base by treatment with sodium ethanolate in ethanol and subsequently treated with an excess of an appropriate acid to generate any pharmaceutically acceptable salt.

Any pharmaceutically acceptable salt of a carbamimidoyl compound of formula (I) can be obtained when a N-hydroxy-carbamimidoyl compound of formula (I) is hydrogenated in a solvent like ethanol, methanol, dioxan or THF, with hydrogen and a catalyst such as palladium, platinum or nickel in the presence of an appropriate acid.

Functional groups in compounds of formula (I) can be modified. As modifications of functional groups in a compound of formula I, one must also consider conversion of a N-hydroxy-carbamimidoyl group into a carbamimidoyl group, the esterification of a carboxy group, the saponification of an ester group and the cleavage of an ether group, such as an arylalkyl ether group, e.g., the benzyl ether group. All of these reactions can be carried out according to methods known per se.

A compound of formula (I) in which $R^1$ represents a hydroxy group can be converted into a compound of formula (I) in which $R^1$ represents hydrogen by hydrogenation in a solvent, such as ethanol, methanol, dioxane, THF or glacial acetic acid, or a solvent mixture, such as ethanol and glacial acetic acid, with hydrogen and a catalyst, such as palladium, platinum or nickel. In so doing, other reactive groups present in the compound of formula I and reactive towards the reducing agent can be modified.

A compound of formula (I) in which $R^1$ represents benzyloxy-carbonyl can be converted into a compound of formula (I) in which $R^1$ represents hydrogen by hydrogenation in a solvent, such as ethanol, methanol, dioxane, THF or glacial acetic acid, or a solvent mixture, such as ethanol and glacial acetic acid, with hydrogen and a catalyst, such as palladium. The reaction can be optionally performed in the presence of an acid such as HCl in a solvent such as EtOH or MeOH. In so doing, other reactive groups present in the compound of formula I and reactive towards the reducing agent can be modified.

A compound of formula (I) in which $R^1$ represents lower-alkoxy-carbonyl or aryl-lower-alkoxy-carbonyl is obtained by reacting a compound of formula (I) in which $R^1$ represents hydrogen with a chloroformic acid lower alkyl ester or a chloroformic acid aryl-lower-alkyl ester in a solvent, such as dichloromethane, dioxane or DMF, or a solvent mixture, such as dichloromethane and water or ethyl acetate and water, in the presence of an organic base, such as pyridine or triethylamine, or an inorganic base, such as sodium hydroxide, sodium carbonate or potassium bicarbonate.

A compound of formula (I) in which $R^1$ represents benzyloxy-carbonyl and $R^2$, $R^3$ and $R^4$ have the significance of hydrogen can be prepared according to general methods known in the art, e.g., by coupling of an acid of formula (III) and [(4-aminomethyl-phenyl)-imino-methyl]-carbamic acid benzyl ester in the presence of coupling reagents as BOP or EDCI/HOBt and a organic base such as triethylamine or diisopropyl ethyl amine in a solvent such as THF.

A compound of formula (I) in which $R^1$ represents lower-alkyl-carbonyl or aryl-carbonyl that is obtained by reacting a compound of formula (I) in which $R^1$ represents hydrogen with a acyl chloride in a solvent, such as dichloromethane, dioxane or DMF, or a solvent mixture, such as dichloromethane and water or ethyl acetate and water, in the presence of an organic base, such as pyridine or triethylamine, or an inorganic base, such as sodium hydroxide, sodium carbonate or potassium bicarbonate.

A compound of formula (II) in which $R^2$, $R^3$, $R^4$, $R^7$, $R^8$, $R^9$, $R^{10}$ or $R^{11}$ has the significance of a hydroxy group, or a compound of formula (I) in which $R^1$ has the significance of benzyloxy-carbonyl and $R^2$, $R^3$, $R^4$, $R^7$, $R^8$, $R^9$, $R^{10}$ or $R^{11}$ has the significance of a hydroxy group can be reacted:

with an alkylating agent such as an appropriately substituted alkyl bromide, alkyl iodide or alkyl mesylate in the presence of a base such as potassium carbonate or caesium carbonate in a solvent such as DMF or acetone, or with an alkene oxide in a solvent like EtOH, or by a Mitsunobu reaction with an appropriately substituted alcohol in the presence of DEAD, DIAD, or di-tert.- butyl-azodicarboxylate, and triphenylphosphine or triphenylphosphine on solid support in a solvent such as THF, dichloromethane or dioxane, or by an oxidative coupling with an aryl boronic acid or a heteroarylboronic acid in the presence of a copper salt like Cu(OAc)$_2$, a base like pyridine or triethylamine and a solvent like dichloromethane or 1,2-dichloroethane, or with trifluorosulfonic acid anhydride and an organic base like triethylamine or pyridine in a solvent such as THF or dichloromethane.

A compound of formula (II) in which $R^2$, $R^3$, $R^4$, $R^7$, $R^8$, $R^9$, $R^{10}$ or $R^{11}$ has the significance of an aniline group or a compound of formula (I) in which $R^1$ has the significance of benzyloxy-carbonyl and $R^2$, $R^3$, $R^4$, $R^7$, $R^8$, $R^9$, $R^{10}$ or $R^{11}$ has the significance of an aniline group can be reacted:

with an alkylating agent such as an appropriately substituted alkyl bromide, alkyl iodide or alkyl mesylate in the presence of an organic base such as triethyl amine or diisopropyl ethyl amine in a solvent such as DMF, or with an acyl or a sulfonyl chloride or a chloroformic acid ester in the presence of an organic base such as triethyl amine or diisopropyl ethyl amine in a solvent such as DMF, THF or acetonitrile, or by reaction with isocyanate in a solvent such as dichloromethane or 1,2-dichloroethane, or by oxidative coupling with an arylboronic acid or a heteroaryl boronic acid with a copper salt like Cu(OAc)$_2$, an organic base such as triethylamine or pyridine and an oxidant like TEMPO in a solvent like dichloromethane or 1,2-dichloroethane.

A compound of formula (II) in which $R^2$, $R^3$, $R^4$, $R^7$, $R^8$, $R^9$, $R^{10}$ or $R^{11}$ has the significance of a bromide or of $CF_3-SO_2-O-$, or a compound of formula (I) in which $R^1$ has the significance of benzyloxy-carbonyl and $R^2$, $R^3$, $R^4$, $R^7$, $R^8$, $R^9$, $R^{10}$ or $R^{11}$ has the significance of of a bromide or of $CF_3-SO_2-O-$ can be reacted, with an aryl boronic acid or a heteroaryl boronic acid in the presence of a base such as solid or aqueous potassium carbonate or sodium carbonate and a palladium catalyst such as tetrakis(triphenylphosphin)palladium (0) or 1,1'-bis(diphenyl-phosphin)ferrocene-palladium dichloride in a solvent such as toluene or THF, or with bis(pinacolato)diboron in the presence of a base such as potassium acetate and a palladium catalyst like bis(triphenylphosphine)palladium(II) chloride and a solvent such as dioxane. The boronic acid ester thus obtained is further converted by reaction with an arylhalogenide or a heteroaryl halogenide and a base such as solid or aqueous potassium carbonate or sodium carbonate and a palladium catalyst such as bis(diphenylphosphin)ferrocene-palladium dichloride in a solvent such as 1,2-dimethoxyethane, or with carbon monoxide in the presence of a catalyst such as Pd(OAc)$_2$, a ligand such as 1,3-bis-(diphenylphosphino)propane, an alcohol such as MeOH or 2-trimethylsilyl ethanol and a solvent such as DMSO, or with an appropriately substituted alkine in the presence of an organic base such as triethylamine and copper(I) iodide in a solvent such as DMF and a palladium catalyst such as tetrakis(triphenylphosphin)palladium (0).

A compound of formula (II) in which $R^2$, $R^3$, $R^4$, $R^7$, $R^8$, $R^9$, $R^{10}$ or $R^{11}$ has the significance of a COOH group or a compound of formula (I) in which $R^1$ has the significance of benzyloxy-carbonyl and $R^2$, $R^3$, $R^4$, $R^7$, $R^8$, $R^9$, $R^{10}$ or $R^{11}$ has the significance of a COOH group can be reacted:

in the presence of coupling reagents such as BOP or EDCI/HOBt and an organic base such as triethylamine or diisopropyl ethyl amine in a solvent such as THF, DMF or dichloromethane.

A compound of formula (II) in which $R^2$, $R^3$, $R^4$, $R^7$, $R^8$, $R^9$, $R^{10}$ or $R^{11}$ has the significance of a CHO group, or a compound of formula (I) in which $R^1$ has the significance of benzyloxy-carbonyl and $R^2$, $R^3$, $R^4$, $R^7$, $R^8$, $R^9$, $R^{10}$ or $R^{11}$ has the significance of a CHO group can be reacted:

by reduction with NaBH$_4$ in EtOH, or by reductive amination with an amine in the presence of a reducing agent such as NaBH$_4$ or NaBH$_3$CN and a solvent such as EtOH, or by reaction with hydroxylamine, hydrochloride in the presence of a base such as NaOAc and a solvent such as EtOH, and subsequent reduction of the intermediate oxime by Zn in HOAc. The aminomethyl derivative thus obtained can be reacted with an acyl chloride or a sulfonyl chloride in the presence of an organic base and a solvent such as THF, dichloromethane or DMF.

The compounds of formula (II) in which X has the significance of an oxygen are prepared according to general methods known in the art, e.g., by coupling of an acid of formula (III) and an appropriately substituted 4-aminomethyl benzonitrile of formula (VI) in the presence of coupling reagents such as BOP or EDCI/HOBt and an organic base such as triethylamine or diisopropyl ethyl amine in a solvent such as THF.

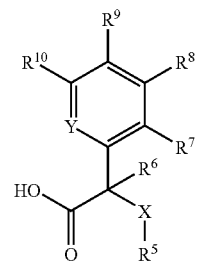

(III)

Compounds of formula (III) in which X has the significance of oxygen are known in the art or can be prepared according to general methods known in the art, e.g., as described hereinafter and/or as described in the Examples or in analogous methods.

For example, a compound of formula (III) in which X has the significance of oxygen and $R^6$ has the significance of hydrogen can be prepared by reaction of an aldehyde of formula (IV) with bromoform or chloroform in a mixture of solvents like dioxane/methanol or dioxane/ethanol in the presence of an inorganic base like sodium hydroxide or potassium hydroxide, or by reaction of an aldehyde of formula (IV) with trimethylsilyl cyanide in the presence of ZnI$_2$ in a solvent such as dichloromethane. The trimethylsilyl cyanohydrine thus obtained is subsequently hydrolysed in concentrated hydrochloric acid to the corresponding α-hydroxy carboxylic acid which is then alkylated to give a compound of formula (III) using an appropiately substituted alkyl halide in the presence of silver oxide in a solvent such as toluene.

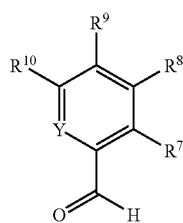

Compounds of formula (IV) are known in the art or can be prepared according to general methods known in the art, e.g., as described hereinafter and/or as described in the Examples or in analogous methods.

Compounds of formula (III) can be prepared from compounds of formula (V) in which $R^7$ and/or $R^{11}$ refers to substituents which have an ortho-directing effect in a metallation reaction by reaction with a strong base like n-butyl lithium, LDA or lithium 2,2,6,6-tetramethyl piperidide, with ethyl glyoxalate as electrophile, with N,N,N',N',N''-pentamethyldiethylentriamine or N,N,N',N'-tetramethylethylendiamine as additive and THF as solvent. The α-hydroxy phenyl acetic acid ester thus obtained is reacted with an alkylating agent such as ethyl iodide or methyl iodide in the presence of silver oxide in toluene as solvent. The α-alkoxy phenyl acetic acid ester is then hydrolysed by a base such as aqueous NaOH or LiOH in a solvent such as THF or EtOH.

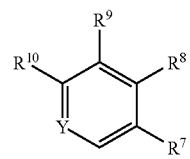

A compound of formula (III) in which X refers to oxygen and $R^6$ refers to methyl can be prepared by reaction of an appropriately substituted acetophenone with bromoform or chloroform in a mixture of solvents like dioxane/methanol or dioxane/ethanol in the presence of an inorganic base like sodium hydroxide or potassium hydroxide.

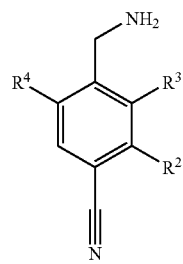

Compounds of formula (VI) can be prepared according to general methods known in the art, e.g., as described hereinafter and/or as described in the Examples or in analogy to these.

For example, a substituted 4-aminomethyl benzonitrile of formula (VI) can be prepared from the corresponding substituted 4-cyano-benzaldehyde by reaction with hydroxylamine hydrochloride in the presence of a base such as NaOAc in a solvent such as EtOH. Subsequently, the oxime thus obtained can be reduced by zinc in acetic acid. Alternatively, a substituted 4-aminomethyl benzonitrile of formula (VI) can be prepared from the corresponding substituted 4-bromomethyl benzonitrile by reaction with hexamethylene tetramine (HMTA) in chloroform and subsequent hydrolysis of the HMTA adduct by concentrated aqueous hydrochloric acid in EtOH.

The compounds of formula (II) in which X refers to an $NR^{12}$ and $R^{12}$ refers to lower-alkyl are prepared according to general methods known in the art, e.g., as described hereinafter and/or as described in the Examples or in analogy to these methods.

For example, a compound of formula (VII)

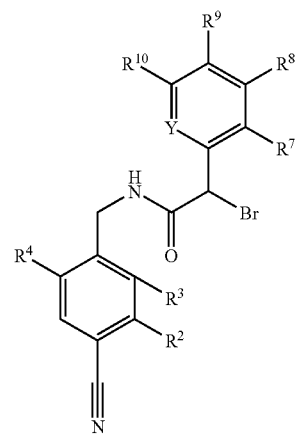

can be reacted with a lower-alkyl amine or a di-lower-alkyl amine or the corresponding ammonium hydrochlorides in the presence of an organic base such as triethylamine and a catalyst such as tetrabutylammonium iodide in a solvent such as THF.

Compounds of formula (II) in which X has the significance of $NR^{12}$ and $R^{12}$ has the significance of lower-alkyl-carbonyl can be obtained by coupling an appropriately substituted N-Boc-phenylglycine and an appropriately substituted 4-aminomethyl benzonitrile in the presence of coupling reagents such as BOP or EDCI/HOBt, and an organic base such as triethylamine or diisopropyl ethyl amine in a solvent such as THF. The Boc group can be cleaved by reaction with trifluoroacetic acid in a solvent like dichloromethane. The amino group thus liberated can then react with an appropriately substituted acyl chloride or acyl anhydride in the presence of an organic amine like triethylamine in a solvent like THF or dichloromethane.

The compounds of formula (II) in which X refers to sulfur are prepared according to general methods known in the art, e.g., as described hereinafter and/or as described in the Examples or in analogous methods. For example, a compound of formula (VII) can be reacted with the sodium salt of a lower-alkyl mercaptane in the presence of a catalyst such as tetrabutylammonium iodide in a solvent such as methanol.

Compounds of formula (II) in which X has the significance of $SO_2$ can be obtained from compounds of formula (II) in which X has the significance of sulfur by reaction with an oxidant such as m-chloro perbenzoic acid in a solvent like dichloromethane.

Compounds of formula (VII) can be obtained by coupling an appropriately substituted α-bromo-phenylacetic acid and an appropriately substituted 4-aminomethyl benzonitrile in the presence of coupling reagents such as BOP or EDCI/HOBt and an organic base as triethylamine or diisopropyl ethyl amine in a solvent such as THF.

Insofar as their preparation is not described in the examples, the compounds of formulae (I), (II), (III), (IV), (V), (VI) and (VII) can be prepared according to analogous methods, or according to the methods set forth above.

Furthermore, the invention relates to compounds of formula (I) as defined above, when manufactured by a process as described above. In another embodiment, the invention relates to the intermediates, the compounds of formula (II)

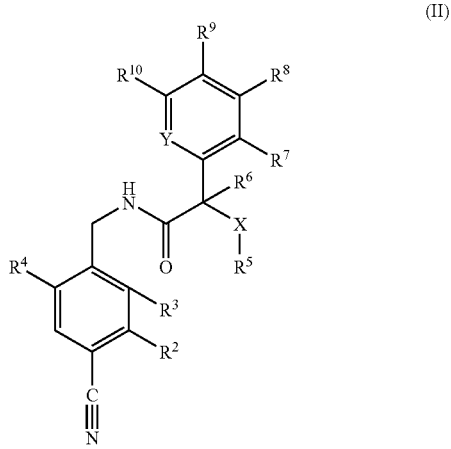

(II)

wherein $R^2$, $R^3$, $R^4$, $R^5$, $R^6$, $R^7$, $R^8$, $R^9$, $R^{10}$, X and Y are defined above.

As described above, the compounds of formula (I) are active compounds and inhibit the formation of coagulation factors Xa, IXa and thrombin induced by factor VIIa and tissue factor or are derivatives which are converted under physiological conditions to such active compounds. These compounds consequently influence both platelet aggregation which is induced by these factors and plasmatic blood coagulation. They therefore inhibit the formation of thrombi and can be used for the treatment and/or prevention of diseases, such as arterial and venous thrombosis, deep vein thrombosis, pulmonary embolism, unstable angina pectoris, cardiac infarction, stroke due to atrial fibrillation, inflammation and arteriosclerosis. Furthermore, these compounds have an effect on tumor cells and prevent metastases. They can therefore also be used as antitumor agents. Prevention and/or treatment thrombosis, particularly arterial or deep vein thrombosis, is the preferred indication.

The invention therefore also relates to pharmaceutical compositions comprising a compound as defined above and a pharmaceutically acceptable carrier and/or adjuvant. The invention likewise embraces compounds as described above for use as therapeutically active substances, especially as therapeutically active substances for the treatment and/or prophylaxis of diseases which are associated with the formation of clotting factors Xa, IXa and thrombin induced by factor VIIa and tissue factor, particularly as therapeutically active substances for the treatment and/or prophylaxis of arterial and venous thrombosis, deep vein thrombosis, pulmonary embolism, unstable angina pectoris, cardiac infarction, stroke due to atrial fibrillation, inflammation, arteriosclerosis and/or tumor.

In another preferred embodiment, the invention relates to a method for the therapeutic and/or prophylactic treatment of diseases which are asscociated with the formation of clotting factors Xa, IXa and thrombin induced by factor VIIa and tissue factor, particularly for the therapeutic and/or prophylactic treatment of arterial and venous thrombosis, deep vein thrombosis, pulmonary embolism, unstable angina pectoris, cardiac infarction, stroke due to atrial fibrillation, inflammation, arteriosclerosis and/or tumor, which method comprises administering a compound as defined above to a human being or animal.

The invention also embraces the use of compounds as defined above for the therapeutic and/or prophylactic treatment of diseases which are asscociated with the formation of clotting factors Xa, IXa and thrombin induced by factor VIIa and tissue factor, particularly for the therapeutic and/or prophylactic treatment of arterial and venous thrombosis, deep vein thrombosis, pulmonary embolism, unstable angina pectoris, cardiac infarction, stroke due to atrial fibrillation, inflammation, arteriosclerosis and/or tumor.

The invention also relates to the use of compounds as described above for the preparation of medicaments for the therapeutic and/or prophylactic treatment of diseases which are asscociated with the formation of clotting factors Xa, IXa and thrombin induced by factor VIIa and tissue factor, particularly for the therapeutic and/or prophylactic treatment of arterial and venous thrombosis, deep vein thrombosis, pulmonary embolism, unstable angina pectoris, cardiac infarction, stroke due to atrial fibrillation, inflammation, arteriosclerosis and/or tumor. Such medicaments comprise a compound as described above.

The inhibition of the amidolytic activity of factor VIIa/tissue factor complex by the compounds in accordance with the invention can be demonstrated with the aid of a chromogenic peptide substrate as described hereinafter.

The measurements were carried out by an automated robotic assay on microtitre plates at room temperature. To this end, 100 μL of a solution of 26 nM of tissue factor, 9 nM of soluble factor VIIa and 8 mM of calcium chloride were added to 25 μL of a solution of the inhibitor in a buffer [pH 7.5, 100 mM, comprising 0.14M NaCl, 0.1M N-(2-hydroxyethyl)piperazine-N'-(2-ethanesulphonic acid) (HEPES), 0.5 mg/l of fatty-acid-free BSA (bovine serum albumin) and 0.05% $NaN_3$] in each well of the plate. After an incubation time of 15 minutes the reaction was started by the addition of 50 μl of chromogenic substrate Chromozym-tPA (3.5 mM, $MeSO_2$-D-Phe-Gly-Arg-paranitroanilide) and the hydrolysis of the substrate was followed spectrophotometrically on a kinetic microtitre plate reader over 10 minutes. Using the plot of the inhibition curves, the Ki values were determined according to the method described in Biochem. J. 55, 1953, 170–171.

The activity of the low molecular weight substances can, moreover, be characterized in the "prothrombin time" (PT) clotting test. The substances are prepared as a 10 mM solution in DMSO or DMSO/0.1M HCl (DHCl) and thereafter made up to the desired dilution in the same solvent. Thereafter, 0.25 ml of human plasma (obtained from whole blood anticoagulated with 1/10 volume of 108 mM Na citrate) was placed in the instrument-specific sample container. In each case 5 μl of each dilution of the substance-dilution series was then mixed with the plasma provided. This plasma/inhibitor mixture was incubated at 37° C. for 2 minutes. Thereafter, there were pipetted to the semi-automatic device (ACL, Automated Coagulation Laboratory (Instrument Laboratory)) 50 µl of plasma/inhibitor mixture in the measurement container. The clotting reaction was initiated by the addition of 0.1 ml of Innovin® (recombinant human tissue factor combined with calcium buffer and synthetic phospholipids (Dade Behring®, Inc.). The time up to the fibrin cross-linking was determined photooptically from the ACL. The inhibitor concentration, which brought about a doubling of the PT clotting time, was determined by means of a graph.

The Ki value of the active compounds of the present invention preferably amounts to about 0.001 to 50 µM, especially about 0.001 to 1 µM. The PT values preferably amount to about 1 to 100 µM, especially to about 1 to 10 µM.

| Example | Ki [µM] |
|---------|---------|
| 24.3 | 2.21 |
| 33.3 | 0.49 |
| 53.3 | 2.26 |
| 72.2 | 2.10 |
| 126.3 | 0.02 |
| 129 | 0.021 |
| 141 | 0.044 |
| 266 | 0.242 |
| 267 | 0.371 |
| 269 | 0.32 |
| 271 | 0.154 |
| 294.2 | 0.586 |
| 323 | 0.065 |
| 325 | 0.077 |
| 329 | 0.121 |
| 335.5 | 0.017 |
| 336.2 | 0.598 |

The compounds of formula I and/or their pharmaceutically acceptable salts can be used as medicaments, e.g., in the form of pharmaceutical preparations for enteral, parenteral or topical administration. They can be administered, for example, perorally, e.g., in the form of tablets, coated tablets, dragées, hard and soft gelatine capsules, solutions, emulsions or suspensions, rectally, e.g., in the form of suppositories, parenterally, e.g., in the form of injection solutions or suspensions or infusion solutions, or topically, e.g., in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 100 mg, comes into consideration. Depending on severity of the disease and the precise pharmacokinetic profile the compound could be administered with one or several daily dosage units, e.g., in 1 to 3 dosage units.

The pharmaceutical preparations conveniently contain about 1–500 mg, preferably 1–100 mg, of a compound of formula I.

The following Examples serve to illustrate the present invention in more detail. They are, however, not intended to limit its scope in any manner.

EXAMPLES

Abbreviations

BOP=(benzotriazol-1-yloxy)-tris-(dimethylamino)-phosphonium-hexafluorophosphat, CAS=Chemical Abstract Services, DEAD=diethyl azodicarboxylate, DMF=dimethyl formamide, EDCI=1-[3-(dimethylamino)propyl]-3-ethylcarbodiimide hydrochloride, EtOH=ethanol, HOBT=1-hydroxybenzotriazole, MS=mass spectroscopy, MeOH=methanol, rt=room temperature, THF=tetrahydrofuran General Procedures General Procedure A: Conversion of an Aromatic Aldehyde into an Aryl-α-alkoxyacetic Acid.

To a stirred solution of the aldehyde (1 eq) and bromoform (1.27 eq) in the appropriate alkohol (MeOH or EtOH, 1 ml/mmol aldehyde) and dioxane (1 ml/mmol aldehyde) is added dropwise a solution of potassium hydroxyde (5 eq) in the appropriate alkohol (MeOH or EtOH, 1 ml/mmol aldehyde) for 15 min. For larger amounts a slight cooling is applied. Stirring at rt. under an argon atmosphere is then continued for 18–48 h. The solid is filtered off and washed with the appropriate alkohol. The filtrate is concentrated (rotavapor). The residue is taken up in water. The resulting solution is washed with Et$_2$O and acidified to pH 1 by dropwise addition of 3.0 N HCl. This is extracted with Et$_2$O, dried (MgSO$_4$), filtered and concentrated (rotavapor). The crude product can be purified by chromatography (silicagel) or by crystallization.

General Procedure B: Coupling of an Aryl-α-alkoxyacetic Acid with a Primary Amine Using EDCI as a Coupling Reagent.

To a stirred solution of the amine (1 eq) in THF is added the acid (1.2 eq), triethylamine (1.2 eq) and EDCI (1.2 eq). HOBT (1.2 eq) can also be added. The mixture is then stirred at rt. under an argon atmosphere for 16–24 h. The mixture is diluted with EtOAc, washed with sat. KHSO$_4$ solution/water (1:1) and water; dried (MgSO$_4$), filtered and concentrated. The crude product can be purified by chromatography (silicagel) or by crystallization.

General Procedure C: Coupling of an Aryl-α-alkoxyacetic Acid with a Primary Amine Using BOP as a Coupling Reagent.

To a stirred solution of the amine (1 eq) in THF is added the acid (1.5 eq), N-diisopropylamine (1.5 eq) and BOP-reagent (1.5 eq). The mixture is then stirred at rt under an argon atmosphere for 16–24 h. The mixture is diluted with EtOAc, washed with water, 1.0 N NaOH and brine; dried (MgSO$_4$), filtered and concentrated. The crude product can be purified by chromatography (silicagel) or by crystallization.

General Procedure D: Conversion of an Aromatic Nitrile into an Amidine (Pinner Reaction).

Dry HCl gas is passed over a cooled (−10° C.), stirred solution of the starting material in CHCl$_3$/EtOH (or MeOH) 5:1 for 15 min. The flask is stoppered and left at 4° C. overnight. If conversion is not complete, the reaction mixture is allowed to warm to rt. The mixture is concentrated (rotavapor and high vacuum) at rt. The residue is dissolved in EtOH and treated with a 2.0 M NH$_3$ solution in EtOH. The resulting mixture is stirred at rt (sensitive compounds) or 60° C. for 2–18 h. The mixture is then concentrated (rotavapor) and purified by chromatography (silicagel).

Example 1

1.1

(S)-(+)-Methoxyphenylacetic acid was coupled with 4-aminomethyl benzonitrile (CAS No: 10406-25-4) according to general procedure C to give (S)-N-(4-cyano-benzyl)-2-methoxy-2-phenyl-acetamide as an off-white solid. MS 281.2 ([M+H]$^+$)

1.2

(S)-N-(4-Cyano-benzyl)-2-methoxy-2-phenyl-acetamide was converted to (S)-N-(4-carbamimidoyl-benzyl)-2-methoxy-2-phenyl-acetamide hydrochloride according to general procedure D. Colorless solid. MS 298 ([M+H]$^+$)

Example 2

2.1

(R)-(+)-Methoxyphenylacetic acid was coupled with 4-aminomethyl benzonitrile (CAS No: 10406-25-4) according to general procedure C to give (R)-N-(4-cyano-benzyl)-2-methoxy-2-phenyl-acetamide as an off-white solid. MS 281.1 ([M+H]$^+$)

2.2

(R)-N-(4-Cyano-benzyl)-2-methoxy-2-phenyl-acetamide was converted to (R)-N-(4-carbamimidoyl-benzyl)-2-methoxy-2-phenyl-acetamide hydrochloride according to general procedure D. Colorless solid. MS 298.2 ([M+H]$^+$)

Example 3

3.1

4-Benzyloxybenzaldehyde was converted to (RS)-(4-benzyloxy-phenyl)-methoxy-acetic acid according to general procedure A. Off-white solid. MS 271.1 ([M−H]$^−$)

3.2

(RS)-(4-Benzyloxy-phenyl)-methoxy-acetic acid was coupled with 4-aminomethyl benzonitrile to give (RS)-2-(4-benzyloxy-phenyl)-N-(4-cyano-benzyl)-2-methoxy-acetamide according to general procedure B. Colorless solid. MS 387.3 ([M+H]$^+$)

3.3

(RS)-2-(4-Benzyloxy-phenyl)-N-(4-cyano-benzyl)-2-methoxy-acetamide was converted to (RS)-2-(4-benzyloxy-phenyl)-N-(4-carbamimidoyl-benzyl)-2-methoxy-acetamide hydrochloride according to general procedure D. Colorless foam. MS 404.5 ([M+H]$^+$)

Example 4

4.1

4-Phenoxybenzaldehyde was converted to (RS)-methoxy-(4-phenoxy-phenyl)-acetic acid according to general procedure A. Yellow oil. MS 257.0 ([M−H]$^−$)

4.2

(RS)-Methoxy-(4-phenoxy-phenyl)-acetic acid was coupled with 4-aminomethyl benzonitrile according to general procedure B to give (RS)-N-(4-cyano-benzyl)-2-methoxy-2-(4-phenoxy-phenyl)-acetamide. Colorless solid. MS 373.3 ([M+H]$^+$)

4.3

(RS)-N-(4-Cyano-benzyl)-2-methoxy-2-(4-phenoxy-phenyl)-acetamide was converted to (RS)-N-(4-carbamimidoyl-benzyl)-2-methoxy-2-(4-phenoxy-phenyl)-acetamide hydrochloride according to general procedure D. Colorless foam. MS 390.3 ([M+H]$^+$)

Example 5

5.1

3-Phenoxybenzaldehyde was converted to (RS)-methoxy-(3-phenoxy-phenyl)-acetic acid according to general procedure A. Light yellow liquid.

5.2

(RS)-Methoxy-(3-phenoxy-phenyl)-acetic acid was coupled with 4-aminomethyl benzonitrile according to general procedure B to give (RS)-N-(4-cyano-benzyl)-2-methoxy-2-(3-phenoxy-phenyl)-acetamide. Light yellow oil. MS 373.3 ([M+H]$^+$)

5.3

(RS)-N-(4-Cyano-benzyl)-2-methoxy-2-(3-phenoxy-phenyl)-acetamide was converted to (RS)-N-(4-carbamimidoyl-benzyl)-2-methoxy-2-(3-phenoxy-phenyl)-acetamide hydrochloride according to general procedure D. Colorless amorphous solid. MS 390.3 ([M+H]$^+$)

Example 6

6.1

Benzaldehyde was converted to (RS)-ethoxy-phenyl-acetic acid according to general procedure A. Light yellow liquid.

6.2

(RS)-Ethoxy-phenyl-acetic acid was coupled with 4-aminomethyl benzonitrile according to general procedure B to give (RS)-N-(4-cyano-benzyl)-2-ethoxy-2-phenyl-acetamide. Light yellow semisolid. MS 295.3 ([M+H]$^+$)

6.3

(RS)-N-(4-Cyano-benzyl)-2-ethoxy-2-phenyl-acetamide was converted to (RS)-N-(4-carbamimidoyl-benzyl)-2-ethoxy-2-phenyl-acetamide hydrochloride according to general procedure D. Colorless amorphous solid. MS 312.2 ([M+H]$^+$)

Example 7

7.1

2-Fluorobenzaldehyde was converted to (RS)-(2-fluoro-phenyl)-methoxy-acetic acid according to general procedure A. Off-white amorphous solid. MS 182.9 ([M−H]$^−$)

7.2

(RS)-(2-Fluoro-phenyl)-methoxy-acetic acid was coupled with 4-aminomethyl benzonitrile according to general procedure B to give (RS)-N-(4-cyano-benzyl)-2-(2-fluoro-phenyl)-2-methoxy-acetamide. Colorless oil. MS 299.2 ([M+H]$^+$)

7.3

(RS)-N-(4-Cyano-benzyl)-2-(2-fluoro-phenyl)-2-methoxy-acetamide was converted to (RS)-N-(4-carbamimidoyl-benzyl)-2-(2-fluoro-phenyl)-2-methoxy-acetamide hydrochloride according to general procedure D. Colorless foam. MS 316.2 ([M+H]$^+$)

Example 8

8.1

3-Benzyloxybenzaldehyde was converted to (RS)-(3-benzyloxy-phenyl)-methoxy-acetic acid according to general procedure A. Colorless solid.

8.2

(RS)-(3-Benzyloxy-phenyl)-methoxy-acetic acid was coupled with 4-aminomethyl benzonitrile according to general procedure B to give (RS)-2-(3-benzyloxy-phenyl)-N-(4-cyano-benzyl)-2-methoxy-acetamide. Light yellow oil.

8.3

(RS)-2-(3-Benzyloxy-phenyl)-N-(4-cyano-benzyl)-2-methoxy-acetamide was converted to (RS)-2-(3-benzyloxy-phenyl)-N-(4-carbamimidoyl-benzyl)-2-methoxy-acetamide hydrochloride according to general procedure D. Colorless amorphous solid. MS 404.5 ([M+H]$^+$)

Example 9

9.1

As a side product of the synthesis of (RS)-2-(3-benzyloxy-phenyl)-N-(4-carbamimidoyl-benzyl)-2-methoxy-acetamide hydrochloride (example 8.3) there was obtained (RS)-N-(4-carbamimidoyl-benzyl)-2-(3-hydroxy-phenyl)-2-methoxy-acetamide hydrochloride. Colorless amorphous solid. MS 314.2 ([M+H]$^+$)

Example 10

10.1

To a stirred solution of 3-nitrobenzaldehyde (4.043 g) at rt in 190 ml CH$_2$Cl$_2$ was added ZnI$_2$ (0.427 g). The mixture was purged with N$_2$ and cooled to 0° C. Trimethylsilyl cyanide (2.92 g as a solution in 10 ml CH$_2$Cl$_2$) was then added dropwise to the mixture for 15 min. The mixture was then allowed to warm to room temperature and stirring was continued for 16 h. Water (250 ml) was then added to the mixture. The layers were separated and the aqueous phase was extracted with CH$_2$Cl$_2$ (125 ml). The combined organics were washed with water (125 ml) and brine (125 ml), dried (MgSO$_4$), filtered and concentrated (rotavapor) to leave the crude (RS)-(3-nitro-phenyl)-trimethylsilanyloxy-acetonitrile (6.56 g) as an orange oil which was used in the next step without further purification.

10.2

(RS)-(3-Nitro-phenyl)-trimethylsilanyloxy-acetonitrile (6.30 g) was dissolved in concentrated HCl with stirring. The mixture was then refluxed for 3 h. After cooling to room temperature, the yellow solution was poured into 200 g of crushed ice. This was extracted with Et$_2$O (150 ml+150 ml+150 ml). The combined organics were washed with water (200 ml) and brine (200 ml), dried (MgSO$_4$), filtered and concentrated (rotavapor) to leave a yellow solid. This solid was triturated in a mixture of n-hexane (20 ml) and Et$_2$O (2 ml), collected by filtration and washed with n-hexane to give (RS)-hydroxy-(3-nitro-phenyl)-acetic acid as a light yellow solid (4.56 g).

10.3

A mixture of (RS)-hydroxy-(3-nitro-phenyl)-acetic acid (1.054 g), Ag$_2$O (2.478 g) and MeI (2.304 g) was heated to reflux in toluene (10 ml). Stirring was then continued for 3 h. After cooling to rt, the solid was filtered off and washed with EtOAc. The filtrate was concentrated (rotavapor) to leave the crude (RS)-methoxy-(3-nitro-phenyl)-acetic acid methyl ester (1.161 g) as a light yellow oil.

10.4

A mixture of (RS)-methoxy-(3-nitro-phenyl)-acetic acid methyl ester (1.039 g) and NaOH (0.239 g) in water (0.75 ml) and methanol (10 ml) was stirred at 0° C. for 4.5 h. The reaction mixture was then concentrated (rotavapor, high vac.) and the residue (light yellow solid) was taken in water (25 ml). The resulting solution was acidified to pH~1 by dropwise addition of 3.0 N HCl. This was extracted with EtOAc (50 ml+25 ml). The combined organics were dried (MgSO4), filtered and concentrated (rotavapor) to leave the crude (RS)-methoxy-(3-nitro-phenyl)-acetic acid (0.944 g) as a light yellow solid.

10.5

(RS)-Methoxy-(3-nitro-phenyl)-acetic acid was coupled with 4-aminomethyl benzonitrile according to general procedure C to give (RS)-N-(4-cyano-benzyl)-2-methoxy-2-(3-nitro-phenyl)-acetamide. Light yellow gum.

10.6

(RS)-N-(4-Cyano-benzyl)-2-methoxy-2-(3-nitro-phenyl)-acetamide was converted to (RS)-N-(4-carbamimidoyl-benzyl)-2-methoxy-2-(3-nitro-phenyl)-acetamide hydrochloride according to general procedure D. Off-white solid. MS 343.2 ([M+H]$^+$)

Example 11

11.1

4-Biphenylaldehyde was converted to (RS)-biphenyl-4-yl-methoxy-acetic acid according to general procedure A. Light brown solid.

11.2

(RS)-Biphenyl-4-yl-methoxy-acetic acid was coupled with 4-aminomethyl benzonitrile according to general procedure C to give (RS)-2-biphenyl-4-yl-N-(4-cyano-benzyl)-2-methoxy-acetamide. Light yellow solid.

11.3

(RS)-2-Biphenyl-4-yl-N-(4-cyano-benzyl)-2-methoxy-acetamide was converted to (RS)-2-biphenyl-4-yl-N-(4-carbamimidoyl-benzyl)-2-methoxy-acetamide hydrochloride according to general procedure D. Off-white solid. MS 374.4 ([M+H]$^+$)

Example 12

12.1

Piperonal was converted to (RS)-benzo[1,3]dioxol-5-yl-methoxy-acetic acid according to general procedure A. Orange oil.

12.2

(RS)-Benzo[1,3]dioxol-5-yl-methoxy-acetic acid was coupled with 4-aminomethyl benzonitrile according to general procedure C to give (RS)-2-benzo[1,3]dioxol-5-yl-N-(4-cyano-benzyl)-2-methoxy-acetamide. Light yellow solid.

12.3

(RS)-2-Benzo[1,3]dioxol-5-yl-N-(4-cyano-benzyl)-2-methoxy-acetamide was converted to (RS)-2-benzo[1,3]dioxol-5-yl-N-(4-carbamimidoyl-benzyl)-2-methoxy-acetamide hydrochloride according to general procedure D (Pinner reaction in EtOH/CHCl$_3$ as a solvent). Off-white solid. MS 342.2 ([M+H]$^+$)

Example 13

13.1

As a side product of the synthesis of (RS)-2-benzo[1,3]dioxol-5-yl-N-(4-carbamimidoyl-benzyl)-2-methoxy-acetamide hydrochloride (example 12.3) there was obtained (RS)-2-benzo[1,3]dioxol-5-yl-N-(4-carbamimidoyl-benzyl)-2-ethoxy-acetamide hydrochloride. Light brown solid. MS 356.3 ([M+H]$^+$)

Example 14

14.1

5-Ethoxy-2-fluoro-3-(1-methyl-piperidin-4-yloxy)-benzaldehyde was converted to (RS)-[5-ethoxy-2-fluoro-3-(1-methyl-piperidin-4-yloxy)-phenyl]-methoxy-acetic acid according to general procedure A. Off-white solid. MS 342.2 ([M+H]$^+$)

14.2

(RS)-[5-Ethoxy-2-fluoro-3-(1-methyl-piperidin-4-yloxy)-phenyl]-methoxy-acetic acid was coupled with 4-aminomethyl benzonitrile according to general procedure B to give (RS)-N-(4-cyano-benzyl)-2-[5-ethoxy-2-fluoro-3-(1-methyl-piperidin-4-yloxy)-phenyl]-2-methoxy-acetamide. Colorless foam. MS 456.5 ([M+H]$^+$)

14.3

(RS)-N-(4-Cyano-benzyl)-2-[5-ethoxy-2-fluoro-3-(1-methyl-piperidin-4-yloxy)-phenyl]-2-methoxy-acetamide was converted to (RS)-N-(4-carbamimidoyl-benzyl)-2-[5-ethoxy-2-fluoro-3-(1-methyl-piperidin-4-yloxy)-phenyl]-2-methoxy-acetamide hydrochloride according to general procedure D. Colorless foam. MS 473.5 ([M+H]$^+$)

Example 15

15.1

2-Fluoro-4-methoxybenzaldehyde was converted to (RS)-(2-fluoro-4-methoxy-phenyl)-methoxy-acetic acid according to general procedure A. Light yellow oil. MS 213.4 ([M–H]$^-$)

15.2

(RS)-(2-Fluoro-4-methoxy-phenyl)-methoxy-acetic acid was coupled with 4-aminomethyl benzonitrile according to general procedure B to give (RS)-N-(4-cyano-benzyl)-2-(2-fluoro-4-methoxy-phenyl)-2-methoxy-acetamide. Colorless oil. MS 329.2 ([M+H]$^+$)

15.3

(RS)-N-(4-Cyano-benzyl)-2-(2-fluoro-4-methoxy-phenyl)-2-methoxy-acetamide was converted to (RS)-N-(4-carbamimidoyl-benzyl)-2-(2-fluoro-4-methoxy-phenyl)-2-methoxy-acetamide hydrochloride according to general procedure D. Colorless foam. MS 346.4 ([M+H]$^+$)

15.4

(RS)-N-(4-Carbamimidoyl-benzyl)-2-(2-fluoro-4-methoxy-phenyl)-2-methoxy-acetamide hydrochloride (example 15.3, 200 mg) was dissolved in DMF (2.2 ml). The flask was placed in an ice bath. Ethyl chloroformate (58 mg) and triethylamine (160 mg) were added dropwise. The reaction mixture was stirred for 1.5 h at 0° C. Ethyl acetate (30 ml) and ice water (40 ml) were added and the mixture was extracted with ethyl acetate. The organic phase was washed with water, dried, filtered and evaporated. The product was purified by chromatography (silicagel, ethylacetate) to give (RS)-[amino-(4-{[2-(2-fluoro-4-methoxy-phenyl)-2-methoxy-acetylamino]-methyl}-phenyl)-methylene]-carbamic acid ethyl ester (218 mg) as a colorless amorphous solid. MS 418.3 ([M+H]$^+$)

15.5

(RS)-N-(4-Cyano-benzyl)-2-(2-fluoro-4-methoxy-phenyl)-2-methoxy-acetamide (example 15.2, 251 mg) was dissolved in methanol (7 ml). Hydroxylamine hydrochloride (212 mg) and triethylamine (618 mg) were added. The mixture was stirred for 19 h at rt. The solvent was evaporated. The residue was dissolved in methylene chloride, washed with water, dried and filtered. The solvent was evaporated to give (RS)-2-(2-fluoro-4-methoxy-phenyl)-N-[4-(N-hydroxycarbamimidoyl)-benzyl]-2-methoxy-acetamide (269 mg) as an off-white foam. MS 362.2 ([M+H]$^+$)

15.6

(RS)-N-(4-Cyano-benzyl)-2-(2-fluoro-4-methoxy-phenyl)-2-methoxy-acetamide (example 15.2, 285 mg) was dissolved in methanol (0.7 ml) and chloroform (3.3 ml). The mixture was placed in an ice-NaCl bath. Dry HCl gas was passed over the reaction mixture for 15 min. The flask was stoppered and left overnight at 4° C. The mixture was concentrated (rotavapor and high vacuum) at rt. The residue was dissolved in methanol (1.9 ml). Hydrazine hydrochloride (66 mg) and triethylamine (264 mg) were added. The mixture was stirred overnight. The solvent was evaporated and the product was purified by chromatography (silica gel, CH$_2$Cl$_2$=>CH$_2$Cl$_2$/MeOH 4:1) to give RS)-2-(2-fluoro-4-methoxy-phenyl)-N-[4-(N-aminocarbamimidoyl)-benzyl]-2-methoxy-acetamide (205 mg) as an off-white foam. MS 361.2 ([M+H]$^+$)

Example 16

16.1
3-Benzyloxy-4-methoxy-benzaldehyde was converted to (RS)-(3-benzyloxy-4-methoxy-phenyl)-methoxy-acetic acid according to general procedure A. Orange solid.

16.2
To a stirred solution of (RS)-(3-benzyloxy-4-methoxy-phenyl)-methoxy-acetic acid (0.923 g) at rt in ethanol was added 10% Pd/C. The mixture was then stirred at rt under a hydrogen atmosphere for 17 h. The catalyst was filtered off and washed with dichloromethane. The filtrate was concentrated (rotavapor) to give (RS)-(3-hydroxy-4-methoxy-phenyl)-methoxy-acetic acid (0.642 g) as an orange gum.

16.3
(RS)-(3-Hydroxy-4-methoxy-phenyl)-methoxy-acetic acid was coupled with 4-aminomethyl benzonitrile according to general procedure C to give (RS)-N-(4-cyano-benzyl)-2-(3-hydroxy-4-methoxy-phenyl)-2-methoxy-acetamide. White foam.

16.4
To a stirred solution of (RS)-N-(4-cyano-benzyl)-2-(3-hydroxy-4-methoxy-phenyl)-2-methoxy-acetamide (0.303 g) at rt in DMF (3 ml) were added $K_2CO_3$ (0.14 g) and ethyl bromoacetate (0.169 g). The reaction mixture was then stirred at rt under an argon atmosphere for 5 h 45. The mixture was diluted with EtOAc (25 ml), washed with water (25 ml) and brine (25 ml), dried ($MgSO_4$), filtered and concentrated (rotavapor) to leave the crude product as a light yellow gum. The product was purified by chromatography (Silicagel (20 g) using a gradient profile: cyclohexane to cyclohexane/EtOAc 35:65) to give (RS)-{5-[(4-cyano-benzylcarbamoyl)-methoxy-methyl]-2-methoxy-phenoxy}-acetic acid ethyl ester (0.342 g) as a white solid.

16.5
(RS)-{5-[(4-Cyano-benzylcarbamoyl)-methoxy-methyl]-2-methoxy-phenoxy}-acetic acid ethyl ester was converted to (RS)-{5-[(4-carbamimidoyl-benzylcarbamoyl)-methoxy-methyl]-2-methoxy-phenoxy}-acetic acid methyl ester hydrochloride according to general procedure D. Off-white solid. MS 416.3 ([M+H]$^+$)

Example 17

17.1
As a side product of the synthesis of (RS)-{5-[(4-carbamimidoyl-benzylcarbamoyl)-methoxy-methyl]-2-methoxy-phenoxy}-acetic acid methyl ester hydrochloride (example 16.5) there was obtained (RS)-N-(4-carbamimidoyl-benzyl)-2-(3-carbamoylmethoxy-4-methoxy-phenyl)-2-methoxy-acetamide hydrochloride. Off-white solid. MS 401.5 ([M+H]$^+$)

Example 18

18.1
3-Benzyloxy-4-methoxy-benzaldehyde was converted to (RS)-(3-benzyloxy-4-methoxy-phenyl)-ethoxy-acetic acid according to general procedure A. Light yellow solid.

18.2
To a stirred solution of (RS)-(3-benzyloxy-4-methoxy-phenyl)-ethoxy-acetic acid (0.801 g) at rt in ethanol was added 10% Pd/C (0.1 g). The mixture was then stirred at rt under a hydrogen atmosphere for 17 h. The catalyst was filtered off and washed with dichloromethane. The filtrate was concentrated (rotavapor). The residue was purified by chromatography to give (RS)-ethoxy-(3-hydroxy-4-methoxy-phenyl)-acetic acid (0.250 g) as a light yellow gum.

18.3
(RS)-Ethoxy-(3-hydroxy-4-methoxy-phenyl)-acetic acid was coupled with 4-aminomethyl benzonitrile according to general procedure C to give (RS)-N-(4-cyano-benzyl)-2-ethoxy-2-(3-hydroxy-4-methoxy-phenyl)-acetamide. Light yellow gum.

18.4
To a stirred solution of (RS)-N-(4-cyano-benzyl)-2-ethoxy-2-(3-hydroxy-4-methoxy-phenyl)-acetamide (0.158 g) at rt in DMF (1.5 ml) were added $K_2CO_3$ (0.067 g) and ethyl bromoacetate (0.081 g). The reaction mixture was then stirred at rt under an argon atmosphere for 24 h. The mixture was diluted with EtOAc (10 ml), washed with water (10 ml+10 ml) and brine (10 ml), dried ($MgSO_4$), filtered and concentrated (rotavapor). The product was purified by chromatography (Silicagel (20 g) using a gradient profile: cyclohexane to cyclohexane/EtOAc 45:55) to give (RS)-{5-[(4-cyano-benzylcarbamoyl)-ethoxy-methyl]-2-methoxy-phenoxy}-acetic acid ethyl ester (0.160 g) as a colorless gum.

18.5
(RS)-{5-[(4-Cyano-benzylcarbamoyl)-ethoxy-methyl]-2-methoxy-phenoxy}-acetic acid ethyl ester was converted to (RS)-{5-[(4-carbamimidoyl-benzylcarbamoyl)-ethoxy-methyl]-2-methoxy-phenoxy}-acetic acid ethyl ester hydrochloride according to general procedure D. Off-white solid. MS 444.4 ([M+H]$^+$)

Example 19

19.1
As a side product of the synthesis of (RS)-{5-[(4-carbamimidoyl-benzylcarbamoyl)-ethoxy-methyl]-2-methoxy-phenoxy}-acetic acid ethyl ester hydrochloride (example 18.5), there was obtained (RS)-N-(4-carbamimidoyl-benzyl)-2-(3-carbamoylmethoxy-4-methoxy-phenyl)-2-ethoxy-acetamide hydrochloride. Off-white solid. MS 415.4 ([M+H]$^+$)

Example 20

20.1
To a stirred suspension of (RS)-{5-[(4-carbamimidoyl-benzylcarbamoyl)-ethoxy-methyl]-2-methoxy-phenoxy}-acetic acid ethyl ester hydrochloride (example 18.5, 0.045 g) at rt in THF (1 ml) and water (0.5 ml) was added 1.0 N NaOH (0.2 ml). The mixture was then stirred at rt under an argon atmosphere for 3 h. The mixture waa acidified to pH 5–6 by addition of 1.0 N HCl. The THF was removed (rotavapor) and the product precipitated out from the remaining water. It was collected by filtration, washed with water and cyclohexane and dried overnight under high vacuum to give (RS)-{5-[(4-carbamimidoyl-benzylcarbamoyl)-ethoxy-methyl]-2-methoxy-phenoxy}-acetic acid (0.027 g) as a white powder. MS 416.3 ([M+H]$^+$)

Example 21

21.1
(RS)-(4-Benzyloxy-phenyl)-methoxy-acetic acid (example 3.1) was hydrogenated at rt and normal pressure using 10% Pd/C as a catalyst and EtOH as a solvent to give (RS)-(4-hydroxy-phenyl)-methoxy-acetic acid as a light grey solid. MS 181.4 ([M–H]$^-$)

21.2
(RS)-(4-Hydroxy-phenyl)-methoxy-acetic acid was coupled with 4-aminomethyl benzonitrile according to general procedure B to give (RS)-N-(4-cyano-benzyl)-2-(4-hydroxy-phenyl)-2-methoxy-acetamide. Colorless foam. MS 295.2 ([M–H]$^-$)

21.3
In analogy to example 16.4, (RS)-N-(4-cyano-benzyl)-2-(4-hydroxy-phenyl)-2-methoxy-acetamide was alkylated with ethyl iodide/cesium carbonate in DMF to give (RS)-N-(4-cyano-benzyl)-2-(4-ethoxy-phenyl)-2-methoxy-acetamide as a colorless solid. MS 325.3 ([M+H]$^+$)

21.4
(RS)-N-(4-Cyano-benzyl)-2-(4-ethoxy-phenyl)-2-methoxy-acetamide was converted to (RS)-N-(4-carbamimidoyl-benzyl)-2-ethoxy-2-(4-ethoxy-phenyl)-acetamid hydrochloride according to general procedure D using EtOH/CHCl$_3$ as a solvent. Off-white amorphous solid. MS 365.3 ([M+H]$^+$)

Example 22

22.1
(RS)-N-(4-Cyano-benzyl)-2-(4-hydroxy-phenyl)-2-methoxy-acetamide (example 21.2, 0.406 g) was dissolved in THF (12 ml). Triphenylphosphine (0.539 g) and 4-hydroxy-N-methylpiperidine (0.237 g) were added. The reaction mixture was cooled to 0° C. Slowly, DEAD (0.384 g) was added. The reaction mixture was stirred at 0° C. for 30 min and at rt for 5 days. The solvent was evaporated and the product was purified by chromatography (silicagel, mobile phase: gradient from CH$_2$Cl$_2$ to CH$_2$Cl$_2$/MeOH 4:1) to give (RS)-N-(4-cyano-benzyl)-2-methoxy-2-[4-(1-methyl-piperidin-4-yloxy)-phenyl]-acetamide as a colorless foam (0.241 g). MS 394.4 ([M+H]$^+$)

22.2
(RS)-N-(4-Cyano-benzyl)-2-methoxy-2-[4-(1-methyl-piperidin-4-yloxy)-phenyl]-acetamide was converted to (RS)-N-(4-carbamimidoyl-benzyl)-2-methoxy-2-[4-(1-methyl-piperidin-4-yloxy)-phenyl]-acetamide hydrochloride according to general procedure D. Colorless foam. MS 411.4 ([M+H]$^+$)

Example 23

23.1
(+/−)-(α-Methoxy-alpha-trifluoromethyl phenylacetic acid was coupled with 4-aminomethyl benzonitrile according to general procedure C to give (RS)-N-(4-cyano-benzyl)-3,3,3-trifluoro-2-methoxy-2-phenyl-propionamide. Off-white solid.

23.2
(RS)-N-(4-Cyano-benzyl)-3,3,3-trifluoro-2-methoxy-2-phenyl-propionamide was converted to (RS)-N-(4-carbamimidoyl-benzyl)-3,3,3-trifluoro-2-methoxy-2-phenyl-propionamide hydrochloride according to general procedure D. White solid. MS 366.2 ([M+H]$^+$)

Example 24

24.1
Fluorveratraldehyde was converted to (RS)-(2-fluoro-4,5-dimethoxy-phenyl)-methoxy-acetic acid according to general procedure A. Light yellow oil. MS 243.1 ([M–H]$^-$)

24.2
(RS)-(2-Fluoro-4,5-dimethoxy-phenyl)-methoxy-acetic acid was coupled with 4-aminomethyl benzonitrile according to general procedure B to give (RS)-N-(4-cyano-benzyl)-2-(2-fluoro-4,5-dimethoxy-phenyl)-2-methoxy-acetamide. Red foam. MS 359.2 ([M+H]$^+$)

24.3
(RS)-N-(4-Cyano-benzyl)-2-(2-fluoro-4,5-dimethoxy-phenyl)-2-methoxy-acetamide was converted to (RS)-N-(4-carbamimidoyl-benzyl)-2-(2-fluoro-4,5-dimethoxy-phenyl)-2-methoxy-acetamide hydrochloride according to general procedure D. Orange solid. MS 376.4 ([M+H]$^+$)

Example 25

25.1
(RS)-(3-Benzyloxy-phenyl)-methoxy-acetic acid (example 8.1) was hydrogenated at rt and normal pressure using 10% Pd/C as a catalyst and EtOH as a solvent to give (RS)-(3-hydroxy-phenyl)-methoxy-acetic acid as a colorless foam.

25.2
(RS)-(3-Hydroxy-phenyl)-methoxy-acetic acid was coupled with 4-aminomethyl benzonitrile according to general procedure B to give (RS)-N-(4-cyano-benzyl)-2-(3-hydroxy-phenyl)-2-methoxy-acetamide. Colorless oil.

25.3
In analogy to example 16.4, (RS)-N-(4-cyano-benzyl)-2-(3-hydroxy-phenyl)-2-methoxy-acetamide was alkylated with 2-iodopropane/cesium carbonate in DMF to give (RS)-N-(4-cyano-benzyl)-2-(3-isopropoxy-phenyl)-2-methoxy-acetamide as a colorless oil. MS 339.2 ([M+H]$^+$)

25.4
(RS)-N-(4-Cyano-benzyl)-2-(3-isopropoxy-phenyl)-2-methoxy-acetamide was converted to (RS)-N-(4-carbamimidoyl-benzyl)-2-(3-isopropoxy-phenyl)-2-methoxy-acetamide hydrochloride according to general procedure D. Colorless amorphous solid. MS 356.3 ([M+H]$^+$)

Example 26

26.1
In analogy to example 22.1, (RS)-N-(4-cyano-benzyl)-2-(4-hydroxy-phenyl)-2-methoxy-acetamide (example 21.2) was reacted with cyclopentanol, triphenylphosphine and DEAD in THF. Further conversion according to general procedure D gave (RS)-N-(4-carbamimidoyl-benzyl)-2-(4-cyclopentyloxy-phenyl)-2-methoxy-acetamide hydrochloride as a light yellow solid. MS 282.3 ([M+H]$^+$)

Example 27

27.1

In analogy to example 16.4, (RS)-N-(4-cyano-benzyl)-2-(4-hydroxy-phenyl)-2-methoxy-acetamide (example 21.2) was alkylated with 2-iodopropane/cesium carbonate in DMF to give (RS)-N-(4-cyano-benzyl)-2-(4-isopropoxy-phenyl)-2-methoxy-acetamide as a colorless solid. MS 339.2 ([M+H]$^+$)

27.2

(RS)-N-(4-Cyano-benzyl)-2-(4-isopropoxy-phenyl)-2-methoxy-acetamide was converted to (RS)-N-(4-carbamimidoyl-benzyl)-2-(4-isopropoxy-phenyl)-2-methoxy-acetamide hydrochloride according to general procedure D. Colorless foam. MS 356.3 ([M+H]$^+$)

Example 28

28.1

In analogy to example 16.4, (RS)-N-(4-cyano-benzyl)-2-(4-hydroxy-phenyl)-2-methoxy-acetamide (example 21.2) was alkylated with ethylbromoacetate/cesium carbonate in DMF to give (RS)-{4-[(4-cyano-benzylcarbamoyl)-methoxy-methyl]-phenoxy}-acetic acid ethyl ester as a colorless solid. MS 383.3 ([M+H]$^+$)

28.2

(RS)-{4-[(4-Cyano-benzylcarbamoyl)-methoxy-methyl]-phenoxy}-acetic acid ethyl ester was converted to (RS)-{4-[(4-carbamimidoyl-benzylcarbamoyl)-methoxy-methyl]-phenoxy}-acetic acid methyl ester hydrochloride according to general procedure D using MeOH/CHCl$_3$ as a solvent. Colorless foam. MS 386.3 ([M+H]$^+$)

Example 29

29.1

In analogy to example 20.1, (RS)-{4-[(4-carbamimidoyl-benzylcarbamoyl)-methoxy-methyl]-phenoxy}-acetic acid methyl ester hydrochloride (example 28.2) was hydrolyzed to (RS)-{4-[(4-carbamimidoyl-benzylcarbamoyl)-methoxy-methyl]-phenoxy}-acetic acid. Colorless solid. MS 370.2 ([M−H]$^-$)

Example 30

30.1

In analogy to example 22.1, (RS)-N-(4-cyano-benzyl)-2-(3-hydroxy-phenyl)-2-methoxy-acetamide (example 25.2) was reacted with tetrahydro-2H-pyran-4-ol, DEAD and triphenylphosphine in THF and subsequently converted into (RS)-N-(4-carbamimidoyl-benzyl)-2-methoxy-2-[3-(tetrahydro-pyran-4-yloxy)-phenyl]-acetamide hydrochloride according to general procedure D. Colorless amorphous solid. MS 398.4 ([M+H]$^+$)

Example 31

31.1

3,5-Diethoxy-2-fluoro-benzaldehyde (CAS 277324-21-7) was converted to (RS)-(3,5-diethoxy-2-fluoro-phenyl)-methoxy-acetic acid according to general procedure A. Yellow oil. MS 271.1 ([M−H]$^-$)

31.2

(RS)-(3,5-Diethoxy-2-fluoro-phenyl)-methoxy-acetic acid was coupled with 4-aminomethyl benzonitrile according to general procedure B to give (RS)-N-(4-cyano-benzyl)-2-(3,5-diethoxy-2-fluoro-phenyl)-2-methoxy-acetamide. Light yellow oil. MS 387.3 ([M+H]$^+$)

31.3

(RS)-N-(4-Cyano-benzyl)-2-(3,5-diethoxy-2-fluoro-phenyl)-2-methoxy-acetamide was converted to (RS)-N-(4-carbamimidoyl-benzyl)-2-(3,5-diethoxy-2-fluoro-phenyl)-2-methoxy-acetamide hydrochloride according to general procedure D. Light brown foam. MS 404.5 ([M+H]$^+$)

Example 32

32.1

5-Ethoxy-2-fluoro-4-(2-hydroxy-ethoxy)-benzaldehyde (CAS 376600-66-7) was converted to (RS)-[5-ethoxy-2-fluoro-4-(2-hydroxy-ethoxy)-phenyl]-methoxy-acetic acid according to general procedure A. Yellow oil. MS 287.0 ([M−H]$^-$)

32.2

(RS)-[5-Ethoxy-2-fluoro-4-(2-hydroxy-ethoxy)-phenyl]-methoxy-acetic acid was coupled with 4-aminomethyl benzonitrile according to general procedure B to give (RS)-N-(4-cyano-benzyl)-2-[5-ethoxy-2-fluoro-4-(2-hydroxy-ethoxy)-phenyl]-2-methoxy-acetamide. Light yellow oil. MS 403.4 ([M+H]$^+$)

32.3

(RS)-N-(4-Cyano-benzyl)-2-[5-ethoxy-2-fluoro-4-(2-hydroxy-ethoxy)-phenyl]-2-methoxy-acetamide was converted to (RS)-N-(4-carbamimidoyl-benzyl)-2-[5-ethoxy-2-fluoro-4-(2-hydroxy-ethoxy)-phenyl]-2-methoxy-acetamide hydrochloride according to general procedure D. Off-white foam. MS 420.3 ([M+H]$^+$)

Example 33

33.1

3,4-Diethoxy-2-fluoro-benzaldehyde was converted to (RS)-(3,4-diethoxy-2-fluoro-phenyl)-methoxy-acetic acid according to general procedure A. Yellow oil. MS 271.1 ([M−H]$^-$)

33.2

(RS)-(3,4-Diethoxy-2-fluoro-phenyl)-methoxy-acetic acid was coupled with 4-aminomethyl benzonitrile according to general procedure B to give (RS)-N-(4-cyano-benzyl)-2-(3,4-diethoxy-2-fluoro-phenyl)-2-methoxy-acetamide. Colorless solid. MS 387.3 ([M+H]$^+$)

33.3

(RS)-N-(4-Cyano-benzyl)-2-(3,4-diethoxy-2-fluoro-phenyl)-2-methoxy-acetamide was converted to (RS)-N-(4-carbamimidoyl-benzyl)-2-(3,4-diethoxy-2-fluoro-phenyl)-2-methoxy-acetamide hydrochloride according to general procedure D. Colorless foam. MS 404.5 ([M+H]$^+$)

Example 34

34.1

4-(Bromomethyl)-3-fluorobenzonitrile (CAS 105942-09-4, 21 g) was dissolved in DMF (90 ml). Phthalimide potassium salt (19.64 g) was added and the mixture was stirred for 9 h at 130° C. After cooling to rt, the mixture was poured on ice. The solid was filtered off. Ethyl acetate and water were added and extracted with ethyl acetate. The organic phase was washed with water, dried, filtered and evaporated to give a light brown solid (14.1 g, 42% pure as judged by NMR). This solid was suspended in ethanol (50 ml). A solution of hydrazine in water (24%, 15 ml) was added and the mixture was refluxed for a total of 14 h. The mixture was filtered and the solvent was evaporated. The product was purified by chromatography (silica gel, $CH_2Cl_2$=>$CH_2Cl_2$/MeOH 4:1) to give 4-aminomethyl-3-fluoro-benzonitrile (0.63 g) as a brown oil.

34.2

(RS)-(2-Fluoro-4-methoxy-phenyl)-methoxy-acetic acid (example 15.1) was coupled with 4-aminomethyl-3-fluoro-benzonitrile according to general procedure B to give (RS)-N-(4-cyano-2-fluoro-benzyl)-2-(2-fluoro-4-methoxy-phenyl)-2-methoxy-acetamide. Yellow oil. MS 347.3 ($[M+H]^+$)

34.3

(RS)-N-(4-Cyano-2-fluoro-benzyl)-2-(2-fluoro-4-methoxy-phenyl)-2-methoxy-acetamide was converted to (RS)-N-(4-carbamimidoyl-2-fluoro-benzyl)-2-(2-fluoro-4-methoxy-phenyl)-2-methoxy-acetamide hydrochloride according to general procedure D. Off-white amorphous solid. MS 364.2 ($[M+H]^+$)

Example 35

35.1

(RS)-(2-Fluoro-4-methoxy-phenyl)-methoxy-acetic acid (example 15.1) was coupled with 4-aminomethyl-2-fluorobenzonitrile (CAS 368426-73-7) according to general procedure B to give (RS)-N-(4-cyano-3-fluoro-benzyl)-2-(2-fluoro-4-methoxy-phenyl)-2-methoxy-acetamide. Light yellow solid. MS 347.3 ($[M+H]^+$)

35.2

(RS)-N-(4-Cyano-3-fluoro-benzyl)-2-(2-fluoro-4-methoxy-phenyl)-2-methoxy-acetamide was converted to (RS)-N-(4-carbamimidoyl-3-fluoro-benzyl)-2-(2-fluoro-4-methoxy-phenyl)-2-methoxy-acetamide hydrochloride according to general procedure D. Off-white amorphous solid. MS 364.2 ($[M+H]^+$)

Example 36

36.1

2,4-Bis-(trifluoromethyl)benzaldehyde was converted to (RS)-(2,4-bis-trifluoromethyl-phenyl)-methoxy-acetic acid according to general procedure A. White solid.

36.2

(RS)-(2,4-Bis-trifluoromethyl-phenyl)-methoxy-acetic acid was coupled with 4-aminomethyl benzonitrile according to general procedure C to give (RS)-2-(2,4-bis-trifluoromethyl-phenyl)-N-(4-cyano-benzyl)-2-methoxy-acetamide. Colorless gum.

36.3

(RS)-2-(2,4-Bis-trifluoromethyl-phenyl)-N-(4-cyano-benzyl)-2-methoxy-acetamide was converted to (RS)-2-(2,4-bis-trifluoromethyl-phenyl)-N-(4-carbamimidoyl-benzyl)-2-methoxy-acetamide hydrochloride according to general procedure D. Off-white solid. MS 434.4 ($[M+H]^+$)

Example 37

37.1

2-Benzyloxy-4-methoxy-benzaldehyde (CAS 32884-23-4) was converted to (RS)-(2-benzyloxy-4-methoxy-phenyl)-methoxy-acetic acid according to general procedure A. Light yellow oil. MS 301.1 ($[M–H]^-$)

37.2

In analogy to example 16.2, (RS)-(2-benzyloxy-4-methoxy-phenyl)-methoxy-acetic acid was hydrogenated to give (RS)-(2-hydroxy-4-methoxy-phenyl)-methoxy-acetic acid. Purple solid. MS 211.0 ($[M–H]$)

37.3

(RS)-(2-Hydroxy-4-methoxy-phenyl)-methoxy-acetic acid was coupled with 4-aminomethyl benzonitrile according to general procedure B to give (RS)-N-(4-cyano-benzyl)-2-(2-hydroxy-4-methoxy-phenyl)-2-methoxy-acetamide. Orange amorphous solid. MS 327.3 ($[M+H]^+$)

37.4

In analogy to example 15.5, (RS)-N-(4-cyano-benzyl)-2-(2-hydroxy-4-methoxy-phenyl)-2-methoxy-acetamide was converted to (RS)-N-[4-(N-hydroxycarbamimidoyl)-benzyl]-2-(2-hydroxy-4-methoxy-phenyl)-2-methoxy-acetamide. White solid. MS 358.1 ($[M–H]^-$)

37.5

A suspension of (RS)-N-[4-(N-hydroxycarbamimidoyl)-benzyl]-2-(2-hydroxy-4-methoxy-phenyl)-2-methoxy-acetamide (240 mg) in ethanol (9 ml) and acetic acid (0.38 ml) was hydrogenated for 7.5 h using 10% Pd/C as a catalyst. The reaction mixture was filtered and the solvent was evaporated. The product was purified by chromatography (silica gel, $CH_2Cl_2$=>$CH_2Cl_2$/MeOH 4:1) to give (RS)-N-(4-carbamimidoyl-benzyl)-2-(2-hydroxy-4-methoxy-phenyl)-2-methoxy-acetamide actetate (12 mg) as an off-white, amorphous solid. MS 344.2 ($[M+H]^+$)

Example 38

38.1

2-Fluoro-3-methoxybenzaldehyde was converted to (RS)-(2-fluoro-5-methoxy-phenyl)-methoxy-acetic acid according to general procedure A. Light yellow oil.

38.2

(RS)-(2-Fluoro-5-methoxy-phenyl)-methoxy-acetic acid was coupled with 4-aminomethyl benzonitrile according to general procedure C to give (RS)-N-(4-cyano-benzyl)-2-(2-fluoro-5-methoxy-phenyl)-2-methoxy-acetamide. Colorless gum.

38.3

(RS)-N-(4-Cyano-benzyl)-2-(2-fluoro-5-methoxy-phenyl)-2-methoxy-acetamide was converted to (RS)-N-(4-carbamimidoyl-benzyl)-2-(2-fluoro-5-methoxy-phenyl)-2-methoxy-acetamide hydrochloride according to general procedure D. White solid. MS 346.2 ($[M+H]^+$)

Example 39

39.1

2,3-Difluorobenzaldehyde was converted to (RS)-(2,3-difluoro-phenyl)-methoxy-acetic acid according to general procedure A. Off-white solid.

39.2

(RS)-(2,3-Difluoro-phenyl)-methoxy-acetic acid was coupled with 4-aminomethyl benzonitrile according to general procedure C to give (RS)-N-(4-cyano-benzyl)-2-(2,3-difluoro-phenyl)-2-methoxy-acetamide. Off-white solid.

39.3

(RS)-N-(4-Cyano-benzyl)-2-(2,3-difluoro-phenyl)-2-methoxy-acetamide was converted to (RS)-N-(4-carbamimidoyl-benzyl)-2-(2,3-difluoro-phenyl)-2-methoxy-acetamide hydrochloride according to general procedure D. White solid. MS 334.3 ([M+H]$^+$)

Example 40

40.1

2,6-Difluorobenzaldehyde was converted to (RS)-(2,6-difluoro-phenyl)-methoxy-acetic acid according to general procedure A. Light yellow solid.

40.2

(RS)-(2,6-Difluoro-phenyl)-methoxy-acetic acid was coupled with 4-aminomethyl benzonitrile according to general procedure C to give (RS)-N-(4-cyano-benzyl)-2-(2,6-difluoro-phenyl)-2-methoxy-acetamide. Off-white solid.

40.3

(RS)-N-(4-Cyano-benzyl)-2-(2,6-difluoro-phenyl)-2-methoxy-acetamide was converted to (RS)-N-(4-carbamimidoyl-benzyl)-2-(2,6-difluoro-phenyl)-2-methoxy-acetamide hydrochloride according to general procedure D. White solid. MS 334.2 ([M+H]$^+$)

Example 41

41.1

4-Bromo-2-fluorobenzaldehyde was converted to (RS)-(4-bromo-2-fluoro-phenyl)-methoxy-acetic acid according to general procedure A using methanol/dioxane as a solvent. Light yellow oil.

41.2

(RS)-(4-Bromo-2-fluoro-phenyl)-methoxy-acetic acid was coupled with 4-aminomethyl benzonitrile according to general procedure C to give (RS)-2-(4-bromo-2-fluoro-phenyl)-N-(4-cyano-benzyl)-2-methoxy-acetamide. Light yellow gum.

41.3

(RS)-2-(4-Bromo-2-fluoro-phenyl)-N-(4-cyano-benzyl)-2-methoxy-acetamide was converted to (RS)-2-(4-bromo-2-fluoro-phenyl)-N-(4-carbamimidoyl-benzyl)-2-methoxy-acetamide hydrochloride according to general procedure D. Off-white solid. MS 394.1 ([M+H]$^+$)

Example 42

42.1

4-Bromo-2-fluorobenzaldehyde was reacted according to general procedure A using ethanol/dioxane as a solvent. The product of this reaction was subsequently coupled with 4-aminomethyl benzonitrile according to general procedure B to give (RS)-2-(4-bromo-2-fluoro-phenyl)-N-(4-cyano-benzyl)-2-ethoxy-acetamide. Light yellow oil. MS 391.1 ([M+H]$^+$)

42.2

(RS)-2-(4-Bromo-2-fluoro-phenyl)-N-(4-cyano-benzyl)-2-ethoxy-acetamide was converted to (RS)-2-(4-bromo-2-fluoro-phenyl)-N-(4-carbamimidoyl-benzyl)-2-ethoxy-acetamide hydrochloride according to general procedure D. Off-white foam. MS 408.2 ([M+H]$^+$)

Example 43

43.1

4-Bromo-2-fluorobenzaldehyde was converted to (RS)-(4-bromo-2-fluoro-phenyl)-propoxy-acetic acid according to general procedure A using n-propanol/dioxane as a solvent. Colorless semisolid.

43.2

(RS)-(4-Bromo-2-fluoro-phenyl)-propoxy-acetic acid was coupled with 4-aminomethyl benzonitrile according to general procedure C to give (RS)-2-(4-bromo-2-fluoro-phenyl)-N-(4-cyano-benzyl)-2-propoxy-acetamide. Colorless oil. MS 405.3 ([M+H]$^+$)

43.3

(RS)-2-(4-Bromo-2-fluoro-phenyl)-N-(4-cyano-benzyl)-2-propoxy-acetamide was converted to (RS)-2-(4-bromo-2-fluoro-phenyl)-N-(4-carbamimidoyl-benzyl)-2-propoxy-acetamide hydrochloride according to general procedure D. Colorless solid. MS 423.3 ([M+H]$^+$)

Example 44

44.1

2-Fluoro-4-(trifluoromethyl)benzaldehyde was converted to (RS)-(2-fluoro-4-trifluoromethyl-phenyl)-methoxy-acetic acid according to general procedure A. Light yellow gum.

44.2

(RS)-(2-Fluoro-4-trifluoromethyl-phenyl)-methoxy-acetic acid was coupled with 4-aminomethyl benzonitrile according to general procedure C to give (RS)-N-(4-cyano-benzyl)-2-(2-fluoro-4-trifluoromethyl-phenyl)-2-methoxy-acetamide. Light yellow gum.

44.3

(RS)-N-(4-Cyano-benzyl)-2-(2-fluoro-4-trifluoromethyl-phenyl)-2-methoxy-acetamide was converted to (RS)-N-(4-carbamimidoyl-benzyl)-2-(2-fluoro-4-trifluoromethyl-phenyl)-2-methoxy-acetamide hydrochloride according to general procedure D. Off-white solid. MS 384.2 ([M+H]$^+$)

Example 45

45.1

In analogy to example 16.4, (RS)-N-(4-cyano-benzyl)-2-(4-hydroxy-phenyl)-2-methoxy-acetamide (example 21.2) was alkylated with bromoethanol/cesium carbonate in DMF to give (RS)-N-(4-cyano-benzyl)-2-[4-(2-hydroxy-ethoxy)-phenyl]-2-methoxy-acetamide as a colorless oil. MS 363.1 ([M+Na]$^+$)

45.2

(RS)-N-(4-Cyano-benzyl)-2-[4-(2-hydroxy-ethoxy)-phenyl]-2-methoxy-acetamide was converted to (RS)-N-(4-carbamimidoyl-benzyl)-2-[4-(2-hydroxy-ethoxy)-phenyl]-2-methoxy-acetamide hydrochloride according to general procedure D. Colorless foam. MS 358.2 ([M+H]$^+$)

Example 46

46.1

4-Dimethylaminobenzaldehyde was converted to (RS)-(4-dimethylamino-phenyl)-methoxy-acetic acid according to general procedure A. Light brown foam. MS 208.2 ([M–H]$^-$)

46.2

(RS)-(4-Dimethylamino-phenyl)-methoxy-acetic acid was coupled with 4-aminomethyl benzonitrile according to general procedure B to give (RS)-N-(4-cyano-benzyl)-2-(4-dimethylamino-phenyl)-2-methoxy-acetamide. Off-white solid. MS 324.2 ([M+H]$^+$)

46.3

(RS)-N-(4-Cyano-benzyl)-2-(4-dimethylamino-phenyl)-2-methoxy-acetamide was converted to (RS)-N-(4-carbamimidoyl-benzyl)-2-(4-dimethylamino-phenyl)-2-methoxy-acetamide hydrochloride according to general procedure D. Colorless solid. MS 341.2 ([M+H]$^+$)

Example 47

47.1

3-Oxo-3,4-dihydro-2H-benzo[1,4]oxazine-6-carbaldehyde (CAS 200195-15-9) was reacted according to general procedure A using methanol/dioxane as a solvent. The product of this reaction was subsequently coupled with 4-aminomethyl benzonitrile according to general procedure C to give (RS)-N-(4-cyano-benzyl)-2-methoxy-2-(3-oxo-3,4-dihydro-2H-benzo[1,4]oxazin-6-yl)-acetamide. Light yellow solid.

47.2

(RS)-N-(4-Cyano-benzyl)-2-methoxy-2-(3-oxo-3,4-dihydro-2H-benzo[1,4]oxazin-6-yl)-acetamide was converted to (RS)-N-(4-carbamimidoyl-benzyl)-2-methoxy-2-(3-oxo-3,4-dihydro-2H-benzo[1,4]oxazin-6-yl)-acetamide hydrochloride according to general procedure D. Off-white solid. MS 369.2 ([M+H]$^+$)

Example 48

48.1

4-(1-Pyrrolidino)benzaldehyde was reacted according to general procedure A using methanol/dioxane as a solvent. The product of this reaction was subsequently coupled with 4-aminomethyl benzonitrile according to general procedure B to give (RS)-N-(4-cyano-benzyl)-2-methoxy-2-(4-pyrrolidin-1-yl-phenyl)-acetamide. Off-white solid. MS 350.4 ([M+H]$^+$)

48.2

(RS)-N-(4-Cyano-benzyl)-2-methoxy-2-(4-pyrrolidin-1-yl-phenyl)-acetamide was converted to (RS)-N-(4-carbamimidoyl-benzyl)-2-methoxy-2-(4-pyrrolidin-1-yl-phenyl)-acetamide hydrochloride according to general procedure D. Light red foam. MS 367.2 ([M+H]$^+$)

Example 49

49.1

2-Chlorobenzaldehyde was converted to (RS)-(2-chloro-phenyl)-methoxy-acetic acid according to general procedure A. Light yellow oil. MS 198.9 ([M–H]$^-$)

49.2

(RS)-(2-Chloro-phenyl)-methoxy-acetic acid was coupled with 4-aminomethyl benzonitrile according to general procedure B to give (RS)-2-(2-chloro-phenyl)-N-(4-cyano-benzyl)-2-methoxy-acetamide. Light yellow oil. MS 315.1 ([M+H]$^+$)

49.3

(RS)-2-(2-Chloro-phenyl)-N-(4-cyano-benzyl)-2-methoxy-acetamide was converted to (RS)-N-(4-carbamimidoyl-benzyl)-2-(2-chloro-phenyl)-2-methoxy-acetamide hydrochloride according to general procedure D. Off-white, amorphous solid. MS 332.2 ([M+H]$^+$)

Example 50

50.1

4-Acetamidbenzaldehyde was converted to (RS)-(4-acetylamino-phenyl)-methoxy-acetic acid according to general procedure A. Yellow, amorphous solid. MS 222.0 ([M–H]$^-$)

50.2

(RS)-(4-Acetylamino-phenyl)-methoxy-acetic acid was coupled with 4-aminomethyl benzonitrile according to general procedure B to give (RS)-2-(4-acetylamino-phenyl)-N-(4-cyano-benzyl)-2-methoxy-acetamide. Off-white, amorphous solid. MS 338.3([M+H]$^+$)

50.3

(RS)-2-(4-Acetylamino-phenyl)-N-(4-cyano-benzyl)-2-methoxy-acetamide was converted to (RS)-2-(4-acetylamino-phenyl)-N-(4-carbamimidoyl-benzyl)-2-methoxy-acetamide hydrochloride according to general procedure D. Orange amorphous solid. MS 355.2 ([M+H]$^+$)

Example 51

51.1

4-(Trifluoromethoxy)benzaldehyde was converted to (RS)-methoxy-(4-trifluoromethoxy-phenyl)-acetic acid according to general procedure A. Light yellow oil. MS 249.3 ([M–H]$^-$)

51.2

(RS)-Methoxy-(4-trifluoromethoxy-phenyl)-acetic acid was coupled with 4-aminomethyl benzonitrile according to general procedure B to give (RS)-N-(4-cyano-benzyl)-2-methoxy-2-(4-trifluoromethoxy-phenyl)-acetamide. Light blue semisolid. MS 365.2 ([M+H]$^+$)

51.3

(RS)-N-(4-Cyano-benzyl)-2-methoxy-2-(4-trifluoromethoxy-phenyl)-acetamide was converted to (RS)-N-(4-carbamimidoyl-benzyl)-2-methoxy-2-(4-trifluoromethoxy-phenyl)-acetamide hydrochloride according to general procedure D. Off-white amorphous solid. MS 382.3 ([M+H]$^+$)

Example 52

52.1

1-(4-Formylphenyl)-1H-imidazole was reacted according to general procedure A using methanol/dioxane as a solvent. The product of this reaction was subsequently coupled with 4-aminomethyl benzonitrile according to general procedure B to give (RS)-N-(4-cyano-benzyl)-2-(4-imidazol-1-yl-phenyl)-2-methoxy-acetamide. Colorless foam. MS 347.2 ([M+H]$^+$)

52.2

(RS)-N-(4-Cyano-benzyl)-2-(4-imidazol-1-yl-phenyl)-2-methoxy-acetamide was converted to (RS)-N-(4-carbamimidoyl-benzyl)-2-(4-imidazol-1-yl-phenyl)-2-methoxy-acetamide hydrochloride according to general procedure D. Light yellow solid. MS 364.3 ([M+H]$^+$)

Example 53e 53.1

6-Methoxy-2-naphtaldehyde was converted to (RS)-methoxy-(6-methoxy-naphthalen-2-yl)-acetic acid according to general procedure A. Light yellow solid. MS 245.2 ([M−H]$^+$)

53.2

(RS)-Methoxy-(6-methoxy-naphthalen-2-yl)-acetic acid was coupled with 4-aminomethyl benzonitrile according to general procedure C to give (RS)-N-(4-cyano-benzyl)-2-methoxy-2-(6-methoxy-naphthalen-2-yl)-acetamide. Off-white foam. MS 361.2 ([M+H]$^+$)

53.3

(RS)-N-(4-Cyano-benzyl)-2-methoxy-2-(6-methoxy-naphthalen-2-yl)-acetamide was converted to (RS)-N-(4-carbamimidoyl-benzyl)-2-methoxy-2-(6-methoxy-naphthalen-2-yl)-acetamide hydrochloride according to general procedure D. Off-white solid. MS 378.3 ([M+H]$^+$)

Example 54

54.1

4-Morpholinobenzaldehyde was reacted according to general procedure A using methanol/dioxane as a solvent. The product of this reaction was subsequently coupled with 4-aminomethyl benzonitrile according to general procedure B to give (RS)-N-(4-cyano-benzyl)-2-methoxy-2-(4-morpholin-4-yl-phenyl)-acetamide. Orange oil. MS 366.2 ([M+H]$^+$)

54.2

(RS)-N-(4-Cyano-benzyl)-2-methoxy-2-(4-morpholin-4-yl-phenyl)-acetamide was converted to (RS)-N-(4-carbamimidoyl-benzyl)-2-methoxy-2-(4-morpholin-4-yl-phenyl)-acetamide hydrochloride according to general procedure D. Orange foam. MS 383.3 ([M+H]$^+$)

Example 55

55.1

Morpholinobenzaldehyde was reacted according to general procedure A using methanol/dioxane as a solvent. The product of this reaction was subsequently coupled with 4-aminomethyl benzonitrile according to general procedure B to give (RS)-N-(4-cyano-benzyl)-2-methoxy-2-(2-morpholin-4-yl-phenyl)-acetamide. Orange oil.

55.2

(RS)-N-(4-Cyano-benzyl)-2-methoxy-2-(2-morpholin-4-yl-phenyl)-acetamide was converted to (RS)-N-(4-carbamimidoyl-benzyl)-2-methoxy-2-(2-morpholin-4-yl-phenyl)-acetamide hydrochloride according to general procedure D. Light brown foam. MS 383.3 ([M+H]$^+$)

Example 56

56.1

4-[3-(Dimethylamino)propoxy]benzaldehyde was reacted according to general procedure A using methanol/dioxane as a solvent. The product of this reaction was subsequently coupled with 4-aminomethyl benzonitrile according to general procedure B to give (RS)-N-(4-cyano-benzyl)-2-[4-(3-dimethylamino-propoxy)-phenyl]-2-methoxy-acetamide. Colorless solid. MS 382.3 ([M+H]$^+$)

56.2

(RS)-N-(4-Cyano-benzyl)-2-[4-(3-dimethylamino-propoxy)-phenyl]-2-methoxy-acetamide was converted to (RS)-N-(4-carbamimidoyl-benzyl)-2-[4-(3-dimethylamino-propoxy)-phenyl]-2-methoxy-acetamide hydrochloride according to general procedure D. Colorless solid. MS 399.2 ([M+H]$^+$)

Example 57

57.1

To a stirred solution of (RS)-2-(4-bromo-2-fluoro-phenyl)-N-(4-cyano-benzyl)-2-methoxy-acetamide (example 41.2, 173 mg) in 1,2-dimethoxyethane (8 ml) were added PdCl$_2$(dppf) (34 mg), an aqueous 10% solution of Na$_2$CO$_3$ (2 ml) and 4-dimethylaminophenylboronic acid (378 mg). The mixture was then stirred at 85° C. under an argon atmosphere for 1.5 h. After cooling to rt, the mixture was diluted with ethyl acetate (15 ml) and washed with water (10 ml). The aqueous layer was extracted with ethyl acetate and the combined organics were washed with water and brine, dried (MgSO$_4$), filtered and concentrated. The product was purified by chromatography (silica gel, gradient cyclohexane=>cyclohexane/ethyl acetate 2:3) to give (RS)-N-(4-cyano-benzyl)-2-(4'-dimethylamino-3-fluoro-biphenyl-4-yl)-2-methoxy-acetamide (167 mg) as a light yellow solid.

57.2

(RS)-N-(4-Cyano-benzyl)-2-(4'-dimethylamino-3-fluoro-biphenyl-4-yl)-2-methoxy-acetamide was converted to (RS)-N-(4-carbamimidoyl-benzyl)-2-(4'-dimethylamino-3-fluoro-biphenyl-4-yl)-2-methoxy-acetamide hydrochloride according to general procedure D. Off-white solid. MS 435.4 ([M+H]$^+$)

Example 58

58.1

In analogy to example 57.1, (RS)-2-(4-bromo-2-fluoro-phenyl)-N-(4-cyano-benzyl)-2-methoxy-acetamide (example 41.2) was reacted with 4-methoxyphenylboronic acid to give (RS)-N-(4-cyano-benzyl)-2-(3-fluoro-4'-methoxy-biphenyl-4-yl)-2-methoxy-acetamide. Off-white solid.

58.2

(RS)-N-(4-Cyano-benzyl)-2-(3-fluoro-4'-methoxy-biphenyl-4-yl)-2-methoxy-acetamide was converted to (RS)-N-(4-carbamimidoyl-benzyl)-2-(3-fluoro-4'-methoxy-biphenyl-4-yl)-2-methoxy-acetamide hydrochloride according to general procedure D. White solid. MS 422.3 ([M+H]$^+$)

Example 59

59.1
In analogy to example 57.1, (RS)-2-(4-bromo-2-fluoro-phenyl)-N-(4-cyano-benzyl)-2-methoxy-acetamide (example 41.2) was reacted with 2-methoxyphenylboronic acid to give (RS)-N-(4-cyano-benzyl)-2-(3-fluoro-2'-methoxy-biphenyl-4-yl)-2-methoxy-acetamide. Light yellow gum.

59.2
(RS)-N-(4-Cyano-benzyl)-2-(3-fluoro-2'-methoxy-biphenyl-4-yl)-2-methoxy-acetamide was converted to (RS)-N-(4-carbamimidoyl-benzyl)-2-(3-fluoro-2'-methoxy-biphenyl-4-yl)-2-methoxy-acetamide hydrochloride according to general procedure D. Off-white solid. MS 422.3 ([M+H]$^+$)

Example 60

60.1
In analogy to example 57.1, (RS)-2-(4-bromo-2-fluoro-phenyl)-N-(4-cyano-benzyl)-2-methoxy-acetamide (example 41.2) was reacted with phenylboronic acid to give (RS)-N-(4-cyano-benzyl)-2-(3-fluoro-biphenyl-4-yl)-2-methoxy-acetamide. Light yellow gum.

60.2
(RS)-N-(4-Cyano-benzyl)-2-(3-fluoro-biphenyl-4-yl)-2-methoxy-acetamide was converted to (RS)-N-(4-carbamimidoyl-benzyl)-2-(3-fluoro-biphenyl-4-yl)-2-methoxy-acetamide hydrochloride according to general procedure D. White solid. MS 392.3 ([M+H]$^+$)

Example 61

61.1
In analogy to example 57.1, (RS)-2-(4-bromo-2-fluoro-phenyl)-N-(4-cyano-benzyl)-2-methoxy-acetamide (example 41.2) was reacted with 3-methoxyphenylboronic acid to give (RS)-N-(4-cyano-benzyl)-2-(3-fluoro-3'-methoxy-biphenyl-4-yl)-2-methoxy-acetamide. Light yellow gum.

61.2
(RS)-N-(4-Cyano-benzyl)-2-(3-fluoro-3'-methoxy-biphenyl-4-yl)-2-methoxy-acetamide was converted to (RS)-N-(4-carbamimidoyl-benzyl)-2-(3-fluoro-3'-methoxy-biphenyl-4-yl)-2-methoxy-acetamide hydrochloride according to general procedure D. White solid. MS 422.3 ([M+H]$^+$)

Example 62

62.1
2,2-Dimethylchromane-6-carbaldehyde was converted to (RS)-(2,2-dimethyl-chroman-6-yl)-methoxy-acetic acid according to general procedure A. Light yellow oil. MS 249.1 ([M−H]$^-$)

62.2
(RS)-(2,2-Dimethyl-chroman-6-yl)-methoxy-acetic acid was coupled with 4-aminomethyl benzonitrile according to general procedure C to give (RS)-N-(4-cyano-benzyl)-2-(2,2-dimethyl-chroman-6-yl)-2-methoxy-acetamide. Off-white semi-solid. MS 365.2 ([M+H]$^+$)

62.3
(RS)-N-(4-Cyano-benzyl)-2-(2,2-dimethyl-chroman-6-yl)-2-methoxy-acetamide was converted to (RS)-N-(4-carbamimidoyl-benzyl)-2-(2,2-dimethyl-chroman-6-yl)-2-methoxy-acetamide hydrochloride according to general procedure D. Light yellow solid. MS 382.4 ([M+H]$^+$)

Example 63

63.1
2-Fluoro-4-methoxybenzaldehyde was converted to (RS)-ethoxy-(2-fluoro-4-methoxy-phenyl)-acetic acid according to general procedure A using ethanol/dioxane as a solvent. Yellow oil. MS 227.2 ([M−H]$^-$)

63.2
(RS)-Ethoxy-(2-fluoro-4-methoxy-phenyl)-acetic acid was coupled with 4-aminomethyl benzonitrile according to general procedure B to give (RS)-N-(4-cyano-benzyl)-2-ethoxy-2-(2-fluoro-4-methoxy-phenyl)-acetamide. Yellow oil. MS 343.2 ([M+H]$^+$)

63.3
(RS)-N-(4-Cyano-benzyl)-2-ethoxy-2-(2-fluoro-4-methoxy-phenyl)-acetamide was converted to (RS)-N-(4-carbamimidoyl-benzyl)-2-ethoxy-2-(2-fluoro-4-methoxy-phenyl)-acetamide hydrochloride according to general procedure D. Colorless foam. MS 360.3 ([M+H]$^+$)

63.4
In analogy to example 15.5, give (RS)-N-(4-cyano-benzyl)-2-ethoxy-2-(2-fluoro-4-methoxy-phenyl)-acetamide (example 63.2) was converted to (RS)-2-ethoxy-2-(2-fluoro-4-methoxy-phenyl)-N-[4-(N-hydroxycarbamimidoyl)-benzyl]-acetamide. Colorless foam. MS 376.3 ([M+H]$^+$)

Example 64

64.1
3-(Cyclopentyloxy)-4-methoxy-benzaldehyde was converted to (RS)-(3-cyclopentyloxy-4-methoxy-phenyl)-methoxy-acetic acid according to general procedure A. Yellow oil. MS 279.2 ([M−H]$^-$)

64.2
(RS)-(3-Cyclopentyloxy-4-methoxy-phenyl)-methoxy-acetic acid was coupled with 4-aminomethyl benzonitrile according to general procedure B to give (RS)-N-(4-cyano-benzyl)-2-(3-cyclopentyloxy-4-methoxy-phenyl)-2-methoxy-acetamide. Colorless solid.

64.3
(RS)-N-(4-Cyano-benzyl)-2-(3-cyclopentyloxy-4-methoxy-phenyl)-2-methoxy-acetamide was converted to (RS)-4-[3-(3-cyclopentyloxy-4-methoxy-phenyl)-3-methoxy-2-oxo-propylamino]-benzamidine hydrochloride according to general procedure D. Off-white foam. MS 412.4 ([M+H]$^+$)

Example 65

65.1
2-Chloro-4-methoxybenzaldehyde (CAS No: 54439-75-7) was converted to (RS)-(2-chloro-4-methoxy-phenyl)-methoxy-acetic acid according to general procedure A. Yellow oil. MS 228.9 ([M−H]$^-$)

65.2
(RS)-(2-Chloro-4-methoxy-phenyl)-methoxy-acetic acid was coupled with 4-aminomethyl benzonitrile according to general procedure B to give (RS)-2-(2-chloro-4-methoxy-phenyl)-N-(4-cyano-benzyl)-2-methoxy-acetamide. Light yellow oil. MS 345.2 ([M+H]$^+$)

65.3

(RS)-2-(2-Chloro-4-methoxy-phenyl)-N-(4-cyano-benzyl)-2-methoxy-acetamide was converted to (RS)-N-(4-carbamimidoyl-benzyl)-2-(2-chloro-4-methoxy-phenyl)-2-methoxy-acetamide hydrochloride according to general procedure D. Colorless foam. MS 362.2 ([M+H]$^+$)

Example 66

66.1

2,6-Difluoro-4-methoxybenzaldehyde (CAS No: 256417-10-4) was converted to (RS)-(2,6-difluoro-4-methoxy-phenyl)-methoxy-acetic acid according to general procedure A. Yellow oil. MS 230.9 ([M–H]$^-$)

66.2

(RS)-(2,6-Difluoro-4-methoxy-phenyl)-methoxy-acetic acid was coupled with 4-aminomethyl benzonitrile according to general procedure B to give (RS)-N-(4-cyano-benzyl)-2-(2,6-difluoro-4-methoxy-phenyl)-2-methoxy-acetamide. Light yellow amorphous solid. MS 347.1 ([M+H]$^+$)

66.3

(RS)-N-(4-Cyano-benzyl)-2-(2,6-difluoro-4-methoxy-phenyl)-2-methoxy-acetamide was converted to (RS)-N-(4-carbamimidoyl-benzyl)-2-(2,6-difluoro-4-methoxy-phenyl)-2-methoxy-acetamide hydrochloride according to general procedure D. Colorless foam. MS 364.2 ([M+H]$^+$)

Example 67

67.1

2-Fluoro-4-methoxybenzaldehyde was reacted according to general procedure A using n-propanol/dioxane as a solvent. The product of this reaction was subsequently coupled with 4-aminomethyl benzonitrile according to general procedure B to give (RS)-N-(4-cyano-benzyl)-2-(2-fluoro-4-methoxy-phenyl)-2-propoxy-acetamide. Light yellow oil. MS 357.2 ([M+H]$^+$)

67.2

(RS)-N-(4-Cyano-benzyl)-2-(2-fluoro-4-methoxy-phenyl)-2-propoxy-acetamide was converted to (RS)-N-(4-carbamimidoyl-benzyl)-2-(2-fluoro-4-methoxy-phenyl)-2-propoxy-acetamide hydrochloride according to general procedure D. Colorless foam. MS 374.2 ([M+H]$^+$)

Example 68

68.1

2-Methoxy-2-(1-naphtyl)propionic acid was coupled with 4-aminomethyl benzonitrile according to general procedure B to give (RS)-N-(4-cyano-benzyl)-2-methoxy-2-naphthalen-1-yl-propionamide. Colorless foam. MS 345.2 ([M+H]$^+$)

68.2

(RS)-N-(4-Cyano-benzyl)-2-methoxy-2-naphthalen-1-yl-propionamide was converted to (RS)-N-(4-carbamimidoyl-benzyl)-2-methoxy-2-naphthalen-1-yl-propionamide hydrochloride according to general procedure D. Colorless foam. MS 362.2 ([M+H]$^+$)

Example 69

69.1

A solution of 1-bromo-3,5-difluorobenzene (16.8 g) in THF (180 ml) was cooled to –75° C. under an argon atmosphere. A 2 M solution of lithiumdiisopropylamide in THF/heptane/ethylbenzene (43.1 ml) was slowly added at below –70° C. The mixture was stirred at –78° C. for 1 h. Dimethylformamide (12.6 ml) was added and the mixture was stirred for 2 h. The cooling bath was removed and the mixture was slowly warmed to rt. The mixture was diluted with diethyl ether and washed with 0.5 M HCl. The aqueous phase was extracted with diethyl ether. The combined organic phase was dried (MgSO$_4$), filtered and the solvent was removed to give the crude 4-bromo-2,6-difluorobenzaldehyde (12.4 g). The crude aldehyde was reacted according to general procedure A using methanol/dioxane as a solvent. The product of this reaction was subsequently coupled with 4-aminomethyl benzonitrile according to general procedure B to give (RS)-2-(4-bromo-2,6-difluoro-phenyl)-N-(4-cyano-benzyl)-2-methoxy-acetamide. Yellow oil. MS 395.0 ([M+H]$^+$)

69.2

(RS)-2-(4-Bromo-2,6-difluoro-phenyl)-N-(4-cyano-benzyl)-2-methoxy-acetamide was converted to (RS)-2-(4-bromo-2,6-difluoro-phenyl)-N-(4-carbamimidoyl-benzyl)-2-methoxy-acetamide hydrochloride according to general procedure D. Off-white solid. MS 412.2 ([M+H]$^+$)

Example 70

70.1

In analogy to example 16.4, 2-fluoro-4-hydroxy-benzaldehyde (CAS-No: 348-27-6) was alkylated with benzylbromide/potassium carbonate in DMF to give 4-benzyloxy-2-fluoro-benzaldehyde. Off-white solid. MS 230.1 ([M+H]$^+$)

70.2

4-Benzyloxy-2-fluoro-benzaldehyde was converted to (RS)-(4-benzyloxy-2-fluoro-phenyl)-methoxy-acetic acid according to general procedure A. White solid. MS 289.1 ([M–H]$^-$)

70.3

(RS)-(4-Benzyloxy-2-fluoro-phenyl)-methoxy-acetic acid was hydrogenated at rt and normal pressure using 10% Pd/C as a catalyst and EtOH as a solvent to give (RS)-(2-fluoro-4-hydroxy-phenyl)-methoxy-acetic acid as a light yellow oil. MS 199.2 ([M–H]$^-$)

70.4

(RS)-(2-Fluoro-4-hydroxy-phenyl)-methoxy-acetic acid was coupled with 4-aminomethyl benzonitrile according to general procedure C to give (RS)-N-(4-cyano-benzyl)-2-(2-fluoro-4-hydroxy-phenyl)-2-methoxy-acetamide. White solid. MS 315.1 ([M+H]$^+$)

70.5

In analogy to example 16.4, (RS)-N-(4-cyano-benzyl)-2-(2-fluoro-4-hydroxy-phenyl)-2-methoxy-acetamide was alkylated with 2-iodopropane and cesium carbonate in DMF to give (RS)-N-(4-cyano-benzyl)-2-(2-fluoro-4-isopropoxy-phenyl)-2-methoxy-acetamide. Light yellow oil. MS 357.2 ([M+H]$^+$)

70.6

(RS)-N-(4-Cyano-benzyl)-2-(2-fluoro-4-isopropoxy-phenyl)-2-methoxy-acetamide was converted to (RS)-N-(4-carbamimidoyl-benzyl)-2-(2-fluoro-4-isopropoxy-phenyl)-2-methoxy-acetamide hydrochloride according to general procedure D. Off-white solid. MS 374.2 ([M+H]$^+$)

Example 71

71.1
In analogy to example 16.4, (RS)-N-(4-cyano-benzyl)-2-(2-fluoro-4-hydroxy-phenyl)-2-methoxy-acetamide (example 70.4) was alkylated with 1-iodo-2-methylpropane and cesium carbonate in DMF to give (RS)-N-(4-cyano-benzyl)-2-(2-fluoro-4-isobutoxy-phenyl)-2-methoxy-acetamide. Off-white, amorphous solid. MS 371.3 ([M+H]$^+$)

71.2
(RS)-N-(4-Cyano-benzyl)-2-(2-fluoro-4-isobutoxy-phenyl)-2-methoxy-acetamide was converted to (RS)-N-(4-carbamimidoyl-benzyl)-2-(2-fluoro-4-isobutoxy-phenyl)-2-methoxy-acetamide hydrochloride according to general procedure D. Off-white solid. MS 388.3 ([M+H]$^+$)

Example 72

72.1
In analogy to example 22.1, (RS)-N-(4-cyano-benzyl)-2-(2-fluoro-4-hydroxy-phenyl)-2-methoxy-acetamide (example 70.4) was reacted with 4-fluorophenethyl alcohol, diethyl azodicarboxylate and triphenyl-phosphine in THF to give (RS)-N-(4-cyano-benzyl)-2-{2-fluoro-4-[2-(4-fluorophenyl)-ethoxy]-phenyl}-2-methoxy-acetamide. Colorless oil. MS 437.3 ([M+H]$^+$)

72.2
(RS)-N-(4-Cyano-benzyl)-2-{2-fluoro-4-[2-(4-fluorophenyl)-ethoxy]-phenyl}-2-methoxy-acetamide was converted to (RS)-N-(4-carbamimidoyl-benzyl)-2-{2-fluoro-4-[2-(4-fluoro-phenyl)-ethoxy]-phenyl}-2-methoxy-acetamide hydrochloride according to general procedure D. Off-white, amorphous solid. MS 454.5 ([M+H]$^+$)

Example 73

73.1
To a stirred solution of (RS)-2-(4-bromo-2-fluoro-phenyl)-N-(4-cyano-benzyl)-2-methoxy-acetamide (example 41.2, 1.16 g) at rt in dioxane were added bis(pinacolato) diboron (1.17 g) and potassium acetate (0.91 g). The mixture was purged with argon and bis(triphenylphosphine)palladium(II) chloride (0.13 g) was added. The mixture was then stirred at 80° C. under an argon atmosphere for 18 h. The solids were filtered off and washed with EtOAc. The filtrate was concentrated to leave the crude product as a dark brown oil. The product was isolated by chromatography (silica gel, gradient cyclohexane=>cyclohexane/EtOAc 3:2) to give (RS)-N-(4-cyano-benzyl)-2-[2-fluoro-4-(4,4,5,5-tetramethyl-[1,3,2]dioxaborolan-2-yl)-phenyl]-2-methoxy-acetamide as brown oil (0.64 g). Brown oil. MS 425.4 ([M+H]$^+$)

73.2
In analogy to example 57.1 (RS)-N-(4-cyano-benzyl)-2-[2-fluoro-4-(4,4,5,5-tetramethyl-[1,3,2]dioxaborolan-2-yl)-phenyl]-2-methoxy-acetamide was reacted with 3-bromopyridine to give (RS)-N-(4-cyano-benzyl)-2-(2-fluoro-4-pyridin-3-yl-phenyl)-2-methoxy-acetamide. Light brown amorphous solid. MS 376.3 ([M+H]$^+$)

73.3
(RS)-N-(4-Cyano-benzyl)-2-(2-fluoro-4-pyridin-3-yl-phenyl)-2-methoxy-acetamide was converted to (RS)-N-(4-carbamimidoyl-benzyl)-2-(2-fluoro-4-pyridin-3-yl-phenyl)-2-methoxy-acetamide; hydrochloride according to general procedure D. Off-white solid. MS 393.2 ([M+H]$^+$)

Example 74

74.1
In analogy to example 57.1 (RS)-N-(4-cyano-benzyl)-2-[2-fluoro-4-(4,4,5,5-tetramethyl-[1,3,2]dioxaborolan-2-yl)-phenyl]-2-methoxy-acetamide (example 73.1) was reacted with 4-bromopyridine, hydrochloride to give (RS)-N-(4-cyano-benzyl)-2-(2-fluoro-4-pyridin-4-yl-phenyl)-2-methoxy-acetamide. Light brown amorphous solid. MS 376.3 ([M+H]$^+$)

74.2
(RS)-N-(4-cyano-benzyl)-2-(2-fluoro-4-pyridin-4-yl-phenyl)-2-methoxy-acetamide was converted to (RS)-N-(4-carbamimidoyl-benzyl)-2-(2-fluoro-4-pyridin-4-yl-phenyl)-2-methoxy-acetamide; hydrochloride according to general procedure D. Off-white solid. MS 393.2 ([M+H]$^+$)

Example 75

75.1
5-Bromo-2-fluorobenzaldehyde was converted to (RS)-(5-bromo-2-fluoro-phenyl)-methoxy-acetic acid according to general procedure A using methanol/dioxane as solvent. Light yellow liquid. MS 262.0 ([M–H]$^-$)

75.2
(RS)-(5-Bromo-2-fluoro-phenyl)-methoxy-acetic acid was reacted with 4-aminomethyl benzonitrile according to general procedure C to give (RS)-2-(5-bromo-2-fluoro-phenyl)-N-(4-cyano-benzyl)-2-methoxy-acetamide. Colorless solid. MS 377.2 ([M+H]$^+$)

75.3
(RS)-2-(5-Bromo-2-fluoro-phenyl)-N-(4-cyano-benzyl)-2-methoxy-acetamide was converted to (RS)-2-(5-bromo-2-fluoro-phenyl)-N-(4-carbamimidoyl-benzyl)-2-methoxy-acetamide hydrochloride according to general procedure D. Colorless solid. MS 394.0 ([M+H]$^+$)

Example 76

76.1
In analogy to example 57.1, (RS)-2-(5-bromo-2-fluoro-phenyl)-N-(4-cyano-benzyl)-2-methoxy-acetamide (example 75.2) was reacted with phenylboronic acid to give (RS)-N-(4-cyano-benzyl)-2-(4-fluoro-biphenyl-3-yl)-2-methoxy-acetamide. Off-white solid. MS 374.1 (M).

76.2
(RS)-N-(4-Cyano-benzyl)-2-(4-fluoro-biphenyl-3-yl)-2-methoxy-acetamide was converted to (RS)-N-(4-carbamimidoyl-benzyl)-2-(4-fluoro-biphenyl-3-yl)-2-methoxy-acetamide hydrochloride according to general procedure D. Colorless solid. MS 392.2 ([M+H]$^+$)

Example 77

77.1
2-Fluoro-5-methylbenzaldehyde was converted to (RS)-(2-fluoro-5-methyl-phenyl)-methoxy-acetic acid according to general procedure A using methanol/dioxane as solvent. Off-white liquid. MS 197.1 ([M–H]$^-$)

77.2

(RS)-(2-Fluoro-5-methyl-phenyl)-methoxy-acetic acid was reacted with 4-aminomethyl benzonitrile according to general procedure C to give (RS)-N-(4-cyano-benzyl)-2-(2-fluoro-5-methyl-phenyl)-2-methoxy-acetamide. Colorless amorphous solid. MS 313.2 ([M+H]$^+$)

77.3

(RS)-N-(4-Cyano-benzyl)-2-(2-fluoro-5-methyl-phenyl)-2-methoxy-acetamide was converted to (RS)-N-(4-carbamimidoyl-benzyl)-2-(2-fluoro-5-methyl-phenyl)-2-methoxy-acetamide hydrochloride according to general procedure D. Colorless solid. MS 330.2 ([M+H]$^+$)

Example 78

78.1

5-(Trifluoromethyl)-2-fluorobenzaldehyde was converted to (RS)-(2-fluoro-5-trifluoromethyl-phenyl)-methoxy-acetic acid according to general procedure A using methanol/dioxane as solvent. Colorless amorphous solid. MS 251.1 ([M–H]$^-$)

78.2

(RS)-(2-Fluoro-5-trifluoromethyl-phenyl)-methoxy-acetic acid was reacted with 4-aminomethyl benzonitrile according to general procedure C to (RS)-N-(4-cyano-benzyl)-2-(2-fluoro-5-trifluoromethyl-phenyl)-2-methoxy-acetamide. Colorless amorphous solid. MS 367.1 ([M+H]$^+$)

78.3

(RS)-N-(4-Cyano-benzyl)-2-(2-fluoro-5-trifluoromethyl-phenyl)-2-methoxy-acetamide was converted to (RS)-N-(4-carbamimidoyl-benzyl)-2-(2-fluoro-5-trifluoromethyl-phenyl)-2-methoxy-acetamide hydrochloride according to general procedure D.

Example 79

79.1

2-Fluoro-6-methoxybenzaldehyde was converted to (RS)-(2-fluoro-6-methoxy-phenyl)-methoxy-acetic acid according to general procedure A using methanol/dioxane as solvent. Off-white liquid. MS 213.1 ([M–H]$^-$)

79.2

(RS)-(2-Fluoro-6-methoxy-phenyl)-methoxy-acetic acid was reacted with 4-aminomethyl benzonitrile according to general procedure C to (RS)-N-(4-cyano-benzyl)-2-(2-fluoro-6-methoxy-phenyl)-2-methoxy-acetamide. Colorless solid. MS 329.2 ([M+H]$^+$)

79.3

(RS)-N-(4-Cyano-benzyl)-2-(2-fluoro-6-methoxy-phenyl)-2-methoxy-acetamide was converted to (RS)-N-(4-carbamimidoyl-benzyl)-2-(2-fluoro-6-methoxy-phenyl)-2-methoxy-acetamide hydrochloride according to general procedure D.

Example 80

80.1

A solution of O-benzyl-3-fluorobenzene (4.66 g) in THF (50 ml) was cooled to −65° C. n-Buthyllithium in hexane (1.5 M, 15.8 ml) was added within 15 minutes. The reaction mixture was stirred at −65° C. for 30 minutes. Then DMF (1.95 ml) was added dropwise. The reaction mixture was warmed to rt overnight, then poured onto ice and extracted with ethyl acetate. The organic layers were washed with brine, dried over MgSO4 and concentrated to give (RS)-2-benzyloxy-6-fluoro-benzaldehyde (4.66 g). Yellow liquid. MS 230.1 ([M]).

80.2

(RS)-2-Benzyloxy-6-fluoro-benzaldehyde was converted to (RS)-(2-benzyloxy-6-fluoro-phenyl)-methoxy-acetic acid according to general procedure A using methanol/dioxane as solvent. Yellow liquid. MS 289.1 ([M–H]$^-$)

80.3

In analogy to example 16.2, (RS)-(2-benzyloxy-6-fluoro-phenyl)-methoxy-acetic acid was converted to (RS)-(2-fluoro-6-hydroxy-phenyl)-methoxy-acetic acid. Colorless amorphous solid. MS 199.1 ([M–H]$^-$)

80.4

(RS)-(2-Fluoro-6-hydroxy-phenyl)-methoxy-acetic acid was reacted with 4-aminomethyl benzonitrile according to general procedure C to give (RS)-N-(4-cyano-benzyl)-2-(2-fluoro-6-hydroxy-phenyl)-2-methoxy-acetamide. Colorless solid. MS 315.1 ([M+H]$^+$)

80.5

(RS)-N-(4-Cyano-benzyl)-2-(2-fluoro-6-hydroxy-phenyl)-2-methoxy-acetamide was converted to (RS)-N-(4-carbamimidoyl-benzyl)-2-(2-fluoro-6-hydroxy-phenyl)-2-methoxy-acetamide hydrochloride according to general procedure D.

Example 81

81.1

α-Bromophenylacetic acid was reacted with 4-aminomethyl benzonitrile according to general procedure C to give (RS)-2-bromo-N-(4-cyano-benzyl)-2-phenyl-acetamide. White solid. MS 329.1 ([M+H]$^+$)

81.2

To a stirred solution of (RS)-2-bromo-N-(4-cyano-benzyl)-2-phenyl-acetamide (200 mg) in THF (10 ml) at rt under an Ar atmosphere were added dimethylamine, hydrochloride (149 mg), triethylamine (0.42 ml) and tetrabutylammonium iodide (34 mg). The reaction mixture was stirred for 19 hrs, then treated with additional dimethylamine, hydrochloride (149 mg) and triethylamine (0.42 ml). After another 8 hrs stirring at rt, the solids were filtered off and washed with EtOAc. The filtrate was washed with water and brine, dried over MgSO4 and concentrated. The product was isolated by chromatography (silica gel, gradient dichloromethane=>dichloromethane/MeOH 9:1) to give (RS)-N-(4-cyano-benzyl)-2-dimethylamino-2-phenyl-acetamide (165 mg). Orange solid. MS 294.3 ([M+H]$^+$)

81.3

(RS)-N-(4-Cyano-benzyl)-2-dimethylamino-2-phenyl-acetamide was converted to (RS)-N-(4-carbamimidoyl-benzyl)-2-dimethylamino-2-phenyl-acetamide hydrochloride according to general procedure D. Off-white solid. MS 311.2 ([M+H]$^+$)

Example 82

82.1

In analogy to example 81.2, (RS)-2-bromo-N-(4-cyano-benzyl)-2-phenyl-acetamide (example 81.1) was reacted with methylamine hydrochloride to give (RS)-N-(4-cyanobenzyl)-2-methylamino-2-phenyl-acetamide. Off-white amorphous solid. MS 280.1 ([M+H]$^+$)

82.2

(RS)-N-(4-Cyano-benzyl)-2-methylamino-2-phenyl-acetamide was converted to (RS)-N-(4-carbamimidoyl-benzyl)-2-methylamino-2-phenyl-acetamide hydrochloride according to general procedure D. Off-white solid. MS 297.3 ([M+H]$^+$)

Example 83

83.1

To a stirred solution of sodium methanethiolate (0.43 g) at rt in methanol (15 ml) were added the (RS)-2-bromo-N-(4-cyano-benzyl)-2-phenyl-acetamide (0.5 g, example 81.1) and a catalytic amount of tetrabutyl ammonium iodide. The mixture was then stirred at rt for 1 hr. The mixture was concentrated. The residue was taken up in EtOAc, washed with 1.0 N and brine, dried over MgSO4, filtered and concentrated. The product was isolated by chromatography (silica gel, cyclohexane/EtOAc 2:1) to give (RS)-N-(4-cyano-benzyl)-2-methylsulfanyl-2-phenyl-acetamide (0.36 g). Colorless solid. MS 297.2 ([M+H]$^+$)

83.2

(RS)-N-(4-Cyano-benzyl)-2-methylsulfanyl-2-phenyl-acetamide was converted to (RS)-N-(4-carbamimidoyl-benzyl)-2-methylsulfanyl-2-phenyl-acetamide hydrochloride according to general procedure D. Colorless solid. MS 314.2 ([M+H]$^+$)

Example 84

84.1

In analogy to example 83.1 (RS)-2-bromo-N-(4-cyano-benzyl)-2-phenyl-acetamide (example 81.1) was reacted with sodium ethanethiolate to give (RS)-N-(4-cyano-benzyl)-2-ethylsulfanyl-2-phenyl-acetamide. Off-white solid. MS 311.2 ([M+H]$^+$)

84.2

(RS)-N-(4-Cyano-benzyl)-2-ethylsulfanyl-2-phenyl-acetamide was converted to (RS)-N-(4-carbamimidoyl-benzyl)-2-ethylsulfanyl-2-phenyl-acetamide hydrochloride according to general procedure D. Colorless solid. MS 328.2 ([M+H]$^+$)

Example 85

85.1

A solution of (RS)-N-(4-cyano-benzyl)-2-methylsulfanyl-2-phenyl-acetamide (0.11 g, example 83.1) in dichloromethane (10 ml) was cooled to −10° C. and treated with mCPBA (0.27 g). The reaction mixture was stirred at 0° C., then diluted with dichloromethane and washed with aqueous sodium hydrogen sulfite solution. The organic layer was further washed with saturated KHCO3 solution and brine, dried over MgSO4, filtered and concentrated. The product was isolated by chromatography (silica gel, gradient cyclohexane=>EtOAc) to give (RS)-N-(4-cyano-benzyl)-2-methanesulfonyl-2-phenyl-acetamide (0.084 g). White solid. MS 329.2 ([M+H]$^+$)

85.2

(RS)-N-(4-Cyano-benzyl)-2-methanesulfonyl-2-phenyl-acetamide was converted to (RS)-N-(4-carbamimidoyl-benzyl)-2-methanesulfonyl-2-phenyl-acetamide hydrochloride according to general procedure D. Colorless solid. MS 346.1 ([M+H]$^+$)

Example 86

86.1

Boc-DL-phenylglycine was reacted with 4-aminomethyl benzonitrile according to general procedure C to give (RS)-[(4-cyano-benzylcarbamoyl)-phenyl-methyl]-carbamic acid tert-butyl ester. Off-white solid. MS 366.2 ([M+H]$^+$)

86.2

(RS)-[(4-Cyano-benzylcarbamoyl)-phenyl-methyl]-carbamic acid tert-butyl ester was converted to (RS)-2-amino-N-(4-carbamimidoyl-benzyl)-2-phenyl-acetamide hydrochloride according to general procedure C. Off-white solid. MS 283.2 ([M+H]$^+$)

Example 87

87.1

A solution of give (RS)-[(4-cyano-benzylcarbamoyl)-phenyl-methyl]-carbamic acid tert-butyl ester (0.77 g, example 86.1) in dichloromethane (20 ml) was cooled to 0° C. and treated with trifluoro acetic acid (5 ml). The reaction mixture was stirred at rt for 5 hrs, then diluted with dichloromethane, cooled to 0° C. and brought to pH 9 by dropwise addition of saturated aqueous Na$_2$CO$_3$. The organic layer was washed with brine, dried over MgSO$_4$, filtered and concentrated to give (RS)-2-amino-N-(4-cyano-benzyl)-2-phenyl-acetamide (0.56 g). Off-white amorphous solid. MS 266.2 ([M+H]$^+$)

87.2

A solution of (RS)-2-amino-N-(4-cyano-benzyl)-2-phenyl-acetamide (0.1 g) in dichloromethane (5 ml) was cooled to 0° C. and treated with triethylamine (58 µl) and acetyl chloride (28 µl). The reaction mixture was stirred at rt for 1 hr, then diluted with dichloromethane, washed with 1N HCl and brine. The organic layer was dried over MgSO4, filtered and concentrated. The product was isolated by chromatography (silica gel, gradient dichloromethane=>dichloromethane/MeOH 9:1) to give (RS)-2-acetylamino-N-(4-cyano-benzyl)-2-phenyl-acetamide (98 mg). Off-white solid. MS 308.2 ([M+H]$^+$)

87.3

(RS)-2-Acetylamino-N-(4-cyano-benzyl)-2-phenyl-acetamide was converted to (RS)-2-acetylamino-N-(4-carbamimidoyl-benzyl)-2-phenyl-acetamide hydrochloride according to general procedure D.

Example 88

88.1

In analogy to example 22.1, (RS)-N-(4-cyano-benzyl)-2-(2-fluoro-4-hydroxy-phenyl)-2-methoxy-acetamide (example 70.4) was reacted with 2-phenoxyethanol, diethyl azodicarboxylate and triphenyl-phosphine in THF to give (RS)-N-(4-cyano-benzyl)-2-[2-fluoro-4-(2-phenoxy-ethoxy)-phenyl]-2-methoxy-acetamide. Colorless oil. MS 435.3 ([M+H]$^+$)

88.2

(RS)-N-(4-Cyano-benzyl)-2-[2-fluoro-4-(2-phenoxy-ethoxy)-phenyl]-2-methoxy-acetamide was converted to (RS)-N-(4-carbamimidoyl-benzyl)-2-[2-fluoro-4-(2-phenoxy-ethoxy)-phenyl]-2-methoxy-acetamide hydrochloride according to general procedure D. White solid. MS 452.2 ([M+H]$^+$)

Example 89

89.1

2-Pyridinecarboxaldehyde was converted to (RS)-methoxy-pyridin-2-yl-acetic acid according to general procedure A using methanol/dioxane as solvent. Brown oil. MS 166.1 ([M–H]$^-$)

89.2

(RS)-Methoxy-pyridin-2-yl-acetic acid was reacted with 4-aminomethyl benzonitrile according to general procedure B to give (RS)-N-(4-cyano-benzyl)-2-methoxy-2-pyridin-2-yl-acetamide. Brown oil. MS 282.2 ([M+H]$^+$)

89.3

(RS)-N-(4-Cyano-benzyl)-2-methoxy-2-pyridin-2-yl-acetamide was converted to (RS)-N-(4-carbamimidoyl-benzyl)-2-methoxy-2-pyridin-2-yl-acetamide hydrochloride according to general procedure D. Off-white, amorphous solid. MS 299.2 ([M+H]$^+$)

Example 90

90.1

Acetophenone was converted to (RS)-2-methoxy-2-phenyl-propionic acid according to general procedure A using methanol/dioxane as solvent. Brown oil. MS 179.1 ([M–H]$^-$)

90.2

(RS)-2-Methoxy-2-phenyl-propionic acid was reacted with 4-aminomethyl benzonitrile according to general procedure B to give (RS)-N-(4-cyano-benzyl)-2-methoxy-2-phenyl-propionamide. Off-white, waxy solid. MS 295.0 ([M+H]$^+$)

90.3

(RS)-N-(4-Cyano-benzyl)-2-methoxy-2-phenyl-propionamide was converted to (RS)-N-(4-carbamimidoyl-benzyl)-2-methoxy-2-phenyl-propionamide hydrochloride according to general procedure D. Off-white, amorphous solid. MS 312.2 ([M+H]$^+$)

Example 91

91.1

The crude 4-bromo-2,6-difluorobenzaldehyde described in example 69.1 was reacted according to general procedure A using ethanol/dioxane as a solvent. The product of this reaction was subsequently coupled with 4-aminomethyl benzonitrile according to general procedure B. The product of this reaction could not be obtained pure and was directly converted to (RS)-2-(4-bromo-2,6-difluoro-phenyl)-N-(4-carbamimidoyl-benzyl)-2-ethoxy-acetamide hydrochloride according to general procedure D. Off-white solid. MS 426.2([M+H]$^+$)

Example 92

92.1

In analogy to example 16.4 (RS)-N-(4-cyano-benzyl)-2-(2-fluoro-6-hydroxy-phenyl)-2-methoxy-acetamide (example 80.4) was reacted with 2-bromoethanol in the presence of cesium carbonat in DMF to give N-(4-cyano-benzyl)-2-[2-fluoro-6-(2-hydroxy-ethoxy)-phenyl]-2-methoxy-acetamide. White solid. MS 359.2([M+H]$^+$)

92.1

N-(4-Cyano-benzyl)-2-[2-fluoro-6-(2-hydroxy-ethoxy)-phenyl]-2-methoxy-acetamide was converted to N-(4-carbamimidoyl-benzyl)-2-[2-fluoro-6-(2-hydroxy-ethoxy)-phenyl]-2-methoxy-acetamide hydrochloride according to general procedure D. White solid. MS 376.3 ([M+H]$^+$)

Example 93

93.1

In analogy to example 16.4 (RS)-N-(4-cyano-benzyl)-2-(2-fluoro-6-hydroxy-phenyl)-2-methoxy-acetamide (example 80.4) was reacted with iodo acetamide in the presence of potassium carbonate in DMF to give 2-(2-carbamoyl-methoxy-6-fluoro-phenyl)-N-(4-cyano-benzyl)-2-methoxy-acetamide. Solid. MS 372.2 ([M+H]$^+$)

93.2

2-(2-Carbamoylmethoxy-6-fluoro-phenyl)-N-(4-cyano-benzyl)-2-methoxy-acetamide was converted to N-(4-carbamimidoyl-benzyl)-2-(2-carbamoylmethoxy-6-fluoro-phenyl)-2-methoxy-acetamide hydrochloride according to general procedure D. White solid. MS 389.2 ([M+H]$^+$)

Example 94

94.1

To a solution of 2-biphenyl-4-yl-2-hydroxy-propionic acid (CAS-6244-54-8, 943 mg) in THF (10 ml), stirred at 0° C. was added NaH (60% in mineral oil, 342 mg). After 50 min, ethyl iodide (0.69 ml) was added and the mixture was stirred at rt for 14 h. DMF (10 ml) was added. After 2 days, 47 mg NaH and 0.16 ml ethyl iodide were added subsequently. In the course of three weeks, a total of 653 mg NaH and 1.32 ml ethyl iodide were added. Water was added and the mixture was extracted with EtOAc (2×). The organic phase was washed with water, dried, filtered and evaporated. The crude product was purified by flash chromatography (EtOAc/cyclohexane 5:95=>1:4) to give (RS)-2-biphenyl-4-yl-2-ethoxy-propionic acid ethyl ester (276 mg) as a light yellow oil. MS 298.1 ([M]$^+$)

94.2

(RS)-2-Biphenyl-4-yl-2-ethoxy-propionic acid ethyl ester was hydrolyzed to (RS)-2-biphenyl-4-yl-2-ethoxy-propionic acid in analogy to example 20.1. Colorless waxy solid. MS 269.1 ([M–H]$^-$)

94.3

(RS)-2-Biphenyl-4-yl-2-ethoxy-propionic acid was coupled with 4-aminomethyl benzonitrile to give (RS)-2-biphenyl-4-yl-N-(4-cyano-benzyl)-2-ethoxy-propionamide according to general procedure C. Colorless solid. MS 385.1 ([M+H]$^+$)

94.4

(RS)-2-Biphenyl-4-yl-N-(4-cyano-benzyl)-2-ethoxy-propionamide was converted to (RS)-2-biphenyl-4-yl-N-(4-carbamimidoyl-benzyl)-2-ethoxy-propionamide hydrochloride according to general procedure D. Colorless solid. MS 402.3 ([M+H]$^+$)

Example 95

95.1
4-(5-Ethoxy-2-fluoro-3-formyl-phenoxy)-piperidine-1-carboxylic acid tert-butyl ester was converted to (RS)-4-[3-(carboxy-methoxy-methyl)-5-ethoxy-2-fluoro-phenoxy]-piperidine-1-carboxylic acid tert-butyl ester according to general procedure A. Off-white solid. MS 445.3 ([M+NH$_4$]$^+$)

95.2
(RS)-4-[3-(Carboxy-methoxy-methyl)-5-ethoxy-2-fluoro-phenoxy]-piperidine-1-carboxylic acid tert-butyl ester was coupled with 4-aminomethyl benzonitrile to give (RS)-4-{3-[(4-cyano-benzylcarbamoyl)-methoxy-methyl]-5-ethoxy-2-fluoro-phenoxy}-piperidine-1-carboxylic acid tert-butyl ester according to general procedure B. Yellow oil. MS 564.4 ([M+Na]$^+$)

95.3
The BOC-protecting group of (RS)-4-{3-[(4-cyano-benzylcarbamoyl)-methoxy-methyl]-5-ethoxy-2-fluoro-phenoxy}-piperidine-1-carboxylic acid tert-butyl ester was removed according to standard procedures (TFA in CH$_2$Cl$_2$) to give (RS)-N-(4-cyano-benzyl)-2-[5-ethoxy-2-fluoro-3-(piperidin-4-yloxy)-phenyl]-2-methoxy-acetamide. Off-white solid. MS 442.3 ([M+H]$^+$)

95.4
To a solution of (RS)-N-(4-cyano-benzyl)-2-[5-ethoxy-2-fluoro-3-(piperidin-4-yloxy)-phenyl]-2-methoxy-acetamide (300 mg) in THF (3 ml) were added benzenesulfonyl chloride (127 mg) and triethylamine (138 mg). The mixture was stirred over the weekend. Ice-water and EtOAc were added and the pH of the aqueous phase was adjusted to 2. The mixture was extracted with EtOAc. The organic phase was washed with saturated NaHCO$_3$ soln. and water, dried, filtered and evaporated to give (RS)-2-[3-(1-benzenesulfonyl-piperidin-4-yloxy)-5-ethoxy-2-fluoro-phenyl]-N-(4-cyano-benzyl)-2-methoxy-acetamide (396 mg) as an off-white solid. MS 582.2 ([M+H]$^+$).

95.5
(RS)-2-[3-(1-Benzenesulfonyl-piperidin-4-yloxy)-5-ethoxy-2-fluoro-phenyl]-N-(4-cyano-benzyl)-2-methoxy-acetamide was converted to (RS)-2-[3-(1-benzenesulfonyl-piperidin-4-yloxy)-5-ethoxy-2-fluoro-phenyl]-N-(4-carbamimidoyl-benzyl)-2-methoxy-acetamide hydrochloride according to general procedure D. Colorless solid. MS 599.3 ([M+H]$^+$)

Using similar conditions to the ones described in examples 95.4 and 95.5, (RS)-N-(4-cyano-benzyl)-2-[5-ethoxy-2-fluoro-3-(piperidin-4-yloxy)-phenyl]-2-methoxy-acetamide was converted to the following compounds:

Example 96

(RS)-N-(4-Carbamimidoyl-benzyl)-2-[5-ethoxy-2-fluoro-3-(1-methanesulfonyl-piperidin-4-yloxy)-phenyl]-2-methoxy-acetamide hydrochloride, MS 537.3 ([M+H]$^+$)

Example 97

(RS)-2-[3-(1-Acetyl-piperidin-4-yloxy)-5-ethoxy-2-fluoro-phenyl]-N-(4-carbamimidoyl-benzyl)-2-methoxy-acetamide hydrochloride, MS 501.3 ([M+H]$^+$)

Example 98

(RS)-2-[3-(1-Benzoyl-piperidin-4-yloxy)-5-ethoxy-2-fluoro-phenyl]-N-(4-carbamimidoyl-benzyl)-2-methoxy-acetamide hydrochloride, MS 563.5 ([M+H]$^+$)

Example 99

99.1
(RS)-(2-Fluoro-4-methoxy-phenyl)-methoxy-acetic acid, described in example 15.1 was coupled with 4-aminomethyl-3-chlorobenzonitrile (CAS 202521-97-9) according to general procedure B to give (RS)-N-(2-chloro-4-cyano-benzyl)-2-(2-fluoro-4-methoxy-phenyl)-2-methoxy-acetamide. Light green solid. MS 361.1 ([M–H]$^-$)

99.2
(RS)-N-(2-Chloro-4-cyano-benzyl)-2-(2-fluoro-4-methoxy-phenyl)-2-methoxy-acetamide was converted to (RS)-N-(4-carbamimidoyl-2-chloro-benzyl)-2-(2-fluoro-4-methoxy-phenyl)-2-methoxy-acetamide hydrochloride according to general procedure D. Off-white solid. MS 378.1 ([M–H]$^-$)

Example 100

100.1
(RS)-Ethoxy-(2-fluoro-4-methoxy-phenyl)-acetic acid, described in example 63.1 was coupled with 4-aminomethyl-3-chlorobenzonitrile (CAS 202521-97-9) according to general procedure C to give (RS)-N-(2-chloro-4-cyano-benzyl)-2-ethoxy-2-(2-fluoro-4-methoxy-phenyl)-acetamide. Yellow oil. MS 377.2 ([M+H]$^+$)

100.2
(RS)-N-(2-chloro-4-cyano-benzyl)-2-ethoxy-2-(2-fluoro-4-methoxy-phenyl)-acetamide was converted to (RS)-N-(4-carbamimidoyl-2-chloro-benzyl)-2-ethoxy-2-(2-fluoro-4-methoxy-phenyl)-acetamide hydrochloride according to general procedure D. Colorless foam. MS 394.1 ([M+H]$^+$)

Example 101

101.1
To a solution of 3,5-difluoroanisole (20 g) in THF (200 ml) was added pentamethyldiethylenetriamine (24.05 g). The mixture was cooled to –75° C. n-butyllithium (85 ml, 1.6 M in hexane) was added in such a way that the temperature did not exceed –67° C. The mixture was stirred for 2 h. Ethylglyoxalate (55.5 g, 50% in toluene) was added and the mixture was stirred for a further 2 h. Afterwards, the mixture was allowed to warm up to rt. Water was added and the mixture was made acidic (pH 3) with 25% HCl. The mixture was extracted with EtOAc. The organic phase was washed with 0.5 N HCl, dried, filtered and concentrated. The product was purified by flash chromatography (SiO$_2$, cyclohexane/EtOAc 7:1) to give (RS)-(2,6-difluoro-4-methoxy-phenyl)-hydroxy-acetic acid ethyl ester (13.09 g). Colorless oil. MS 246.1 ([M]$^+$)

101.2
To a suspension of (RS)-(2,6-difluoro-4-methoxy-phenyl)-hydroxy-acetic acid ethyl ester (13.06 g) and Ag$_2$O (24.58 g) in toluene (100 ml) was added ethyl iodide (24.81 g). The mixture was heated to reflux for 2.5 h. Ethyl iodide (24.81 g) and Ag$_2$O (12.29 g) were added and the mixture was refluxed for a further 7 h. The solid was filtered off and the filtrate was concentrated to give (RS)-(2,6-difluoro-4- methoxy-phenyl)-ethoxy-acetic acid ethyl ester (14.6 g). Light yellow oil. MS 274.1 ([M]$^+$)

101.3

(RS)-(2,6-Difluoro-4-methoxy-phenyl)-ethoxy-acetic acid ethyl ester was hydrolyzed to (RS)-(2,6-difluoro-4-methoxy-phenyl)-ethoxy-acetic acid in analogy to example 20.1. MS Light yellow oil 245.2 ([M−H]$^-$)

101.4

(RS)-(2,6-Difluoro-4-methoxy-phenyl)-ethoxy-acetic acid was coupled with 4-aminomethyl-3-chlorobenzonitrile (CAS 202521-97-9) according to general procedure C to give (RS)-N-(2-chloro-4-cyano-benzyl)-2-(2,6-difluoro-4-methoxy-phenyl)-2-ethoxy-acetamide. Colorless oil. MS 395.0 ([M+H]$^+$)

101.5

(RS)-N-(2-Chloro-4-cyano-benzyl)-2-(2,6-difluoro-4-methoxy-phenyl)-2-ethoxy-acetamide was converted to (RS)-N-(4-carbamimidoyl-2-chloro-benzyl)-2-(2,6-difluoro-4-methoxy-phenyl)-2-ethoxy-acetamide hydrochloride according to general procedure D. Colorless foam. MS 412.3 ([M+H]$^+$)

Example 102

102.1

(RS)-(2,6-Difluoro-4-methoxy-phenyl)-methoxy-acetic acid, described in example 66.1 was coupled with 4-aminomethyl-3-chlorobenzonitrile (CAS 202521-97-9) according to general procedure C to give (RS)-N-(2-chloro-4-cyano-benzyl)-2-(2,6-difluoro-4-methoxy-phenyl)-2-methoxy-acetamide. Light yellow oil. MS 379.2 ([M−H]$^-$)

102.2

(RS)-N-(2-Chloro-4-cyano-benzyl)-2-(2,6-difluoro-4-methoxy-phenyl)-2-methoxy-acetamide was converted to (RS)-N-(4-carbamimidoyl-2-chloro-benzyl)-2-(2,6-difluoro-4-methoxy-phenyl)-2-methoxy-acetamide hydrochloride according to general procedure D. Colorless foam. MS 398.2 ([M+H]$^+$)

Example 103

103.1

(RS)-Ethoxy-(2-fluoro-4-methoxy-phenyl)-acetic acid, described in example 63.1 was coupled with 4-aminomethyl-2-chlorobenzonitrile (CAS 202522-15-4) according to general procedure C to give (RS)-N-(3-chloro-4-cyano-benzyl)-2-ethoxy-2-(2-fluoro-4-methoxy-phenyl)-acetamide. Yellow oil. MS 377.2 ([M+H]$^+$)

103.2

(RS)-N-(3-Chloro-4-cyano-benzyl)-2-ethoxy-2-(2-fluoro-4-methoxy-phenyl)-acetamide was converted to (RS)-N-[3-chloro-4-(N-hydroxycarbamimidoyl)-benzyl]-2-ethoxy-2-(2-fluoro-4-methoxy-phenyl)-acetamide according to general procedure D. Colorless solid. MS 410.0 ([M+H]$^+$)

103.3

In analogy to example 37.5, (RS)-N-[3-chloro-4-(N-hydroxycarbamimidoyl)-benzyl]-2-ethoxy-2-(2-fluoro-4-methoxy-phenyl)-acetamide was reduced to give (RS)-N-(4-carbamimidoyl-3-chloro-benzyl)-2-ethoxy-2-(2-fluoro-4-methoxy-phenyl)-acetamide acetate. Colorless solid. MS 394.2 ([M+H]$^+$)

Example 104

The crude 4-bromo-2,6-difluorobenzaldehyde described in example 69.1 was reacted according to general procedure A using ethanol/dioxane as a solvent. The product of this reaction was subsequently coupled with 4-aminomethyl-3-methoxy-benzonitrile (CAS 182159-14-4) according to general procedure B. The product of this reaction could not be obtained pure and was directly converted to (RS)-2-(4-bromo-2,6-difluoro-phenyl)-N-(4-carbamimidoyl-2-methoxy-benzyl)-2-ethoxy-acetamide hydrochloride according to general procedure D. Off-white solid. MS 456.1 ([M+H]$^+$)

Example 105

105.1

(RS)-Ethoxy-(2-fluoro-4-methoxy-phenyl)-acetic acid, described in example 63.1 was coupled with 4-aminomethyl-3-methoxy-benzonitrile (CAS 182159-14-4) according to general procedure B to give (RS)-N-(4-cyano-2-methoxy-benzyl)-2-ethoxy-2-(2-fluoro-4-methoxy-phenyl)-acetamide. Yellow oil. MS 373.2 ([M+H]$^+$)

105.2

(RS)-N-(4-Cyano-2-methoxy-benzyl)-2-ethoxy-2-(2-fluoro-4-methoxy-phenyl)-acetamide was converted to (RS)-N-(4-carbamimidoyl-2-methoxy-benzyl)-2-ethoxy-2-(2-fluoro-4-methoxy-phenyl)-acetamide hydrochloride according to general procedure D. Colorless solid. MS 390.3 ([M+H]$^+$)

Example 106

106.1

A suspension of 3-fluoro-4-formyl-benzonitrile (CAS 105942-10-7, 3 g), phenol (2.14 g) and potassium carbonate (3.14 g) in DMF (20 ml) was stirred at 120° C. for 90 min. After cooling down to rt, water was added and the mixture was extracted with diethyl ether. The organic phase was washed with 0.1 M NaOH and brine, dried, filtered and evaporated. The crude 4-formyl-3-phenoxy-benzonitrile (brown oil, 3.75 g) was used in the next step without further purification.

106.2

To a solution of 4-formyl-3-phenoxy-benzonitrile (2.21 g) in dry ethanol (45 ml) was added sodium acetate (0.894 g) and hydroxylamine hydrochloride (0.757 g). The mixture was stirred at rt for 4.5 h. The solvent was evaporated and the product was purified by flash chromatography (cyclohexane/EtOAc 8:2=>3:7) to give 4-(hydroxyimino-methyl)-3-phenoxy-benzonitrile (1.42 g). Light yellow solid. MS 238.1 ([M]$^+$)

106.3

A solution of 4-(hydroxyimino-methyl)-3-phenoxy-benzonitrile (200 mg) in acetic acid (1.2 ml) was stirred at 65° C. Zinc powder (500 mg) was added portionwise during 30 min. After stirring for a further 1 h, the reaction mixture was filtered and the filtrate was concentrated to near dryness. Water was added and the mixture was washed with diethyl ether. The organic phase was extracted (1×) with diluted acetic acid. The pH of the combined aqueous phases was adjusted to 11 using 2 N NaOH. The mixture was extracted with EtOAc. The organic phase was dried, filtered and concentrated to give 4-aminomethyl-3-phenoxy-benzonitrile (165 mg) as a light yellow oil.

106.4

(RS)-Ethoxy-(2-fluoro-4-methoxy-phenyl)-acetic acid, described in example 63.1 was coupled with 4-aminomethyl-3-phenoxy-benzonitrile according to general procedure B to give (RS)-N-(4-cyano-2-phenoxy-benzyl)-2-ethoxy-2-(2-fluoro-4-methoxy-phenyl)-acetamide. Colorless oil. MS 435.2 ([M+H]$^+$)

106.5

(RS)-N-(4-Cyano-2-phenoxy-benzyl)-2-ethoxy-2-(2-fluoro-4-methoxy-phenyl)-acetamide was converted to (RS)-N-(4-carbamimidoyl-2-phenoxy-benzyl)-2-ethoxy-2-(2-fluoro-4-methoxy-phenyl)-acetamide hydrochloride according to general procedure D. Colorless solid. MS 452.4 ([M+H]$^+$)

Using similar procedures to the ones described in example 106, 3-fluoro-4-formyl-benzonitrile (CAS 105942-10-7) was converted to the following compounds:

Example 107

(RS)-N-(4-Carbamimidoyl-2-o-tolyloxy-benzyl)-2-ethoxy-2-(2-fluoro-4-methoxy-phenyl)-acetamide hydrochloride, MS 466.5 ([M+H]$^+$)

Example 108

(RS)-N-[4-Carbamimidoyl-2-(4-fluoro-phenoxy)-benzyl]-2-ethoxy-2-(2-fluoro-4-methoxy-phenyl)-acetamide hydrochloride, MS 470.3 ([M+H]$^+$)

Example 109

(RS)-N-[4-Carbamimidoyl-2-(pyridin-3-yloxy)-benzyl]-2-ethoxy-2-(2-fluoro-4-methoxy-phenyl)-acetamide acetic acid, MS 453.5 ([M+H]$^+$)

Example 110

110.1

To a solution of 4-formyl-3-hydroxy-benzonitrile (CAS 84102-89-6) (6.90 g) in dry ethanol (165 ml) was added sodium acetate (4.23 g) and hydroxylamine hydrochloride (3.58 g). The mixture was stirred at rt for 1 h. The solvent was evaporated and the product was purified by flash chromatography (cyclohexane/EtOAc 8:2=>1:1) to give 3-hydroxy-4-(hydroxyimino-methyl)-benzonitrile (4.70 g). Light yellow solid. MS 162.0 ([M]$^+$)

110.2

A solution of 3-hydroxy-4-(hydroxyimino-methyl)-benzonitrile (1.79 g) in acetic acid (16.6 ml) was stirred at 65° C. Zinc powder (6.59 g) was added portionwise during 30 min. After stirring for a further 1.5 h, the reaction mixture was filtered and the filtrate was concentrated to dryness. 1 N HCl (55.3 ml) was added and the solvent was evaporated. The same procedure was repeated with with water (2x), EtOH (2x) and toluene (2x). The resulting colorless solid was dissolved in diethyl ether, filtered and the filtrate was concentrated to give 4-aminomethyl-3-hydroxy-benzonitrile hydrochloride (colorless solid, 2.5 g) which was used in the next step without further purification. MS 149.2 ([M+H]$^+$)

110.3

(RS)-Ethoxy-(2-fluoro-4-methoxy-phenyl)-acetic acid, described in example 63.1 was coupled with 4-aminomethyl-3-hydroxy-benzonitrile hydrochloride according to general procedure B to give (RS)-N-(4-cyano-2-hydroxybenzyl)-2-ethoxy-2-(2-fluoro-4-methoxy-phenyl)-acetamide. Colorless solid. MS 457.1 ([M−H]$^-$)

110.4

To a solution of (RS)-N-(4-cyano-2-hydroxy-benzyl)-2-ethoxy-2-(2-fluoro-4-methoxy-phenyl)-acetamide (310 mg) and 2-chloro-5-nitropyridine (205 mg) in DMSO (2 ml) was added cesium carbonate (423 mg). The mixture was stirred at 50° C. for 5 h. The solvent was evaporated, the residue was dissolved in EtOAc and washed with water (2x) and brine (1x). The organic phase was dried, filtered and concentrated. The product was purified by flash chromatography (cyclohexane/EtOAc 9:1=>4:6) to give (RS)-N-[4-cyano-2-(5-nitro-pyridin-2-yloxy)-benzyl]-2-ethoxy-2-(2-fluoro-4-methoxy-phenyl)-acetamide. Light yellow foam. MS 481.4 ([M+H]$^+$)

110.5

(RS)-N-[4-Cyano-2-(5-nitro-pyridin-2-yloxy)-benzyl]-2-ethoxy-2-(2-fluoro-4-methoxy-phenyl)-acetamide was converted to (RS)-N-[4-carbamimidoyl-2-(5-nitro-pyridin-2-yloxy)-benzyl]-2-ethoxy-2-(2-fluoro-4-methoxy-phenyl)-acetamide hydrochloride according to general procedure D. Off-white solid. MS 498.3 ([M+H]$^+$)

Example 111

(RS)-N-[4-Carbamimidoyl-2-(5-nitro-pyridin-2-yloxy)-benzyl]-2-ethoxy-2-(2-fluoro-4-methoxy-phenyl)-acetamide hydrochloride was hydrogenated at rt and normal pressure in EtOH/THF using Pd (10% on charcoal) as a catalyst to give (RS)-N-[2-(5-amino-pyridin-2-yloxy)-4-carbamimidoyl-benzyl]-2-ethoxy-2-(2-fluoro-4-methoxy-phenyl)-acetamide hydrochloride. Light yellow solid. MS 468.1 ([M+H]$^+$)

Example 112

112.1

A solution of (RS)-N-(4-cyano-2-hydroxy-benzyl)-2-ethoxy-2-(2-fluoro-4-methoxy-phenyl)-acetamide (example 17.3, 626 mg), 4-dimethylamino pyridine (22 mg) and triethylamine (407 mg) in dichloromethane (14 ml) was stirred at −20° C. Trifluoromethanesulfonic acid anhydride (604 mg) was added dropwise. The cooling bath was removed and the mixture was stirred at rt overnight. The mixture was diluted with dichloromethane and washed with 0.1 N HCl and with water. The organic phase was dried, filtered and concentrated. The product was purified by flash chromatography (CH$_2$Cl$_2$=>CH$_2$Cl$_2$:MeOH 9:1) to give 766 mg of the triflate as a light brown oil.

The triflate (358 mg) was dissolved in 1,2-dimethoxyethane (7.4 ml) and isopropanol (0.9 ml). Phenylboronic acid (184 mg) and Na$_2$CO$_3$ (10% as a solution in water, 1.6 ml) were added and the mixture was stirred for 30 min under an argon atmosphere. Tetrakis-(triphenylphosphine)-palladium (42 mg) was added and the mixture was heated to reflux for 4 h and stirred at rt overnight. The mixture was filtered and the filtrate was diluted with EtOAc and washed with 1 N NaOH (2x) and with water (2x). The organic phase was dried, filtered and concentrated. The product was purified by flash chromatography (EtOAc/cyclohexane 3:7=>6:4) to give (RS)-N-(5-cyano-biphenyl-2-ylmethyl)-2-ethoxy-2-(2-fluoro-4-methoxy-phenyl)-acetamide (157 mg). Colorless foam. MS 419.3 ([M+H]$^+$)

112.2

(RS)-N-(5-Cyano-biphenyl-2-ylmethyl)-2-ethoxy-2-(2-fluoro-4-methoxy-phenyl)-acetamide was converted to (RS)-N-(5-carbamimidoyl-biphenyl-2-ylmethyl)-2-ethoxy-2-(2-fluoro-4-methoxy-phenyl)-acetamide hydrochloride according to general procedure D. White solid. MS 436.2 ([M+H]$^+$)

Example 113

113.1

In analogy to example 16.4, (RS)-N-(4-cyano-2-hydroxy-benzyl)-2-ethoxy-2-(2-fluoro-4-methoxy-phenyl)-acetamide (example 110.3) was alkylated with ethyl bromoacetate/cesium carbonate in DMF to give (RS)-(5-cyano-2-{[2-ethoxy-2-(2-fluoro-4-methoxy-phenyl)-acetylamino]-methyl}-phenoxy)-acetic acid ethyl ester as a colorless solid. MS 443.4 ([M−H])

113.2

(RS)-(5-Cyano-2-{[2-ethoxy-2-(2-fluoro-4-methoxy-phenyl)-acetylamino]-methyl}-phenoxy)-acetic acid ethyl ester was converted to (RS)-(5-carbamimidoyl-2-{[2-ethoxy-2-(2-fluoro-4-methoxy-phenyl)-acetylamino]-methyl}-phenoxy)-acetic acid ethyl ester hydrochloride according to general procedure D. Colorless foam. MS 462.2 ([M+H]$^+$)

Using similar procedures to the ones described in example 113, (RS)-N-(4-cyano-2-hydroxy-benzyl)-2-ethoxy-2-(2-fluoro-4-methoxy-phenyl)-acetamide (example 110.3) was converted to the following compounds:

Example 114

(RS)-N-(4-Carbamimidoyl-2-carbamoylmethoxy-benzyl)-2-ethoxy-2-(2-fluoro-4-methoxy-phenyl)-acetamide hydrochloride, MS 433.3 ([M+H]$^+$)

Example 115

(RS)-N-(4-Carbamimidoyl-2-isopropoxy-benzyl)-2-ethoxy-2-(2-fluoro-4-methoxy-phenyl)-acetamide hydrochloride, MS 418.3 ([M+H]$^+$)

Example 116

(RS)-N-[4-Carbamimidoyl-2-(2-hydroxy-ethoxy)-benzyl]-2-ethoxy-2-(2-fluoro-4-methoxy-phenyl)-acetamide hydrochloride, MS 420.2 ([M+H]$^+$)

Example 117

2-(5-Carbamimidoyl-2-{[2-ethoxy-2-(2-fluoro-4-methoxy-phenyl)-acetylamino]-methyl}-phenoxy)-N-isopropyl-2-phenyl-acetamide hydrochloride, MS 551.2 ([M+H]$^+$)

The starting material for the preparation of 2-(5-carbamimidoyl-2-{[2-ethoxy-2-(2-fluoro-4-methoxy-phenyl)-acetylamino]-methyl}-phenoxy)-N-isopropyl-2-phenyl-acetamide hydrochloride, 2-chloro-N-isopropyl-2-phenyl-acetamide, was prepared from alpha-chlorophenylacetyl chloride with isopropyl amine in CH$_2$Cl$_2$/aq. NaOH.

Example 118

In analogy to example 20.1, (RS)-(5-carbamimidoyl-2-{[2-ethoxy-2-(2-fluoro-4-methoxy-phenyl)-acetylamino]-methyl}-phenoxy)-acetic acid ethyl ester hydrochloride (example 113.2) was hydrolysed to give (RS)-(5-carbamimidoyl-2-{[2-ethoxy-2-(2-fluoro-4-methoxy-phenyl)-acetylamino]-methyl}-phenoxy)-acetic acid. Colorless solid. MS 434.2 ([M+H]$^+$)

Example 119

In analogy to example 22.1, (RS)-N-(4-cyano-2-hydroxy-benzyl)-2-ethoxy-2-(2-fluoro-4-methoxy-phenyl)-acetamide (example 110.3) was reacted in a Mitsunobu reaction with methyl-(R)-(+)-lactate. The product of this reaction was converted to (RS)-(S)-2-(5-carbamimidoyl-2-{[2-ethoxy-2-(2-fluoro-4-methoxy-phenyl)-acetylamino]-methyl}-phenoxy)-propionic acid ethyl ester hydrochloride according to general procedure D. Colorless foam. MS 476.3 ([M+H]$^+$)

Example 120

As a side product of the synthesis of (RS)-(S)-2-(5-carbamimidoyl-2-{[2-ethoxy-2-(2-fluoro-4-methoxy-phenyl)-acetylamino]-methyl}-phenoxy)-propionic acid ethyl ester hydrochloride (example 119), there was obtained ((RS)-S)-2-(5-carbamimidoyl-2-{[2-ethoxy-2-(2-fluoro-4-methoxy-phenyl)-acetylamino]-methyl}-phenoxy)-propionamide hydrochloride as a colorless foam. MS 447.3 ([M+H]$^+$)

Using similar procedures to the ones described in examples 119 and 120, (RS)-N-(4-cyano-2-hydroxy-benzyl)-2-ethoxy-2-(2-fluoro-4-methoxy-phenyl)-acetamide (example 110.3) was converted to the following compounds:

Example 121

(RS)-(R)-2-(5-Carbamimidoyl-2-{[2-ethoxy-2-(2-fluoro-4-methoxy-phenyl)-acetylamino]-methyl}-phenoxy)-propionic acid ethyl ester hydrochloride, MS 476.1 ([M+H]$^+$)

Example 122

(RS)-(R)-2-(5-Carbamimidoyl-2-{[2-ethoxy-2-(2-fluoro-4-methoxy-phenyl)-acetylamino]-methyl}-phenoxy)-propionamide hydrochloride, MS 447.3 ([M+H]$^+$)

Example 123

123.1

To a solution of 4-aminomethyl-3-hydroxy-benzonitrile hydrochloride (example 110.2, 2.0 g) and triethylamine (2.19 g) in dichloromethane (20 ml) was added di-tert.-butyldicarbonate (2.41 g). The mixture was stirred at rt for 3.5 h. The mixture was washed with water (3×), dried, filtered and concentrated. The crude product was dissolved in DMF (15.5 ml). Cesium carbonate (4.00 g) and iodoacetamide (2.27 g) were added and the mixture was stirred at rt for 3 days. Water was added and the mixture was extracted with EtOAc. The organic phase was washed with water, dried, filtered and concentrated. The crude product was dissolved in MeOH and then concentrated to obtain a thick suspension. The solid was filtered off and washed with a small amount of MeOH. This procedure was repeated with the mother liquor to give (2-carbamoylmethoxy-4-cyano-benzyl)-carbamic acid tert-butyl ester (a total of 1.88 g) as a colorless solid. MS 304.2 ([M−H]$^-$)

123.2

The BOC protecting group of (2-carbamoylmethoxy-4-cyano-benzyl)-carbamic acid tert-butyl ester was removed using HCl in dioxane to give 2-(2-aminomethyl-5-cyano-phenoxy)-acetamide hydrochloride as an off-white powder. MS 206.1 ([M+H]$^+$)

123.3

(RS)-(2-Fluoro-4-methoxy-phenyl)-methoxy-acetic acid (example 15.1) was coupled with 2-(2-aminomethyl-5-cyano-phenoxy)-acetamide hydrochloride according to general procedure C. The product of this reaction was converted to (RS)-N-(4-carbamimidoyl-2-carbamoylmethoxy-benzyl)-2-(2-fluoro-4-methoxy-phenyl)-2-methoxy-acetamide hydrochloride according to general procedure D. Colorless foam. MS 419.3 ([M+H]$^+$)

Example 124

124.1

(RS)-(2,6-Difluoro-4-methoxy-phenyl)-ethoxy-acetic acid (example 101.3) was coupled with 4-aminomethyl-3-phenoxy-benzonitrile (example 106.3) according to general procedure C to give (RS)-N-(4-cyano-2-phenoxy-benzyl)-2-(2,6-difluoro-4-methoxy-phenyl)-2-ethoxy-acetamide. Colorless foam. MS 453.1 ([M+H]$^+$)

124.2

(RS)-N-(4-Cyano-2-phenoxy-benzyl)-2-(2,6-difluoro-4-methoxy-phenyl)-2-ethoxy-acetamide was converted to (RS)-N-(4-carbamimidoyl-2-phenoxy-benzyl)-2-(2,6-difluoro-4-methoxy-phenyl)-2-ethoxy-acetamide hydrochloride according to general procedure D. Colorless foam. MS 470.2 ([M+H]$^+$)

Example 125

125.1

(RS)-(2,6-Difluoro-4-methoxy-phenyl)-ethoxy-acetic acid (example 101.3) was coupled with 4-aminomethyl-3-methoxy-benzonitrile (CAS 182159-14-4) according to general procedure B to give (RS)-4-[3-(2,6-difluoro-4-methoxy-phenyl)-3-ethoxy-2-oxo-propylamino]-3-methoxy-benzonitrile. Colorless oil. MS 391.1 ([M+H]$^+$)

(RS)-4-[3-(2,6-Difluoro-4-methoxy-phenyl)-3-ethoxy-2-oxo-propylamino]-3-methoxy-benzonitrile was converted to (RS)-N-(4-carbamimidoyl-2-methoxy-benzyl)-2-(2,6-difluoro-4-methoxy-phenyl)-2-ethoxy-acetamide hydrochloride according to general procedure D. Colorless foam. MS 408.2 ([M+H]$^+$)

Example 126

126.1

(RS)-(2,6-Difluoro-4-methoxy-phenyl)-ethoxy-acetic acid (example 101.3) was coupled with 4-aminomethyl-3-hydroxy-benzonitrile hydrochloride (example 110.2) according to general procedure B to give (RS)-N-(4-cyano-2-hydroxy-benzyl)-2-(2,6-difluoro-4-methoxy-phenyl)-2-ethoxy-acetamide. Colorless foam. MS 375.4 ([M–H]$^-$)

126.2

In analogy to example 16.4, (RS)-N-(4-cyano-2-hydroxy-benzyl)-2-(2,6-difluoro-4-methoxy-phenyl)-2-ethoxy-acetamide was alkylated with iodoacetamide/cesium carbonate in DMF to give (RS)-N-(2-carbamoylmethoxy-4-cyano-benzyl)-2-(2,6-difluoro-4-methoxy-phenyl)-2-ethoxy-acetamide as a colorless solid. MS 434.3 ([M+H]$^+$)

126.3

(RS)-N-(2-Carbamoylmethoxy-4-cyano-benzyl)-2-(2,6-difluoro-4-methoxy-phenyl)-2-ethoxy-acetamide was converted to (RS)-N-(4-carbamimidoyl-2-carbamoylmethoxy-benzyl)-2-(2,6-difluoro-4-methoxy-phenyl)-2-ethoxy-acetamide hydrochloride according to general procedure D. Colorless foam. MS 451.3 ([M+H]$^+$)

Using similar procedures to the ones described in example 126, (RS)-N-(4-cyano-2-hydroxy-benzyl)-2-(2,6-difluoro-4-methoxy-phenyl)-2-ethoxy-acetamide (example 126.1) was converted to the following compounds in Examples 127–129:

Example 127

(RS)-N-[4-Carbamimidoyl-2-(2-fluoro-benzyloxy)-benzyl]-2-(2,6-difluoro-4-methoxy-phenyl)-2-ethoxy-acetamide hydrochloride, MS 502.3 ([M+H]$^+$)

Example 128

(RS)-N-[4-Carbamimidoyl-2-(5-chloro-2-fluoro-benzyloxy)-benzyl]-2-(2,6-difluoro-4-methoxy-phenyl)-2-ethoxy-acetamide hydrochloride, MS 536.3 ([M+H]$^+$)

Example 129

(RS)-N-{4-Carbamimidoyl-2-[(2-methoxy-ethylcarbamoyl)-methoxy]-benzyl}-2-(2,6-difluoro-4-methoxy-phenyl)-2-ethoxy-acetamide hydrochloride, MS 509.5 ([M+H]$^+$)

The starting material for the preparation of (RS)-N-{4-carbamimidoyl-2-[(2-methoxy-ethylcarbamoyl)-methoxy]-benzyl}-2-(2,6-difluoro-4-methoxy-phenyl)-2-ethoxy-acetamide hydrochloride, 2-chloro-N-(2-methoxy-ethyl)-acetamide, was prepared from chloroacetyl chloride with 2-methoxyethyl amine and triethylamine in CH$_2$Cl$_2$.

Example 130

(RS)-N-{4-Carbamimidoyl-2-[(2-morpholin-4-yl-ethylcarbamoyl)-methoxy]-benzyl}-2-(2,6-difluoro-4-methoxy-phenyl)-2-ethoxy-acetamide hydrochloride, MS 564.3 ([M+H]$^+$)

The starting material for the preparation of (RS)-N-{4-carbamimidoyl-2-[(2-morpholin-4-yl-ethylcarbamoyl)-methoxy]-benzyl}-2-(2,6-difluoro-4-methoxy-phenyl)-2-ethoxy-acetamide hydrochloride, 2-chloro-N-(2-morpholin-4-yl-ethyl)-acetamide hydrochloride, was prepared from chloroacetyl chloride with morpholine in CH$_2$Cl$_2$.

Example 131

(RS)-N-{4-Carbamimidoyl-2-[(2-diethylamino-ethylcarbamoyl)-methoxy]-benzyl}-2-(2,6-difluoro-4-methoxy-phenyl)-2-ethoxy-acetamide hydrochloride, MS 550.3 ([M+H]$^+$)

The starting material for the preparation of (RS)-N-{4-carbamimidoyl-2-[(2-diethylamino-ethylcarbamoyl)-methoxy]-benzyl}-2-(2,6-difluoro-4-methoxy-phenyl)-2-ethoxy-acetamide hydrochloride, 2-chloro-N-(2-diethylamino-ethyl)-acetamide hydrochloride, was prepared from chloroacetyl chloride with diethylamine in CH$_2$Cl$_2$.

Examples 132 and 133

In analogy to example 16.4, (RS)-N-(4-cyano-2-hydroxy-benzyl)-2-(2,6-difluoro-4-methoxy-phenyl)-2-ethoxy-acetamide (example 126.1) was alkylated with 3-(chloromethyl)-

1,2,4-oxadiazole/cesium carbonate in DMF to give a mixture of N-[4-cyano-2-([1,2,4]oxadiazol-3-ylmethoxy)-benzyl]-2-(2,6-difluoro-4-methoxy-phenyl)-2-ethoxy-acetamide and N-(4-cyano-2-cyanomethoxy-benzyl)-2-(2,6-difluoro-4-methoxy-phenyl)-2-ethoxy-acetamide. These compounds were converted according to general procedure D to give (RS)-N-{4-Carbamimidoyl-2-[(2-diethylamino-ethylcarbamoyl)-methoxy]-benzyl}-2-(2,6-difluoro-4-methoxy-phenyl)-2-ethoxy-acetamide hydrochloride.

Example 132

(RS)-N-[4-Carbamimidoyl-2-([1,2,4]oxadiazol-3-yl-methoxy)-benzyl]-2-(2,6-difluoro-4-methoxy-phenyl)-2-ethoxy-acetamide hydrochloride, MS 476.1 ([M+H]$^+$)

Example 133

(RS)-N-(4-Carbamimidoyl-2-carbamimidoylmethoxy-benzyl)-2-(2,6-difluoro-4-methoxy-phenyl)-2-ethoxy-acetamide hydrochloride, MS 450.1 ([M+H]$^+$)

Example 134

In analogy to example 22.1, (RS)-N-(4-cyano-2-hydroxy-benzyl)-2-(2,6-difluoro-4-methoxy-phenyl)-2-ethoxy-acetamide (example 126.1) was reacted in a Mitsunobu reaction with 1H-benzimidazole-2-methanol. The product of this reaction could not be obtained pure and was directly converted to (RS)-N-[2-(1H-benzoimidazol-2-ylmethoxy)-4-carbamimidoyl-benzyl]-2-(2,6-difluoro-4-methoxy-phenyl)-2-ethoxy-acetamide hydrochloride according to general procedure D. Off-white foam. MS 524.4 ([M+H]$^+$)

Example 135

135.1
In analogy to example 22.1, (RS)-N-(4-cyano-2-hydroxy-benzyl)-2-(2,6-difluoro-4-methoxy-phenyl)-2-ethoxy-acetamide (example 126.1) was reacted in a Mitsunobu reaction with [3aS,5R,6aR]-2,2-dimethyl-tetrahydro-cyclopenta[1,3]dioxol-5-ol (CAS 25494-07-9) to give (RS)-N-[4-cyano-2-((3aS,5S,6aR)-2,2-dimethyl-tetrahydro-cyclopenta[1,3]dioxol-5-yloxy)-benzyl]-2-(2,6-difluoro-4-methoxy-phenyl)-2-ethoxy-acetamide. Colorless oil. MS 517.3 ([M+H]$^+$)

135.2
(RS)-N-[4-Cyano-2-((3aS,5S,6aR)-2,2-dimethyl-tetrahydro-cyclopenta[1,3]dioxol-5-yloxy)-benzyl]-2-(2,6-difluoro-4-methoxy-phenyl)-2-ethoxy-acetamide was converted to (RS)-N-[4-carbamimidoyl-2-((1S,3R,4S)-3,4-dihydroxy-cyclopentyloxy)-benzyl]-2-(2,6-difluoro-4-methoxy-phenyl)-2-ethoxy-acetamide hydrochloride according to general procedure D. Off-white solid. MS 494.4 ([M+H]$^+$)

Example 136

136.1
To a solution of (RS)-N-(4-cyano-2-hydroxy-benzyl)-2-(2,6-difluoro-4-methoxy-phenyl)-2-ethoxy-acetamide (example 126.1, 200 mg) and cyclopentene oxide (894 mg) in ethanol (2 ml) was added potassium carbonate (18 mg). The mixture was stirred at 105° C. for 17 h. The mixture was concentrated and the crude product was purified by flash chromatography (cyclohexane=>cyclohexane/EtOAc 1:1) to give a mixture of (RS) and (SR)-N-[4-cyano-2-((1R,2R)-2-hydroxy-cyclopentyloxy)-benzyl]-2-(2,6-difluoro-4-methoxy-phenyl)-2-ethoxy-acetamide (148 mg). Light yellow oil. MS 461 ([M+H]$^+$)

136.2
A mixture of (RS) and (SR)-N-[4-Cyano-2-((1R,2R)-2-hydroxy-cyclopentyloxy)-benzyl]-2-(2,6-difluoro-4-methoxy-phenyl)-2-ethoxy-acetamide was converted to a mixture of (RS) and (SR)-N-[4-Carbamimidoyl-2-((1RS,2RS)-2-hydroxy-cyclopentyloxy)-benzyl]-2-(2,6-difluoro-4-methoxy-phenyl)-2-ethoxy-acetamide hydrochloride according to general procedure D. Colorless solid. MS 478.1 ([M+H]$^+$)

Example 137

(RS)-(2,6-Difluoro-4-methoxy-phenyl)-methoxy-acetic acid (example 66.1) was coupled with 2-(2-aminomethyl-5-cyano-phenoxy)-acetamide hydrochloride (example 123.2) according to general procedure C. The product of this reaction was converted to (RS)-N-(4-carbamimidoyl-2-carbamoylmethoxy-benzyl)-2-(2,6-difluoro-4-methoxy-phenyl)-2-methoxy-acetamide hydrochloride according to general procedure D. Colorless foam. MS 437.4 ([M+H]$^+$)

Example 138

138.1
(RS)-(2,6-Difluoro-4-methoxy-phenyl)-methoxy-acetic acid (example 66.1) was coupled with 4-aminomethyl-3-hydroxy-benzonitrile hydrochloride (example 110.2) according to general procedure C to give (RS)-N-(4-cyano-2-hydroxy-benzyl)-2-(2,6-difluoro-4-methoxy-phenyl)-2-methoxy-acetamide. Colorless foam. MS 361.1 ([M−H]$^-$)

138.2
In analogy to example 16.4, (RS)-N-(4-cyano-2-hydroxy-benzyl)-2-(2,6-difluoro-4-methoxy-phenyl)-2-methoxy-acetamide was alkylated with 2-chloro-N-methylacetamide/cesium carbonate in DMF to give (RS)-N-(4-cyano-2-methylcarbamoylmethoxy-benzyl)-2-(2,6-difluoro-4-methoxy-phenyl)-2-methoxy-acetamide as a colorless foam. MS 434.2 ([M+H]$^+$)

138.3
(RS)-N-(4-Cyano-2-methylcarbamoylmethoxy-benzyl)-2-(2,6-difluoro-4-methoxy-phenyl)-2-methoxy-acetamide was converted to (RS)-N-(4-carbamimidoyl-2-methylcarbamoylmethoxy-benzyl)-2-(2,6-difluoro-4-methoxy-phenyl)-2-methoxy-acetamide hydrochloride according to general procedure D. Colorless solid. MS 451.2 ([M+H]$^+$)

Using similar procedures to the ones described in example 138.2 and 138.3, (RS)-N-(4-cyano-2-hydroxy-benzyl)-2-(2,6-difluoro-4-methoxy-phenyl)-2-methoxy-acetamide (example 138.1) was converted to the following compounds:

Example 139

(RS)-N-[4-Carbamimidoyl-2-(isopropylcarbamoyl-methoxy)-benzyl]-2-(2,6-difluoro-4-methoxy-phenyl)-2-methoxy-acetamide hydrochloride, MS 479.3 ([M+H]$^+$)

Example 140

(RS)-N-{4-Carbamimidoyl-2-[(4-fluoro-phenylcarbamoyl)-methoxy]-benzyl}-2-(2,6-difluoro-4-methoxy-phenyl)-2-methoxy-acetamide hydrochloride, MS 531.2 ([M+H]$^+$)

Example 141

In analogy to example 22.1, (RS)-N-(4-cyano-2-hydroxy-benzyl)-2-(2,6-difluoro-4-methoxy-phenyl)-2-methoxy-acetamide (example 138.1) was reacted in a Mitsunobu reaction with 2-hydroxymethylpyridine. The product of this reaction could not be obtained pure and was directly converted to (RS)-N-[4-carbamimidoyl-2-(pyridin-2-yl-methoxy)-benzyl]-2-(2,6-difluoro-4-methoxy-phenyl)-2-methoxy-acetamide hydrochloride according to general procedure D. Colorless foam. MS 471.2 ([M+H]$^+$)

Example 142

142.1

A solution of 3-fluoro-4-formyl-benzonitrile (CAS 105942-10-7, 1 g) in THF (25 ml) was cooled to 0° C. under argon. Trifluoroethanol (3.36 g) and potassium tert.-butylate (0.83 g) were added subsequently. The mixture was stirred for 2 h. The mixture was diluted with EtOAc and washed with water. The organic phase was dried, filtered and concentrated. The product was purified by flash chromatography (SiO$_2$, cyclohexane/EtOAc 1:1) to give 4-formyl-3-(2,2,2-trifluoro-ethoxy)-benzonitrile. Yellow solid.

142.2

In analogy to example 106.2, 4-formyl-3-(2,2,2-trifluoro-ethoxy)-benzonitrile was reacted with hydroxylamine hydrochloride and sodium acetate in ethanol to give 4-(hydroxyimino-methyl)-3-(2,2,2-trifluoro-ethoxy)-benzonitrile as a yellow solid.

142.3

In analogy to example 106.3, 4-(hydroxyimino-methyl)-3-(2,2,2-trifluoro-ethoxy)-benzonitrile was reduced to 4-aminomethyl-3-(2,2,2-trifluoro-ethoxy)-benzonitrile using zinc in acetic acid.

142.4

(RS)-(2,6-Difluoro-4-methoxy-phenyl)-methoxy-acetic acid (example 66.1) was coupled with 4-aminomethyl-3-(2,2,2-trifluoro-ethoxy)-benzonitrile according to general procedure B to give (RS)-N-[4-cyano-2-(2,2,2-trifluoro-ethoxy)-benzyl]-2-(2,6-difluoro-4-methoxy-phenyl)-2-methoxy-acetamide. Colorless solid. MS 445.0 ([M+H]$^+$)

142.5

(RS)-N-[4-Cyano-2-(2,2,2-trifluoro-ethoxy)-benzyl]-2-(2,6-difluoro-4-methoxy-phenyl)-2-methoxy-acetamide was converted to (RS)-N-[4-carbamimidoyl-2-(2,2,2-trifluoro-ethoxy)-benzyl]-2-(2,6-difluoro-4-methoxy-phenyl)-2-methoxy-acetamide hydrochloride according to general procedure D. Colorless solid. MS 462.1 ([M+H]$^+$)

Examples 143 and 144

Using similar procedures to the ones described in example 138.2 and 138.3, (RS)-N-(4-cyano-2-hydroxy-benzyl)-2-(2,6-difluoro-4-methoxy-phenyl)-2-methoxy-acetamide (example 138.1) was converted to the following compounds:

Example 143

(RS)-N-[4-Carbamimidoyl-2-(pyridin-3-ylmethoxy)-benzyl]-2-(2,6-difluoro-4-methoxy-phenyl)-2-methoxy-acetamide hydrochloride, MS 471.2 ([M+H]$^+$)

Example 144

(RS)-N-[4-Carbamimidoyl-2-(pyridin-4-ylmethoxy)-benzyl]-2-(2,6-difluoro-4-methoxy-phenyl)-2-methoxy-acetamide hydrochloride, MS 471.1 ([M+H]$^+$)

Example 145

To a well stirred ice cooled solution of 3,5-difluorophenol (30.0 g) in CH$_2$Cl$_2$ (500 ml) under N$_2$ were added tert-butyldiphenylchlorosilane (63.4 g) and imidazole (17.3 g). The reaction mixture was stirred 15 min before removing the cooling bath. After 3.5 h the reaction was stopped by washing 1 N HCl sol. (2×300 ml and 1×200 ml), sat. aq. Na$_2$CO$_3$ sol. (200 ml) and brine (200 ml). The aqueous layers were extracted with more CH$_2$Cl$_2$ (200 ml). After drying (MgSO$_4$) the solvent was evaporated to obtain 84.8 g (100%) of tert-butyl-(3,5-difluoro-phenoxy)-diphenyl-silane. Colorless oil. MS 368.1 (M$^+$).

Example 146

A well stirred solution under N$_2$ of tert-butyl-(3,5-difluoro-phenoxy)-diphenyl-silane (20.0 g) and N,N,N',N'-pentamethyldiethylenetriamine (9.9 g) in dry THF (600 ml) was cooled to −75° C. A 1.6 M sol. of BuLi in Hex (35.6 ml) was added via syringe. The reaction mixture was stirred 1 h under cooling (−78° C.). A white precipitate was formed. Glyoxalic acid ethyl ester (50% in Tol, 22.2 g) was added and it was stirred 2 h at −78° C. The cooling bath was removed and the clear solution was left to warm to −10° C. (1 h). After dilution with TBME (500 ml) the mixture was washed with 1 N HCl (2×500 ml) and brine (250 ml), dried over MgSO$_4$ and the solvent was evaporated. The crude product was purified by CC (Hept, then Hept/CH$_2$Cl$_2$ 1:4). 27.9 g (60%) of (RS)-[4-(tert-butyl-diphenyl-silanyloxy)-2,6-difluoro-phenyl]-hydroxy-acetic acid ethyl ester were obtained next to 7.3 g (36%) of recovered starting material. Colorless viscous oil. MS 488.4 ([M+NH$_4$]$^+$).

Example 147

To a well stirred solution under N$_2$ of (RS)-[4-(tert-butyl-diphenyl-silanyloxy)-2,6-difluoro-phenyl]-hydroxy-acetic acid ethyl ester (14.9 g) in Tol (100 ml) was added Ag$_2$O (14.7 g). The mixture was heated in an oil bath at 115–120° C. and iodoethane (12.8 ml) in Tol (50 ml) was slowly added from a dropping funnel. After a total of 2 h and 4 h more iodoethane (7.7 ml each) was added. After a total of 5.5 h heating was stopped and the mixture was left to stir over night at RT. The solids were filtered away over 1 cm of dicalite and were washed with AcOEt. The solvent was evaporated to obtain 16.3 g of crude product as a yellow oil. CC (Hept/CH$_2$Cl$_2$ 9:1 to pure CH$_2$Cl$_2$) afforded 10.5 (66%) of (RS)-[4-(tert-butyl-diphenyl-silanyloxy)-2,6-difluoro-phenyl]-ethoxy-acetic acid ethyl ester next to 2.6 g (17%) of recovered starting material. Colorless oil. MS 453.2 (4, [M−OEt]$^+$), 441.1 (24, [M−tBu]$^+$)425.2 (100, [M−COOEt]$^+$).

Example 148

To a solution of (RS)-[4-(tert-butyl-diphenyl-silanyloxy)-2,6-difluoro-phenyl]-ethoxy-acetic acid ethyl ester (10.4 g) in a THF (50 ml), MeOH (50 ml) and H$_2$O (20 ml) mixture was added LiOH.H$_2$O (1.75 g) and it was stirred 2 h at 60° C. After cooling water (240 ml) was added and the solution was washed with TBME (240 ml). The aqueous layer was collected, TBME was added (240 ml) and the mixture was acidified with 1 N HCl sol. The aqueous layer was extracted with one more portion of TBME. The combined organic layers were dried (MgSO$_4$) and the solvent was evaporated to obtained an oil. Solid (RS)-(2,6-difluoro-4-hydroxy-phenyl)-ethoxy-acetic acid (4.6 g, 95%) was obtained after addition of AcOEt, evaporation of it and drying on the high vacuum over night. Off-white solid. MS 231.1 ([M–H]$^-$).

Example 149

(RS)-(2,6-Difluoro-4-hydroxy-phenyl)-ethoxy-acetic acid (2.3 g) was dissolved in DMF (75 ml) and [(4-aminomethyl-phenyl)-imino-methyl]-carbamic acid benzyl ester dihydrochloride [Prepared according to Ch. Lila, Ph. Gloanec, L. Cadet, Y. Hervé, J. Fournier, F. Leborgne, T. J. Verbeuren, G. De Nanteuil, Synthetic Communications 1998, 28, 23, 4419–4429] (3.18 g) and HOBt (2.15 g) were successively added. The slurry was cooled in an ice bath and N-(3-dimethylaminopropyl)-N'-ethylcarbodiimide hydrochloride (3.05 g) was added. Et$_3$N (8.0 ml) was slowly added. The resulting mixture was left to stir over night warming up to rt. After removing the solvent precipitation from CH$_2$Cl$_2$/MeOH 19:1 yielded the product. Drying over night on the high vacuum afforded 3.0 g (60 g) of pure (RS)-[(4-{[2-(2,6-difluoro-4-hydroxy-phenyl)-2-ethoxy-acetylamino]-methyl}-phenyl)-imino-methyl]-carbamic acid benzyl ester. White solid. MS 498.3 ([M+H]$^+$).

Example 150

(RS)-[4-(tert-Butyl-diphenyl-silanyloxy)-2,6-difluoro-phenyl]-ethoxy-acetic acid ethyl ester (6.85 g) was dissolved in THF (135 ml) and a 1 M TBAF sol. in THF (15.1 ml) was added. After 3 h the reaction mixture was poured on AcOEt (300 ml) and H$_2$O (300 ml). The aqueous layer was extracted with two more portions of AcOEt (100 ml). The combined organic layers were washed with brine and dried (MgSO$_4$) and the solvent was evaporated. Crystallization from ice cold CH$_2$Cl$_2$ afforded 3.08 g (86%) of (RS)-(2,6-difluoro-4-hydroxy-phenyl)-ethoxy-acetic acid ethyl ester. White crystals. MS 258.9 ([M–H]$^+$).

Example 151

(RS)-[(4-{[2-(2,6-difluoro-4-hydroxy-phenyl)-2-ethoxy-acetylamino]-methyl}-phenyl)-imino-methyl]-carbamic acid benzyl ester (100 mg) was dissolved in EtOH (2 ml). 1.25 M HCl in EtOH (0.1 ml) was added and the mixture was hydrogenated 1.5 h at 1 atm H$_2$ in the presence of a catalytic amount of 10% Pd/C. After filtration of the catalyst the solvent was removed to obtain 71 mg (88%) of (RS)-N-(4-carbamimidoyl-benzyl)-2-(2,6-difluoro-4-hydroxy-phenyl)-2-ethoxy-acetamide hydrochloride. White powder. MS 364.3 ([M+H]$^+$).

Example 152

152.1

To a mixture of (RS)-[(4-{[2-(2,6-difluoro-4-hydroxy-phenyl)-2-ethoxy-acetylamino]-methyl}-phenyl)-imino-methyl]-carbamic acid benzyl ester (100 mg), N-(2-hydroxyethyl)morpholine (29 mg) and polymer bound triphenylphosphine (~3 mmol/g, 167 mg) in CH$_2$Cl$_2$ (2 ml) was added di-tert-butyl azodicarboxylate (93 mg) before shaking 22 h at rt. After filtration of the polymer the solvent was evaporated and the residue was purified by HPLC to obtain 28 mg of (23%) (RS)-{[4-({2-[2,6-difluoro-4-(2-morpholin-4-yl-ethoxy)-phenyl]-2-ethoxy-acetylamino}-methyl)-phenyl]-imino-methyl}-carbamic acid benzyl ester.

152.2

(RS)-[4-({2-[2,6-Difluoro-4-(2-morpholin-4-yl-ethoxy)-phenyl]-2-ethoxy-acetylamino)-methyl)-phenyl]-imino-methyl}-carbamic acid benzyl ester (25 mg) was dissolved in EtOH (2 ml) and hydrogenated 2 h at rt and 1 atm H$_2$ in presence of a catalytic amount of 10% Pd/C. The catalyst was filtered off, the solvent was evaporated and (RS)-N-(4-carbamimidoyl-benzyl)-2-[2,6-difluoro-4-(2-morpholin-4-yl-ethoxy)-phenyl]-2-ethoxy-acetamide dihydrochloride was obtained in quantitative yield by precipitation from AcOEt with a 4.6 N HCl sol. in AcOEt. White solid. MS 477.2 ([M+H]$^+$).

Examples 153 and 154

Examples 153 and 154 were obtained in analogy to example 152.

153

(RS)-N-(4-Carbamimidoyl-benzyl)-2-(2,6-difluoro-4-phenethyloxy-phenyl)-2-ethoxy-acetamide hydrochloride from phenethyl alcohol. White solid. MS 468.2 ([M+H]$^+$).

154

(RS)-N-(4-Carbamimidoyl-benzyl)-2-(4-cyclopropylmethoxy-2,6-difluoro-phenyl)-2-ethoxy-acetamide hydrochloride from hydroxymethylcyclopropane. White solid. MS 418.3 ([M+H]$^+$).

Example 155

To a mixture of (RS)-[(4-{[2-(2,6-difluoro-4-hydroxy-phenyl)-2-ethoxy-acetylamino]-methyl}-phenyl)-imino-methyl]-carbamic acid benzyl ester (300 mg), ethanol (61 mg) and polymer bound triphenylphosphine (~3 mmol/g, 501 mg) in CH$_2$Cl$_2$ (6 ml) and DMF (1.5 ml) was added di-tert-butyl azodicarboxylate (555 mg) before shaking 60 h at rt. After filtration of the polymer the solvent was evaporated and the residue was purified by HPLC. The resulting material was dissolved in MeOH (10 ml) and the solution was acidified with 2 ml of 1.25 M HCl in MeOH and hydrogenated 2 h at rt and 1 atm H$_2$ in the presence of a catalytic amount of 10% PdC. After filtration, evaporation of the solvent, HPLC purification and hydrochloride formation 27 mg (10%) of (RS)-N-(4-carbamimidoyl-benzyl)-2-ethoxy-2-(4-ethoxy-2,6-difluoro-phenyl)-acetamide hydrochloride are obtained. Light yellow solid. MS 392.1 ([M+H]$^+$).

Example 156

156.1

(RS)-(2,6-Difluoro-4-hydroxy-phenyl)-ethoxy-acetic acid ethyl ester (500 mg) was dissolved in CH$_2$Cl$_2$ (20 ml). Cu(OAc)$_2$ (349 mg), 4-methoxyphenylboronic acid (876 mg) and MS4 Å were added followed by pyridine (760 mg). The mixture was stirred over night before filtration and evaporation of the solvent. CC (Hept/CH$_2$Cl$_2$ 1:4) afforded 455 mg (65%) of (RS)-[2,6-difluoro-4-(4-methoxy-phenoxy)-phenyl]-ethoxy-acetic acid ethyl ester. Yellow oil.

156.2

(RS)-[2,6-Difluoro-4-(4-methoxy-phenoxy)-phenyl]-ethoxy-acetic acid ethyl ester (455 mg) was dissolved in THF (2.4 ml), MeOH (2.4 ml) and H$_2$O (1.0 ml) and LiOH.H$_2$O (104 mg) was added. The reaction mixture was stirred 1 h at 60° C. The solution was diluted with cold H$_2$O (15 ml) and TBME (15 ml) and acidified with 1 N HCl. The aqueous layer was extracted with two more portions of TBME (15 ml). The combined organic layers were dried (MgSO$_4$) and the solvent was evaporated to obtain 398 mg (95%) of (RS)-[2,6-difluoro-4-(4-methoxy-phenoxy)-phenyl]-ethoxy-acetic acid. White waxy solid. MS 336.9 ([M−H]$^-$).

156.3

(RS)-[2,6-Difluoro-4-(4-methoxy-phenoxy)-phenyl]-ethoxy-acetic acid (398 mg) was dissolved in DMF (15 ml). [(4-aminomethyl-phenyl)-imino-methyl]-carbamic acid benzyl ester dihydrochloride [Prepared according to Ch. Lila, Ph. Gloanec, L. Cadet, Y. Hervé, J. Fournier, F. Leborgne, T. J. Verbeuren, G. De Nanteuil, Synthetic Communications 1998, 28, 23, 4419–4429] (367 mg) and 1-hydroxybenzotriazole (254 mg) were added and the mixture was cooled to 0° C. N-(3-Dimethylaminopropyl)-N'-ethyl-carbodiimide hydrochloride (254 mg) and triethylamine (1.38 ml) were added and it was stirred 1 h at 0° C. and 5.5 h at rt. The solvent was evaporated and the residue was taken up in H$_2$O (40 ml) and CH$_2$Cl$_2$ (30 ml). The organic layer was separated, washed with brine and dried (MgSO$_4$). The aqueous layers were extracted with two more portions CH$_2$Cl$_2$. After evaporation of the solvent CC(CH$_2$Cl$_2$ to CH$_2$Cl$_2$/MeOH 98:2) afforded 228 mg (32%) of (RS)-[4-(12-[2,6-difluoro-4-(4-methoxy-phenoxy)-phenyl]-2-ethoxy-acetylamino)-methyl)-phenyl]-imino-methyl}-carbamic acid benzyl ester. White foam. MS 602.0 ([M−H]$^-$).

156.4

(RS)-{[4-({2-[2,6-Difluoro-4-(4-methoxy-phenoxy)-phenyl]-2-ethoxy-acetylamino}-methyl)-phenyl]-imino-methyl}-carbamic acid benzyl ester (181 mg) was hydrogenated 3 h in MeOH (3 ml) at rt and 1 atm H$_2$ in the presence of 10% Pd/C (6 mg) and 2 M NH$_3$ sol. in MeOH (75 µL). The free benzamidine was isolated by filtration and evaporation of the solvent, dissolved in AcOEt (3 ml) and treated with 1 N HCl to obtain 109 mg (72%) of (RS)-N-(4-carbamimidoyl-benzyl)-2-[2,6-difluoro-4-(4-methoxy-phenoxy)-phenyl]-2-ethoxy-acetamide. White solid. MS 470.1 ([M+H]$^+$).

Examples 157–161

Examples 157–161 were prepared in analogy to example 156.

157.1

(RS)-[4-(3,4-Dimethoxy-phenoxy)-2,6-difluoro-phenyl]-ethoxy-acetic acid ethyl ester. Yellow oil.

157.2

(RS)-[4-(3,4-Dimethoxy-phenoxy)-2,6-difluoro-phenyl]-ethoxy-acetic acid. Yellow oil. MS 366.9 ([M−H]$^-$).

157.3

(RS)-{[4-({2-[4-(3,4-Dimethoxy-phenoxy)-2,6-difluoro-phenyl]-2-ethoxy-acetylamino}-methyl)-phenyl]-imino-methyl}-carbamic acid benzyl ester. White foam. MS 632.2 ([M−H]$^-$).

157.4

(RS)-N-(4-Carbamimidoyl-benzyl)-2-[4-(3,4-dimethoxy-phenoxy)-2,6-difluoro-phenyl]-2-ethoxy-acetamide hydrochloride. White solid. MS 500.5 ([M+H]$^+$).

158.1

(RS)-[2,6-Difluoro-4-(3-methoxy-phenoxy)-phenyl]-ethoxy-acetic acid ethyl ester. Colorless oil. MS 384.4 ([M+NH$_4$]$^+$).

158.2

(RS)-[2,6-Difluoro-4-(3-methoxy-phenoxy)-phenyl]-ethoxy-acetic acid. Off-white semisolid. MS 356.4 ([M+NH$_4$]$^+$).

158.3

(RS)-{[4-({2-[2,6-Difluoro-4-(3-methoxy-phenoxy)-phenyl]-2-ethoxy-acetylamino}-methyl)-phenyl]-imino-methyl}-carbamic acid benzyl ester. Yellow foam. MS 604.3 ([M+H]$^+$).

158.4

(RS)-N-(4-Carbamimidoyl-benzyl)-2-[2,6-difluoro-4-(3-methoxy-phenoxy)-phenyl]-2-ethoxy-acetamide hydrochloride. White powder. MS 470.4 ([M+H]$^+$).

159.1

(RS)-[4-(3-Acetylamino-phenoxy)-2,6-difluoro-phenyl]-ethoxy-aceticacidethyl ester. Colorless oil. MS 392.1 ([M−H]$^-$).

159.2

(RS)-[4-(3-Acetylamino-phenoxy)-2,6-difluoro-phenyl]-ethoxy-acetic acid. Light yellow foam. MS 364.1 ([M−H]$^-$).

159.3

(RS)-{[4-({2-[4-(3-Acetylamino-phenoxy)-2,6-difluoro-phenyl]-2-ethoxy-acetylamino}-methyl)-phenyl]-imino-methyl}-carbamic acid benzyl ester. Colorless oil. MS 631.2 ([M+H]$^+$).

159.4

(RS)-2-[4-(3-Acetylamino-phenoxy)-2,6-difluoro-phenyl]-N-(4-carbamimidoyl-benzyl)-2-ethoxy-acetamide hydrochloride. Off-white solid. MS 495.4 ([M−H]$^-$).

160.1

(RS)-[4-(4-Cyano-phenoxy)-2,6-difluoro-phenyl]-ethoxy-acetic acid ethyl ester. White solid.

160.2

(RS)-[4-(4-Cyano-phenoxy)-2,6-difluoro-phenyl]-ethoxy-acetic acid. Yellowish gum. MS 332.4 ([M−H]$^-$).

160.3

(RS)-{[4-({2-[4-(4-Cyano-phenoxy)-2,6-difluoro-phenyl]-2-ethoxy-acetylamino}-methyl)-phenyl]-imino-methyl}-carbamic acid benzyl ester. Orange powder. MS 599.5 ([M+H]$^+$).

160.4

(RS)-N-(4-Carbamimidoyl-benzyl)-2-[4-(4-cyano-phenoxy)-2,6-difluoro-phenyl]-2-ethoxy-acetamide hydrochloride. Yellowish foam. MS 465.5 ([M+H]$^+$).

161.1

(RS-)[2,6-Difluoro-4-(3-trifluoromethoxy-phenoxy)-phenyl]-ethoxy-acetic acid ethyl ester. Colorless oil. MS 438.3 ([M+NH$_4$]$^+$).

161.2

(RS)-[2,6-Difluoro-4-(3-trifluoromethoxy-phenoxy)-phenyl]-ethoxy-acetic acid. Yellowish oil. MS 391.3 ([M−H]$^-$).

161.3

(RS)-{[4-({2-[2,6-Difluoro-4-(3-trifluoromethoxy-phenoxy)-phenyl]-2-ethoxy-acetylamino}-methyl)-phenyl]-imino-methyl}-carbamic acid benzyl ester. Off-white powder. MS 658.3 ([M+H]$^+$).

161.4

(RS)-N-(4-Carbamimidoyl-benzyl)-2-[2,6-difluoro-4-(3-trifluoromethoxy-phenoxy)-phenyl]-2-ethoxy-acetamide hydrochloride. White foam. MS 524.5 ([M+H]$^+$).

Example 162

A solution of (RS)-(2,6-difluoro-4-hydroxy-phenyl)-ethoxy-acetic acid ethyl ester (500 mg) in pyridine (5 ml) was placed under $N_2$ and cooled to 0° C. $Tf_2O$ (813 mg) was added and the resulting solution was left to stir in the ice bath. After 18 h the reaction mixture was poured on a mixture of 50 ml 1 N HCl and ice. The product was extracted with AcOEt. The organic layer was washed with more 1 N HCl (50 ml), water (50 ml) and brine (30 ml). The aqueous layers were extracted with more AcOEt. After drying ($MgSO_4$) the solvent was evaporated to obtain 738 mg (98%) of (RS)-(2,6-difluoro-4-trifluoromethanesulfonyloxy-phenyl)-ethoxy-acetic acid ethyl ester. Yellow oil. MS 393.4 ([M+H]$^+$).

Example 163

To a solution of (RS)-(2,6-difluoro-4-trifluoromethanesulfonyloxy-phenyl)-ethoxy-acetic acid ethyl ester (200 mg) and 2-(trimethylsilyl)ethanol (603 mg) in DMSO (2.5 ml) was added triethylamine (1.8 ml) followed by Pd(OAc)$_2$ (6 mg) and 1,3-bis(diphenylphosphino)propane (11 mg). The flask was put under carbon monoxide and the reaction mixture was stirred 2 h at 70° C. AcOEt (30 ml) was added and it was washed with 1 N HCl (2×40 ml), water (2×40 ml) and brine (30 ml). After drying (MgSO$_4$) the solvent was evaporated. CC (Hept/AcOEt 98:2) afforded 151 mg (76%) of (RS)-4-(ethoxy-ethoxycarbonyl-methyl)-3,5-difluoro-benzoic acid 2-trimethylsilanyl-ethyl ester. Colorless oil. MS 406.6 ([M+NH$_4$]$^+$).

Example 164

(RS-4-(Ethoxy-ethoxycarbonyl-methyl)-3,5-difluoro-benzoic acid 2-trimethylsilanyl-ethyl ester (414 mg) was dissolved in DMF (1 ml) and a 1 M TBAF sol. in THF (1.12 ml) was added. After 3.5 h more TBAF sol. (0.5 ml) was added. AcOEt (15 ml) was added and the solution was washed with 1 N HCl (15 ml), water (15 ml) and brine (15 ml). After drying (Na$_2$SO$_4$) the solvent was evaporated to yield 32 mg (100%) of (RS)-4-(ethoxy-ethoxycarbonyl-methyl)-3,5-difluoro-benzoic acid. Colorless oil. MS 287.0 ([M−H]$^-$).

Example 165

165.1

1,1'-Carbonyldiimidazole (88 mg) was dissolved in THF (1 ml) and a solution of (RS)-4-(ethoxy-ethoxycarbonyl-methyl)-3,5-difluoro-benzoic acid (156 mg) in THF (1 ml) was added. After 30 min stirring at rt isobutylamine (41 mg) was added and the mixture was stirred 3 h. AcOEt (20 ml) was added and the solution was washed with 1 N HCl (20 ml). The aqueous layer was extracted with two more portions AcOEt (20 ml), the the combined organic layers were dried (Na$_2$SO$_4$) and the solvent was evaporated. CC (Hept/AcOET 3:1) afforded 125 mg (67%) of (RS)-(2,6-difluoro-4-isobutylcarbamoyl-phenyl)-ethoxy-acetic acid ethyl ester. White solid.

165.2

To a solution of (RS)-(2,6-difluoro-4-isobutylcarbamoyl-phenyl)-ethoxy-acetic acid ethyl ester (125 mg) in a mixture of THF (1 ml), MeOH (1 ml) and H$_2$O (0.5 ml) was added LiOH.H$_2$O (31 mg). After stirring 1.5 h at 60° C. AcOEt was added (10 ml) and the product was extracted with H$_2$O (10 ml). The aqueous layer was collected, acidified with 1 N HCl and extracted with AcOEt (2×15 ml). The combined organic layers were dried (Na$_2$SO$_4$) and the solvent is evaporated to obtain 76 mg (66%) of (RS)-(2,6-difluoro-4-isobutylcarbamoyl-phenyl)-ethoxy-acetic acid. Off-white solid. MS 333.4 ([M+H]$^+$).

165.3

(RS)-(2,6-Difluoro-4-isobutylcarbamoyl-phenyl)-ethoxy-acetic acid (71 mg) was dissolved in DMF (3.5 ml) and [(4-aminomethyl-phenyl)-imino-methyl]-carbamic acid benzyl ester dihydrochloride [Prepared according to Ch. Lila, Ph. Gloanec, L. Cadet, Y. Hervé, J. Fournier, F. Leborgne, T. J. Verbeuren, G. De Nanteuil, Synthetic Communications 1998, 28, 23, 4419–4429] (88 mg), disopropylamine (114 mg) and 2-(1H-benzotriazole-1-yl) 1,1,3,3-tetramethyluronium tetrafluoroborate (TBTU) (80 mg) were subsequently added. After 30 min stirring at rt AcOEt (10 ml) was added and the organic layer was washed with 1 N HCl (2×10 ml), H$_2$O (10 ml) and brine. The aqueous layers were extracted with more AcOEt (10 ml). After drying (MgSO$_4$) the solvent was evaporated and the crude product was purified by HPLC to obtain 30 mg (23%) of (RS)-[(4-{[2-(2,6-difluoro-4-isobutylcarbamoyl-phenyl)-2-ethoxy-acetylamino]-methyl}-phenyl)-imino-methyl]-carbamic acid benzyl ester. White solid. MS 581.4 ([M+H]$^+$).

165.4

To a solution of [(4-{[2-(2,6-difluoro-4-isobutylcarbamoyl-phenyl)-2-ethoxy-acetylamino]-methyl}-phenyl)-imino-methyl]-carbamic acid benzyl ester (27 mg) in MeOH (1 ml) and 2 M NH$_3$ in MeOH (0.3 ml) was added a spatula tip of 10% Pd/C. The mixture was placed under 1 atm H$_2$ and stirred 4 h at rt. Filtration and evaporation of the solvent afforded 14 mg (64%) of 4-(RS)-[(4-carbamimidoyl-benzylcarbamoyl)-ethoxy-methyl]-3,5-difluoro-N-isobutyl-benzamide hydrochloride. White solid. MS 447.5 ([M+H]$^+$).

Examples 166–170

Examples 166–170 were prepared in analogy to example 165. Instead of using CDI for the first coupling step, the products were prepared by following the TBTU mediated coupling procedure described in example 165.3.

166

(RS)-4-[(4-Carbamimidoyl-benzylcarbamoyl)-ethoxy-methyl]-N-ethyl-3,5-difluoro-benzamide hydrochloride. Yellowish solid. MS 419.4 ([M+H]$^+$).

167

(RS)-4-[(4-Carbamimidoyl-benzylcarbamoyl)-ethoxy-methyl]-3,5-difluoro-N-(2-methoxy-ethyl)-benzamide hydrochloride. Yellow foam. MS 449.5 ([M+H]$^+$).

168

(RS)-4-[(4-Carbamimidoyl-benzylcarbamoyl)-ethoxy-methyl]-N-cyclopentyl-3,5-difluoro-benzamide hydrochloride. Yellow powder. MS 459.6 ([M+H]$^+$).

169

(RS)-4-[(4-Carbamimidoyl-benzylcarbamoyl)-ethoxymethyl]-3,5-difluoro-N-(2,2,2-trifluoro-ethyl)-benzamide hydrochloride. Yellowish powder. MS 473.3 ([M+H]$^+$).

170

(RS)-4-[(4-Carbamimidoyl-benzylcarbamoyl)-ethoxymethyl]-N-cyclopropylmethyl-3,5-difluoro-benzamide hydrochloride. MS 445.5 ([M+H]$^+$).

Example 171 tert-Butydiphenylchlorosilane (76.8 g) was added over 30 min to a cooled (0° C.) solution of 2,4-difluorophenol (34.6 g) and imidazole (19.9 G) in $CH_2Cl_2$ (400 ml). The cooling bath was removed and the reaction mixture was stirred 2 h at rt before washing it with $H_2O$ (400 ml), 5% aq. $NaHCO_3$ (300 ml) and brine. The aqueous layers were extracted with two more portions of $CH_2Cl_2$ (150 ml). The combined organic layers were dried ($Na_2SO_4$) and the solvent was evaporated to obtain 102 g (99%) of tert-butyl-(2,4-difluorophenoxy)-diphenyl-silane. Colorless liquid.

Example 172

A solution under Ar of tert-butyl-(2,4-difluoro-phenoxy)-diphenyl-silane (102 g) and 1,1,4,7,7-pentamethyldiethylenetriamine (50.6 g) in DME (800 ml) was cooled to −70° C. before addition of 1.6 N n-BuLi in hexane (182 ml) over a period of 1 h. The yellow solution was stirred 1 h at −70° C. 50% glyoxalic acid ethylester in toluene (113 g) was added over a period of 1 h. The reaction mixture was stirred 2 h more at −70° C. before heating up over 1 h to 0° C. Sat. $NH_4$ sol. (300 ml) was added and the pH was lowered to pH=6 with 2 N HCl. The product was extracted with AcOEt (2×400 ml). The organic layers were washed with brine (500 ml) and dried ($Na_2SO_4$) and the solvent was evaporated. CC (Hept to Hept/AcOEt 9:1) afforded 70.8 g (54%) of (RS)-[3-(tert-butyl-diphenyl-silanyloxy)-2,6-difluoro-phenyl]-hydroxy-acetic acid ethyl ester. Yellowish oil. MS 488.5 ([M+H]$^+$).

Example 173

A mixture of (RS)-[3-(tert-butyl-diphenyl-silanyloxy)-2,6-difluoro-phenyl]-hydroxy-acetic acid ethyl ester (70.8 g), $Ag_2O$ (69.7 g) and iodoethane (117 g) in Tol (700 ml) was stirred 68 h at 90° C. After filtration and evaporation of the solvent the product was separated from the remaining starting material by MPLC (Hept to Hept/AcOEt 1:9). The procedure was repeated with the recovered starting material. 62.5 g (83%) of (RS)-[3-(tert-butyl-diphenyl-silanyloxy)-2,6-difluoro-phenyl]-ethoxy-acetic acid ethyl ester were obtained. Light yellow oil. MS 498.3 (1, M$^+$); 441.1 (73, [M−tBu]$^+$); 425.2 (33, [M−COOEt]$^+$).

Example 174

To a solution of (RS)-[3-(tert-butyl-diphenyl-silanyloxy)-2,6-difluoro-phenyl]-ethoxy-acetic acid ethyl ester (62.5 g) in THF (250 ml) and MeOH (250 ml) was added $H_2O$ (200 ml) and LiOH.$H_2O$ (10.5 g) and it was stirred 2 h at 65° C. MeOH and THF were evaporated and the aqueous residue was washed with Hept/$Et_2O$ 9:1 (2×150 ml). The organic layers were extracted with two portions of $H_2O$ (200 ml). The combined aqueous layers were cooled in an ice bath and acidified with 35 ml 25% aq. HCl. Extraction with AcOEt (3×200 ml) followed by washing with brine, drying ($Na_2SO_4$) and evaporation of the solvent afforded 28.7 g (99%) of (RS)-(2,6-difluoro-3-hydroxy-phenyl)-ethoxyacetic acid. Yellow viscous oil. MS 231.2 ([M−H]$^-$).

Example 174a

A solution of (RS)-(2,6-difluoro-3-hydroxy-phenyl)-ethoxy-acetic acid (14.8 g) in EtOH (200 ml) and 1.25 N HCl in EtOH (60 ml) was stirred over night at rt. The solvent was evaporated and the residue was purified by CC (AcOEt/Hept 1:1) to obtain 15.5 g (93%) of (RS)-(2,6-difluoro-3-hydroxy-phenyl)-ethoxy-acetic acid ethyl ester. Off-white solid. MS 258.9 ([M−H]$^-$).

Example 175

To a solution of (RS)-(2,6-difluoro-3-hydroxy-phenyl)-ethoxy-acetic acid (12.0 g) in DMF (600 ml) was added [(4-aminomethyl-phenyl)-imino-methyl]-carbamic acid benzyl ester dihydrochloride [Prepared according to Ch. Lila, Ph. Gloanec, L. Cadet, Y. Hervé, J. Fournier, F. Leborgne, T. J. Verbeuren, G. De Nanteuil, Synthetic Communications 1998, 28, 23, 4419–4429] (18.2 g) and 1-hydroxybenzotriazole. The mixture was cooled to 0–5° C. and EDC (15.8 g) and trietylamine (62 ml) were added. The mixture was stirred 1 h at 0–5° C. and over night at rt. The solvent was evaporated and the residue was dissolved in $CH_2Cl_2$ and washed with $H_2O$ (600 ml), and brine (300 ml). The aqueous layers were extracted with more $CH_2Cl_2$ (2×300 ml). The combined organic layers were dried ($Na_2SO_4$) and the solvent was evaporated. CC($CH_2Cl_2$/2 N $NH_3$ in MeOH 97:3 to 19:1) afforded 10.2 g (40%) of (RS)-[(4-{[2-(2,6-difluoro-3-hydroxy-phenyl)-2-ethoxy-acetylamino]-methyl}-phenyl)-imino-methyl]-carbamic acid benzyl ester. White foam. MS 498.2 ([M+H]$^+$).

Example 176

(RS)-[(4-{[2-(2,6-Difluoro-3-hydroxy-phenyl)-2-ethoxy-acetylamino]-methyl}-phenyl)-imino-methyl]-carbamic acid benzyl ester (250 mg) was dissolved in EtOH (20 ml) and 0.9 N HCl in EtOH (5 ml) was added. After 10 min stirring 10% Pd/C (11 mg) was added and the mixture was hydrogenated 2 h at rt under 1 atm $H_2$. Filtration, evaporation of the solvent and trituration with MeCN (4 ml) afforded the solid product that was washed with two portions of $Et_2O$ (5 ml). After drying on the vacuum at 50° C. 175 mg (87%) of (RS)-N-(4-carbamimidoyl-benzyl)-2-(2,6-difluoro-3-hydroxy-phenyl)-2-ethoxy-acetamide hydrochloride were obtained. White solid. MS 364.0 ([M+H]$^+$).

Examples 177–207, 207a, 207b

Examples 177–207b were prepared in two steps (E1/E2 and F1/F2) from (RS)-[(4-{[2-(2,6-difluoro-3-hydroxy-phenyl)-2-ethoxy-acetylamino]-methyl}-phenyl)-imino-methyl]-carbamic acid benzyl ester and an appropriate alcohol by the following procedures:

Procedure E1: A mixture of 1.0 equivalent of (RS)-[(4-{[2-(2,6-difluoro-3-hydroxy-phenyl)-2-ethoxy-acetylamino]-methyl}-phenyl)-imino-methyl]-carbamic acid benzyl ester, 1.1 equivalents of alcohol, ca. 2 equivalents of polymer bound triphenylphosphine (~3 mM/g) and 2.0 equivalents of di-tert-butylazodicarboxylate are shaken 2 days at rt. The reaction mixture is absorbed on a 20 g silica gel samplet and the product is purified by chromatography ($CH_2Cl_2$/2 N $NH_3$ in MeOH system)

Procedure E2: As E1 but with 1.25 equivalents alcohol and stirring 40 h.

Procedure F1: The products from procedure E were hydrogenated at rt and 1 atm $H_2$ in EtOH/1.25 N HCl in EtOH 5:1 in the presence of a catalytic amount of 10% Pd/C. Filtration and evaporation of the solvent afforded the final compounds.

Procedure F2: As F1 but in MeOH instead of EtOH. Were necessary the final compounds were purified by HPLC.

| No. | Name | Alcohol | Proc. | Appearance | MS $[M + H]^+$ |
|---|---|---|---|---|---|
| 177 | (RS)-N-(4-Carbamimidoyl-benzyl)-2-ethoxy-2-{3-[2-(2-ethoxy-ethoxy)-ethoxy]-2,6-difluoro-phenyl}-acetamide hydrochloride | Diethylene glycol monoethyl ether | E1/F1 | Brownish foam | 480.1 |
| 178 | (RS)-N-(4-Carbamimidoyl-benzyl)-2-[3-(3-dimethylamino-propoxy)-2,6-difluoro-phenyl]-2-ethoxy-acetamide dihydrochloride | 3-Dimethyl-amino-1-propanol | E1/F1 | Yellowish foam | 449.1 |
| 179 | (RS)-N-(4-Carbamimidoyl-benzyl)-2-(2,6-difluoro-3-{2-[2-(2-methoxy-ethoxy)-ethoxy]-ethoxy}-phenyl)-2-ethoxy-acetamide hydrochloride | Triethylene glycol monomethyl ether | E1/F1 | Brownish foam | 510.3 |
| 180 | (RS)-N-(4-Carbamimidoyl-benzyl)-2-[2,6-difluoro-3-(3-pyridin-4-yl-propoxy)-phenyl]-2-ethoxy-acetamide dihydrochloride | 4-Pyridine-propanol | E1/F1 | Brownish foam | 483.1 |
| 181 | (RS)-N-(4-Carbamimidoyl-benzyl)-2-[2,6-difluoro-3-(2-pyrrolidin-1-yl-ethoxy)-phenyl]-2-ethoxy-acetamide dihydrochloride | 1-(2-Hydroxy-ethyl)-pyrrolidine | E1/F1 | Brownish foam | 461.0 |
| 182 | (RS)-N-(4-Carbamimidoyl-benzyl)-2-[2,6-difluoro-3-(1-methyl-cyclopropylmethoxy)-phenyl]-2-ethoxy-acetamide hydrochloride | 1-Methyl-cyclopropane-methanol | E1/F1 | White solid | 432.0 |
| 183 | (RS)-N-(4-Carbamimidoyl-benzyl)-2-[2,6-difluoro-3-(2-piperidin-1-yl-ethoxy)-phenyl]-2-ethoxy-acetamide dihydrochloride | 1(2-Hydroxy-ethyl)-piperidine | E2/F2 | Yellow foam | 475.8 |
| 184 | (RS,RS)-N-(4-Carbamimidoyl-benzyl)-2-[3-(3-chloro-2-hydroxymethyl-2-methyl-propoxy)-2,6-difluoro-phenyl]-2-ethoxy-acetamide hydrochloride | 3-Methyl-3-oxetane-methanol | E2/F1 | Off-white foam | 484.2 |
| 185 | (RS)-N-(4-Carbamimidoyl-benzyl)-2-ethoxy-2-[3-(2-ethoxy-ethoxy)-2,6-difluoro-phenyl]-acetamide hydrochloride | 2-Ethoxy-ethanol | E2/F2 | Brownish foam | 436.2 |
| 186 | (RS)-N-(4-Carbamimidoyl-benzyl)-2-[2,6-difluoro-3-(2-methoxy-ethoxy)-phenyl]-2-ethoxy-acetamide hydrochloride | 2-Methoxy-ethanol | E2/F2 | Brownish foam | 422.1 |
| 187 | (RS)-N-(4-Carbamimidoyl-benzyl)-2-[3-(3-dimethylamino-2,2-dimethyl-propoxy)-2,6-difluoro-phenyl]-2-ethoxy-acetamide dihydrochloride | 3-Dimethyl-amino-2,2-dimethyl-1-propanol | E2/F2 | White foam | 477.1 |
| 188 | (RS)-N-(4-Carbamimidoyl-benzyl)-2-[2,6-difluoro-3-(2-thiophen-2-yl-ethoxy)-phenyl]-2-ethoxy-acetamide hydrochloride | 2-(2-Thienyl)-ethanol | E2/F2 | Brownish foam | 474.1 |

-continued

| No. | Name | Alcohol | Proc. | Appearance | MS [M + H]+ |
|---|---|---|---|---|---|
| 189 | (RS,RS)-N-(4-Carbamimidoyl-benzyl)-2-[2,6-difluoro-3-(tetrahydro-furan-2-ylmethoxy)-phenyl]-2-ethoxy-acetamide hydrochloride | Tetrahydro-furfuryl alcohol | E2/F2 | Brownish foam | 448.1 |
| 190 | (RS)-N-(4-Carbamimidoyl-benzyl)-2-(2,6-difluoro-3-isobutoxy-phenyl)-2-ethoxy-acetamide hydrochloride | 2-Methyl propanol | E2/F2 | White solid | 420.1 |
| 191 | (RS,RS,RS)-N-(4-Carbamimidoyl-benzyl)-2-[2,6-difluoro-3-(2-methyl-cyclopropylmethoxy)-phenyl]-2-ethoxy-acetamide hydrochloride | 2-Methyl-cyclopropane-methanol | E2/F2 | Brownish foam | 432.0 |
| 192 | (RS)-N-(4-Carbamimidoyl-benzyl)-2-[3-(2-cyclopropyl-ethoxy)-2,6-difluoro-phenyl]-2-ethoxy-acetamide hydrochloride | 2-Cyclopropyl-ethanol | E2/F2 | White foam | 432.2 |
| 193 | (RS)-N-(4-Carbamimidoyl-benzyl)-2-ethoxy-2-(3-ethoxy-2,6-difluoro-phenyl)-acetamide hydrochloride | Ethanol | E2/F2 | Yellowish foam | 391.9 |
| 194 | (RS)-N-(4-Carbamimidoyl-benzyl)-2-(2,6-difluoro-3-propoxy-phenyl)-2-ethoxy-acetamide hydrochloride | 1-Propanol | E2/F2 | Brownish foam | 406.0 |
| 195 | (RS)-N-(4-Carbamimidoyl-benzyl)-2-(3-cyclopropylmethoxy-2,6-difluoro-phenyl)-2-ethoxy-acetamide hydrochloride | Hydroxy-methyl-cyclopropane | E2/F2 | Brownish foam | 417.9 |
| 196 | (RS)-N-(4-Carbamimidoyl-benzyl)-2-[3-(2-dimethylamino-ethoxy)-2,6-difluoro-phenyl]-2-ethoxy-acetamide dihydrochloride | 2-Dimethyl-aminoethanol | E2/F2 | Brownish foam | 434.9 |
| 197 | (RS)-N-(4-Carbamimidoyl-benzyl)-2-(3-cyclobutylmethoxy-2,6-difluoro-phenyl)-2-ethoxy-acetamide hydrochloride | Cyclobutane-methanol | E2/F2 | Brownish foam | 432.0 |
| 198 | (RS)-N-(4-Carbamimidoyl-benzyl)-2-{2,6-difluoro-3-[2-(2-oxo-pyrrolidin-1-yl)-ethoxy]-phenyl}-2-ethoxy-acetamide hydrochloride | N-(2-Hydroxy-ethyl)-2-pyrrolidone | E2/F2 | Brownish foam | 475.0 |
| 199 | (RS)-N-(4-Carbamimidoyl-benzyl)-2-[2,6-difluoro-3-(3,3,3-trifluoro-propoxy)-phenyl]-2-ethoxy-acetamide hydrochloride | 3,3,3-Trifluoro-1-propanol | E2/F2 | Brownish foam | 460.1 |
| 200 | (RS)-N-(4-Carbamimidoyl-benzyl)-2-[2,6-difluoro-3-(2-pyridin-3-yl-ethoxy)-phenyl]-2-ethoxy-acetamide dihydrochloride | 3-(2-Hydroxy-ethyl)pyridine | E2/F2 | Yellow foam | 469.9 |
| 201 | (RS)-N-(4-Carbamimidoyl-benzyl)-2-(3-diethylcarbamoylmethoxy-2,6-difluoro-phenyl)-2-ethoxy-acetamide hydrochloride | N,N-Diethyl-2-hydroxy-acetamide | E2/F2 | Brownish foam | 477.1 |
| 202 | (RS)-N-(4-Carbamimidoyl-benzyl)-2-[2,6-difluoro-3-(2-morpholin-4-yl-ethoxy)-phenyl]-2-ethoxy-acetamide dihydrochloride | N-(2-Hydroxy-ethyl)-morpholine | E2/F2 | Brownish foam | 477.0 |
| 203 | (RS,RS)-N-(4-Carbamimidoyl-benzyl)-2-[2,6-difluoro-3-(1-methyl-piperidin-3-ylmethoxy)-phenyl]-2-ethoxy-acetamide dihydrochloride | 1-Methyl-3-piperidine-methanol | E2/F2 | Brownish foam | 475.0 |

-continued

| No. | Name | Alcohol | Proc. | Appearance | MS [M + H]+ |
|---|---|---|---|---|---|
| 204 | (RS,RS)-N-(4-Carbamimidoyl-benzyl)-2-[2,6-difluoro-3-(1-methyl-piperidin-2-ylmethoxy)-phenyl]-2-ethoxy-acetamide dihydrochloride | 1-Methyl-2-piperidine-methanol | E2/F2 | Brownish oil | 475.2 |
| 205 | (RS)-N-(4-Carbamimidoyl-benzyl)-2-[2,6-difluoro-3-(2-pyridin-2-yl-ethoxy)-phenyl]-2-ethoxy-acetamide dihydrochloride | 2-(2-Hydroxy-ethyl)pyridine | E2/F2 | Yellow foam | 469.0 |
| 206 | (RS,RS)-N-(4-Carbamimidoyl-benzyl)-2-[2,6-difluoro-3-(2-piperidin-2-yl-ethoxy)-phenyl]-2-ethoxy-acetamide dihydrochloride | 2-Piperidine-ethanol | E2/F2 | Brownish foam | 475.0 |
| 207 | (RS)-N-(4-Carbamimidoyl-benzyl)-2-(2,6-difluoro-3-methoxy-phenyl)-2-ethoxy-acetamide hydrochloride | Methanol (3 equivalents) | E2/F2 | Off-white foam | 378.5 |
| 207a | (RS)-N-(4-Carbamimidoyl-benzyl)-2-(3-cyclohexyloxy-2,6-difluoro-phenyl)-2-ethoxy-acetamide hydrochloride | Cyclohexanol | E2/F2 | Off-white solid | 446.0 |
| 207b | (RS)-N-(4-Carbamimidoyl-benzyl)-2-[2,6-difluoro-3-(piperidin-4-yloxy)-phenyl]-2-ethoxy-acetamide dihydrochloride | 1-tert-Butoxy-carbonyl-4-hydroxy-piperdine | E2/F2 | Off-white foam | 447.5 |

Example 208

208.1

To a solution under Ar of (RS)-(2,6-difluoro-3-hydroxy-phenyl)-ethoxy-acetic acid ethyl ester (320 mg) in $CH_2Cl_2$ (10 ml) was added copper(II)acetate (230 mg), 4-fluorobenzeneboronic acid 516 mg) and powdered MS4 Å (2 g). After addition of triethlyamine (622 mg) the mixture was stirred 40 h at rt. The solids were filtered away and the solvent was evaporated. Column chromatography (CC) (AcOEt:Hept 1:9 to 1:1) afforded 154 mg of (RS)-[2,6-difluoro-3-(4-fluoro-phenoxy)-phenyl]-ethoxy-acetic acid ethyl ester as a brownish oil.

208.2

(R,S)-[2,6-Difluoro-3-(4-fluoro-phenoxy)-phenyl]-ethoxy-acetic acid ethyl ester (145 mg) was dissolved in MeOH/THF 1:1 (2 ml) and $H_2O$ (0.5 ml) and $LiOH.H_2O$ (36 mg) were added. The solution was stirred 2 h at 60° C. THF and MeOH were evaporated and the residue was diluted with $H_2O$ (10 ml) and acidified with 1 N HCl (pH=2). The product was extracted with AcOEt (2×30 ml). The organic layers were washed with brine (20 ml). Drying ($Na_2SO_4$) and evaporation of the solvent afforded 140 mg of (RS)-[2,6-difluoro-3-(4-fluoro-phenoxy)-phenyl]-ethoxy-acetic acid as a yellowish oil.

208.3

To a solution of (RS)-[2,6-difluoro-3-(4-fluoro-phenoxy)-phenyl]-ethoxy-acetic acid (140 mg) in DMF (5 ml) was added [(4-aminomethyl-phenyl)-imino-methyl]-carbamic acid benzyl ester dihydrochloride (149 mg) and 1-hydroxy-benzotriazole (92 mg). The mixture was cooled to 0–5° C. and EDC (130 mg) and triethylamine (0.5 ml) were added. After stirring 2 h at 0–5° C. the solvent was evaporated and the residue was partitioned between $H_2O$ (25 ml) and AcOEt (25 ml). The aqueous layer was extracted with more AcOEt (25 ml). The organic layers were washed with brine (25 ml) and dried ($Na_2SO_4$) and the solvent was evaporated. CC (AcOEt/Hept 1:3 to 4:1) afforded 120 mg of (R,S)-N-[4-(amino-benzyloxycarbonimidoylimino-methyl)-benzyl]-2-[2,6-difluoro-3-(4-fluoro-phenoxy)phenyl)-2-ethoxy-acetamide as white crystals.

208.4

(R,S)-N-[4-(Amino-benzyloxycarbonimidoylimino-methyl)-benzyl]-2-[2,6-difluoro-3-(4-fluoro-phenoxy)phenyl)-2-ethoxy-acetamide (120 mg) was dissolved in MeOH (10 ml) and 1.25 N HCl in MeOH (2 ml) was added. The mixture was hydrogenated 1 h at 1 atm $H_2$ and rt in presence of 10% Pd/C (12 mg). After filtration and evaporation of the solvent (R,S)-N-(4-carbamimidoyl-benzyl)-2-[2,6-difluoro-3-(4-fluoro-phenoxy)-phenyl]-2-ethoxy-acetamide hydrochloride was obtained by crystallization from $MeCN/Et_2O$. White solid. MS 458.5 ([M+H]+).

Examples 209–212

Examples 209–212 were prepared in analogy to example 208:

| No. | Name | Appearance | MS [M + H]+ |
|---|---|---|---|
| 209 | (RS)-N-(4-Carbamimidoyl-benzyl)-2-[2,6-difluoro-3-(pyridin-3-yloxy)-phenyl]-2-ethoxy-acetamide dihydrochloride | Off-white foam | 441.5 |
| 210 | (RS)-N-(4-Carbamimidoyl-benzyl)-2-[2,6-difluoro-3-(3-trifluoromethyl-phenoxy)-phenyl]-2-ethoxy-acetamide hydrochloride | White crystals | 508.1 |
| 211 | (RS)-N-(4-Carbamimidoyl-benzyl)-2-(2,6-difluoro-3-m-tolyloxy-phenyl)-2-ethoxy-acetamide hydrochloride | White crystals | 454.1 |

-continued

| No. | Name | Appearance | MS [M + H]⁺ |
|---|---|---|---|
| 212 | (RS)-N-(4-Carbamimidoyl-benzyl)-2-ethoxy-2-[3-(3-ethoxy-phenoxy)-2,6-difluoro-phenyl]-acetamide hydrochloride | White crystals | 484.1 |

Example 213

To an ice cooled mixture under Ar of (RS)-(2,6-difluoro-3-hydroxy-phenyl)-ethoxy-acetic acid, 4-aminomethyl-benzonitrile hydrochloride (10.6 g) and 1-hydroxybenzotriazole (9.8 g) in DMF (140 ml) was added EDC (13.9 g) and triethylamine (55 ml). The mixture was stirred 2.5 h at 0° C. and 2 d at rt. The solvent was evaporated and H₂O (250 ml) was added. The product was extracted with AcOEt (2×200 ml). The organic layers were washed with 5% NaHCO₃ aq. sol. (100 ml), brine 100 ml). After drying (Na₂SO₄) the solvent was evaporated. CC (AcOEt/Hept 2:3) afforded 7.66 g (49%) of (RS)-N-(4-cyano-benzyl)-2-(2,6-difluoro-3-hydroxy-phenyl)-2-ethoxy-acetamide. White solid. MS 364.1 ([M+NH₄]⁺).

General procedure G for the preparation of the N-hydroxy-benzamidines: 1.0 equivalent of the benzonitrile was dissolved in EtOH and 5.0 equivalents of hydroxylamine hydrochloride and triethylamine were added. The solution was stirred over night before addition of 5.0 equivalents more of hydroxylamine hydrochloride and triethylamine. After stirring again over night the products were isolated by evaporation of the solvent and CC.

General procedure H for the reduction of the N-hydroxy-benzamidines: The n-hydroxy-benzamidines were hydrogenated in EtOH over night at rt and 1 atm H₂ in presence of a catalytic amount of 10% Pd/C and 10 equivalents of AcOH. The products were isolated by filtration and evaporation of the solvent. Where necessary a crystallization or CC were carried out.

Example 214

To a solution under Ar of (RS)-N-(4-cyano-benzyl)-2-(2,6-difluoro-3-hydroxy-phenyl)-2-ethoxy-acetamide (200 mg) in DMF (10 ml) was added CSCO₃ (226 mg) and 3-bromopentane (105 mg). The solution was stirred over night at 80° C. The solvent was evaporated and the residue was taken up in H₂O (50 ml). The product was extracted with AcOEt (2×100 ml). The organic layers were washed with H₂O (2×50 ml) and dried (Na₂SO₄) and the solvent was evaporated. CC (AcOEt/Hept 2:3 to AcOEt) afforded 190 mg (79%) of (RS)-N-(4-cyano-benzyl)-2-ethoxy-2-[3-(1-ethyl-propoxy)-2,6-difluoro-phenyl]-acetamide. This material was converted to (RS)-N-(4-carbamimidoyl-benzyl)-2-ethoxy-2-[3-(1-ethyl-propoxy)-2,6-difluoro-phenyl]-acetamide acetate by the sequence of procedures G and H. Off-white solid. MS 434.4 ([M+H]⁺).

Examples 215–216

Example 215 was prepared in analogy to example 214. Example 216 was prepared from (RS)-N-(4-cyano-benzyl)-2-(2,6-difluoro-3-hydroxy-phenyl)-2-ethoxy-acetamide by a sequence of procedures E2, G and H.

| No. | Name | Appearance | MS [M + H]⁺ |
|---|---|---|---|
| 215 | (RS)-N-(4-Carbamimidoyl-benzyl)-2-(3-cyclopentyloxy-2,6-difluoro-phenyl)-2-ethoxy-acetamide acetate | Brown solid | 432.5 |
| 216 | (RS)-N-(4-Carbamimidoyl-benzyl)-2-[2,6-difluoro-3-(tetrahydro-pyran-4-yloxy)-phenyl]-2-ethoxy-acetamide acetate | White solid | 448.1 |

Example 217

A solution under Ar of (RS)-N-(4-cyano-benzyl)-2-(2,6-difluoro-3-hydroxy-phenyl)-2-ethoxy-acetamide (5.0 g) in pyridine (50 ml) was cooled to −10° C. and trifluoromethanesulfonic acid anhydride (4.5 g) was added over a period of 10 min. The reaction mixture was stirred 2 h at 0° C. More trifluoromethanesulfonic acid anhydride was added (4.5 g) over 30 min and it was stirred 30 min more at 0° C. Pyridine was evaporated, H₂O (200 ml) was added and the product was extracted with AcOEt (2×100 ml). The organic layers were washed with brine, combined and dried (Na₂SO₄) before evaporation of the solvent. CC (AcOEt/Hept to AcOEt) afforded 6.2 g (89%) of (R,S)-trifluoromethanesulfonic acid 3-[(4-cyano-benzylcarbamoyl)-ethoxy-methyl]-2,4-difluoro-phenyl ester. Yellow oil. MS 479.1 ([M+H]⁺).

General procedure I for the Reduction of the N-Hydroxy-Benzamidines:

To a 0.015 M solution of the N-hydroxy-benzamidine in EtOH was added AcOH (10 equivalents) and Raney-Ni (2.5 equivalents, Degussa 313 Z type). The reaction mixture was stirred over night at rt. The catalyst was filtered away, the solvent was evaporated, H₂O (⅗ of the initial EtOH volume) was added and the mixture was treated with 25% aq. NH₄OH (⅕ of the initial EtOH volume). The solvent was evaporated and the residue was purified by CC(CH₂Cl₂/MeOH/25% aq. NH₄OH). The products were isolated as the hydrochlorides after treatment of a methanolic solution with 1.25 N HCl/MeOH.

Example 218

218.1

To a solution of (RS)-trifluoro-methanesulfonic acid 3-[(4-cyano-benzylcarbamoyl)-ethoxy-methyl]-2,4-difluoro-phenyl ester (570 mg) in dioxane (20 ml) was added bis(pinacolato)diboron (454 mg), dry KOAc (351 mg) and [PdCl$_2$(PPh$_3$)$_2$] (25 mg). The reaction mixture was stirred 24 h at 100° C. After cooling to rt 5-bromopyridine (377 mg), 2 N aq. Na$_2$CO$_3$ sol. (6 ml) and [PdCl$_2$(PPh$_3$)$_2$] (25 mg) were added. The resulting mixture was stirred 1 h at 90° C. The solids were filtered away and washed with H$_2$O (100 ml) and AcOEt (80 ml). The aqueous layer was isolated and extracted with more AcOEt (100 ml). The organic layers were washed with brine (2×80 ml), combined and dried over Na$_2$SO$_4$. The solvent was evaporated and the crude product was purified by CC (AcOEt/Hept 3:7 to 3:1) to obtain 315 mg (65%) of (RS)-N-(4-cyano-benzyl)-2-(2,6-difluoro-3-pyridin-2-yl-phenyl)-2-ethoxy-acetamide. Colorless oil. MS 408.3 ([M+H]$^+$).

218.2

(RS)-N-(4-Cyano-benzyl)-2-(2,6-difluoro-3-pyridin-2-yl-phenyl)-2-ethoxy-acetamide (310 mg) was converted into (RS)-2-(2,6-difluoro-3-pyridin-2-yl-phenyl)-2-ethoxy-N-[4-(N-hydroxycarbamimidoyl)-benzyl]-acetamide (320 mg, 95%) following procedure G. Colorless oil. MS 441.3 ([M+H]$^+$).

218.3

(RS)-2-(2,6-Difluoro-3-pyridin-2-yl-phenyl)-2-ethoxy-N-[4-(N-hydroxycarbamimidoyl)-benzyl]-acetamide (315 mg) was converted into (RS)-N-(4-carbamimidoyl-benzyl)-2-(2,6-difluoro-3-pyridin-2-yl-phenyl)-2-ethoxy-acetamide dihydrochloride (225 mg, 63%) following procedure I. Off-white foam. MS 425.3 ([M+H]$^+$).

Examples 219–222

Examples 219–222 were prepared in analogy to example 218:

| No. | Name | Aryl-X | Appearance | MS [M + H]$^+$ |
|---|---|---|---|---|
| 219 | (RS)-N-(4-Carbamimidoyl-benzyl)-2-[2,6-difluoro-3-(6-methoxy-pyridin-3-yl)-phenyl]-2-ethoxy-acetamide dihydrochloride | 5-Bromo-2-methoxy-pyridine | Off-white foam | 455.5 |
| 220 | (RS)-N-(4-Carbamimidoyl-benzyl)-2-(2,6-difluoro-3-pyridin-3-yl-phenyl)-2-ethoxy-acetamide dihydrochloride | 3-Bromo-pyridine | Off-white foam | 425.4 |
| 221 | (RS)-N-(4-Carbamimidoyl-benzyl)-2-(2,6-difluoro-3-pyrimidin-5-yl-phenyl)-2-ethoxy-acetamide dihydrochloride | 5-Bromo-pyrimidine | White foam | 426.4 |
| 222 | (RS)-N-(4-Carbamimidoyl-benzyl)-2-(2,6-difluoro-3-pyridin-4-yl-phenyl)-2-ethoxy-acetamide dihydrochloride | 4-Iodopyridine | Yellowish foam | 425.3 |

Example 223

(RS)-[3-(tert-Butyl-diphenyl-silanyloxy)-2,6-difluoro-phenyl]-methoxy-acetic acid ethyl ester was prepared in analogy to example 173 from (RS)-[3-(tert-butyl-diphenyl-silanyloxy)-2,6-difluoro-phenyl]-hydroxy-acetic acid ethyl ester and iodomethane. Yellowish oil. MS 484.2 (4, [M+]$^+$); 427.1 (29, [M–tBu]$^+$); 411.2 (14, [M–COOEt]$^+$).

Example 224

A 1.0 M solution of TBAF in THF (100 ml) was added under stirring to a solution of (RS)-(2,6-difluoro-3-hydroxy-phenyl)-methoxy-acetic acid ethyl ester (38.5 g) in THF (500 ml). The reaction mixture was stirred over night at rt before evaporation of the solvent. The residue was partitioned between 600 ml AcOEt/H$_2$O 1:1 and extracted with more AcOEt (200 ml). The organic layers were washed with brine 200 ml, combined and dried over Na$_2$SO$_4$. After evaporation of the solvent CC(CH$_2$Cl$_2$, then CH$_2$Cl$_2$/2 N NH$_3$ in MeOH 97:3) yielded 18.3 g (94%) of (RS)-(2,6-difluoro-3-hydroxy-phenyl)-methoxy-acetic acid ethyl ester. Yellowish solid. MS 245.3 ([M–H]$^-$).

Example 225

A solution of (RS)-(2,6-difluoro-3-hydroxy-phenyl)-methoxy-acetic acid ethyl ester (11.6 g) and LiOH.H$_2$O in THF (40 ml), MeOH (40 ml) and H$_2$O was stirred 2 h at 65° C. The organic solvents were evaporated, H$_2$O was added (50 ml) and the pH was lowered with 2 N HCl to pH=2. The product was extracted with AcOEt (3×50 ml). The organic layers were washed with brine (100 ml), combined and dried (Na$_2$SO$_4$). Evaporation of the solvent afforded 9.6 g (94%) of (RS)-(2,6-difluoro-3-hydroxy-phenyl)-methoxy-acetic acid. White solid. MS 217.1 ([M–H]$^-$).

Example 226

(RS)-N-(4-Cyano-benzyl)-2-(2,6-difluoro-3-hydroxy-phenyl)-2-methoxy-acetamide was prepared from (RS)-(2,6-difluoro-3-hydroxy-phenyl)-methoxy-acetic acid in analogy to (RS)-N-(4-cyano-benzyl)-2-(2,6-difluoro-3-hydroxy-phenyl)-2-ethoxy-acetamide (example 213). White foam. MS 330.8 ([M–H]$^-$).

Example 227

(RS)-Trifluoro-methanesulfonic acid 3-[(4-cyano-benzyl-carbamoyl)-methoxy-methyl]-2,4-difluoro-phenyl ester was prepared from (RS)-N-(4-cyano-benzyl)-2-(2,6-difluoro-3-hydroxy-phenyl)-2-methoxy-acetamide in analogy to (RS)-trifluoro-methanesulfonic acid 3-[(4-cyano-benzylcarbamoyl)-ethoxy-methyl]-2,4-difluoro-phenyl ester (example 217). Yellow oil. MS 482.3 ([M+NH$_4$]$^+$).

General Procedure K for the Suzuki Coupling Reaction:

To a 0.1 M solution in Tol of (RS)-trifluoro-methanesulfonic acid 3-[(4-cyano-benzylcarbamoyl)-methoxy-methyl]-2,4-difluoro-phenyl ester (1.0 equivalent) was added K$_2$CO$_3$ (1.5 equivalents) and the boronic acid (2.0 equivalents). The solution was degassed by bubbling 10 min Ar through it before adding [Pd(PPh)$_4$] (0.03 equivalents). The reaction mixture was stirred over night at 100° C. before isolation of the product by CC (AcOEtHept).

Examples 228–233

Examples 228–233 were prepared from (RS)-trifluoro-methanesulfonic acid 3-[(4-cyano-benzylcarbamoyl)-methoxy-methyl]-2,4-difluoro-phenyl ester by subsequently carrying out procedures K, G and H. Procedure H was modified by replacing HCl with 10 equivalents of AcOH.

| No. | Name | RB(OH)$_2$ | Appearance | MS [M + H]$^+$ |
|---|---|---|---|---|
| 228 | (RS)-N-(4-Carbamimidoyl-benzyl)-2-(2,4-difluoro-3'-methyl-biphenyl-3-yl)-2-methoxy-acetamide | m-Tolyl-boronic acid | White crystals | 424.0 |
| 229 | (RS)-N-(4-Carbamimidoyl-benzyl)-2-(2,4-difluoro-4'-methyl-biphenyl-3-yl)-2-methoxy-acetamide hydrochloride | 4-Methyl-benzene boronic acid | Orange foam | 424.4 |
| 230 | (RS)-N-(4-Carbamimidoyl-benzyl)-2-methoxy-2-(2,4,4'-trifluoro-biphenyl-3-yl)-acetamide acetate | 4-Fluoro-benzene boronic acid | White solid | 428.5 |
| 231 | (RS)-N-(4-Carbamimidoyl-benzyl)-2-(2,4-difluoro-4'-methylsulfanyl-biphenyl-3-yl)-2-methoxy-acetamide hydrochloride | 4-(Methylthio)-phenyl-boronic acid | White solid | 456.4 |
| 232 | (RS)-N-(4-Carbamimidoyl-benzyl)-2-(2,4-difluoro-3'-trifluoromethyl-biphenyl-3-yl)-2-methoxy-acetamide acetate | 3-(Trifluoromethyl)phenyl boronic acid | White solid | 478.3 |
| 233 | (RS)-N-(4-Carbamimidoyl-benzyl)-2-(2,4-difluoro-4'-methoxy-biphenyl-3-yl)-2-methoxy-acetamide hydrochloride | 4-Methoxy-phenylboronic acid | White solid | 440.5 |

Example 234

To a solution in DMSO (40 ml) of (RS)-trifluoro-methanesulfonic acid 3-[(4-cyano-benzylcarbamoyl)-methoxymethyl]-2,4-difluoro-phenyl ester (5.0 g) was added MeOH (21.8 ml), Et$_3$N (4.5 ml), [Pd(OAc)$_2$] (73 mg) and 1,3-bis-(diphenylphosphino)propane. The solution was saturated with carbon monoxide. The dark reaction mixture was stirred 2 h at 70° C. and 1 atm carbon monoxide. The mixture was poured on ice cold H$_2$O (400 ml) and 2 N aq. HCl sol. (30 ml). The product was extracted with AcOEt (2×200 ml). The organic layers were washed with brine (2×200 ml), combined and dried over Na$_2$SO$_4$. The solvent was evaporated and the residue was fractionated by CC (AcOEt/Hept 1:9 to 4:1) to obtain 2.45 g (61%) of (RS)-3-[(4-cyano-benzylcarbamoyl)-methoxy-methyl]-2,4-difluoro-benzoic acid methyl ester. Yellowish solid.

Example 235

A solution of (RS)-3-[(4-cyano-benzylcarbamoyl)-methoxy-methyl]-2,4-difluoro-benzoic acid methyl ester (2.05 g) and LiOH.H$_2$O (241 mg) in THF/MeOH/H$_2$O 1:1:0.5 (75 ml) was stirred 1 h at rt. The organic solvents were evaporated, ice cold H$_2$O (50 ml) was added and the pH was lowered (pH=2) by addition of 2 N aq. HCl sol. The product was extracted with AcOEt (2×120 ml). The organic layers were washed with brine (100 ml), combined and dried over Na$_2$SO$_4$. Evaporation of the solvent yielded 1.80 g of (RS)-3-[(4-cyano-benzylcarbamoyl)-methoxy-methyl]-2,4-difluoro-benzoic acid. White solid. MS 359.4 ([M−H]).

Example 236

236.1

To a solution under Ar of (RS)-3-[(4-cyano-benzylcarbamoyl)-methoxy-methyl]-2,4-difluoro-benzoic acid (150 mg) in DMF (2 ml) was added 1,1'-carbonyldiimidazole (74 mg). The reaction mixture was stirred 15 min at rt before addition of morpholine. After stirring 2 h at rt hydroxylamine hydrochloride (289 mg) and Et$_3$N (0.3 ml) were added. The reaction mixture was stirred 20 h at rt, then it was poured on H$_2$O (20 ml) and extracted with AcOEt (2×20 ml). The organic layers were washed with brine and dried (Na$_2$SO$_4$) and the solvent was evaporated. CC (AcOEt/MeOH 99:1 to 9:1) yielded 111 mg (58%) of (RS)-2-[2,6-difluoro-3-(morpholine-4-carbonyl)-phenyl]-N-[4-(N-hydroxycarbamimidoyl)-benzyl]-2-methoxy-acetamide. White solid. MS 463.5 ([M+H]$^+$).

236.2

A solution of (RS)-2-[2,6-difluoro-3-(morpholine-4-carbonyl)-phenyl]-N-[4-(N-hydroxycarbamimidoyl)-benzyl]-2-methoxy-acetamide (125 mg) was hydrogenated 2 days at rt and 1 atm H$_2$ in presence of 10% Pd/C (13 mg) and AcOH (143 mg). The catalyst was filtered away and the solvent was evaporated to obtain 115 mg of (RS)-N-(4-carbamimidoyl-benzyl)-2-[2,6-difluoro-3-(morpholine-4-carbonyl)-phenyl]-2-methoxy-acetamide acetate. Off-white solid, MS 447.1 ([M+H]$^+$).

Examples 237–2441

Examples 237–241 were prepared in analogy to example 236:

| No. | Name | Amine | Appearance | MS [M + H]⁺ |
|---|---|---|---|---|
| 237 | (RS)-3-[(4-Carbamimidoyl-benzylcarbamoyl)-methoxy-methyl]-N-ethyl-2,4-difluoro-benzamide acetate | Ethylamine hydrochloride | Off-white solid | 405.3 |
| 238 | (RS)-3-[(4-Carbamimidoyl-benzylcarbamoyl)-methoxy-methyl]-2,4-difluoro-N-(2-methoxy-ethyl)-benzamide acetate | 2-Methoxy-ethylamine | Off-white solid | 435.3 |
| 239 | (RS)-3-[(4-Carbamimidoyl-benzylcarbamoyl)-methoxy-methyl]-N,N-diethyl-2,4-difluoro-benzamide acetate | Diethylamine | Off-white foam | 433.4 |
| 240 | (RS)-3-[(4-Carbamimidoyl-benzylcarbamoyl)-methoxy-methyl]-2,4-difluoro-N-(2,2,2-trifluoro-ethyl)-benzamide acetate | 2,2,2-Trifluoro-ethylamine | Off-white solid | 459.1 |
| 241 | (RS)-3-[(4-Carbamimidoyl-benzylcarbamoyl)-methoxy-methyl]-N-cyclopropylmethyl-2,4-difluoro-benzamide acetate | Aminomethyl-cyclopropane | Off-white solid | 431.4 |

Examples 242–244

Example 242–244 were prepared from (RS)-N-(4-cyano-benzyl)-2-(2,6-difluoro-3-hydroxy-phenyl)-2-methoxy-acetamide by a sequence consisting of a Mitsunobu reaction (procedure E2), the formation of the N-hydroxy-benzamidines (procedure G) and the reduction to the benzamidines (procedure I).

| No. | Name | ROH | Appearance | MS [M + H]⁺ |
|---|---|---|---|---|
| 242 | (RS)-N-(4-Carbamimidoyl-benzyl)-2-[2,6-difluoro-3-(pyridin-2-ylmethoxy)-phenyl]-2-methoxy-acetamide dihydrochloride | 2-(Hydroxy-methyl)pyridine) | White foam | 441.5 |
| 243 | (RS)-N-(4-Carbamimidoyl-benzyl)-2-[2,6-difluoro-3-(pyridin-3-ylmethoxy)-phenyl]-2-methoxy-acetamide dihydrochloride | 3-(Hydroxy-methyl)pyridine | Off-white foam | 441.3 |
| 244 | (RS)-N-(4-Carbamimidoyl-benzyl)-2-[2,6-difluoro-3-(pyridin-4-ylmethoxy)-phenyl]-2-methoxy-acetamide dihydrochloride | 4-(Hydroxy-methyl)pyridine | Greenish foam | 441.4 |

Example 245

(RS)-N-(4-Carbamimidoyl-benzyl)-2-[2,6-difluoro-3-(4-fluoro-phenoxy)-phenyl]-2-methoxy-acetamide acetate

245.1

To a solution of (RS)-N-(4-cyano-benzyl)-2-(2,6-difluoro-3-hydroxy-phenyl)-2-methoxy-acetamide (370 mg) in 1,2-dichloroethane (10 ml) was added copper(II)acetate (222 mg), 4-fluorobenzoic acid (467 mg) and powdered MS4 Å (2 g). Et₃N (563 mg) was added and the mixture was stirred 2 days at rt. The mixture was passed over silica gel eluting with AcOEt. CC (AcOEt/Hept 1:3 to 3:1) yielded 203 mg (61%) of (RS)-N-(4-cyano-benzyl)-2-[2,6-difluoro-3-(4-fluoro-phenoxy)-phenyl]-2-methoxy-acetamide. Yellow oil. MS 427.0 ([M+H]⁺).

245.2

(RS)-N-(4-Cyano-benzyl)-2-[2,6-difluoro-3-(4-fluoro-phenoxy)-phenyl]-2-methoxy-acetamide (200 mg) was transformed in (RS)-2-[2,6-difluoro-3-(4-fluoro-phenoxy)-phenyl]-N-[4-(N-hydroxycarbamimidoyl)-benzyl]-2-methoxy-acetamide (174 mg, 81%) by procedure G.

245

Reduction of (RS)-2-[2,6-difluoro-3-(4-fluoro-phenoxy)-phenyl]-N-[4-(N-hydroxycarbamimidoyl)-benzyl]-2-methoxy-acetamide (173 mg) by procedure H afforded 176 mg (93%) of (RS)-N-(4-carbamimidoyl-benzyl)-2-[2,6-difluoro-3-(4-fluoro-phenoxy)-phenyl]-2-methoxy-acetamide acetate. White crystals. MS 444.1 ([M+H]$^+$).

Example 246

(RS)-N-(4-Carbamimidoyl-benzyl)-2-[2,6-difluoro-3-(pyridin-3-yloxy)-phenyl]-2-methoxy-acetamide acetate was prepared analogously with example 245. Off-white crystals. MS 427.1 ([M+H]$^+$).

Example 247

247.1

To a solution of (RS)-2-(4-bromo-2,6-difluoro-phenyl)-N-(4-cyano-benzyl)-2-methoxy-acetamide (example 69.1, 247 mg) in 1,2-dimethoxyethane (5 ml) was added tetrakis(triphenylphosphine) palladium (0) (73 mg). A solution of phenylboronic acid (118 mg) in EtOH (2.1 ml) and a solution of sodium carbonate (563 mg) in water (3 ml) were added. The mixture was stirred for 1.5 h at 85° C. The solids were filtered off and the filtrate was evaporated. The product was purified by flash chromatography (cyclohexane/EtOAc 2:1=>EtOAc) to give (RS)-N-(4-cyano-benzyl)-2-(3,5-difluoro-biphenyl-4-yl)-2-methoxy-acetamide (172 mg). Off-white solid. MS 393.1 ([M+H]$^+$)

247.2

(RS)-N-(4-Cyano-benzyl)-2-(3,5-difluoro-biphenyl-4-yl)-2-methoxy-acetamide was converted to (RS)-N-(4-carbamimidoyl-benzyl)-2-(3,5-difluoro-biphenyl-4-yl)-2-methoxy-acetamide hydrochloride according to general procedure D. Off-white solid. MS 410.2 ([M+H]$^+$)

Example 248

248.1

The crude 4-bromo-2,6-difluorobenzaldehyde described in example 69.1 was reacted according to general procedure A using ethanol/dioxane as a solvent. The product of this reaction was subsequently coupled with 4-aminomethyl benzonitrile according to general procedure B to give (RS)-2-(4-bromo-2,6-difluoro-phenyl)-N-(4-cyano-benzyl)-2-ethoxy-acetamide. Yellow oil.

248.2

In analogy to example 247.1, (RS)-2-(4-bromo-2,6-difluoro-phenyl)-N-(4-cyano-benzyl)-2-ethoxy-acetamide was reacted with phenylboronic acid to give (RS)-N-(4-cyano-benzyl)-2-(3,5-difluoro-biphenyl-4-yl)-2-ethoxy-acetamide. Yellow solid. MS 407.3 ([M+H]$^+$)

248.3

(RS)-N-(4-Cyano-benzyl)-2-(3,5-difluoro-biphenyl-4-yl)-2-ethoxy-acetamide was converted to (RS)-N-(4-carbamimidoyl-benzyl)-2-(3,5-difluoro-biphenyl-4-yl)-2-ethoxy-acetamide hydrochloride according to general procedure D. Off-white solid. MS 424.4 ([M+H]$^+$)

Example 249

Using similar procedures to the ones described in example 248.2 and 248.3, (RS)-2-(4-bromo-2,6-difluoro-phenyl)-N-(4-cyano-benzyl)-2-ethoxy-acetamide was converted to (RS)-N-(4-carbamimidoyl-benzyl)-2-[2,6-difluoro-4-(1H-indol-5-yl)-phenyl]-2-ethoxy-acetamide acetic acid. Colorless solid. MS 463.0 ([M+H]$^+$)

Example 250

250.1

Analogous to example 247.1, (RS)-2-(4-bromo-2,6-difluoro-phenyl)-N-(4-cyano-benzyl)-2-ethoxy-acetamide (example 248.1) was reacted with 2-furanboronic acid to give (RS)-N-(4-cyano-benzyl)-2-(2,6-difluoro-4-furan-2-yl-phenyl)-2-ethoxy-acetamide. Off-white solid. MS 397.0 ([M+H]$^+$)

250.2

In analogy to example 15.5, (RS)-N-(4-cyano-benzyl)-2-(2,6-difluoro-4-furan-2-yl-phenyl)-2-ethoxy-acetamide was reacted with hydroxylamine hydrochloride to give (RS)-2-(2,6-difluoro-4-furan-2-yl-phenyl)-2-ethoxy-N-[4-(N-hydroxycarbamimidoyl)-benzyl]-acetamide. Colorless solid. MS 430.0 ([M+H]$^+$)

250.3

In analogy to example 37.5, (RS)-2-(2,6-difluoro-4-furan-2-yl-phenyl)-2-ethoxy-N-[4-(N-hydroxycarbamimidoyl)-benzyl]-acetamide was reduced to give (RS)-N-(4-carbamimidoyl-benzyl)-2-(2,6-difluoro-4-furan-2-yl-phenyl)-2-ethoxy-acetamide acetate. Colorless solid. MS 414.0 ([M+H]$^+$)

Example 251

As a side product of example 250.3, there was obtained N-(4-carbamimidoyl-benzyl)-2-[2,6-difluoro-4-(tetrahydro-furan-2-yl)-phenyl]-2-ethoxy-acetamide acetic acid. Off-white solid. MS 418.0 ([M+H]$^+$)

Example 252

252.1

In analogy to example 247.1, (RS)-2-(4-bromo-2,6-difluoro-phenyl)-N-(4-cyano-benzyl)-2-ethoxy-acetamide (example 248.1) was reacted with 3-hydroxyphenylboronic acid. The product of this reaction was alkylated with ethylbromoacetate and cesiumcarbonate in DMF (analogous to example 16.4) to give (RS)-{4'-[(4-cyano-benzylcarbamoyl)-ethoxy-methyl]-3',5'-difluoro-biphenyl-3-yloxy}-acetic acid ethyl ester. Colorless oil. MS 509.1 ([M+H]$^+$)

252.2

(RS)-{4'-[(4-Cyano-benzylcarbamoyl)-ethoxy-methyl]-3',5'-difluoro-biphenyl-3-yloxy}-acetic acid ethyl ester was converted to (RS)-4'-[(4-carbamimidoyl-benzylcarbamoyl)-ethoxy-methyl]-3',5'-difluoro-biphenyl-3-yloxy-acetic acid ethyl ester hydrochloride according to general procedure D. Colorless foam. MS 526.2 ([M+H]$^+$)

252.3

In analogy to example 20.1, (RS)-{4'-[(4-carbamimidoyl-benzylcarbamoyl)-ethoxy-methyl]-3',5'-difluoro-biphenyl-3-yloxy}-acetic acid ethyl ester hydrochloride was hydrolyzed to (RS)-{4'-[(4-carbamimidoyl-benzylcarbamoyl)-ethoxy-methyl]-3',5'-difluoro-biphenyl-3-yloxy}1-acetic acid. Colorless solid. MS 498.3 ([M+H]$^+$)

Using similar procedures to the ones described in example 252.1 and 252.2, (RS)-2-(4-bromo-2,6-difluoro-phenyl)-N-(4-cyano-benzyl)-2-ethoxy-acetamide (example 248.1) was converted to the following compounds:

Example 253

(RS)-N-(4-Carbamimidoyl-benzyl)-2-(3'-carbamoyl-methoxy-3,5-difluoro-biphenyl-4-yl)-2-ethoxy-acetamide hydrochloride, MS 497.2 ([M+H]$^+$)

Example 254

RS)-N-(4-Carbamimidoyl-benzyl)-2-[3,5-difluoro-3'-(2-hydroxy-ethoxy)-biphenyl-4-yl]-2-ethoxy-acetamide hydrochloride, MS 484.3 ([M+H]$^+$)

Example 255

(RS)-N-(4-Carbamimidoyl-benzyl)-2-[3'-(3-dimethylamino-propoxy)-3,5-difluoro-biphenyl-4-yl]-2-ethoxy-acetamide hydrochloride, MS 525.3 ([M+H]$^+$)

Example 256

256.1
In analogy to example 247.1, (RS)-2-(4-bromo-2,6-difluoro-phenyl)-N-(4-cyano-benzyl)-2-ethoxy-acetamide (example 248.1) was reacted with 2-hydroxyphenylboronic acid to give (RS)-N-(4-cyano-benzyl)-2-(3,5-difluoro-2'-hydroxy-biphenyl-4-yl)-2-ethoxy-acetamide. Off-white solid. MS 423.0 ([M+H]$^+$)

256.2
In analogy to example 22.1, (RS)-N-(4-cyano-benzyl)-2-(3,5-difluoro-2'-hydroxy-biphenyl-4-yl)-2-ethoxy-acetamide was reacted in a Mitsunobu reaction with 2-benzyloxy-ethanol, diethyl azodicarboxylate and triphenyl phosphine in THF to give (RS)-2-[2'-(2-benzyloxy-ethoxy)-3,5-difluoro-biphenyl-4-yl]-N-(4-cyano-benzyl)-2-ethoxy-acetamide. Yellow oil. MS 557.2 ([M+H]$^+$)

256.3
(RS)-2-[2'-(2-Benzyloxy-ethoxy)-3,5-difluoro-biphenyl-4-yl]-N-(4-cyano-benzyl)-2-ethoxy-acetamide was converted to (RS)-2-[2'-(2-benzyloxy-ethoxy)-3,5-difluoro-biphenyl-4-yl]-N-(4-carbamimidoyl-benzyl)-2-ethoxy-acetamide hydrochloride according to general procedure D. Colorless solid. MS 574.3 ([M+H]$^+$)

Example 257

257.1
In analogy to example 16.4, (RS)-N-(4-cyano-benzyl)-2-(3,5-difluoro-2'-hydroxy-biphenyl-4-yl)-2-ethoxy-acetamide (example 256.1) was alkylated with 1-chloro-2-dimethylaminoethane hydrochloride and cesium carbonate in DMF to give (RS)-N-(4-cyano-benzyl)-2-[2'-(2-dimethylamino-ethoxy)-3,5-difluoro-biphenyl-4-yl]-2-ethoxy-acetamide. Colorless solid. MS 494.1 ([M+H]$^+$)

257.2
(RS)-N-(4-Cyano-benzyl)-2-[2'-(2-dimethylamino-ethoxy)-3,5-difluoro-biphenyl-4-yl]-2-ethoxy-acetamide was converted to (RS)-N-(4-carbamimidoyl-benzyl)-2-[2'-(2-dimethylamino-ethoxy)-3,5-difluoro-biphenyl-4-yl]-2-ethoxy-acetamide hydrochloride according to general procedure D. Colorless solid. MS 511.1 ([M+H]$^+$)

Using similar procedures to the ones described in example 257.1 and 257.2, (RS)-N-(4-cyano-benzyl)-2-(3,5-difluoro-2'-hydroxy-biphenyl-4-yl)-2-ethoxy-acetamide (example 256.1) was converted to the following compounds:

Example 258

(RS)-N-(4-Carbamimidoyl-benzyl)-2-[3,5-difluoro-2'-(2-hydroxy-ethoxy)-biphenyl-4-yl]-2-ethoxy-acetamide hydrochloride, MS 484.1 ([M+H]$^+$)

Example 259

(RS)-{4'-[(4-Carbamimidoyl-benzylcarbamoyl)-ethoxy-methyl]-3',5'-difluoro-biphenyl-2-yloxy}-acetic acid ethyl ester hydrochloride, MS 526.2 ([M+H]$^+$)

Example 260

In analogy to example 20.1, (RS)-14'-[(4-carbamimidoyl-benzylcarbamoyl)-ethoxy-methyl]-3',5'-difluoro-biphenyl-2-yloxy]-acetic acid ethyl ester hydrochloride was hydrolyzed to (RS)-{4'-[(4-carbamimidoyl-benzylcarbamoyl)-ethoxy-methyl]-3',5'-difluoro-biphenyl-2-yloxy}-acetic acid. Colorless solid. MS 496.4 ([M−H]$^-$)

Example 261

261.1
In analogy to example 16.4, (RS)-N-(4-cyano-benzyl)-2-(3,5-difluoro-2'-hydroxy-biphenyl-4-yl)-2-ethoxy-acetamide (example 256.1) was alkylated with iodoacetamide and cesium carbonate in DMF. The product of this reaction was reacted with hydroxylamine hydrochloride in analogy to example 15.5 to give (RS)-2-(2'-carbamoylmethoxy-3,5-difluoro-biphenyl-4-yl)-2-ethoxy-N-[4-(N-hydroxycarbamimidoyl)-benzyl]-acetamide. Colorless solid. MS 513.1 ([M+H]$^+$)

261.2
In analogy to example 37.5, (RS)-2-(2'-carbamoyl-methoxy-3,5-difluoro-biphenyl-4-yl)-2-ethoxy-N-[4-(N-hydroxycarbamimidoyl)-benzyl]-acetamide was reduced to give (RS)-N-(4-carbamimidoyl-benzyl)-2-(2'-carbamoyl-methoxy-3,5-difluoro-biphenyl-4-yl)-2-ethoxy-acetamide acetate. Colorless solid. MS 497.2 ([M+H]$^+$)

Example 262

262.1
To a solution of (RS)-2-(4-bromo-2,6-difluoro-phenyl)-N-(4-cyano-benzyl)-2-ethoxy-acetamide (example 248.1, 800 mg) in DMSO (9 ml) were added bis(pinacolato)diboron (546 mg), potassium acetate (581 mg) and dichloro (1,1'-bis(diphenylphosphino)ferrocene)palladium(II) (44 mg). The mixture was stirred at 85° C. for 5 h and at 50° C. overnight. Dichloro(1,1'-bis(diphenylphosphino)ferrocene)palladium(II) (44 mg) was added and the mixture was stirred at 85° C. for 8 h and at 50° C. overnight. After cooling to rt, ice water was added. The mixture was filtered and the filtrate was extracted with EtOAc. The org. phase was dried, filtered and concentrated. The product was purified by chromatography (SiO$_2$, cyclohexane/EtOAc 4:1=>EtOAc) to give (RS)-N-(4-cyano-benzyl)-2-[2,6-difluoro-4-(4,4,5,5-tetramethyl-[1,3,2]dioxaborolan-2-yl)-phenyl]-2-ethoxy-acetamide (625 mg). Off-white solid. MS 457.3 ([M+H]$^+$)

262.2
To a stirred solution of (RS)-N-(4-cyano-benzyl)-2-[2,6-difluoro-4-(4,4,5,5-tetramethyl-[1,3,2]dioxaborolan-2-yl)-phenyl]-2-ethoxy-acetamide (300 mg) in 1,2-dimethoxy-ethane (8 ml) was added 4-bromopyridine hydrochloride (387 mg). A solution of sodium carbonate (210 mg) in water (2.1 ml) and dichloro(1,1'-bis(diphenylphosphino)ferrocene)palladium (II) (48 mg) were added. The mixture was stirred at 85° C. for 4 h and at rt overnight. After cooling to rt, ice water was added. The mixture was filtered and the filtrate was extracted with EtOAc. The org. phase was washed with brine, dried, filtered and concentrated. The product was purified by chromatography (SiO2, cyclohexane/EtOAc 2:1=>EtOAc) to give (RS)-N-(4-cyano-benzyl)-2-(2,6-difluoro-4-pyridin-4-yl-phenyl)-2-ethoxy-acetamide (189 mg). Off-white solid. MS 408.2 ([M+H]$^+$)

262.3

(RS)-N-(4-Cyano-benzyl)-2-(2,6-difluoro-4-pyridin-4-yl-phenyl)-2-ethoxy-acetamide was converted to (RS)-N-(4-carbamimidoyl-benzyl)-2-(2,6-difluoro-4-pyridin-4-yl-phenyl)-2-ethoxy-acetamide hydrochloride according to general procedure D. Colorless solid. MS 425.2 ([M+H]$^+$)

Using similar procedures to the ones described in example 262.2 and 262.3, (RS)-N-(4-cyano-benzyl)-2-[2,6-difluoro-4-(4,4,5,5-tetramethyl-[1,3,2]dioxaborolan-2-yl)-phenyl]-2-ethoxy-acetamide (example 262.1) was converted to the following compounds:

Example 263

(RS)-N-(4-Carbamimidoyl-benzyl)-2-(2,6-difluoro-4-pyrimidin-5-yl-phenyl)-2-ethoxy-acetamide hydrochloride, MS 426.2 ([M+H]$^+$)

Example 264

(RS)-N-(4-Carbamimidoyl-benzyl)-2-(2,6-difluoro-4-pyrimidin-2-yl-phenyl)-2-ethoxy-acetamide hydrochloride, MS 426.1 ([M+H]$^+$)

Example 265

(RS)-N-(4-Carbamimidoyl-benzyl)-2-(2,6-difluoro-4-pyridin-2-yl-phenyl)-2-ethoxy-acetamide hydrochloride, MS 425.1 ([M+H]$^+$)

Example 266

(RS)-2-[4-(2-Amino-pyrimidin-5-yl)-2,6-difluoro-phenyl]-N-(4-carbamimidoyl-benzyl)-2-ethoxy-acetamide hydrochloride, MS 441.0 ([M+H]$^+$)

Example 267

(RS)-N-(4-Carbamimidoyl-benzyl)-2-(2,6-difluoro-4-pyridin-3-yl-phenyl)-2-ethoxy-acetamide hydrochloridr, MS 424.6 ([M]$^+$)

Example 268

(RS)-2-[4-(6-Amino-pyridin-2-yl)-2,6-difluoro-phenyl]-N-(4-carbamimidoyl-benzyl)-2-ethoxy-acetamide hydrochloride, MS 440.1 ([M+H]$^+$)

Example 269

(RS)-2-[4-(5-Amino-pyridin-2-yl)-2,6-difluoro-phenyl]-N-(4-carbamimidoyl-benzyl)-2-ethoxy-acetamide hydrochloride, MS 440.0 ([M+H]$^+$)

Example 270

(RS)-4'-[(4-Carbamimidoyl-benzylcarbamoyl)-ethoxy-methyl]-3',5'-difluoro-biphenyl-3-carboxylic acid methyl ester hydrochloride, MS 482.1 ([M+H]$^+$)

Example 271

(RS)-(2-[4-(6-Amino-pyridin-3-yl)-2,6-difluoro-phenyl]-N-(4-carbamimidoyl-benzyl)-2-ethoxy-acetamide hydrochloride, MS 440.3 ([M+H]$^+$)

Example 272

In analogy to example 20.1, (RS)-4'-[(4-carbamimidoyl-benzylcarbamoyl)-ethoxy-methyl]-3',5'-difluoro-biphenyl-3-carboxylic acid methyl ester hydrochloride (example 270) was hydrolyzed to (RS)-4'-[(4-carbamimidoyl-benzylcarbamoyl)-ethoxy-methyl]-3',5'-difluoro-biphenyl-3-carboxylic acid. Off-white solid. MS 468.1 ([M+H]$^+$)

Example 273

Analogous to example 15.4, (RS)-(2-[4-(6-amino-pyridin-3-yl)-2,6-difluoro-phenyl]-N-(4-carbamimidoyl-benzyl)-2-ethoxy-acetamide hydrochloride (example 271) was reacted with ethylchloroformate and triethylamine in DMF to give (RS)-[amino-[4-({2-[4-(6-amino-pyridin-3-yl)-2,6-difluoro-phenyl]-2-ethoxy-acetylamino]-methyl)-phenyl]-methylene}-carbamic acid ethyl ester. Off-white solid. MS 512.1 ([M+H]$^+$)

Example 274

To a solution of (RS)-(2-[4-(6-amino-pyridin-3-yl)-2,6-difluoro-phenyl]-N-(4-carbamimidoyl-benzyl)-2-ethoxy-acetamide hydrochloride (example 271, 60 mg) in DMF (1 ml) were added hydroxylamine hydrochloride (27 mg) and triethylamine (38 mg). The mixture was stirred at 50° C. for 2.5 h. After cooling to rt, the mixture was partitioned between EtOAc and ice water and extracted with EtOAc. The organic phase was washed with water, dried, filtered and concentrated to give (RS)2-[4-(6-amino-pyridin-3-yl)-2,6-difluoro-phenyl]-2-ethoxy-N-[4-(N-hydroxycarbamimidoyl)-benzyl]-acetamide (57 mg). Colorless solid. MS 456.0 ([M+H]$^+$)

Example 275

275.1

In analogy to example 262.2, (RS)-N-(4-cyano-benzyl)-2-[2,6-difluoro-4-(4,4,5,5-tetramethyl-[1,3,2]dioxaborolan-2-yl)-phenyl]-2-ethoxy-acetamide (example 262.1) was reacted with 2-bromobenzaldehyde to give (RS)-N-(4-cyano-benzyl)-2-(3,5-difluoro-2'-formyl-biphenyl-4-yl)-2-ethoxy-acetamide. Off-white solid. MS 435.0 ([M+H]$^+$)

275.2

To a suspension of (RS)-N-(4-cyano-benzyl)-2-(3,5-difluoro-2'-formyl-biphenyl-4-yl)-2-ethoxy-acetamide (500 mg) in EtOH (1.2 ml) at 0° C. was added sodium borohydride (91 mg). After 5 min the ice bath was removed. Ice water was added and the mixture was extracted with EtOAc. The organic phase was dried, filtered and concentrated. The product was purified by chromatography (SiO$_2$, cyclohexane/EtOAc 1:2=>EtOAc) to give (RS)-N-(4-cyano-benzyl)-2-(3,5-difluoro-2'-hydroxymethyl-biphenyl-4-yl)-2-ethoxy-acetamide (413 mg). Colorless solid. MS 437.0 ([M+H]$^+$)

275.3

(RS)-N-(4-Cyano-benzyl)-2-(3,5-difluoro-2'-hydroxymethyl-biphenyl-4-yl)-2-ethoxy-acetamide was converted to (RS)-N-(4-carbamimidoyl-benzyl)-2-(3,5-difluoro-2'-hydroxymethyl-biphenyl-4-yl)-2-ethoxy-acetamide hydrochloride according to general procedure D. Colorless solid. MS 454.0 ([M+H]$^+$)

Example 276

As a side product of example 275.3, there was obtained (RS)-N-(4-carbamimidoyl-benzyl)-2-(2'-chloromethyl-3,5-difluoro-biphenyl-4-yl)-2-ethoxy-acetamide. Colorless solid. MS 472.0 ([M+H]$^+$)

Example 277

277.1

In analogy to example 15.5, (RS)-N-(4-cyano-benzyl)-2-(3,5-difluoro-2'-formyl-biphenyl-4-yl)-2-ethoxy-acetamide (example 275.1) was reacted with hydroxylamine hydrochloride to give (RS)-2-[3,5-difluoro-2'-(hydroxyimino-methyl)-biphenyl-4-yl]-2-ethoxy-N-[4-(N-hydroxycarbamimidoyl)-benzyl]-acetamide. Colorless solid. MS 483.1 ([M+H]$^+$)

277.2

In analogy to example 37.5, (RS)-2-[3,5-difluoro-2'-(hydroxyimino-methyl)-biphenyl-4-yl]-2-ethoxy-N-[4-(N-hydroxycarbamimidoyl)-benzyl]-acetamide was reduced to give (RS)-2-(2'-aminomethyl-3,5-difluoro-biphenyl-4-yl)-N-(4-carbamimidoyl-benzyl)-2-ethoxy-acetamide acetate. Light green solid. MS 453.4 ([M+H]$^+$)

Example 278

278.1

2-Fluoro-3-hydroxy-4-methoxy-benzaldehyde (CAS 79418-73-8) was benzylated to give 3-benzyloxy-2-fluoro-4-methoxy-benzaldehyde in analogy to example 16.4. Light yellow oil. MS 260.1 ([M]$^+$)

278.2

3-Benzyloxy-2-fluoro-4-methoxy-benzaldehyde was converted to (RS)-(3-benzyloxy-2-fluoro-4-methoxy-phenyl)-methoxy-acetic acid according to general procedure A. Colorless gum. MS 319.1 ([M–H]$^+$)

278.3

(RS)-(3-Benzyloxy-2-fluoro-4-methoxy-phenyl)-methoxy-acetic acid was debenzylated by hydrogenation in analogy to example 16.2 and then coupled with 4-aminobenzonitrile according to general procedure C to give (RS)-N-(4-cyano-benzyl)-2-(2-fluoro-3-hydroxy-4-methoxy-phenyl)-2-methoxy-acetamide. Off-white foam. MS 345.1 ([M+H]$^+$)

278.4

A mixture of (RS)-N-(4-cyano-benzyl)-2-(2-fluoro-3-hydroxy-4-methoxy-phenyl)-2-methoxy-acetamide (150 mg), phenyl boronic acid (58 mg), copper (II) acetate (79 mg), pyridine (0.18 ml) and activated molecular sieves (4 A) at rt in CH$_2$Cl$_2$ under an argon atmosphere was stirred for 24 h. More copper (II) acetate (40 mg), phenyl boronic acid (29 mg) and pyridine (0.9 ml) were added to the mixture and stirring was continued for 16 h. The mixture was filtered and the cake washed with 15 ml CH$_2$Cl$_2$. The filtrate was washed with 1.0 N HCl (25 ml), 1.0 N NaOH (25 ml) and brine (25 ml), dried (MgSO$_4$), filtered and concentrated (rotavapor) to leave the crude product as a brown gum. The crude product was purified by flash chromatography (cyclohexane=5 cyclohexane/EtOAc 2:3) to give (RS)-N-(4-Cyano-benzyl)-2-(2-fluoro-4-methoxy-3-phenoxy-phenyl)-2-methoxy-acetamide (107 mg) as an off-white foam. MS 421.2 ([M+H]$^+$)

278.5

(RS)-N-(4-Cyano-benzyl)-2-(2-fluoro-4-methoxy-3-phenoxy-phenyl)-2-methoxy-acetamide was converted to (RS)-N-(4-carbamimidoyl-benzyl)-2-(2-fluoro-4-methoxy-3-phenoxy-phenyl)-2-methoxy-acetamide hydrochloride according to general procedure D. Colorless solid. MS 438.3 ([M+H]$^+$)

Example 279

279.1

To a solution of (RS)-N-(4-cyano-benzyl)-2-(2-fluoro-6-hydroxy-phenyl)-2-methoxy-acetamide (1 g, example 80.4) in dichloromethane (25 ml) were triethylamine (1.02 ml) and DMAP (39 mg). While maintaining temperature at 0° C. by cooling with an ice bath, trifluormethane sulfonic anhydride (0.63 ml) was added slowly. The ice bath was removed after 15 min. Stirring was continued for 5 hrs at rt. The reaction mixture was diluted with dichloromethane, and washed with water, KHCO$_3$ solution (10%) and again water. The organic layer was dried over MgSO$_4$, filtered and concentrated. The crude product was purified by flash chromatography (cyclohexane=>cyclohexane/EtOAc 1:1) to give (RS)-trifluoro-methanesulfonic acid 2-[(4-cyano-benzylcarbamoyl)-methoxy-methyl]-3-fluoro-phenyl ester (1.16 g) as light yellow solid. MS 447.2 ([M+H]$^+$)

279.2

A solution of (RS)-trifluoro-methanesulfonic acid 2-[(4-cyano-benzylcarbamoyl)-methoxy-methyl]-3-fluoro-phenyl ester (600 mg) and PPh$_3$ (42 mg) in TEA (10 ml) was deoxygenated by passing a stream of argon through the reaction mixture. Ethynyltrimethylsilane (0.28 ml) and palladium(II)acetate (9 mg) were added. The mixture was stirred for 5 hrs at 50° C. After cooling to rt, the reaction mixture was diluted with water and extracted with EtOAc. The organic layers were combined, dried over MgSO$_4$, filtrated and concentrated. The crude product was purified by flash chromatography (cyclohexane=>cyclohexane/EtOAc 7:3) to give (RS)-N-(4-cyano-benzyl)-2-(2-fluoro-6-trimethylsilanylethynyl-phenyl)-2-methoxy-acetamide (278 mg) as off-white solid. MS 395.2 ([M+H]$^+$)

279.3

A solution of (RS)-N-(4-cyano-benzyl)-2-(2-fluoro-6-trimethylsilanylethynyl-phenyl)-2-methoxy-acetamide (214 mg) in EtOH (10 ml) was treated with K$_2$CO$_3$ (82 mg). The reaction mixture was stirred over night at r.t, then concentrated. The residue was taken up in water and extracted with EtOAc. The organic layers were combined, dried over MgSO$_4$ and concentrated to give (RS)-N-(4-cyano-benzyl)-2-(2-fluoro-6-trimethylsilanylethynyl-phenyl)-2-methoxy-acetamide (150 mg) as off-white solid. MS 323.2 ([M+H]$^+$)

279.4

(RS)-N-(4-Cyano-benzyl)-2-(2-fluoro-6-trimethylsilanylethynyl-phenyl)-2-methoxy-acetamide was converted to (RS)-N-(4-carbamimidoyl-benzyl)-2-(2-ethynyl-6-fluoro-phenyl)-2-methoxy-acetamide hydrochloride according to general procedure D. Light yellow solid. MS 340.1 ([M+H]$^+$)

Example 280

(RS)-N-(4-carbamimidoyl-benzyl)-2-(2-ethynyl-6-fluoro-phenyl)-2-methoxy-acetamide hydrochloride according was hydrogenated in analogy to example 16.2 to give (RS)-N-(4-carbamimidoyl-benzyl)-2-(2-ethyl-6-fluoro-phenyl)-2-methoxy-acetamide hydrochloride. Off-white solid. MS 344.2 ([M+H]$^+$)

Example 281

281.1

A suspension of (RS)-trifluoro-methanesulfonic acid 2-[(4-cyano-benzylcarbamoyl)-methoxy-methyl]-3-fluoro-phenyl ester (520 mg, example 279.1) in DMF (10 ml) was heated to 100° C. and treated with TEA (0.49 ml), tetrahydro-2-(2-propynyloxy)-2H-pyrane (0.33 ml) and Cu(I)I (18 mg). The reaction mixture was degassed by passing a stream of Argon through the reaction mixture. Then bis(triphenylphosphine)palladium(II)chloride (32 mg) was added. The reaction was heated for 6 hrs at 100° C. After cooling to rt, the mixture was concentrated. The residue was taken up in EtOAc and H$_2$O. After filtration through a glass microfibre filter, phases were separated. The organic layer was washed with brine, dried over MgSO$_4$, filtered and concentrated. The crude product was purified by flash chromatography (cyclohexane=>cyclohexane/EtOAc 3:2) to give (RS)-N-(4-cyano-benzyl)-2-{2-fluoro-6-[3-(tetrahydro-pyran-2-yloxy)-prop-1-ynyl]-phenyl}-2-methoxy-acetamide as off-white solid. MS 454.3 ([M+NH$_4$]$^+$)

281.2

(RS)-N-(4-Cyano-benzyl)-2-{2-fluoro-6-[3-(tetrahydro-pyran-2-yloxy)-prop-1-ynyl]-phenyl}-2-methoxy-acetamide was converted to (RS)-N-(4-carbamimidoyl-benzyl)-2-[2-fluoro-6-(3-hydroxy-prop-1-ynyl)-phenyl]-2-methoxy-acetamide hydrochloride according to procedure D. Light yellow solid. MS 370.2 ([M+H]$^+$)

Example 282

(RS)-N-(4-carbamimidoyl-benzyl)-2-[2-fluoro-6-(3-hydroxy-prop-1-ynyl)-phenyl]-2-methoxy-acetamide hydrochloride was hydrogenated in analogy to example 16.2 to give (RS)-N-(4-carbamimidoyl-benzyl)-2-[2-fluoro-6-(3-hydroxy-propyl)-phenyl]-2-methoxy-acetamide hydrochloride. White solid. MS 374.2 ([M+H]$^+$)

Example 283

283.1

Using a similar procedure as described in example 57.1 (RS)-trifluoro-methanesulfonic acid 2-[(4-cyano-benzylcarbamoyl)-methoxy-methyl]-3-fluoro-phenyl ester (example 279.1) was reacted with phenyl boronic acid to give (RS)-N-(4-cyano-benzyl)-2-(3-fluoro-biphenyl-2-yl)-2-methoxy-acetamide. Solid. MS 375.3 ([M+H]$^+$)

283.2

(RS)-N-(4-Cyano-benzyl)-2-(3-fluoro-biphenyl-2-yl)-2-methoxy-acetamide was converted to (RS)-N-(4-carbamimidoyl-benzyl)-2-(3-fluoro-biphenyl-2-yl)-2-methoxy-acetamide hydrochloride according to general procedure D. Off-white solid. MS 392.3 ([M+H]$^+$)

Using a similar procedure as described in example 283 (RS)-trifluoro-methanesulfonic acid 2-[(4-cyano-benzylcarbamoyl)-methoxy-methyl]-3-fluoro-phenyl este (example 279.1) was converted to the following compounds in Examples 284–286.

Example 284

(RS)-2-(3'-Amino-3-fluoro-biphenyl-2-yl)-N-(4-carbamimidoyl-benzyl)-2-methoxy-acetamide hydrochloride. White solid. MS 407.4 ([M+H]$^+$)

Example 285

(RS)-N-(4-Carbamimidoyl-benzyl)-2-(3-fluoro-3'-nitro-biphenyl-2-yl)-2-methoxy-acetamide hydrochloride. Off-white solid. MS 437.2 ([M+H]$^+$)

Example 286

(RS)-2-[2-(6-Amino-pyridin-2-yl)-6-fluoro-phenyl]-N-(4-carbamimidoyl-benzyl)-2-methoxy-acetamide acetate. Off-white solid. MS 408.3 ([M+H]$^+$)

Example 287

287.1

In analogy to example 16.4 (RS)-N-(4-cyano-benzyl)-2-(2-fluoro-6-hydroxy-phenyl)-2-methoxy-acetamide (example 80.4) was reacted with ethyl bromoacetate to give (RS)-{2-[(4-cyano-benzylcarbamoyl)-methoxy-methyl]-3-fluoro-phenoxy}-acetic acid methyl ester. Yellow oil. MS 387.2 ([M+H]$^+$)

287.2

(RS)-{2-[(4-Cyano-benzylcarbamoyl)-methoxy-methyl]-3-fluoro-phenoxy}-acetic acid methyl ester was converted to (RS)-{2-[(4-carbamimidoyl-benzylcarbamoyl)-methoxy-methyl]-3-fluoro-phenoxy}-acetic acid methyl ester acetate according to general procedure D. White solid. MS 404.3 ([M+H]$^+$)

Example 288

In analogy to example 20.1 (RS)-{2-[(4-carbamimidoyl-benzylcarbamoyl)-methoxy-methyl]-3-fluoro-phenoxy}-acetic acid methyl ester acetate was converted to (RS)-N-(4-Carbamimidoyl-benzyl)-2-(2-fluoro-6-phenoxy-phenyl)-2-methoxy-acetamide hydrochloride. White solid. MS 390.2 ([M+H]$^+$)

Example 289

Using a similar procedure as describe in example 287 (RS)-N-(4-cyano-benzyl)-2-(2-fluoro-6-hydroxy-phenyl)-2-methoxy-acetamide (example 80.4) was converted to (RS)-N-(4-carbamimidoyl-benzyl)-2-[2-(3-dimethylamino-propoxy)-6-fluoro-phenyl]-2-methoxy-acetamide hydrochloride. White solid. MS 417.2 ([M+H]$^+$)

Example 290

Using a similar procedure as describe in example 278.4 and example 278.5 (RS)-N-(4-cyano-benzyl)-2-(2-fluoro-6-hydroxy-phenyl)-2-methoxy-acetamide (example 80.4) was converted to (4-carbamimidoyl-benzyl)-2-(2-fluoro-6-phenoxy-phenyl)-2-methoxy-acetamide hydrochloride. White solid. MS 408.2 ([M+H]$^+$)

Example 291

291.1

(RS)-(2,6-Difluoro-4-methoxy-phenyl)-ethoxy-acetic acid (example 101.3) was coupled with 4-amino benzonitrile according to general procedure B to give (RS)-N-(4-cyano-benzyl)-2-(2,6-difluoro-4-methoxy-phenyl)-2-ethoxy-acetamide. Colorless oil.

291.2

(RS)-N-(4-Cyano-benzyl)-2-(2,6-difluoro-4-methoxy-phenyl)-2-ethoxy-acetamide was converted to (RS)-N-(4-carbamimidoyl-benzyl)-2-(2,6-difluoro-4-methoxy-phenyl)-2-ethoxy-acetamide hydrochloride according to general procedure D. White solid. MS 378.3 ([M+H]$^+$)

Example 292

292.1

Using analogous procedures as described in 101.1, 101.2 and 101.3 1-benzyloxy-3,5-difluoro-benzene (CAS 176175-97-6) was converted to (RS)-(4-benzyloxy-2,6-difluoro-phenyl)-ethoxy-acetic acid. Light yellow oil. MS 321.1 ([M−H]$^−$)

292.2

(RS)-(4-benzyloxy-2,6-difluoro-phenyl)-ethoxy-acetic acid was converted to (RS)-2-(4-benzyloxy-2,6-difluoro-phenyl)-N-(4-cyano-benzyl)-2-ethoxy-acetamide according to general procedure B. Colorless oil. MS 437.2 ([M+H]$^+$)

292.3

(RS)-2-(4-Benzyloxy-2,6-difluoro-phenyl)-N-(4-cyano-benzyl)-2-ethoxy-acetamide was converted to (RS)-2-(4-benzyloxy-2,6-difluoro-phenyl)-N-(4-carbamimidoyl-benzyl)-2-ethoxy-acetamide hydrochloride according to general procedure D. Colorless solid. MS 454.3 ([M+H]$^+$)

Example 293

293.1

In analogy to example 16.2 (RS)-(4-benzyloxy-2,6-difluoro-phenyl)-ethoxy-acetic acid (example 292.1) was debenzylated to give (RS)-(2,6-difluoro-4-hydroxy-phenyl)-ethoxy-acetic acid. Light yellow solid. MS 255.1 ([M+Na]$^+$)

293.2

According to general procedure B (RS)-(2,6-difluoro-4-hydroxy-phenyl)-ethoxy-acetic acid was reacted with 4-amino benzonitrile to give (RS)-N-(4-cyano-benzyl)-2-(2,6-difluoro-4-hydroxy-phenyl)-2-ethoxy-acetamide. Colorless solid. MS 345.0 ([M−H]$^−$)

293.3

In analogy to example 16.4 (RS)-N-(4-cyano-benzyl)-2-(2,6-difluoro-4-hydroxy-phenyl)-2-ethoxy-acetamide was reacted with isopropyl iodide to give (RS)-N-(4-cyano-benzyl)-2-(2,6-difluoro-4-isopropoxy-phenyl)-2-ethoxy-acetamide. Colorless oil. MS 387.1 ([M−H]$^−$)

293.4

(RS)-N-(4-Cyano-benzyl)-2-(2,6-difluoro-4-isopropoxy-phenyl)-2-ethoxy-acetamide was converted to (RS)-N-(4-carbamimidoyl-benzyl)-2-(2,6-difluoro-4-isopropoxy-phenyl)-2-ethoxy-acetamide hydrochloride according to general procedure D. Colorless foam. MS 406.2 ([M+H]$^+$)

Example 294

294.1

In analogy to example 22.1 (RS)-N-(4-cyano-benzyl)-2-(2,6-difluoro-4-hydroxy-phenyl)-2-ethoxy-acetamide (example 293.2) was reacted with 2-(hydroxymethyl)-pyridine to give (RS)-(4-cyano-benzyl)-2-[2,6-difluoro-4-(pyridin-2-ylmethoxy)-phenyl]-2-ethoxy-acetamide. Colorless oil.

294.2

According to general procedure D (RS)-(4-cyano-benzyl)-2-[2,6-difluoro-4-(pyridin-2-ylmethoxy)-phenyl]-2-ethoxy-acetamide was converted to (RS)-N-(4-carbamimidoyl-benzyl)-2-[2,6-difluoro-4-(pyridin-2-ylmethoxy)-phenyl]-2-ethoxy-acetamide hydrochloride. Colorless solid. MS 455.2 ([M+H]$^+$)

Example 295

In analogy to example 15.5 (RS)-(4-cyano-benzyl)-2-[2,6-difluoro-4-(pyridin-2-ylmethoxy)-phenyl]-2-ethoxy-acetamide (example 294.1) was converted to (RS)-2-[2,6-difluoro-4-(pyridin-2-ylmethoxy)-phenyl]-2-ethoxy-N-[4-(N-hydroxycarbamimidoyl)-benzyl]-acetamide. Colorless foam. MS 471.2 ([M+H]$^+$)

Example 296

In analogy to example 15.4 (RS)-(4-cyano-benzyl)-2-[2,6-difluoro-4-(pyridin-2-ylmethoxy)-phenyl]-2-ethoxy-acetamide (example 294.1) was reacted ethyl chloroformate to give (RS)-{amino-[4-({2-[2,6-difluoro-4-(pyridin-2-ylmethoxy)-phenyl]-2-ethoxy-acetylamino}-methyl)-phenyl]-methylene}-carbamic acid ethyl ester. Colorless foam. MS 527.2 ([M+H]$^+$)

Using analogous procedures as described in example 294.1 and 294.2 (RS)-N-(4-cyano-benzyl)-2-(2,6-difluoro-4-hydroxy-phenyl)-2-ethoxy-acetamide (example 293.2) was converted to the following compounds in Examples 297 and 298.

Example 297

(RS)-N-(4-carbamimidoyl-benzyl)-2-[2,6-difluoro-4-(pyridin-3-ylmethoxy)-phenyl]-2-ethoxy-acetamide hydrochloride. Colorless foam. MS 455.2 ([M+H]$^+$)

Example 298

(RS)-N-(4-carbamimidoyl-benzyl)-2-[2,6-difluoro-4-(pyridin-4-ylmethoxy)-phenyl]-2-ethoxy-acetamide hydrochloride. Light yellow foam. MS 455.2 ([M+H]$^+$)

Example 299

299.1

In analogy to example 278.4 (RS)-N-(4-cyano-benzyl)-2-(2,6-difluoro-4-hydroxy-phenyl)-2-ethoxy-acetamide (example 293.2) was reacted with phenyl boronic acid to give (RS)-N-(4-cyano-benzyl)-2-(2,6-difluoro-4-phenoxy-phenyl)-2-ethoxy-acetamide. Light yellow solid. MS 423.1 ([M+H]$^+$)

299.2

(RS)-N-(4-Cyano-benzyl)-2-(2,6-difluoro-4-phenoxy-phenyl)-2-ethoxy-acetamide was converted to (RS)-N-(4-carbamimidoyl-benzyl)-2-(2,6-difluoro-4-phenoxy-phenyl)-2-ethoxy-acetamide hydrochloride according to general procedure D. White solid. MS 440.2 ([M+H]$^+$)

Example 300

Using analogous procedures as described in example 22 (RS)-N-(4-cyano-benzyl)-2-(2,6-difluoro-4-hydroxy-phenyl)-2-ethoxy-acetamide (example 293.2) was converted to RS)-N-(4-carbamimidoyl-benzyl)-2-[2,6-difluoro-4-(pyridin-3-yloxy)-phenyl]-2-ethoxy-acetamide hydrochloride. Colorless foam. MS 441.2 ([M+H]$^+$)

Using analogous procedures as described in example 293.3 and 293.4 (RS)-N-(4-cyano-benzyl)-2-(2,6-difluoro-3-hydroxy-phenyl)-2-ethoxy-acetamide (example 213) was converted to ?

Example 301

(RS)-N-(4-Carbamimidoyl-benzyl)-2-(2,6-difluoro-3-isopropoxy-phenyl)-2-ethoxy-acetamide hydrochloride. Colorless foam. MS 406.3 ([M+H]$^+$)

Example 302

(RS)-N-(4-Carbamimidoyl-benzyl)-2-(3-carbamoyl-methoxy-2,6-difluoro-phenyl)-2-ethoxy-acetamide hydrochloride. Colorless foam. MS 421.1 ([M+H]$^+$) Using analogous procedures as described in example 294 (RS)-N-(4-cyano-benzyl)-2-(2,6-difluoro-3-hydroxy-phenyl)-2-ethoxy-acetamide (example 213) was converted to the compound of Example 303.

Example 303

(RS)-2-[3-(2-Benzyloxy-ethoxy)-2,6-difluoro-phenyl]-N-(4-carbamimidoyl-benzyl)-2-ethoxy-acetamide hydrochloride. Colorless foam. MS 498.3 ([M+H]$^+$)

Example 304

The product (below) was isolated as a side product in the preparation of example 26. (RS)-N-(4-carbamimidoyl-benzyl)-2-[2,6-difluoro-3-(2-hydroxy-ethoxy)-phenyl]-2-ethoxy-acetamide hydrochloride. Colorless foam. MS 408.3 ([M+H]$^+$)

Example 305

Using analogous procedures to example 299 (RS)-N-(4-cyano-benzyl)-2-(2,6-difluoro-3-hydroxy-phenyl)-2-ethoxy-acetamide (example 213) was converted to (RS)-N-(4-carbamimidoyl-benzyl)-2-(2,6-difluoro-3-phenoxy-phenyl)-2-ethoxy-acetamide acetate. Solid. MS 408.3 ([M+H]$^+$)

Example 306

Using analogous procedures to example 283 (RS)-N-(4-cyano-benzyl)-2-(2,6-difluoro-3-hydroxy-phenyl)-2-ethoxy-acetamide (example 213) was converted to (RS)-N-(4-carbamimidoyl-benzyl)-2-(2,4-difluoro-biphenyl-3-yl)-2-ethoxy-acetamide hydrochloride. Colorless solid. MS 424.2 ([M+H]$^+$)

Example 307

307.1

A stirred solution of 2,4-difluorbenzoic acid (20.8 g) and N-ethyldiisopropylamine (26.8 ml) in dioxane (80 ml) was treated with diphenyl phosphory azide (37.9 ml; very exothermic!) and tert-butanol (80 ml) at rt and under an argon atmosphere. The mixture was then heated to 90° C. and stirring was continued for 16 h. The mixture (brown solution) was cooled to rt, diluted with EtOAc, washed with water and brine, dried over MgSO$_4$ and treated at the same time with decolorizing charcoal, and finally filtered over a celite pad. The yellow filtrate was concentrated to leave the crude product as an orange oil. The crude product was purified by flash chromatography (cyclohexane/EtOAc 85:15). The product-containing fractions were combined and concentrated. The residue (yellow oil containing white solid) was taken up in 50 ml heptane. The solid (symmetric urea which was formed as by-product during the Curtius reaction) was filtered off. The filtrate was concentrated. The residue was destilled in a Kugelrohr oven (0.73 mbar, 120° C.) to give (2,4-difluoro-phenyl)-carbamic acid tert-butyl ester (24.9 g) as light yellow oil.

307.2

To a stirred, cooled (–78° C.) solution of (2,4-difluoro-phenyl)-carbamic acid tert-butyl ester (5 g) in THF (50 ml) under an argon atmosphere was added dropwise a 1.6 M solution of BuLi in hexanes (28.6 ml) for 20 min (temperature below –68° C. during the addition). When addition was complete, the mixture (turning to orange, then to light red) was stirred at –78° C. for 1 h 30. DMF (7.55 ml) was then added for 10 min (temperature below –70° C.) and stirring at –78° C. was continued for 15 min. As the mixture had turned to a compact mas (no more stirring), it was allowed to warm to room temperature. Water (50 ml) was added and the pH was set to 3 by the dropwise addition of 3 N HCl. EtOAc (50 ml) was added. The organic phase was washed with water and brine dried over MgSO$_4$, filtered and concentrated. The crude product was purified by flash chromatography (cyclohexane=>cyclohexane/EtOAc 85:15) to give (2,4-difluoro-3-formyl-phenyl)-carbamic acid tert-butyl ester (1.75 g) as an off-white solid.

307.3

According to general procedure A (2,4-difluoro-3-formyl-phenyl)-carbamic acid tert-butyl ester was converted to (RS)-(3-tert-butoxycarbonylamino-2,6-difluoro-phenyl)-methoxy-acetic acid. Orange gum. MS 316.1 ([M–H]$^-$)

307.4

According to general procedure C(RS)-(3-tert-butoxycarbonylamino-2,6-difluoro-phenyl)-methoxy-acetic acid was reacted with 4-amino benzonitrile to give (RS)-{3-[(4-cyano-benzylcarbamoyl)-methoxy-methyl]-2,4-difluoro-phenyl}-carbamic acid tert-butyl ester. Solid. MS 430.3 ([M–H]$^-$)

307.5

To a stirred solution of (RS)-{3-[(4-cyano-benzylcarbamoyl)-methoxy-methyl]-2,4-difluoro-phenyl}-carbamic acid tert-butyl ester (514 mg) at rt in dioxane (10 ml) under an argon atmosphere was added 4 M HCl solution in dioxane (6 ml). Stirring at rt was then continued for 3 h. The light yellow solution was concentrated. The solid residue was suspended in EtOAc and washed with 1 N NaOH. The organic layer was dried over MgSO$_4$, filtered and concentrated. The crude product was purified by flash chromatography (cyclohexane=>cyclohexane/EtOAc 2:3) to give (RS)-2-(3-amino-2,6-difluoro-phenyl)-N-(4-cyano-benzyl)-2-methoxy-acetamide (215 mg) as an off-white solid. MS 332.3 ([M+H]$^+$)

307.6

To a stirred solution of (RS)-2-(3-amino-2,6-difluoro-phenyl)-N-(4-cyano-benzyl)-2-methoxy-acetamide (130 mg) at rt in dichloromethane were added sucessively dry 4A molecular sieves (50 mg), phenyl boronic acid (96 mg), triethylamine (0.11 ml), copper (II) acetate (71 mg) and TEMPO (67 mg). A "CaCl$_2$ trap" was placed over the flask and stirring at rt was continued over the week-end. Then the solids were filtered off and washed with EtOAc. The dark brown filtrate was concentrated to leave a dark brown residue. The crude product was purified by flash chromatography (cyclohexane=>cyclohexane/EtOAc 3:2) to give (RS)-N-(4-cyano-benzyl)-2-(2,6-difluoro-3-phenylamino-phenyl)-2-methoxy-acetamide (123 mg) as light grey gum. MS 408.3 ([M+H]$^+$)

307.7

In analogy to example 15.5 (RS)-N-(4-cyano-benzyl)-2-(2,6-difluoro-3-phenylamino-phenyl)-2-methoxy-acetamide was converted to (RS)-2-(2,6-difluoro-3-phenylamino-phenyl)-N-[4-(N-hydroxycarbamimidoyl)-benzyl]-2-methoxy-acetamide. Off-white solid. MS 441.6 ([M+H]$^+$)

307.8

To a stirred solution of (RS)-2-(2,6-difluoro-3-phenylamino-phenyl)-N-[4-(N-hydroxycarbamimidoyl)-benzyl]-2-methoxy-acetamide (106 mg) at rt in ethanol (5 ml) under an argon atmosphere were added 5 drops of acetic acid and and a catalytic amount of Raney-Nickel. The mixture was then stirred at rt under a hydrogen atmosphere for 23 h. The catalyst was filtered off and the filtrate was concentrated. The crude product was purified using flash chromatography (EtOAc/acetone/H$_2$O/HOAc 6:2:1:1) to give (RS)-N-(4-carbamimidoyl-benzyl)-2-(2,6-difluoro-3-phenylamino-phenyl)-2-methoxy-acetamide acetate (92 mg) as on off-white solid. MS 425.5 ([M+H]$^+$)

Example 308

308.1

To a stirred solution of (RS)-2-(3-amino-2,6-difluoro-phenyl)-N-(4-cyano-benzyl)-2-methoxy-acetamide (example 307.5) 81 mg) at rt in THF (5 ml) under an argon atmosphere were added N-ethyldiisopropylamine (0.017 ml) and 2-iodopropane (0.01 ml). The mixture was heated to reflux and stirring was continued for 17 h. More 2-iodopropane (0.1 ml) and N-ethyldiisopropylamine (0.17 ml) were added and stirring at reflux was continued for 7 h. DMF (5 ml) was added and the mixture was stirred at 120° C. for 21 h. The mixture had turned to light brown. More DMF (5 ml), N-ethyldiisopropylamine (0.35 ml,) and 2-iodopropane (0.2 ml) were added and stirring at 90° C. was continued for 17 h. The mixture was cooled to rt, diluted with 20 ml water and extracted with EtOAc. The combined organics were washed with water and brine, dried (MgSO$_4$), filtered and concentrated. The crude product was purified by column chromatography (cyclohexane=>cyclohexane/EtOAc 1:1) to give N-(4-cyano-benzyl)-2-(2,6-difluoro-3-isopropylamino-phenyl)-2-methoxy-acetamide (28 mg) as light brown gum.

308.2

In analogy to example 307.7 and 307.8 N-(4-cyano-benzyl)-2-(2,6-difluoro-3-isopropylamino-phenyl)-2-methoxy-acetamide was converted to (RS)-N-(4-carbamimidoyl-benzyl)-2-(2,6-difluoro-3-isopropylamino-phenyl)-2-methoxy-acetamide acetate. Light green crystals. MS 391.3 ([M+H]$^+$)

Example 309

309.1

In analogy to example 87.2 (RS)-2-(3-amino-2,6-difluoro-phenyl)-N-(4-cyano-benzyl)-2-methoxy-acetamide (example 30.5) was reacted with acetyl chloride to give (RS)-2-(3-acetylamino-2,6-difluoro-phenyl)-N-(4-cyano-benzyl)-2-methoxy-acetamide as white foam.

309.2

Using general procedure D (RS)-2-(3-acetylamino-2,6-difluoro-phenyl)-N-(4-cyano-benzyl)-2-methoxy-acetamide was converted to (RS)-2-(3-acetylamino-2,6-difluoro-phenyl)-N-(4-carbamimidoyl-benzyl)-2-methoxy-acetamide hydrochloride. Off-white solid. MS 391.3 ([M+H]$^+$)

Example 310

3608.1

In analogy to example 309 (RS)-2-(3-amino-2,6-difluoro-phenyl)-N-(4-cyano-benzyl)-2-methoxy-acetamide (example 30.5) was converted to (RS)-(4-carbamimidoyl-benzyl)-2-(2,6-difluoro-3-phenylacetylamino-phenyl)-2-methoxy-acetamide hydrochloride. Off-white solid. MS 467.4 ([M+H]$^+$)

Example 311

311.1

A stirred solution of 2,4-difluorobenzaldehyde (15.4 ml) in toluene (200 ml) was treated with ethylene glycol (23.2 ml) and p-toluene sulfonic acid (0.53 g). The reaction mixture was heated to reflux during 5 hrs (Dean-Stark trap), then it was cooled to r.t and poured onto ice. The organic layer was separated off, washed with 10% KHCO$_3$-solution and brine, dried over MgSO$_4$, filtered and concentrated to give 2-(2,4-difluoro-phenyl)-[1,3]dioxolane (26.8 g) as a light yellow oil. MS 186.1 ([M]$^+$)

311.2

In analogy to procedures 101.1, 101.2 and 101.3 2-(2,4-difluoro-phenyl)-dioxolane was converted to (RS)-(3-[1,3]dioxolan-2-yl-2,6-difluoro-phenyl)-ethoxy-acetic acid. During the acidic work-up after the final ester hydrolysis, the acetal protecting group was partly lost. It was completely cleaved off by treating the mixture of protected and unprotected compound with 3N aqueous HCl/THF/H$_2$O 1:10:1 overnight at rt. Upon complete deprotection, the THF was distilled off and the product was isolated by extraction with EtOAc. No further purification. (RS)-(2,6-Difluoro-3-formyl-phenyl)-ethoxy-acetic acid. Yellow oil. MS 262.0 ([M+NH$_4$]$^+$)

311.3

According to general procedure B (RS)-(2,6-difluoro-3-formyl-phenyl)-ethoxy-acetic acid was reacted with 4-aminomethyl benzonitrile to give (RS)-N-(4-cyano-benzyl)-2-(2,6-difluoro-3-formyl-phenyl)-2-ethoxy-acetamide. Amorphous off-white solid. MS 359.2 ([M+H]$^+$)

311.4

A suspension of (RS)-N-(4-cyano-benzyl)-2-(2,6-difluoro-3-formyl-phenyl)-2-ethoxy-acetamide (300 mg) in EtOH (1 ml) was treated with NaBH$_4$ (66 mg) at 0°. The reaction mixture was stirred for 4 hrs at rt, then poured onto ice and extracted with EtOAc. The organic layers were combined, dried over MgSO$_4$, filtrated and concentrated. The crude product was isolated by flash chromatography (CH$_2$CH$_{12}$=>CH$_2$C$_{2-12}$MeOH 4:1) to give (RS)-N-(4-cyano-benzyl)-2-(2,6-difluoro-3-hydroxymethyl-phenyl)-2-ethoxy-acetamide (174 mg) as amourphous white solid. MS 361.3 ([M+H]$^+$)

311.5

(RS)-N-(4-Cyano-benzyl)-2-(2,6-difluoro-3-hydroxymethyl-phenyl)-2-ethoxy-acetamide was converted according to general procedure D to give (RS)-N-(4-carbamimidoyl-benzyl)-2-(2,6-difluoro-3-hydroxymethyl-phenyl)-2-ethoxy-acetamide hydrochloride as amorphous white solid. MS 378.3 ([M+H]$^+$)

Example 312

312.1

In analogy to example 106.2 (RS)-N-(4-cyano-benzyl)-2-(2,6-difluoro-3-formyl-phenyl)-2-ethoxy-acetamide (example 311.3) was converted to (RS)-N-(4-cyano-benzyl)-2-[2,6-difluoro-3-(hydroxyimino-methyl)-phenyl]-2-ethoxy-acetamide. Off-white amorphous solid. MS 374.3 ([M+H]$^+$)

312.2

In analogy to example 106.3 (RS)-N-(4-cyano-benzyl)-2-[2,6-difluoro-3-(hydroxyimino-methyl)-phenyl]-2-ethoxy-acetamide was converted to (RS)-2-(3-aminomethyl-2,6-difluoro-phenyl)-N-(4-cyano-benzyl)-2-ethoxy-acetamide acetic acid. Yellow oil. MS 360.3 ([M+H]$^+$)

312.3

In analogy to example 87.2 (RS)-2-(3-aminomethyl-2,6-difluoro-phenyl)-N-(4-cyano-benzyl)-2-ethoxy-acetamide acetic acid was reacted with acetyl chloride to give (RS)-2-[3-(acetylamino-methyl)-2,6-difluoro-phenyl]-N-(4-cyano-benzyl)-2-ethoxy-acetamide. White foam. MS 402.5 ([M+H]$^+$)

312.4

According to general procedure D (RS)-2-[3-(acetylamino-methyl)-2,6-difluoro-phenyl]-N-(4-cyano-benzyl)-2-ethoxy-acetamide was converted to (RS)-2-[3-(acetylamino-methyl)-2,6-difluoro-phenyl]-N-(4-carbamimidoyl-benzyl)-2-ethoxy-acetamide hydrochloride. White solid. MS 419.2 ([M+H]$^+$)

Example 313

313.1

In analogy to example 15.5 (RS)-N-(4-cyano-benzyl)-2-(2,6-difluoro-3-formyl-phenyl)-2-ethoxy-acetamide (example 311.3) was converted to (RS)-2-[2,6-difluoro-3-(hydroxyimino-methyl)-phenyl]-2-ethoxy-N-[4-(N-hydroxycarbamimidoyl)-benzyl]-acetamide. Amorphous off-white solid. MS 407.2 ([M+H]$^+$)

313.2

In analogy to example 307.8 (RS)-2-[2,6-difluoro-3-(hydroxyimino-methyl)-phenyl]-2-ethoxy-N-[4-(N-hydroxycarbamimidoyl)-benzyl]-acetamide was hydrogenated to give (RS)-2-(3-aminomethyl-2,6-difluoro-phenyl)-N-(4-carbamimidoyl-benzyl)-2-ethoxy-acetamide acetic acid 1:4. White solid. MS 377.3 ([M+H]$^+$)

Example 314

314.1

To a solution of (RS)-N-(4-cyano-benzyl)-2-(2,6-difluoro-3-formyl-phenyl)-2-ethoxy-acetamide (250 mg, example 311.3) in EtOH (5 ml) was added aniline (64 mg). The suspension was stirred over night, then cooled to 0° C. and treated with NaBH$_4$ (38 mg). The reaction mixture was stirred 1 h at 0° and 1 h at rt, then poured onto ice and extracted with EtOAc. The organic layer was dried over MgSO$_4$, filtrated and concentrated. The crude product was purified by flash chromatography (cyclohexane/EtOAc 1:4=>EtOAc) to give (RS)-N-(4-cyano-benzyl)-2-(2,6-difluoro-3-phenylaminomethyl-phenyl)-2-ethoxy-acetamide (230 mg) as off-white amourphous solid. MS 436.3 ([M+H]$^+$)

314.2

According to general procedure D (RS)-N-(4-cyano-benzyl)-2-(2,6-difluoro-3-phenylaminomethyl-phenyl)-2-ethoxy-acetamide was converted to (RS)-(4-carbamimidoyl-benzyl)-2-(2,6-difluoro-3-phenylaminomethyl-phenyl)-2-ethoxy-acetamide hydrochloride. Amorphous white solid. MS 453.5 ([M+H]$^+$)

Using analogous procedures as described in example 37 (RS)-N-(4-cyano-benzyl)-2-(2,6-difluoro-3-formyl-phenyl)-2-ethoxy-acetamide (example 311.3) was converted to the compounds of Examples 315 and 316.

Example 315

(RS)-(4-Carbamimidoyl-benzyl)-2-(2,6-difluoro-3-morpholin-4-ylmethyl-phenyl)-2-ethoxy-acetamide hydrochloride. White solid. MS 447.2 ([M+H]$^+$)

Example 316

(RS)-(4-Carbamimidoyl-benzyl)-2-(2,6-difluoro-3-piperidin-1-ylmethyl-phenyl)-2-ethoxy-acetamide hydrochloride. Amorphous off-white solid. MS 445.2 ([M+H]$^+$)

Example 317

In analogy to example 307.8 (RS)-2-(3-diethoxymethyl-2,6-difluoro-phenyl)-2-ethoxy-N-[4-(N-hydroxycarbamimidoyl)-benzyl]-acetamide (obtained side product in the synthesis of example 312.1) was converted to (RS)-(4-carbamimidoyl-benzyl)-2-(2,6-difluoro-3-formyl-phenyl)-2-ethoxy-acetamide acetic acid (1:4). White solid. MS 376.3 ([M+H]$^+$)

Example 318

318.1

In analogy to procedures 106.2 and 106.3 3,5-difluoro-4-formyl-benzonitrile (CAS 467442-15-5) was converted to 4-aminomethyl-3,5-difluoro-benzonitrile hydrochloride. Off-white solid. MS 169.2 ([M+H]$^+$)

318.2

According to general procedure C 4-aminomethyl-3,5-difluoro-benzonitrile hydrochloride was reacted with (RS)-(2,6-difluoro-4-methoxy-phenyl)-ethoxy-acetic acid (example 101.3) give to (RS)-N-(4-cyano-2,6-difluoro-benzyl)-

2-(2,6-difluoro-4-methoxy-phenyl)-2-ethoxy-acetamide. Off-white solid. MS 397.1 ([M+H]$^+$)

318.3

According to general procedure D (RS)-N-(4-cyano-2,6-difluoro-benzyl)-2-(2,6-difluoro-4-methoxy-phenyl)-2-ethoxy-acetamide was converted to (RS)-N-(4-carbamimidoyl-2,6-difluoro-benzyl)-2-(2,6-difluoro-4-methoxy-phenyl)-2-ethoxy-acetamide hydrochloride. White solid. MS 414.2 ([M+H]$^+$)

Using similar procedures as described in example 318, 4-aminomethyl-3)$_5$-difluoro-benzonitrile hydrochloride (example 318.1) was coupled with the appropriate acids and converted to the following amidine products:

Example 319

(RS)-N-(4-Carbamimidoyl-2,6-difluoro-benzyl)-2-ethoxy-2-(2-fluoro-4-methoxy-phenyl)-acetamide acetate (coupling with acid (RS)-ethoxy-(2-fluoro-4-methoxy-phenyl)-acetic acid, example 63.1). Off-white powder. MS 396.1 ([M+H]$^+$)

Example 320

(RS)-N-(4-Carbamimidoyl-2,6-difluoro-benzyl)-2-(2,6-difluoro-4-methoxy-phenyl)-2-methoxy-acetamid acetate (coupling with acid (RS)-(2,6-difluoro-4-methoxy-phenyl)-methoxy-acetic acid, example 66.1). Off-white solid. MS 400.5 ([M+H]$^+$)

Example 321

(RS)-N-(4-Carbamimidoyl-2,6-difluoro-benzyl)-2-(2-fluoro-4-methoxy-phenyl)-2-methoxy-acetamide acetate (coupling with acid (RS)-(2-fluoro-4-methoxy-phenyl)-methoxy-acetic acid, example 15.1). Off-white solid. MS 382.3 ([M+H]$^+$)

Example 322

322.1

To a mechanically stirred solution of 4-bromomethyl-3-nitro-benzonitrile (21.7 g, CAS 223 512-70-7) in chloroform (250 ml) under argon atmosphere was added hexamethylenetetramine (7.1 g). A white precipitate appeared a few minutes after the addition. After 3 hrs heating to reflux (oil bath 80° C.) the mixture was cooled to rt. The solid was collected by filtration, washed with chloroform and dried under high vacuum) to give 1-(4-cyano-2-nitro-benzyl)-3,5,7-triaza-1-azonia-tricyclodecane hydrobromide (13.8 g). Off-white powder.

322.2

To a mechanically stirred suspension of 1-(4-cyano-2-nitro-benzyl)-3,5,7-triaza-1-azonia-tricyclodecane hydrobromide (13.8 g) in ethanol (150 ml) under argon atmosphere, was added concentrated aqueous HCl (20 ml). After 6 hours stirring at reflux the mixture was concentrated, diluted with NaOH 1N until pH>12. The product was extracted with EtOAc. The combined organic phases were washed twice with water and with brine. Then the solution was dried over MgSO$_4$), filtered and concentrated to give 4-aminomethyl-3-nitro-benzonitrile (5.8 g) as yellow solid.

322.3

According to general procedure B, 4-aminomethyl-3-nitro-benzonitrile was reacted with (RS)-ethoxy-(2-fluoro-4-methoxy-phenyl)-acetic acid (example 63.1) to give (RS)-(4-cyano-2-nitro-benzyl)-2-ethoxy-2-(2-fluoro-4-methoxy-phenyl)-acetamide. Yellow foam. MS 388.1 ([M+H]$^+$)

322.4

To a stirred solution of (RS)-(4-cyano-2-nitro-benzyl)-2-ethoxy-2-(2-fluoro-4-methoxy-phenyl)-acetamide in THF (5 ml) and ethanol (15 ml) was added palladium/C (250 mg). After 24 hrs stirring at rt under hydrogen atmosphere the mixture was filtered, and the filtrate was concentrated to leave a light yellow foam. The crude product was purified by flash chromatography (cyclohexane=>cyclohexane/EtOAc 1:1) to give (RS)-(2-amino-4-cyano-benzyl)-2-ethoxy-2-(2-fluoro-4-methoxy-phenyl)-acetamide (4.45 g) as light yellow foam. MS 358.7 ([M+H]$^+$)

322.5

To a stirred solution of (RS)-(2-amino-4-cyano-benzyl)-2-ethoxy-2-(2-fluoro-4-methoxy-phenyl)-acetamide (470 mg) in DMF (8 ml) were added iodoacetamide (376 mg) and N-ethyldiisopropylamine (0.34 ml). After 50 hrs stirring at 110° C. under argon atmosphere. The mixture was diluted with EtOAc and water. The organic phase was separated and washed with water and brine, dried ovef MgSO$_4$, filtered and concentrated. The crude product was purified by flash chromatography (CH$_2$Cl$_2$=>CH$_2$Cl$_2$/MeOH 4:1) to give (RS)-[2-(carbamoylmethyl-amino)-4-cyano-benzyl]-2-ethoxy-2-(2-fluoro-4-methoxy-phenyl)-acetamide (133 mg) as an off-white solid. MS 415.1([M+H]$^+$)

322.6

According to general procedure D, (RS)-[2-(carbamoylmethyl-amino)-4-cyano-benzyl]-2-ethoxy-2-(2-fluoro-4-methoxy-phenyl)-acetamide was converted to (RS)-[4-carbamimidoyl-2-(carbamoylmethyl-amino)-benzyl]-2-ethoxy-2-(2-fluoro-4-methoxy-phenyl)-acetamide hydrochloride. Off-white solid. MS 432 ([M+H]$^+$) Using similar procedures as described in example 322.4 and 322.6 (RS)-(2-amino-4-cyano-benzyl)-2-ethoxy-2-(2-fluoro-4-methoxy-phenyl)-acetamide (example 322.4) was converted to the compounds of Examples 323 to 328.

Example 323

(RS)-N-(2-Benzylamino-4-carbamimidoyl-benzyl)-2-ethoxy-2-(2-fluoro-4-methoxy-phenyl)-acetamide acetate. Off-white solid. MS 465 ([M+H]$^+$)

Example 324

(RS)-[4-Carbamimidoyl-2-(2-fluoro-benzylamino)-benzyl]-2-ethoxy-2-(2-fluoro-4-methoxy-phenyl)-acetamide hydrochloride. Off-white solid. MS 483.3 ([M+H]$^+$)

Example 325

(RS)-{4-Carbamimidoyl-2-[(pyridin-2-ylmethyl)-amino]-benzyl}-2-ethoxy-2-(2-fluoro-4-methoxy-phenyl)-acetamide hydrochloride. Off-white solid. MS 466.4 ([M+H]$^+$)

Example 326

(RS)-[4-Carbamimidoyl-2-(4-chloro-2-fluoro-benzylamino)-benzyl]-2-ethoxy-2-(2-fluoro-4-methoxy-phenyl)-acetamide hydrochloride. Off-white solid. MS 517.3 ([M+H]$^+$)

Example 327

(RS)-(4-Carbamimidoyl-2-phenethylamino-benzyl)-2-ethoxy-2-(2-fluoro-4-methoxy-phenyl)-acetamide hydrochloride. Off-white foam. MS 479.5 ([M+H]$^+$)

Example 328

(RS)-(5-Carbamimidoyl-2-{[2-ethoxy-2-(2-fluoro-4-methoxy-phenyl)-acetylamino]-methyl}-phenylamino)-acetic acid ethyl ester hydrochloride. Off-white solid. MS 461.1 ([M+H]$^+$)

Example 329

In analogy to example 20.1 (RS)-(5-carbamimidoyl-2-{[2-ethoxy-2-(2-fluoro-4-methoxy-phenyl)-acetylamino]-methyl}-phenylamino)-acetic acid ethyl ester hydrochloride (example 328) was hydrolysed to give (RS)-(5-carbamimidoyl-2-j [2-ethoxy-2-(2-fluoro-4-methoxy-phenyl)-acetylamino]-methyl)-phenylamino)-acetic acid acetate. Off-white solid. MS 433.4 ([M+H]$^+$)

Example 330

330.1

In analogy to example 95.4, (RS)-(2-amino-4-cyano-benzyl)-2-ethoxy-2-(2-fluoro-4-methoxy-phenyl)-acetamide (example 322.4) was reacted with benzyl sulfonylchloride to give (RS)-(4-cyano-2-phenylmethanesulfonylamino-benzyl)-2-ethoxy-2-(2-fluoro-4-methoxy-phenyl)-acetamide. Off-white foam. MS 512.3 ([M+H]$^+$)

330.2

According to general procedure D (RS)-(4-cyano-2-phenylmethanesulfonylamino-benzyl)-2-ethoxy-2-(2-fluoro-4-methoxy-phenyl)-acetamide was converted to (RS)-(4-carbamimidoyl-2-phenylmethanesulfonylamino-benzyl)-2-ethoxy-2-(2-fluoro-4-methoxy-phenyl)-acetamide hydrochloride. Off-white solid. MS 529.2 ([M+H]$^+$

Example 331

Using similar procedures as described in example 330 (RS)-(2-amino-4-cyano-benzyl)-2-ethoxy-2-(2-fluoro-4-methoxy-phenyl)-acetamide (example 322.4) was reacted with benzylisocyanate and subsequently converted into the corresponding amidine to give (RS)-[2-(3-benzyl-ureido)-4-carbamimidoyl-benzyl]-2-ethoxy-2-(2-fluoro-4-methoxy-phenyl)-acetamide acetate as a white solid. MS 508.4 ([M+H]$^+$)

Example 332

Using similar procedures as described in example 53 (RS)-(2-amino-4-cyano-benzyl)-2-ethoxy-2-(2-fluoro-4-methoxy-phenyl)-acetamide (example 322.4) was reacted with benzyl chloroformate and subsequently converted into the corresponding amidine to give (RS)-(5-carbamimidoyl-2-{[2-ethoxy-2-(2-fluoro-4-methoxy-phenyl)-acetylamino]-methyl}-phenyl)-carbamic acid benzyl ester hydrochloride. White solid. MS 509.4 ([M+H]$^+$)

Example 333

333.1

In analogy to example 30.6 (RS)-(2-amino-4-cyano-benzyl)-2-ethoxy-2-(2-fluoro-4-methoxy-phenyl)-acetamide (example 322.4) was reacted with phenyl boronic acid to give (RS)-(4-cyano-2-phenylamino-benzyl)-2-ethoxy-2-(2-fluoro-4-methoxy-phenyl)-acetamide. Off-white foam. MS 434.1 ([M+H]$^+$)

333.2

According to general procedure D (RS)-(4-cyano-2-phenylamino-benzyl)-2-ethoxy-2-(2-fluoro-4-methoxy-phenyl)-acetamide was converted to (RS)-(4-carbamimidoyl-2-phenylamino-benzyl)-2-ethoxy-2-(2-fluoro-4-methoxy-phenyl)-acetamide hydrochloride. Light green solid. MS 451.1 ([M+H]$^+$)

Example 334

334.1

A solution of (RS)-(2,6-difluoro-4-trifluoromethanesulfonyloxy-phenyl)-ethoxy-acetic acid ethyl ester (3.5 g, example 162) in dioxane (115 ml) was treated with bis(pinacolato)diboron (3.43 g) and K$_2$CO$_3$ (2.65 g). The solution was deoxygenated by passing a stream of argon through it. Then bis(triphenylphosphine)palladium(II) chloride (0.62 g) was added. The reaction mixuter was heated to 100° for 16 hrs, then cooled to r.t and filtrated. The solids were washed with dioxane/EtOAc. The filtrate was concentrated. The crude product was isolated by flash chromatography (cyclohexane/EtOAc 1:1=>EtOAc) to give (RS)-[2,6-difluoro-4-(4,4,5,5-tetramethyl-[1,3,2]dioxaborolan-2-yl)-phenyl]-ethoxy-acetic acid ethyl ester (3.51 g) as yellow oil. MS 388.0 ([M+NH$_4$]$^+$)

334.2

A solution of (RS)-[2,6-difluoro-4-(4,4,5,5-tetramethyl-[1,3,2]dioxaborolan-2-yl)-phenyl]-ethoxy-acetic acid ethyl ester in 1,2-dimethoxyethane was treated with 2-amino-5-bromopyridine and CsF. The reaction mixture was deoxygenated by passing a stream of argon through it. Tetrakis(triphenylphosphine)palladium(0) was added. The reaction mixture was heated to 80° for 2 days, then cooled to rt and concentrated. The crude product was isolated by flash chromatography (cyclohexane/EtOAc 2:1=>EtOAc) to give (RS)-[4-(6-amino-pyridin-3-yl)-2,6-difluoro-phenyl]-ethoxy-acetic acid ethyl ester as amorphous brown solid.

This material which was contaminated with triphenyl phosphinoxid was dissolved in THF and treated with 4.5 ml 1N NaOH and stirred for 18 hrs at rt. The solution was neutralized with 1N HCl, then concentrated. The residue was taken up in Et$_2$O. The solid was filtered off and washed with ether to give (RS)-[4-(6-amino-pyridin-3-yl)-2,6-difluoro-phenyl]-ethoxy-acetic acid (1.36 g, contains 2 equivalent of NaCl).

According to general method B this material (350 mg) which was contaminated with triphenyl phosphinoxid was reacted with 2-(2-aminomethyl-5-cyano-phenoxy)-acetamide hydrochloride (example 123.2) to give (RS)-2-[4-(6-amino-pyridin-3-yl)-2,6-difluoro-phenyl]-N-(2-carbamoyl-methoxy-4-cyano-benzyl)-2-ethoxy-acetamide (186 mg) as off-white solid. MS 496.3 ([M+H]$^+$)

334.3

According to general procedure D, (RS)-2-[4-(6-amino-pyridin-3-yl)-2,6-difluoro-phenyl]-N-(2-carbamoylmethoxy-4-cyano-benzyl)-2-ethoxy-acetamide was converted to (RS)-2-[4-(6-amino-pyridin-3-yl)-2,6-difluoro-phenyl]-N-(4-carbamimidoyl-2-carbamoylmethoxy-benzyl)-2-ethoxy-acetamide hydrochloride acetic acid (1:1:2). Off-white solid. MS 513.3 ([M+H]$^+$)

Example 335

335.1
In analogy to example 22.1 (RS)-(2,6-difluoro-4-hydroxy-phenyl)-ethoxy-acetic acid ethyl ester (example L6) was reacted with 2-(hydroxymethyl)pyridine to give (RS)-[2,6-difluoro-4-(pyridin-2-ylmethoxy)-phenyl]-ethoxy-acetic acid ethyl ester as a yellow semisolid. This material was hydrolysed in analogy to example 101.3 to give (RS)-[2,6-difluoro-4-(pyridin-2-ylmethoxy)-phenyl]-ethoxy-acetic acid. White solid. MS 324.1 ([M+H]$^+$)

335.2
According to general procedure C, (RS)-[2,6-difluoro-4-(pyridin-2-ylmethoxy)-phenyl]-ethoxy-acetic acid was reacted with 2-(2-aminomethyl-5-cyano-phenoxy)-acetamide hydrochloride (example 123.2) to give (RS)-(2-carbamoylmethoxy-4-cyano-benzyl)-2-[2,6-difluoro-4-(pyridin-2-ylmethoxy)-phenyl]-2-ethoxy-acetamide. Amorphous off-white solid. MS 511.3 ([M+H]$^+$)

335.3
According to general procedure D, (RS)-(2-carbamoylmethoxy-4-cyano-benzyl)-2-[2,6-difluoro-4-(pyridin-2-ylmethoxy)-phenyl]-2-ethoxy-acetamide was converted to (RS)-(4-carbamimidoyl-2-carbamoylmethoxy-benzyl)-2-[2,6-difluoro-4-(pyridin-2-ylmethoxy)-phenyl]-2-ethoxy-acetamide hydrochloride. Off-white solid. MS 528.2 ([M+H]$^+$)

Example 336

336.1
According to general procedure C, (RS)-[4-(6-amino-pyridin-3-yl)-2,6-difluoro-phenyl]-ethoxy-acetic acid (intermediate from example 334.4, contains 2 equivalent of NaCl) was reacted with 4-aminomethyl-3,5-difluoro-benzonitrile hydrochloride (example 318.1) to give (RS)-2-[4-(6-amino-pyridin-3-yl)-2,6-difluoro-phenyl]-N-(4-cyano-2,6-difluoro-benzyl)-2-ethoxy-acetamide as off-white solid. MS 459.6 ([M+H]$^+$)

336.2
In analogy to example 307.7 and 307.8, (RS)-2-[4-(6-amino-pyridin-3-yl)-2,6-difluoro-phenyl]-N-(4-cyano-2,6-difluoro-benzyl)-2-ethoxy-acetamide was converted to (RS)-2-[4-(6-amino-pyridin-3-yl)-2,6-difluoro-phenyl]-N-(4-carbamimidoyl-2,6-difluoro-benzyl)-2-ethoxy-acetamide acetate. White powder. MS 476.5 ([M+H]$^+$)

Example 337

337.1
A suspension of (RS)-N-(4-carbamimidoyl-benzyl)-2-(2,6-difluoro-4-methoxy-phenyl)-2-methoxy-acetamide hydrochloride (600 mg, example 66.3) in CH$_2$Cl$_2$ (15 ml), H$_2$O (7.5 ml) and saturated Na$_2$CO$_3$-solution (7.5 ml) was treated with Boc$_2$O (333 mg) and stirred for 6 hrs at rt. The mixture was poured onto ice and extracted with CH$_2$Cl$_2$. The organic layers were dried over MgSO$_4$, filtrated and concentrated. The crude product was purified by flash chromatography (cyclohexane/EtOAc 4:1=>EtOAc) to give (RS)-[(4-{[2-(2,6-difluoro-4-methoxy-phenyl)-2-methoxy-acetylamino]-methyl}-phenyl)-imino-methyl]-carbamic acid tert-butyl ester (630 mg). Amorphous off-white solid.

337.2
The racemic (RS)-[(4-{[2-(2,6-difluoro-4-methoxy-phenyl)-2-methoxy-acetylamino]-methyl}-phenyl)-imino-methyl]-carbamic acid tert-butyl ester (620 mg) was separated by HPLC on ChiralPakAD (15% EtOH in heptane) to give (S)-[(4-{[2-(2,6-difluoro-4-methoxy-phenyl)-2-methoxy-acetylamino]-methyl}-phenyl)-imino-methyl]-carbamic acid tert-butyl ester (193 mg) as a white foam and (R)-[(4-{[2-(2,6-difluoro-4-methoxy-phenyl)-2-methoxy-acetylamino]-methyl}-phenyl)-imino-methyl]-carbamic acid tert-butyl ester (223 mg) as a white foam.

337.3
A suspension of (S)-[(4-{[2-(2,6-difluoro-4-methoxy-phenyl)-2-methoxy-acetylamino]-methyl}-phenyl)-imino-methyl]-carbamic acid tert-butyl ester in water was treated with formic acid. The solution was stirred for 8 hrs at rt, then concentrated, redissolved twice in water, concentrated and dried to give (S)-N-(4-carbamimidoyl-benzyl)-2-(2,6-difluoro-4-methoxy-phenyl)-2-methoxy-acetamide formiate (78 mg) as white foam. MS 364.1 ([M+H]$^+$)

337.4
In analogy to example 341.3, (R)-[(4-{[2-(2,6-difluoro-4-methoxy-phenyl)-2-methoxy-acetylamino]-methyl}-phenyl)-imino-methyl]-carbamic acid tert-butyl ester was converted to (R)-N-(4-carbamimidoyl-benzyl)-2-(2,6-difluoro-4-methoxy-phenyl)-2-methoxy-acetamide formiate. White foam. MS 364.1 ([M+H]$^+$)

Example 338

338.1
A solution of (RS)-ethoxy-(2-fluoro-4-methoxy-phenyl)-acetic acid (7.26 g, example 63.1), ethanol (16.7 ml) and DMAP (1.57 g) in dichloromethane (120 ml) was cooled to 0° and treated with EDCI (6.59 g). The reaction stirred was stirred at rt for 18 hrs, then washed with 0.5 N HCl, H$_2$O, saturated NaHCO$_3$ and brine. The organic layer was dried over MgSO$_4$, filtrated and concentrated. The crude product was purified by flash chromatography (cyclohexane=>cyclohexane/EtOAc 85:15) to give (RS)-ethoxy-(2-fluoro-4-methoxy-phenyl)-acetic acid ethyl ester (4.42 g) as yellow oil. MS 256.2 ([M]$^+$)

338.2
An emulsion of (RS)-ethoxy-(2-fluoro-4-methoxy-phenyl)-acetic acid ethyl ester (1.11 g) in 0.1M NaCl, 3 mM Natriumphosphat buffer pH 7.0 (260 ml) was cooled to 4–5° C. and treated with lipase from Rhizomucor miehei. The reaction mixture was stirred for 4 days at 4–5° while maintaining the pH at 7 by gradual addition of 0.1N NaOH (totally 25.5 ml), then extracted with CH$_2$Cl$_2$ and then EtOAc. The organic layers were dried over Na$_2$SO$_4$, then concentrated to give (R)-ethoxy-(2-fluoro-4-methoxy-phenyl)-acetic acid ethyl ester (330 mg, 98.9% ee).

An emulsion of (R)-ethoxy-(2-fluoro-4-methoxy-phenyl)-acetic acid ethyl ester (416 mg) in 0.1M NaCl, 3 mM Natriumphosphat buffer pH 7.0 (75 ml) was cooled to 4–5° C. was treated with hog liver esterase suspension (0.175 ml). The reaction mixture was stirred for 4 days while maintaining the pH at 7 by gradual addition of 0.1N NaOH (totally 12.8 ml). The reaction mixture was washed with CH$_2$Cl$_2$, then brought to pH 2 by the addition of 2N HCl and extracted with EtOAc. The EtOAc layer was dried over Na$_2$SO$_4$, filtrated and concentrated to give (R)-ethoxy-(2-fluoro-4-methoxy-phenyl)-acetic acid (304 mg, 97.1% ee) as yellow semisolid.

338.3

According to general procedure B (R)-ethoxy-(2-fluoro-4-methoxy-phenyl)-acetic acid was reacted with [amino-(4-aminomethyl-phenyl)-methylene]-carbamic acid benzyl ester hydrochloride 1:2 (prepared according to Ch. Lila, Ph. Gloanec, L. Cadet, Y. Hervé, J. Fournier, F. Leborgne, T. J. Verbeuren, G. De Nanteuil, Synthetic Communications 1998, 28, 23, 4419–4429) to give [1-amino-1-(4-{[(R)-2-ethoxy-2-(2-fluoro-4-methoxy-phenyl)-acetylamino]-methyl}-phenyl)-meth-(E)-ylidene]-carbamic acid benzyl ester (96.5% ee). Off-white solid.

338.4

A solution of [1-amino-1-(4-{[(R)-2-ethoxy-2-(2-fluoro-4-methoxy-phenyl)-acetylamino]-methyl}-phenyl)-meth-(E)-ylidene]-carbamic acid benzyl ester (195 mg) in EtOH (20 ml) was treated with HOAc (0.05 ml) and Pd/C 10% (20 mg) and hydrogenated over night at normal pressure. The catalyst was filtered off, the filtrate was concentrated to give (R)-N-(4-carbamimidoyl-benzyl)-2-ethoxy-2-(2-fluoro-4-methoxy-phenyl)-acetamide acetate (151 mg, 96.3% ee) as white solid.

Example 339

Using general procedure C(RS)-ethoxy-(2-fluoro-4-methoxy-phenyl)-acetic acid (example 63.1) was reacted with [amino-(4-aminomethyl-phenyl)-methylene]-carbamic acid benzyl ester hydrochloride 1:2 (prepared according to Ch. Lila, Ph. Gloanec, L. Cadet, Y. Hervé, J. Fournier, F. Leborgne, T. J. Verbeuren, G. De Nanteuil, Synthetic Communications 1998, 28, 23, 4419–4429) to give (RS)-[amino-(4-{[2-ethoxy-2-(2-fluoro-4-methoxy-phenyl)-acetylamino]-methyl}-phenyl)-methylene]-carbamic acid benzyl ester. White solid. MS 494.3 ([M+H]$^+$)

Example 340

(RS)-[(4-{[2-(2,6-Difluoro-4-methoxy-phenyl)-2-methoxy-acetylamino]-methyl}-phenyl)-imino-methyl]-carbamic acid benzyl ester was prepared using a similar procedure as described in example 339. MS 498.4 ([M+H]$^+$)

Example 341

341.1

Using analogous procedures as described in examples Li-L4,3,5-difluoro-phenol was converted to (RS)-(2,6-difluoro-4-hydroxy-phenyl)-methoxy-acetic acid ethyl ester. White solid. MS 245.2 ([M−H]$^-$)

341.2

Using analoguous procedures as described in examples 279.1 and 334.3 (RS)-(2,6-difluoro-4-hydroxy-phenyl)-methoxy-acetic acid ethyl ester was converted to (RS)-[2,6-difluoro-4-(4,4,5,5-tetramethyl-[1,3,2]dioxaborolan-2-yl)-phenyl]-methoxy-acetic acid ethyl ester. Yellow oil. MS 356.2 ([M]$^+$)

341.3

Using a similar procedure as describe in example 57.1 (RS)-[2,6-difluoro-4-(4,4,5,5-tetramethyl-[1,3,2]dioxaborolan-2-yl)-phenyl]-methoxy-acetic acid ethyl ester was converted to (RS)-(2,6-difluoro-4-pyridin-4-yl-phenyl)-methoxy-acetic acid ethyl ester. Waxy off-white solid.

341.4

A solution of (RS)-(2,6-difluoro-4-pyridin-4-yl-phenyl)-methoxy-acetic acid ethyl ester (1.83 g) in CH$_2$Cl$_2$ (25 ml) was treated with mCPBA (1.61 g). After stirring overnight at rt additional mCPBA (0.6 g) was added and stirring continued for 24 hrs. The reaction mixture was poured onto ice and saturated Na$_2$CO$_3$-solution, then extracted with dichloromethane. The organic layer was washed with saturated Na$_2$CO$_3$-solution and brine, dried over MgSO$_4$, filtered and concentrated. The crude product was isolated by flash chromatography (cyclohexane/EtOAc 1:4=>EtOAc; then CH$_2$Cl$_2$/MeOH 9:1=>4:1) to give (RS)-[2,6-difluoro-4-(1-oxy-pyridin-4-yl)-phenyl]-methoxy-acetic acid ethyl ester (474 mg) as yellow oil. MS 324.2 ([M+H]$^+$)

341.5

A solution of (RS)-[2,6-dfluoro-4-(1-oxy-pyridin-4-yl)-phenyl]-methoxy-acetic acid ethyl ester (509 mg) in THF was treated with 1N NaOH (3.15 ml) and stirred for 5 hrs at rt. Then, the reaction mixture was neutralized with 1N HCl (1.57 ml) and concentrated. The residue was taken up in diethyl ether. The solid was filtered off, washed with diethyl ether and dried to give (RS)-[2,6-difluoro-4-(1-oxy-pyridin-4-yl)-phenyl]-methoxy-acetic acid (599 mg, contains 1 equivalent of NaCl) as off-white solid. MS 296.2 ([M+H]$^+$)

341.6

(RS)-[2,6-Difluoro-4-(1-oxy-pyridin-4-yl)-phenyl]-methoxy-acetic acid was coupled with 4-aminomethyl-benzamidine hydrochloride (CAS 217313-79-6) according to general procedure C to give (RS)-(4-carbamimidoyl-benzyl)-2-[2,6-difluoro-4-(1-oxy-pyridin-4-yl)-phenyl]-2-methoxy-acetamide hydrochloride as amorphous white solid. MS 427.4 ([M+H]$^+$)

Example 342

342.1

To a stirred solution of (RS)-N-(4-Cyano-benzyl)-2-[2,6-difluoro-4-(4,4,5,5-tetramethyl-[1,3,2]dioxaborolan-2-yl)-phenyl]-2-ethoxy-acetamide (350 mg, example 262.1) at rt in dioxane (3 ml) under an argon atmosphere were added trifluoro-methanesulfonic acid 3,6-dihydro-2H-pyran-4-yl ester (196 mg, CAS 188975-30-6, solution in 2 ml dioxane), KOH (86 mg), PdCl$_2$(dppf) (31 mg) and 1,1'-bis(diphenylphosphino)ferrocene (21 mg). The mixture was then heated to 80° C. for 6 hrs. The mixture was concentrated to leave a dark brown solid. The crude product was isolated by column chromatography (cyclohexane=>cyclohexane/EtOAc 55:45) to give (RS)-(4-cyano-benzyl)-2-[4-(3,6-dihydro-2H-pyran-4-yl)-2,6-difluoro-phenyl]-2-ethoxy-acetamide (107 mg) as light yellow gum. MS 413.1 ([M+H]$^+$)

342.2

In analogy to example 307.7 and 307.8 (RS)-(4-cyano-benzyl)-2-[4-(3,6-dihydro-2H-pyran-4-yl)-2,6-difluorophenyl]-2-ethoxy-acetamide was converted to (RS)-(4-carbamimidoyl-benzyl)-2-[2,6-difluoro-4-(tetrahydro-pyran-4-yl)-phenyl]-2-ethoxy-acetamide acetate. Off-white powder. MS 432.4 ([M+H]$^+$)

Example 343

Using similar procedures as described in example 342 (RS)-N-(4-cyano-benzyl)-2-[2,6-difluoro-4-(4,4,5,5-tetramethyl-[1,3,2]dioxaborolan-2-yl)-phenyl]-2-ethoxy-acetamide (example 262.1) was converted to (RS)-(4-carbamimidoyl-benzyl)-2-(4-cyclohexyl-2,6-difluoro-phenyl)-2-ethoxy-acetamide acetate. Off-white powder. MS 430.4 ([M+H]$^+$)

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcristalline cellulose and the mixture is granulated with a solution of polyvinylpyrrolidon in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene Glycol 400 | 150.0 mg |
| Acetic Acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by Acetic Acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| | |
|---|---|
| Capsule contents | |
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula (I) | 50.0 mg |
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesiumstearate | 10.0 mg |
| Flavoring additives | 1.0 mg |

The active ingredient is mixed with lactose, microcristalline cellulose and sodium carboxymethyl cellulose and granulated with a mixture of polyvinylpyrrolidon in water. The granulate is mixed with magnesiumstearate and the flavouring additives and filled into sachets.

What is claimed is:

1. A compound of the formula (I)

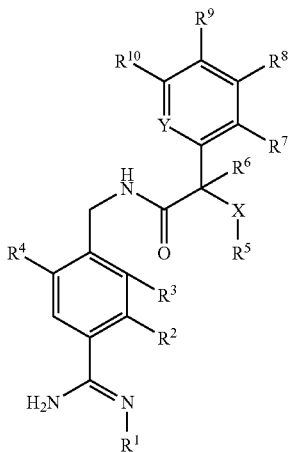

wherein
R¹ is hydrogen, OH, NH₂, lower-alkoxy-carbonyl, aryl-lower-alkoxy-carbonyl, aryloxy-carbonyl, lower-alkyl-carbonyl, aryl-carbonyl, or halogen substituted lower-alkoxy-carbonyl;

R², R³ and R⁴ independently from each other are selected from the group consisting of hydrogen, halogen, hydroxy, carboxy-lower-alkyl-NH, carbamoyl-lower-alkyl-NH, lower-alkoxy-carbonyl-lower-alkyl-NH, hydroxy-cycloalkyl-oxy, dihydroxy-cycloalkyl-oxy, aryl, aryloxy, aryl-NH, aryl-lower-alkyl-NH, aryl-lower-alkyl-SO₂—NH, aryl-lower-alkoxy-carbonyl-NH, aryl-lower-alkyl-NH-carbonyl-NH, heteroaryloxy, heteroaryl-lower-alkyl-NH, lower-alkoxy, and lower-alkoxy substituted with hydroxy, carboxy, carbamoyl, carbamimidoyl, CF₃, aryl, heteroaryl, lower-alkyl-carbamoyl, lower-alkoxy-carbonyl, aryl-carbamoyl, lower-alkoxy-lower-alkyl-carbamoyl, heterocyclyl-lower-alkyl-carbamoyl, or N(lower-alkyl)₂-lower-alkyl-carbamoyl;

R⁵ is lower-alkyl or cycloalkyl, or, if X is O or NR¹², R⁵ is lower alkyl, cycloalkyl or hydrogen;

R⁶ is hydrogen, lower-alkyl, or fluoro-lower-alkyl;

Y is N or C—R¹¹;

R⁷, R⁸, R⁹, R¹⁰ and R¹¹ independently from each other are selected from the group consisting of hydrogen, hydroxy, halogen, amino, lower-alkyl-amino, di-lower-alkyl-amino, lower-alkyl-carbonyl-amino, NO₂, fluoro-lower-alkyl, lower-alkoxy, hydroxy-lower-alkoxy, fluoro-lower-alkoxy, lower-alkinyl, hydroxy-lower-alkinyl, aryl, aryl-lower-alkoxy, aryloxy, aryloxy-lower-alkoxy, heterocyclyl, heterocyclyloxy, lower-alkoxy-carbonyl-lower-alkoxy, carbamoyl-lower-alkoxy, carboxy-lower-alkoxy, cycloalkyloxy, heteroaryl, amino-lower-alkoxy, lower-alkyl-amino-lower-alkoxy, and di-lower-alkyl-amino-lower-alkoxy, lower-alkyl-carbonyl-amino-lower-alkyl,
HO—N=CH, HCO, fluoro-lower-alkyl-SO₂—O, (lower-alkoxy)₂₋₄, CH(lower-alkoxy)₂, hydroxy-chloro-lower-alkoxy, aryl-lower-alkoxy-lower-alkoxy, aryl-NH, aryl-NH-lower-alkyl, aryl-lower-alkyl-carbonyl-NH, heterocyclyl-lower-alkyl, heterocyclyl-carbonyl, heterocyclyl-lower-alkoxy, lower-alkyl-carbamoyl, fluoro-lower-alkyl-carbamoyl, cycloalkyl-carbamoyl, cycloalkyl-lower-alkyl-carbamoyl, di-lower-alkyl-carbamoyl, lower-alkoxy-lower-alkyl-carbamoyl, di-lower-alkyl-carbamoyl-lower-alkoxy, heteroaryloxy, heteroaryl-lower-alkoxy, amino-lower-alkyl, lower-alkyl, hydroxy-lower-alkyl, cycloalkyl, cycloalkyl-lower-alkoxy, and cycloalkyl-lower-alkoxy substituted with lower-alkyl; or R⁸ and R⁹ or R⁸ and R⁷ are bound to each other to form a ring together with the carbon atoms to which they are attached and R⁸ and R⁹ together or R⁸ and R⁷ together are —O—CH₂—O—, —O—CH₂—CO—NH—, —O—CH₂—CH₂—CH₂—, —CH=CH—CH=CH—, or —CH=CH—CH=CH— substituted with lower-alkyl or lower-alkoxy, and R¹⁰, R¹¹ and R⁷ or R⁹ respectively are as defined above;

X is O, S, NR¹², or SO₂;

R¹² is hydrogen, lower-alkyl, or lower-alkyl-carbonyl;
or a pharmaceutically acceptable salt thereof.

2. The compound according to claim 1, wherein
R¹ is hydrogen, OH, NH₂, lower-alkoxy-carbonyl, aryl-lower-alkoxy-carbonyl, aryloxy-carbonyl, lower-alkyl-carbonyl, aryl-carbonyl, or halogen substituted lower-alkoxy-carbonyl;

R², R³ and R⁴ independently from each other are selected from the group consisting of hydrogen, halogen, hydroxy, and lower-alkoxy, and lower-alkoxy substituted with hydroxy, carboxy or carbamoyl;

R⁵ is lower-alkyl or cycloalkyl, or, if X is O or NR¹², R⁵ is lower alkyl, cycloalkyl or hydrogen;

R⁶ is hydrogen, lower-alkyl, or fluoro-lower-alkyl;

Y is N or C—R¹¹;

R⁷, R⁸, R⁹, R¹⁰ and R¹¹ independently from each other are selected from the group consisting of hydrogen, hydroxy, halogen, amino, lower-alkyl-amino, di-lower-alkyl-amino, lower-alkyl-carbonyl-amino, NO₂, fluoro-lower-alkyl, lower-alkoxy, hydroxy-lower-alkoxy, fluoro-lower-alkoxy, lower-alkinyl, hydroxy-lower-alkinyl, aryl, aryl-lower-alkoxy, aryloxy, aryloxy-lower-alkoxy, heterocyclyl, heterocyclyloxy, lower-alkoxy-carbonyl-lower-alkoxy, carbamoyl-lower-alkoxy, carboxy-lower-alkoxy, cycloalkyloxy, heteroaryl, amino-lower-alkoxy, lower-alkyl-amino-lower-alkoxy, and di-lower-alkyl-amino-lower-alkoxy, or R⁸ and R⁹ or R⁸ and R⁷ are bound to each other to form a ring together with the carbon atoms to which they are attached and R⁸ and R⁹ together or R⁸ and R⁷ together are —O—CH₂—O—, —O—CH₂—CO—NH—, —O—CH₂—CH₂—CH₂—, —CH=CH—CH=CH—, or —CH=CH—CH=CH— substituted with lower-alkyl or lower-alkoxy, and R¹⁰, R¹¹ and R⁷ or R⁹ respectively are as defined above;

X is O, S, NR², or SO₂;

R¹² is hydrogen, lower-alkyl, or lower-alkyl-carbonyl;
or a pharmaceutically acceptable salt thereof.

3. The compound according to claim 1, wherein R¹ is hydrogen, OH, NH₂, or lower-alkoxy-carbonyl.

4. The compound according to claim 1, wherein R¹ is hydrogen, OH, or lower-alkoxy-carbonyl.

5. The compound according to claim 1, wherein R¹ is hydrogen, OH, or ethoxycarbonyl.

6. The compound according to claim 1, wherein R¹ is hydrogen.

7. The compounds according to any of claims 1–6, wherein R², R³ and R⁴ independently from each other are hydrogen or halogen.

8. The compound according to claim 1, wherein $R^2$, $R^3$ and $R^4$ are hydrogen.

9. The compound according to claim 1, wherein $R^2$ and $R^4$ are hydrogen.

10. The compound according to claim 1, wherein $R^3$ is hydrogen, halogen, hydroxy, carboxy-lower-alkyl-NH, carbamoyl-lower-alkyl-NH, lower-alkoxy-carbonyl-lower-alkyl-NH, hydroxy-cycloalkyl-oxy, dihydroxy-cycloalkyl-oxy, aryl, aryloxy, aryl-NH, aryl-lower-alkyl-NH, aryl-lower-alkyl-SO$_2$—NH, aryl-lower-alkoxy-carbonyl-NH, aryl-lower-alkyl-NH-carbonyl-NH, heteroaryloxy, heteroaryl-lower-alkyl-NH, lower-alkoxy, or lower-alkoxy substituted with hydroxy, carboxy, carbamoyl, carbamimidoyl, CF$_3$, aryl, heteroaryl, lower-alkyl-carbamoyl, lower-alkoxy-carbonyl, aryl-carbamoyl, lower-alkoxy-lower-alkyl-carbamoyl, heterocyclyl-lower-alkyl-carbamoyl, or N(lower-alkyl)$_2$-lower-alkyl-carbamoyl.

11. The compound according to claim 1, wherein $R^3$ is hydrogen, halogen, carboxy-lower-alkyl-NH, aryl-lower-alkyl-NH, heteroaryl-lower-alkyl-NH, lower-alkoxy, or lower-alkoxy substituted with carbamoyl, heteroaryl, or lower-alkoxy-lower-alkyl-carbamoyl.

12. The compound according to claim 1, wherein $R^3$ is hydrogen, fluorine, carbamoylmethoxy, (2-methoxy-ethyl-carbamoyl)-methoxy, pyridin-2-yl-methoxy, benzylamino, carboxymethl-amino, or pyridin-2-ylmethyl-amino.

13. The compound according to claim 1, wherein X is O.

14. The compound according to claim 1, wherein $R^5$ is lower-alkyl.

15. The compound according to claim 1, wherein $R^5$ is methyl or ethyl.

16. The compound according to claim 1, wherein $R^6$ is hydrogen, methyl, or CF$_3$.

17. The compound according to claim 1, wherein $R^6$ is hydrogen.

18. The compound according to claim 1, wherein Y is C—$R^{11}$ and $R^7$, $R^8$, $R^9$, $R^{10}$ and $R^{11}$ independently from each other are selected from the group consisting of hydrogen, hydroxy, halogen, di-lower-alkyl-amino, lower-alkyl-carbonyl-amino, NO$_2$, fluoro-lower-alkyl, lower-alkoxy, hydroxy-lower-alkoxy, fluoro-lower-alkoxy, aryl, aryl-lower-alkoxy, aryloxy, aryloxy-lower-alkoxy, heterocyclyl, heterocyclyloxy, lower-alkoxy-carbonyl-lower-alkoxy, carbamoyl-lower-alkoxy, carboxy-lower-alkoxy, cycloalkyloxy, heteroaryl, and di-lower-alkyl-amino-lower-alkoxy.

19. The compound according to claim 1, wherein Y is C—$R^{11}$ and $R^7$, $R^8$, $R^9$, $R^{10}$ and $R^{11}$ independently from each other are selected from the group consisting of hydrogen, halogen, lower-alkoxy, and pyridyl.

20. The compound according to claim 1, wherein Y is C—$R^{11}$ and $R^7$, $R^8$, $R^9$, $R^{10}$ and $R^{11}$ independently from each other are selected from the group consisting of hydrogen, fluoro, bromo, methoxy, and pyridyl.

21. The compound according to claim 1, wherein Y is C—$R^{11}$, $R^8$ and $R^9$ or $R^8$ and $R^7$ are bound to each other to form a ring together with the carbon atoms to which they are attached and $R^8$ and $R^9$ together or $R^8$ and $R^7$ together are —O—CH$_2$—O—, —O—CH$_2$—CO—NH—, —O—CH$_2$—CH$_2$—CH$_2$—, —CH=CH—CH=CH—, or —CH=CH—CH=CH— substituted with lower-alkyl or lower-alkoxy, and $R^{10}$, $R^{11}$ and $R^7$ or $R^9$ respectively are hydrogen.

22. The compound according to claim 1, wherein Y is C—$R^{11}$ and $R^7$, $R^8$, $R^9$, $R^{10}$ and $R^{11}$ independently from each other are selected from the group consisting of hydrogen, halogen, lower-alkoxy and heteroaryl.

23. The compound according to claim 1, wherein Y is C—$R^{11}$, $R^7$ is halogen, $R^8$ is hydrogen, $R^9$ is lower-alkoxy, heteroaryl or heteroaryl-lower-alkoxy, $R^{10}$ is hydrogen and $R^{11}$ is hydrogen or halogen.

24. The compound according to claim 1, wherein Y is C—$R^{11}$, $R^7$ is fluorine, $R^8$ is hydrogen, $R^9$ is methoxy, pyridin-3-yl, 5-amino-pyridin-2-yl, 6-amino-pyridin-3-yl, pyridin-2-ylmethoxy, or 2-amino-pyrimidin-5-yl, $R^{10}$ is hydrogen and $R^{11}$ is hydrogen or fluorine.

25. The compound according to claim 1, selected from the group consisting of
  (S)-N-(4-Carbamimidoyl-benzyl)-2-methoxy-2-phenyl-acetamide hydrochloride,
  (RS)-N-(4-Carbamimidoyl-benzyl)-2-(2-fluoro-4-methoxy-phenyl)-2-methoxy-acetamide hydrochloride,
  (RS)-[Amino-(4-{[2-(2-fluoro-4-methoxy-phenyl)-2-methoxy-acetylamino]-methyl}-phenyl)-methylene]-carbamic acid ethyl ester,
  (RS)-2-(2-Fluoro-4-methoxy-phenyl)-N-[4-(N-hydroxy-carbamimidoyl)-benzyl]-2-methoxy-acetamide,
  (RS)-N-(4-Carbamimidoyl-benzyl)-2-(3-fluoro-3'-methoxy-biphenyl-4-yl)-2-methoxy-acetamide hydrochloride,
  (RS)-N-(4-Carbamimidoyl-benzyl)-2-ethoxy-2-(2-fluoro-4-methoxy-phenyl)-acetamide hydrochloride,
  (RS)-N-(4-Carbamimidoyl-benzyl)-2-(2,6-difluoro-4-methoxy-phenyl)-2-methoxy-acetamide hydrochloride,
  (RS)-N-(4-Carbamimidoyl-benzyl)-2-(2-fluoro-4-pyridin-3-yl-phenyl)-2-methoxy-acetamide hydrochloride, and
  (RS)-2-(4-Bromo-2,6-difluoro-phenyl)-N-(4-carbamimidoyl-benzyl)-2-ethoxy-acetamide hydrochloride,
or a pharmaceutically acceptable salt thereof.

26. The compound according to claim 1, selected from the group consisting of
  (RS)-N-(4-Carbamimidoyl-2-carbamoylmethoxy-benzyl)-2-(2,6-difluoro-4-methoxy-phenyl)-2-ethoxy-acetamide hydrochloride,
  (RS)-N-{4-Carbamimidoyl-2-[(2-methoxy-ethylcarbamoyl)-methoxy]-benzyl}-2-(2,6-difluoro-4-methoxy-phenyl)-2-ethoxy-acetamide hydrochloride,
  (RS)-N-[4-Carbamimidoyl-2-(pyridin-2-ylmethoxy)-benzyl]-2-(2,6-difluoro-4-methoxy-phenyl)-2-methoxy-acetamide hydrochloride,
  (RS)-2-[4-(2-Amino-pyrimidin-5-yl)-2,6-difluoro-phenyl]-N-(4-carbamimidoyl-benzyl)-2-ethoxy-acetamide hydrochloride,
  (RS)-N-(4-Carbamimidoyl-benzyl)-2-(2,6-difluoro-4-pyridin-3-yl-phenyl)-2-ethoxy-acetamide hydrochloride,
  (RS)-2-[4-(5-Amino-pyridin-2-yl)-2,6-difluoro-phenyl]-N-(4-carbamimidoyl-benzyl)-2-ethoxy-acetamide hydrochloride,
  (RS)-(2-[4-(6-Amino-pyridin-3-yl)-2,6-difluoro-phenyl]-N-(4-carbamimidoyl-benzyl)-2-ethoxy-acetamide hydrochloride,
  (RS)-N-(4-Carbamimidoyl-benzyl)-2-[2,6-difluoro-4-(pyridin-2-ylmethoxy)-phenyl]-2-ethoxy-acetamide hydrochloride,
  (RS)-N-(2-Benzylamino-4-carbamimidoyl-benzyl)-2-ethoxy-2-(2-fluoro-4-methoxy-phenyl)-acetamide acetate,
  (RS)-(5-Carbamimidoyl-2-{[2-ethoxy-2-(2-fluoro-4-methoxy-phenyl)-acetylamino]-methyl}-phenylamino)-acetic acid acetate,
  (RS)-(4-Carbamimidoyl-2-carbamoylmethoxy-benzyl)-2-[2,6-difluoro-4-(pyridin-2-ylmethoxy)-phenyl]-2-ethoxy-acetamide hydrochloride, (RS)-2-[4-(6-Amino-pyridin-3-yl)-2,6-difluoro-phenyl]-N-(4-carbamimidoyl-2,6-difluoro-benzyl)-2-ethoxy-acetamide acetate, and (RS)-{4-Carbamimidoyl-2-[(pyridin-2-ylmethyl)-amino]-benzyl}-2-ethoxy-2-(2-fluoro-4-methoxy-phenyl)-acetamide hydrochloride, or a pharmaceutically acceptable salt thereof.

27. The compound according to claim 1, selected from the group consisting of
- (S)-N-(4-Carbamimidoyl-benzyl)-2-methoxy-2-phenyl-acetamide hydrochloride,
- (R)-N-(4-Carbamimidoyl-benzyl)-2-methoxy-2-phenyl-acetamide hydrochloride,
- (RS)-2-(4-Benzyloxy-phenyl)-N-(4-carbamimidoyl-benzyl)-2-methoxy-acetamide hydrochloride,
- (RS)-N-(4-Carbamimidoyl-benzyl)-2-methoxy-2-(4-phenoxy-phenyl)-acetamide hydrochloride,
- (RS)-N-(4-Carbamimidoyl-benzyl)-2-methoxy-2-(3-phenoxy-phenyl)-acetamide hydrochloride,
- (RS)-N-(4-Carbamimidoyl-benzyl)-2-ethoxy-2-phenyl-acetamide hydrochloride,
- (RS)-N-(4-Carbamimidoyl-benzyl)-2-(2-fluoro-phenyl)-2-methoxy-acetamide hydrochloride,
- (RS)-2-(3-Benzyloxy-phenyl)-N-(4-carbamimidoyl-benzyl)-2-methoxy-acetamide hydrochloride,
- (RS)-N-(4-Carbamimidoyl-benzyl)-2-(3-hydroxy-phenyl)-2-methoxy-acetamide hydrochloride, and
- (RS)-N-(4-Carbamimidoyl-benzyl)-2-methoxy-2-(3-nitro-phenyl)-acetamide hydrochloride, or a pharmaceutically acceptable salt thereof.

28. The compound according to claim 1, selected from the group consisting of
- (RS)-2-Biphenyl-4-yl-N-(4-carbamimidoyl-benzyl)-2-methoxy-acetamide hydrochloride,
- (RS)-2-Benzo[1,3]dioxol-5-yl-N-(4-carbamimidoyl-benzyl)-2-methoxy-acetamide hydrochloride,
- (RS)-2-Benzo[1,3]dioxol-5-yl-N-(4-carbamimidoyl-benzyl)-2-ethoxy-acetamide hydrochloride,
- (RS)-N-(4-Carbamimidoyl-benzyl)-2-[5-ethoxy-2-fluoro-3-(1-methyl-piperidin-4-yloxy)-phenyl]-2-methoxy-acetamide hydrochloride,
- (RS)-N-(4-Carbamimidoyl-benzyl)-2-(2-fluoro-4-methoxy-phenyl)-2-methoxy-acetamide hydrochloride,
- (RS)-[Amino-(4-{[2-(2-fluoro-4-methoxy-phenyl)-2-methoxy-acetylamino]-methyl}-phenyl)-methylene]-carbamic acid ethyl ester,
- (RS)-2-(2-Fluoro-4-methoxy-phenyl)-N-[4-(N-hydroxycarbamimidoyl)-benzyl]-2-methoxy-acetamide,
- RS)-2-(2-Fluoro-4-methoxy-phenyl)-N-[4-(N-aminocarbamimidoyl)-benzyl]-2-methoxy-acetamide,
- (RS)-{5-[(4-Carbamimidoyl-benzylcarbamoyl)-methoxy-methyl]-2-methoxy-phenoxy}-acetic acid methyl ester hydrochloride, and
- (RS)-N-(4-Carbamimidoyl-benzyl)-2-(3-carbamoylmethoxy-4-methoxy-phenyl)-2-methoxy-acetamide hydrochloride, or a pharmaceutically acceptable salt thereof.

29. The compound according to claim 1, selected from the group consisting of
- (RS)-{5-[(4-Carbamimidoyl-benzylcarbamoyl)-ethoxymethyl]-2-methoxy-phenoxy}-acetic acid ethyl ester hydrochloride,
- (RS)-N-(4-Carbamimidoyl-benzyl)-2-(3-carbamoylmethoxy-4-methoxy-phenyl)-2-ethoxy-acetamide hydrochloride,
- (RS)-{5-[(4-Carbamimidoyl-benzylcarbamoyl)-ethoxymethyl]-2-methoxy-phenoxy}-acetic acid,
- (RS)-N-(4-Carbamimidoyl-benzyl)-2-ethoxy-2-(4-ethoxy-phenyl)-acetamid hydrochloride,
- (RS)-N-(4-Carbamimidoyl-benzyl)-2-methoxy-2-[4-(1-methyl-piperidin-4-yloxy)-phenyl]-acetamide hydrochloride,
- (RS)-N-(4-Carbamimidoyl-benzyl)-3,3,3-trifluoro-2-methoxy-2-phenyl-propionamide hydrochloride,
- (RS)-N-(4-Carbamimidoyl-benzyl)-2-(2-fluoro-4,5-dimethoxy-phenyl)-2-methoxy-acetamide hydrochloride,
- (RS)-N-(4-Carbamimidoyl-benzyl)-2-(3-isopropoxy-phenyl)-2-methoxy-acetamide hydrochloride,
- (RS)-N-(4-Carbamimidoyl-benzyl)-2-(4-cyclopentyloxy-phenyl)-2-methoxy-acetamide hydrochloride, and
- (RS)-N-(4-Carbamimidoyl-benzyl)-2-(4-isopropoxy-phenyl)-2-methoxy-acetamide hydrochloride, or a pharmaceutically acceptable salt thereof.

30. The compound according to claim 1, selected from the group consisting of
- (RS)-{4-[(4-Carbamimidoyl-benzylcarbamoyl)-methoxy-methyl]-phenoxy}-acetic acid methyl ester hydrochloride,
- (RS)-{4-[(4-Carbamimidoyl-benzylcarbamoyl)-methoxy-methyl]-phenoxy}-acetic acid,
- (RS)-N-(4-Carbamimidoyl-benzyl)-2-methoxy-2-[3-(tetrahydro-pyran-4-yloxy)-phenyl]-acetamide hydrochloride,
- (RS)-N-(4-Carbamimidoyl-benzyl)-2-(3,5-diethoxy-2-fluoro-phenyl)-2-methoxy-acetamide hydrochloride,
- (RS)-N-(4-Carbamimidoyl-benzyl)-2-[5-ethoxy-2-fluoro-4-(2-hydroxy-ethoxy)-phenyl]-2-methoxy-acetamide hydrochloride,
- (RS)-N-(4-Carbamimidoyl-benzyl)-2-(3,4-diethoxy-2-fluoro-phenyl)-2-methoxy-acetamide hydrochloride,
- (RS)-N-(4-Carbamimidoyl-2-fluoro-benzyl)-2-(2-fluoro-4-methoxy-phenyl)-2-methoxy-acetamide hydrochloride,
- (RS)-N-(4-Carbamimidoyl-3-fluoro-benzyl)-2-(2-fluoro-4-methoxy-phenyl)-2-methoxy-acetamide hydrochloride,
- (RS)-2-(2,4-Bis-trifluoromethyl-phenyl)-N-(4-carbamimidoyl-benzyl)-2-methoxy-acetamide hydrochloride, and
- (RS)-N-[4-(N-Hydroxycarbamimidoyl)-benzyl]-2-(2-hydroxy-4-methoxy-phenyl)-2-methoxy-acetamide, or a pharmaceutically acceptable salt thereof.

31. The compound according to claim 1, selected from the group consisting of
- (RS)-N-(4-Carbamimidoyl-benzyl)-2-(2-hydroxy-4-methoxy-phenyl)-2-methoxy-acetamide actetate,
- (RS)-N-(4-Carbamimidoyl-benzyl)-2-(2-fluoro-5-methoxy-phenyl)-2-methoxy-acetamide hydrochloride,
- (RS)-N-(4-Carbamimidoyl-benzyl)-2-(2,3-difluoro-phenyl)-2-methoxy-acetamide hydrochloride,
- (RS)-N-(4-Carbamimidoyl-benzyl)-2-(2,6-difluoro-phenyl)-2-methoxy-acetamide hydrochloride,
- (RS)-2-(4-Bromo-2-fluoro-phenyl)-N-(4-carbamimidoyl-benzyl)-2-methoxy-acetamide hydrochloride,
- (RS)-2-(4-Bromo-2-fluoro-phenyl)-N-(4-carbamimidoyl-benzyl)-2-ethoxy-acetamide hydrochloride,
- (RS)-2-(4-Bromo-2-fluoro-phenyl)-N-(4-carbamimidoyl-benzyl)-2-propoxy-acetamide hydrochloride,
- (RS)-N-(4-Carbamimidoyl-benzyl)-2-(2-fluoro-4-trifluoromethyl-phenyl)-2-methoxy-acetamide hydrochloride, (RS)-N-(4-Carbamimidoyl-benzyl)-2-[4-(2-hydroxy-ethoxy)-phenyl]-2-methoxy-acetamide hydrochloride, and
(RS)-N-(4-Carbamimidoyl-benzyl)-2-(4-dimethylamino-phenyl)-2-methoxy-acetamide hydrochloride, or
a pharmaceutically acceptable salt thereof.

32. The compound according to claim 1, selected from the group consisting of
(RS)-N-(4-Carbamimidoyl-benzyl)-2-methoxy-2-(3-oxo-3,4-dihydro-2H-benzo[1,4]oxazin-6-yl)-acetamide hydrochloride,
(RS)-N-(4-Carbamimidoyl-benzyl)-2-methoxy-2-(4-pyrrolidin-1-yl-phenyl)-acetamide hydrochloride,
(RS)-N-(4-Carbamimidoyl-benzyl)-2-(2-chloro-phenyl)-2-methoxy-acetamide hydrochloride,
(RS)-2-(4-Acetylamino-phenyl)-N-(4-carbamimidoyl-benzyl)-2-methoxy-acetamide hydrochloride,
(RS)-N-(4-Carbamimidoyl-benzyl)-2-methoxy-2-(4-trifluoromethoxy-phenyl)-acetamide hydrochloride,
(RS)-N-(4-Carbamimidoyl-benzyl)-2-(4-imidazol-1-yl-phenyl)-2-methoxy-acetamide hydrochloride,
(RS)-N-(4-Carbamimidoyl-benzyl)-2-methoxy-2-(6-methoxy-naphthalen-2-yl)-acetamide hydrochloride,
(RS)-N-(4-Carbamimidoyl-benzyl)-2-methoxy-2-(4-morpholin-4-yl-phenyl)-acetamide hydrochloride,
(RS)-N-(4-Carbamimidoyl-benzyl)-2-methoxy-2-(2-morpholin-4-yl-phenyl)-acetamide hydrochloride, and
(RS)-N-(4-Carbamimidoyl-benzyl)-2-[4-(3-dimethylamino-propoxy)-phenyl]-2-methoxy-acetamide hydrochloride, or
a pharmaceutically acceptable salt thereof.

33. The compound according to claim 1, selected from the group consisting of
(RS)-N-(4-Carbamimidoyl-benzyl)-2-(4'-dimethylamino-3-fluoro-biphenyl-4-yl)-2-methoxy-acetamide hydrochloride,
(RS)-N-(4-Carbamimidoyl-benzyl)-2-(3-fluoro-4'-methoxy-biphenyl-4-yl)-2-methoxy-acetamide hydrochloride,
(RS)-N-(4-Carbamimidoyl-benzyl)-2-(3-fluoro-2'-methoxy-biphenyl-4-yl)-2-methoxy-acetamide hydrochloride,
(RS)-N-(4-Carbamimidoyl-benzyl)-2-(3-fluoro-biphenyl-4-yl)-2-methoxy-acetamide hydrochloride,
(RS)-N-(4-Carbamimidoyl-benzyl)-2-(3-fluoro-3'-methoxy-biphenyl-4-yl)-2-methoxy-acetamide hydrochloride,
(RS)-N-(4-Carbamimidoyl-benzyl)-2-(2,2-dimethyl-chroman-6-yl)-2-methoxy-acetamide hydrochloride,
(RS)-N-(4-Carbamimidoyl-benzyl)-2-ethoxy-2-(2-fluoro-4-methoxy-phenyl)-acetamide hydrochloride,
(RS)-2-Ethoxy-2-(2-fluoro-4-methoxy-phenyl)-N-[4-(N-hydroxycarbamimidoyl)-benzyl]-acetamide,
(RS)-4-[3-(3-Cyclopentyloxy-4-methoxy-phenyl)-3-methoxy-2-oxo-propylamino]-benzamidine hydrochloride, and
(RS)-N-(4-Carbamimidoyl-benzyl)-2-(2-chloro-4-methoxy-phenyl)-2-methoxy-acetamide hydrochloride, or
a pharmaceutically acceptable salt thereof.

34. The compound selected from claim 1, selected from the group consisting of
(RS)-N-(4-Carbamimidoyl-benzyl)-2-(2,6-difluoro-4-methoxy-phenyl)-2-methoxy-acetamide hydrochloride,
(RS)-N-(4-Carbamimidoyl-benzyl)-2-(2-fluoro-4-methoxy-phenyl)-2-propoxy-acetamide hydrochloride,
(RS)-N-(4-Carbamimidoyl-benzyl)-2-methoxy-2-naphthalen-1-yl-propionamide hydrochloride,
(RS)-2-(4-Bromo-2,6-difluoro-phenyl)-N-(4-carbamimidoyl-benzyl)-2-methoxy-acetamide hydrochloride,
(RS)-N-(4-Carbamimidoyl-benzyl)-2-(2-fluoro-4-isopropoxy-phenyl)-2-methoxy-acetamide hydrochloride,
(RS)-N-(4-Carbamimidoyl-benzyl)-2-(2-fluoro-4-isobutoxy-phenyl)-2-methoxy-acetamide hydrochloride,
(RS)-N-(4-Carbamimidoyl-benzyl)-2-{2-fluoro-4-[2-(4-fluoro-phenyl)-ethoxy]-phenyl}-2-methoxy-acetamide hydrochloride,
(RS)-N-(4-Carbamimidoyl-benzyl)-2-(2-fluoro-4-pyridin-3-yl-phenyl)-2-methoxy-acetamide hydrochloride,
(RS)-N-(4-Carbamimidoyl-benzyl)-2-(2-fluoro-4-pyridin-4-yl-phenyl)-2-methoxy-acetamide hydrochloride, and
(RS)-2-(5-Bromo-2-fluoro-phenyl)-N-(4-carbamimidoyl-benzyl)-2-methoxy-acetamide hydrochloride, or
a pharmaceutically acceptable salt thereof.

35. The compound according to claim 1, selected from the group consisting of
(RS)-N-(4-Carbamimidoyl-benzyl)-2-(4-fluoro-biphenyl-3-yl)-2-methoxy-acetamide hydrochloride,
(RS)-N-(4-Carbamimidoyl-benzyl)-2-(2-fluoro-5-methyl-phenyl)-2-methoxy-acetamide hydrochloride,
(RS)-N-(4-Carbamimidoyl-benzyl)-2-(2-fluoro-5-trifluoromethyl-phenyl)-2-methoxy-acetamide hydrochloride,
(RS)-N-(4-Carbamimidoyl-benzyl)-2-(2-fluoro-6-methoxy-phenyl)-2-methoxy-acetamide hydrochloride,
(RS)-N-(4-Carbamimidoyl-benzyl)-2-(2-fluoro-6-hydroxy-phenyl)-2-methoxy-acetamide hydrochloride,
(RS)-N-(4-Carbamimidoyl-benzyl)-2-dimethylamino-2-phenyl-acetamide hydrochloride,
(RS)-N-(4-Carbamimidoyl-benzyl)-2-methylamino-2-phenyl-acetamide hydrochloride,
(RS)-N-(4-Carbamimidoyl-benzyl)-2-methylsulfanyl-2-phenyl-acetamide hydrochloride,
(RS)-N-(4-Carbamimidoyl-benzyl)-2-ethylsulfanyl-2-phenyl-acetamide hydrochloride, and
(RS)-N-(4-Carbamimidoyl-benzyl)-2-methanesulfonyl-2-phenyl-acetamide hydrochloride, or
a pharmaceutically acceptable salt thereof.

36. The compound according to claim 1, selected from the group consisting of
(RS)-2-Amino-N-(4-carbamimidoyl-benzyl)-2-phenyl-acetamide hydrochloride,
(RS)-2-Acetylamino-N-(4-carbamimidoyl-benzyl)-2-phenyl-acetamide hydrochloride,
(RS)-N-(4-Carbamimidoyl-benzyl)-2-[2-fluoro-4-(2-phenoxy-ethoxy)-phenyl]-2-methoxy-acetamide hydrochloride,
(RS)-N-(4-Carbamimidoyl-benzyl)-2-methoxy-2-pyridin-2-yl-acetamide hydrochloride,
(RS)-N-(4-Carbamimidoyl-benzyl)-2-methoxy-2-phenyl-propionamide hydrochloride,
(RS)-2-(4-Bromo-2,6-difluoro-phenyl)-N-(4-carbamimidoyl-benzyl)-2-ethoxy-acetamide hydrochloride,
N-(4-Carbamimidoyl-benzyl)-2-[2-fluoro-6-(2-hydroxy-ethoxy)-phenyl]-2-methoxy-acetamide hydrochloride, and
N-(4-Carbamimidoyl-benzyl)-2-(2-carbamoylmethoxy-6-fluoro-phenyl)-2-methoxy-acetamide hydrochloride,
or a pharmaceutically acceptable salt thereof.

37. The compound according to claim 1, selected from the group consisting of
(RS)-2-Biphenyl-4-yl-N-(4-carbamimidoyl-benzyl)-2-ethoxy-propionamide hydrochloride, (RS)-2-[3-(1-Benzenesulfonyl-piperidin-4-yloxy)-5-ethoxy-2-fluoro-phenyl]-N-(4-carbamimidoyl-benzyl)-2-methoxy-acetamide hydrochloride,
(RS)-N-(4-Carbamimidoyl-benzyl)-2-[5-ethoxy-2-fluoro-3-(1-methanesulfonyl-piperidin-4-yloxy)-phenyl]-2-methoxy-acetamide hydrochloride,
(RS)-2-[3-(1-Acetyl-piperidin-4-yloxy)-5-ethoxy-2-fluoro-phenyl]-N-(4-carbamimidoyl-benzyl)-2-methoxy-acetamide hydrochloride,
(RS)-2-[3-(1-Benzoyl-piperidin-4-yloxy)-5-ethoxy-2-fluoro-phenyl]-N-(4-carbamimidoyl-benzyl)-2-methoxy-acetamide hydrochloride,
(RS)-N-(4-Carbamimidoyl-2-chloro-benzyl)-2-(2-fluoro-4-methoxy-phenyl)-2-methoxy-acetamide hydrochloride,
(RS)-N-(4-Carbamimidoyl-2-chloro-benzyl)-2-ethoxy-2-(2-fluoro-4-methoxy-phenyl)-acetamide hydrochloride,
(RS)-N-(4-Carbamimidoyl-2-chloro-benzyl)-2-(2,6-difluoro-4-methoxy-phenyl)-2-ethoxy-acetamide hydrochloride,
(RS)-N-(4-Carbamimidoyl-2-chloro-benzyl)-2-(2,6-difluoro-4-methoxy-phenyl)-2-methoxy-acetamide hydrochloride, and
(RS)-N-[3-Chloro-4-(N-hydroxycarbamimidoyl)-benzyl]-2-ethoxy-2-(2-fluoro-4-methoxy-phenyl)-acetamide, or a pharmceutically acceptable salt thereof.

38. The compound according to claim 1, selected from the group consisting of
(RS)-N-(4-Carbamimidoyl-3-chloro-benzyl)-2-ethoxy-2-(2-fluoro-4-methoxy-phenyl)-acetamide acetate,
(RS)-2-(4-Bromo-2,6-difluoro-phenyl)-N-(4-carbamimidoyl-2-methoxy-benzyl)-2-ethoxy-acetamide hydrochloride,
(RS)-N-(4-Carbamimidoyl-2-methoxy-benzyl)-2-ethoxy-2-(2-fluoro-4-methoxy-phenyl)-acetamide hydrochloride,
(RS)-N-(4-Carbamimidoyl-2-phenoxy-benzyl)-2-ethoxy-2-(2-fluoro-4-methoxy-phenyl)-acetamide hydrochloride,
(RS)-N-(4-Carbamimidoyl-2-o-tolyloxy-benzyl)-2-ethoxy-2-(2-fluoro-4-methoxy-phenyl)-acetamide hydrochloride,
(RS)-N-[4-Carbamimidoyl-2-(4-fluoro-phenoxy)-benzyl]-2-ethoxy-2-(2-fluoro-4-methoxy-phenyl)-acetamide hydrochloride,
(RS)-N-[4-Carbamimidoyl-2-(pyridin-3-yloxy)-benzyl]-2-ethoxy-2-(2-fluoro-4-methoxy-phenyl)-acetamide acetic acid,
(RS)-N-[4-Carbamimidoyl-2-(5-nitro-pyridin-2-yloxy)-benzyl]-2-ethoxy-2-(2-fluoro-4-methoxy-phenyl)-acetamide hydrochloride,
(RS)-N-[2-(5-Amino-pyridin-2-yloxy)-4-carbamimidoyl-benzyl]-2-ethoxy-2-(2-fluoro-4-methoxy-phenyl)-acetamide hydrochloride, and
(RS)-N-(5-Carbamimidoyl-biphenyl-2-ylmethyl)-2-ethoxy-2-(2-fluoro-4-methoxy-phenyl)-acetamide hydrochloride, or a pharmaceutically acceptable salt thereof.

39. The compound according to claim 1, selected from the group consisting of
(RS)-(5-Carbamimidoyl-2-{[2-ethoxy-2-(2-fluoro-4-methoxy-phenyl)-acetylamino]-methyl}-phenoxy)-acetic acid ethyl ester hydrochloride,
(RS)-N-(4-Carbamimidoyl-2-carbamoylmethoxy-benzyl)-2-ethoxy-2-(2-fluoro-4-methoxy-phenyl)-acetamide hydrochloride,
(RS)-N-(4-Carbamimidoyl-2-isopropoxy-benzyl)-2-ethoxy-2-(2-fluoro-4-methoxy-phenyl)-acetamide hydrochloride,
(RS)-N-[4-Carbamimidoyl-2-(2-hydroxy-ethoxy)-benzyl]-2-ethoxy-2-(2-fluoro-4-methoxy-phenyl)-acetamide hydrochloride,
2-(5-Carbamimidoyl-2-{[2-ethoxy-2-(2-fluoro-4-methoxy-phenyl)-acetylamino]-methyl}-phenoxy)-N-isopropyl-2-phenyl-acetamide hydrochloride,
(RS)-(5-Carbamimidoyl-2-{[2-ethoxy-2-(2-fluoro-4-methoxy-phenyl)-acetylamino]-methyl}-phenoxy)-acetic acid,
(RS)-(S)-2-(5-Carbamimidoyl-2-{[2-ethoxy-2-(2-fluoro-4-methoxy-phenyl)-acetylamino]-methyl}-phenoxy)-propionic acid ethyl ester hydrochloride,
((RS)-S)-2-(5-Carbamimidoyl-2-{[2-ethoxy-2-(2-fluoro-4-methoxy-phenyl)-acetylamino]-methyl}-phenoxy)-propionamide hydrochloride,
(RS)-(R)-2-(5-Carbamimidoyl-2-{[2-ethoxy-2-(2-fluoro-4-methoxy-phenyl)-acetylamino]-methyl}-phenoxy)-propionic acid ethyl ester hydrochloride, and
(RS)-(R)-2-(5-Carbamimidoyl-2-{[2-ethoxy-2-(2-fluoro-4-methoxy-phenyl)-acetylamino]-methyl}-phenoxy)-propionamide hydrochloride, or a pharmaceutically acceptable salt thereof.

40. The compound according to claim 1, selected from the group consisting of
(RS)-N-(4-Carbamimidoyl-2-carbamoylmethoxy-benzyl)-2-(2-fluoro-4-methoxy-phenyl)-2-methoxy-acetamide hydrochloride,
(RS)-N-(4-Carbamimidoyl-2-phenoxy-benzyl)-2-(2,6-difluoro-4-methoxy-phenyl)-2-ethoxy-acetamide hydrochloride,
(RS)-N-(4-Carbamimidoyl-2-methoxy-benzyl)-2-(2,6-difluoro-4-methoxy-phenyl)-2-ethoxy-acetamide hydrochloride,
(RS)-N-(4-Carbamimidoyl-2-carbamoylmethoxy-benzyl)-2-(2,6-difluoro-4-methoxy-phenyl)-2-ethoxy-acetamide hydrochloride,
(RS)-N-[4-Carbamimidoyl-2-(2-fluoro-benzyloxy)-benzyl]-2-(2,6-difluoro-4-methoxy-phenyl)-2-ethoxy-acetamide hydrochloride,
(RS)-N-[4-Carbamimidoyl-2-(5-chloro-2-fluoro-benzyloxy)-benzyl]-2-(2,6-difluoro-4-methoxy-phenyl)-2-ethoxy-acetamide hydrochloride,
(RS)-N-{4-Carbamimidoyl-2-[(2-methoxy-ethylcarbamoyl)-methoxy]-benzyl}-2-(2,6-difluoro-4-methoxy-phenyl)-2-ethoxy-acetamide hydrochloride,
(RS)-N-{4-Carbamimidoyl-2-[(2-morpholin-4-yl-ethylcarbamoyl)-methoxy]-benzyl}-2-(2,6-difluoro-4-methoxy-phenyl)-2-ethoxy-acetamide hydrochloride,
(RS)-N-{4-Carbamimidoyl-2-[(2-diethylamino-ethylcarbamoyl)-methoxy]-benzyl}-2-(2,6-difluoro-4-methoxy-phenyl)-2-ethoxy-acetamide hydrochloride, and
(RS)-N-[4-Carbamimidoyl-2-([1,2,4]oxadiazol-3-yl-methoxy)-benzyl]-2-(2,6-difluoro-4-methoxy-phenyl)-2-ethoxy-acetamide hydrochloride, or a pharmaceutically acceptable salt thereof.

41. The compound according to claim 1, selected from the group consisting of
(RS)-N-(4-Carbamimidoyl-2-carbamimidoylmethoxy-benzyl)-2-(2,6-difluoro-4-methoxy-phenyl)-2-ethoxy-acetamide hydrochloride, (RS)-N-[2-(1H-Benzoimidazol-2-ylmethoxy)-4-carbamimidoyl-benzyl]-2-(2,6-difluoro-4-methoxy-phenyl)-2-ethoxy-acetamide hydrochloride,
(RS)-N-[4-Carbamimidoyl-2-((1S,3R,4S)-3,4-dihydroxy-cyclopentyloxy)-benzyl]-2-(2,6-difluoro-4-methoxy-phenyl)-2-ethoxy-acetamide hydrochloride,
a mixture of (RS) and (SR)-N-[4-Carbamimidoyl-2-((1RS,2RS)-2-hydroxy-cyclopentyloxy)-benzyl]-2-(2,6-difluoro-4-methoxy-phenyl)-2-ethoxy-acetamide hydrochloride,
(RS)-N-(4-Carbamimidoyl-2-carbamoylmethoxy-benzyl)-2-(2,6-difluoro-4-methoxy-phenyl)-2-methoxy-acetamide hydrochloride,
(RS)-N-(4-Carbamimidoyl-2-methylcarbamoylmethoxy-benzyl)-2-(2,6-difluoro-4-methoxy-phenyl)-2-methoxy-acetamide hydrochloride,
(RS)-N-[4-Carbamimidoyl-2-(isopropylcarbamoyl-methoxy)-benzyl]-2-(2,6-difluoro-4-methoxy-phenyl)-2-methoxy-acetamide hydrochloride,
(RS)-N-{4-Carbamimidoyl-2-[(4-fluoro-phenylcarbamoyl)-methoxy]-benzyl}-2-(2,6-difluoro-4-methoxy-phenyl)-2-methoxy-acetamide hydrochloride,
(RS)-N-[4-Carbamimidoyl-2-(pyridin-2-ylmethoxy)-benzyl]-2-(2,6-difluoro-4-methoxy-phenyl)-2-methoxy-acetamide hydrochloride, and
(RS)-N-[4-Carbamimidoyl-2-(2,2,2-trifluoro-ethoxy)-benzyl]-2-(2,6-difluoro-4-methoxy-phenyl)-2-methoxy-acetamide hydrochloride, or
a pharmaceutically acceptable salt thereof.

42. The compound according to claim 1, selected from the group consisting of
(RS)-N-[4-Carbamimidoyl-2-(pyridin-3-ylmethoxy)-benzyl]-2-(2,6-difluoro-4-methoxy-phenyl)-2-methoxy-acetamide hydrochloride,
(RS)-N-[4-Carbamimidoyl-2-(pyridin-4-ylmethoxy)-benzyl]-2-(2,6-difluoro-4-methoxy-phenyl)-2-methoxy-acetamide hydrochloride,
(RS)-N-(4-Carbamimidoyl-benzyl)-2-(2,6-difluoro-4-hydroxy-phenyl)-2-ethoxy-acetamide hydrochloride,
(RS)-N-(4-Carbamimidoyl-benzyl)-2-[2,6-difluoro-4-(2-morpholin-4-yl-ethoxy)-phenyl]-2-ethoxy-acetamide dihydrochloride,
(RS)-{[4-({2-[2,6-Difluoro-4-(2-morpholin-4-yl-ethoxy)-phenyl]-2-ethoxy-acetylamino}-methyl)-phenyl]-imino-methyl}-carbamic acid benzyl ester,
(RS)-N-(4-Carbamimidoyl-benzyl)-2-(2,6-difluoro-4-phenethyloxy-phenyl)-2-ethoxy-acetamide hydrochloride,
(RS)-N-(4-Carbamimidoyl-benzyl)-2-(4-cyclopropylmethoxy-2,6-difluoro-phenyl)-2-ethoxy-acetamide hydrochloride,
(RS)-N-(4-Carbamimidoyl-benzyl)-2-ethoxy-2-(4-ethoxy-2,6-difluoro-phenyl)-acetamide hydrochloride,
(RS)-N-(4-Carbamimidoyl-benzyl)-2-[2,6-difluoro-4-(4-methoxy-phenoxy)-phenyl]-2-ethoxy-acetamide, and
(RS)-N-(4-Carbamimidoyl-benzyl)-2-[4-(3,4-dimethoxy-phenoxy)-2,6-difluoro-phenyl]-2-ethoxy-acetamide hydrochloride, or
a pharmaceutically acceptable salt thereof.

43. The compound according to claim 1, selected from the group consisting of
(RS)-N-(4-Carbamimidoyl-benzyl)-2-[2,6-difluoro-4-(3-methoxy-phenoxy)-phenyl]-2-ethoxy-acetamide hydrochloride,
(RS)-2-[4-(3-Acetylamino-phenoxy)-2,6-difluoro-phenyl]-N-(4-carbamimidoyl-benzyl)-2-ethoxy-acetamide hydrochloride,
(RS)-N-(4-Carbamimidoyl-benzyl)-2-[4-(4-cyano-phenoxy)-2,6-difluoro-phenyl]-2-ethoxy-acetamide hydrochloride,
(RS)-N-(4-Carbamimidoyl-benzyl)-2-[2,6-difluoro-4-(3-trifluoromethoxy-phenoxy)-phenyl]-2-ethoxy-acetamide hydrochloride,
(RS)-4-[(4-Carbamimidoyl-benzylcarbamoyl)-ethoxy-methyl]-3,5-difluoro-N-isobutyl-benzamide hydrochloride,
(RS)-4-[(4-Carbamimidoyl-benzylcarbamoyl)-ethoxy-methyl]-N-ethyl-3,5-difluoro-benzamide hydrochloride,
(RS)-4-[(4-Carbamimidoyl-benzylcarbamoyl)-ethoxy-methyl]-3,5-difluoro-N-(2-methoxy-ethyl)-benzamide hydrochloride,
(RS)-4-[(4-Carbamimidoyl-benzylcarbamoyl)-ethoxy-methyl]-N-cyclopentyl-3,5-difluoro-benzamide hydrochloride, and
(RS)-4-[(4-Carbamimidoyl-benzylcarbamoyl)-ethoxy-methyl]-3,5-difluoro-N-(2,2,2-trifluoro-ethyl)-benzamide hydrochloride, or
a pharmaceutically acceptable salt thereof.

44. The compound according to claim 1, selected from the group consisting of
(RS)-4-[(4-Carbamimidoyl-benzylcarbamoyl)-ethoxy-methyl]-N-cyclopropylmethyl-3,5-difluoro-benzamide hydrochloride,
(RS)-[(4-{[2-(2,6-Difluoro-3-hydroxy-phenyl)-2-ethoxy-acetylamino]-methyl}-phenyl)-imino-methyl]-carbamic acid benzyl ester,
(RS)-N-(4-Carbamimidoyl-benzyl)-2-(2,6-difluoro-3-hydroxy-phenyl)-2-ethoxy-acetamide hydrochloride,
(RS)-N-(4-Carbamimidoyl-benzyl)-2-ethoxy-2-{3-[2-(2-ethoxy-ethoxy)-ethoxy]-2,6-difluoro-phenyl}-acetamide hydrochloride,
(RS)-N-(4-Carbamimidoyl-benzyl)-2-[3-(3-dimethylamino-propoxy)-2,6-difluoro-phenyl]-2-ethoxy-acetamide dihydrochloride,
(RS)-N-(4-Carbamimidoyl-benzyl)-2-(2,6-difluoro-3-{2-[2-(2-methoxy-ethoxy)-ethoxy]-ethoxy}-phenyl)-2-ethoxy-acetamide hydrochloride,
(RS)-N-(4-Carbamimidoyl-benzyl)-2-[2,6-difluoro-3-(3-pyridin-4-yl-propoxy)-phenyl]-2-ethoxy-acetamide dihydrochloride,
(RS)-N-(4-Carbamimidoyl-benzyl)-2-[2,6-difluoro-3-(2-pyrrolidin-1-yl-ethoxy)-phenyl]-2-ethoxy-acetamide dihydrochloride,
(RS)-N-(4-Carbamimidoyl-benzyl)-2-[2,6-difluoro-3-(1-methyl-cyclopropylmethoxy)-phenyl]-2-ethoxy-acetamide hydrochloride, and
(RS)-N-(4-Carbamimidoyl-benzyl)-2-[2,6-difluoro-3-(2-piperidin-1-yl-ethoxy)-phenyl]-2-ethoxy-acetamide dihydrochloride, or
a pharmaceutically acceptable salt thereof.

45. The compound according to claim 1, selected from the group consisting of
(RS,RS)-N-(4-Carbamimidoyl-benzyl)-2-[3-(3-chloro-2-hydroxymethyl-2-methyl-propoxy)-2,6-difluoro-phenyl]-2-ethoxy-acetamide hydrochloride,
(RS)-N-(4-Carbamimidoyl-benzyl)-2-ethoxy-2-[3-(2-ethoxy-ethoxy)-2,6-difluoro-phenyl]-acetamide hydrochloride,
(RS)-N-(4-Carbamimidoyl-benzyl)-2-[2,6-difluoro-3-(2-methoxy-ethoxy)-phenyl]-2-ethoxy-acetamide hydrochloride, (RS)-N-(4-Carbamimidoyl-benzyl)-2-[3-(3-dimethylamino-2,2-dimethyl-propoxy)-2,6-difluoro-phenyl]-2-ethoxy-acetamide dihydrochloride, (RS)-N-(4-Carbamimidoyl-benzyl)-2-[2,6-difluoro-3-(2-thiophen-2-yl-ethoxy)-phenyl]-2-ethoxy-acetamide hydrochloride, (RS,RS)-N-(4-Carbamimidoyl-benzyl)-2-[2,6-difluoro-3-(tetrahydro-furan-2-ylmethoxy)-phenyl]-2-ethoxy-acetamide hydrochloride, (RS)-N-(4-Carbamimidoyl-benzyl)-2-(2,6-difluoro-3-isobutoxy-phenyl)-2-ethoxy-acetamide hydrochloride, (RS,RS,RS)-N-(4-Carbamimidoyl-benzyl)-2-[2,6-difluoro-3-(2-methyl-cyclopropylmethoxy)-phenyl]-2-ethoxy-acetamide hydrochloride, (RS)-N-(4-Carbamimidoyl-benzyl)-2-[3-(2-cyclopropyl-ethoxy)-2,6-difluoro-phenyl]-2-ethoxy-acetamide hydrochloride, and (RS)-N-(4-Carbamimidoyl-benzyl)-2-ethoxy-2-(3-ethoxy-2,6-difluoro-phenyl)-acetamide hydrochloride, or a pharmaceutically acceptable salt thereof.

46. The compound according to claim 1, selected from the group consisting of (RS)-N-(4-Carbamimidoyl-benzyl)-2-(2,6-difluoro-3-propoxy-phenyl)-2-ethoxy-acetamide hydrochloride, (RS)-N-(4-Carbamimidoyl-benzyl)-2-(3-cyclopropylmethoxy-2,6-difluoro-phenyl)-2-ethoxy-acetamide hydrochloride, (RS)-N-(4-Carbamimidoyl-benzyl)-2-[3-(2-dimethylamino-ethoxy)-2,6-difluoro-phenyl]-2-ethoxy-acetamide dihydrochloride, (RS)-N-(4-Carbamimidoyl-benzyl)-2-(3-cyclobutylmethoxy-2,6-difluoro-phenyl)-2-ethoxy-acetamide hydrochloride, (RS)-N-(4-Carbamimidoyl-benzyl)-2-{2,6-difluoro-3-[2-(2-oxo-pyrrolidin-1-yl)-ethoxy]-phenyl}-2-ethoxy-acetamide hydrochloride, (RS)-N-(4-Carbamimidoyl-benzyl)-2-[2,6-difluoro-3-(3,3,3-trifluoro-propoxy)-phenyl]-2-ethoxy-acetamide hydrochloride, (RS)-N-(4-Carbamimidoyl-benzyl)-2-[2,6-difluoro-3-(2-pyridin-3-yl-ethoxy)-phenyl]-2-ethoxy-acetamide dihydrochloride, (RS)-N-(4-Carbamimidoyl-benzyl)-2-(3-diethylcarbamoylmethoxy-2,6-difluoro-phenyl)-2-ethoxy-acetamide hydrochloride, (RS)-N-(4-Carbamimidoyl-benzyl)-2-[2,6-difluoro-3-(2-morpholin-4-yl-ethoxy)-phenyl]-2-ethoxy-acetamide dihydrochloride, and (RS,RS)-N-(4-Carbamimidoyl-benzyl)-2-[2,6-difluoro-3-(1-methyl-piperidin-3-ylmethoxy)-phenyl]-2-ethoxy-acetamide dihydrochloride, or a pharmaceutically acceptable salt thereof.

47. The compound according to claim 1, selected from the group consisting of (RS,RS)-N-(4-Carbamimidoyl-benzyl)-2-[2,6-difluoro-3-(1-methyl-piperidin-2-ylmethoxy)-phenyl]-2-ethoxy-acetamide dihydrochloride, (RS)-N-(4-Carbamimidoyl-benzyl)-2-[2,6-difluoro-3-(2-pyridin-2-yl-ethoxy)-phenyl]-2-ethoxy-acetamide dihydrochloride, (RS,RS)-N-(4-Carbamimidoyl-benzyl)-2-[2,6-difluoro-3-(2-piperidin-2-yl-ethoxy)-phenyl]-2-ethoxy-acetamide dihydrochloride, (RS)-N-(4-Carbamimidoyl-benzyl)-2-(2,6-difluoro-3-methoxy-phenyl)-2-ethoxy-acetamide hydrochloride, (RS)-N-(4-Carbamimidoyl-benzyl)-2-(3-cyclohexyloxy-2,6-difluoro-phenyl)-2-ethoxy-acetamide hydrochloride, (RS)-N-(4-Carbamimidoyl-benzyl)-2-[2,6-difluoro-3-(piperidin-4-yloxy)-phenyl]-2-ethoxy-acetamide dihydrochloride, (R,S)-N-(4-Carbamimidoyl-benzyl)-2-[2,6-difluoro-3-(4-fluoro-phenoxy)-phenyl]-2-ethoxy-acetamide hydrochloride, (RS)-N-(4-Carbamimidoyl-benzyl)-2-[2,6-difluoro-3-(pyridin-3-yloxy)-phenyl]-2-ethoxy-acetamide dihydrochloride, (RS)-N-(4-Carbamimidoyl-benzyl)-2-[2,6-difluoro-3-(3-trifluoromethyl-phenoxy)-phenyl]-2-ethoxy-acetamide hydrochloride, and (RS)-N-(4-Carbamimidoyl-benzyl)-2-(2,6-difluoro-3-m-tolyloxy-phenyl)-2-ethoxy-acetamide hydrochloride, or a pharmaceutically acceptable salt thereof.

48. The compound according to claim 1, selected from the group consisting of (RS)-N-(4-Carbamimidoyl-benzyl)-2-ethoxy-2-[3-(3-ethoxy-phenoxy)-2,6-difluoro-phenyl]-acetamide hydrochloride, (RS)-N-(4-Carbamimidoyl-benzyl)-2-ethoxy-2-[3-(1-ethyl-propoxy)-2,6-difluoro-phenyl]-acetamide acetate, (RS)-N-(4-Carbamimidoyl-benzyl)-2-(3-cyclopentyloxy-2,6-difluoro-phenyl)-2-ethoxy-acetamide acetate, (RS)-N-(4-Carbamimidoyl-benzyl)-2-[2,6-difluoro-3-(tetrahydro-pyran-4-yloxy)-phenyl]-2-ethoxy-acetamide acetate, (RS)-N-(4-Carbamimidoyl-benzyl)-2-(2,6-difluoro-3-pyridin-2-yl-phenyl)-2-ethoxy-acetamide dihydrochloride, (RS)-N-(4-Carbamimidoyl-benzyl)-2-[2,6-difluoro-3-(6-methoxy-pyridin-3-yl)-phenyl]-2-ethoxy-acetamide dihydrochloride, (RS)-N-(4-Carbamimidoyl-benzyl)-2-(2,6-difluoro-3-pyridin-3-yl-phenyl)-2-ethoxy-acetamide dihydrochloride, (RS)-N-(4-Carbamimidoyl-benzyl)-2-(2,6-difluoro-3-pyrimidin-5-yl-phenyl)-2-ethoxy-acetamide dihydrochloride, (RS)-N-(4-Carbamimidoyl-benzyl)-2-(2,6-difluoro-3-pyridin-4-yl-phenyl)-2-ethoxy-acetamide dihydrochloride, and (RS)-N-(4-Carbamimidoyl-benzyl)-2-(2,4-difluoro-3'-methyl-biphenyl-3-yl)-2-methoxy-acetamide, or a phamaceutically acceptable salt thereof.

49. The compound according to claim 1, selected from the group consisting of (RS)-N-(4-Carbamimidoyl-benzyl)-2-(2,4-difluoro-4'-methyl-biphenyl-3-yl)-2-methoxy-acetamide hydrochloride, (RS)-N-(4-Carbamimidoyl-benzyl)-2-methoxy-2-(2,4,4'-trifluoro-biphenyl-3-yl)-acetamide acetate, (RS)-N-(4-Carbamimidoyl-benzyl)-2-(2,4-difluoro-4'-methylsulfanyl-biphenyl-3-yl)-2-methoxy-acetamide hydrochloride, (RS)-N-(4-Carbamimidoyl-benzyl)-2-(2,4-difluoro-3'-trifluoromethyl-biphenyl-3-yl)-2-methoxy-acetamide acetate, (RS)-N-(4-Carbamimidoyl-benzyl)-2-(2,4-difluoro-4'-methoxy-biphenyl-3-yl)-2-methoxy-acetamide hydrochloride, (RS)-N-(4-Carbamimidoyl-benzyl)-2-[2,6-difluoro-3-(morpholine-4-carbonyl)-phenyl]-2-methoxy-acetamide acetate, (RS)-2-[2,6-difluoro-3-(morpholine-4-carbonyl)-phenyl]-N-[4-(N-hydroxycarbamimidoyl)-benzyl]-2-methoxy-acetamide, (RS)-3-[(4-Carbamimidoyl-benzylcarbamoyl)-methoxymethyl]-N-ethyl-2,4-difluoro-benzamide acetate, (RS)-3-[(4-Carbamimidoyl-benzylcarbamoyl)-methoxymethyl]-2,4-difluoro-N-(2-methoxy-ethyl)-benzamide acetate, and (RS)-3-[(4-Carbamimidoyl-benzylcarbamoyl)-methoxymethyl]-N,N-diethyl-2,4-difluoro-benzamide acetate, or a pharmaceutically acceptable salt thereof.

50. The compound according to claim 1, selected from the group consisting of (RS)-3-[(4-Carbamimidoyl-benzylcarbamoyl)-methoxymethyl]-2,4-difluoro-N-(2,2,2-trifluoro-ethyl)-benzamide acetate, (RS)-3-[(4-Carbamimidoyl-benzylcarbamoyl)-methoxymethyl]-N-cyclopropylmethyl-2,4-difluoro-benzamide acetate, (RS)-N-(4-Carbamimidoyl-benzyl)-2-[2,6-difluoro-3-(pyridin-2-ylmethoxy)-phenyl]-2-methoxy-acetamide dihydrochloride, (RS)-N-(4-Carbamimidoyl-benzyl)-2-[2,6-difluoro-3-(pyridin-3-ylmethoxy)-phenyl]-2-methoxy-acetamide dihydrochloride, (RS)-N-(4-Carbamimidoyl-benzyl)-2-[2,6-difluoro-3-(pyridin-4-ylmethoxy)-phenyl]-2-methoxy-acetamide dihydrochloride, (RS)-N-(4-Carbamimidoyl-benzyl)-2-[2,6-difluoro-3-(4-fluoro-phenoxy)-phenyl]-2-methoxy-acetamide acetate, (RS)-2-[2,6-difluoro-3-(4-fluoro-phenoxy)-phenyl]-N-[4-(N-hydroxycarbamimidoyl)-benzyl]-2-methoxy-acetamide, (RS)-N-(4-Carbamimidoyl-benzyl)-2-[2,6-difluoro-3-(pyridin-3-yloxy)-phenyl]-2-methoxy-acetamide acetate, (RS)-N-(4-Carbamimidoyl-benzyl)-2-(3,5-difluoro-biphenyl-4-yl)-2-methoxy-acetamide hydrochloride, and (RS)-N-(4-Carbamimidoyl-benzyl)-2-(3,5-difluoro-biphenyl-4-yl)-2-ethoxy-acetamide hydrochloride, or a pharmaceutically acceptable salt thereof.

51. The compound according to claim 1, selected from the group consisting of (RS)-N-(4-Carbamimidoyl-benzyl)-2-[2,6-difluoro-4-(1H-indol-5-yl)-phenyl]-2-ethoxy-acetamide acetic acid, (RS)-2-(2,6-Difluoro-4-furan-2-yl-phenyl)-2-ethoxy-N-[4-(N-hydroxycarbamimidoyl)-benzyl]-acetamide, (RS)-N-(4-Carbamimidoyl-benzyl)-2-(2,6-difluoro-4-furan-2-yl-phenyl)-2-ethoxy-acetamide acetate, N-(4-Carbamimidoyl-benzyl)-2-[2,6-difluoro-4-(tetrahydro-furan-2-yl)-phenyl]-2-ethoxy-acetamide acetic acid, (RS)-{4'-[(4-Carbamimidoyl-benzylcarbamoyl)-ethoxymethyl]-3',5'-difluoro-biphenyl-3-yloxy}-acetic acid ethyl ester hydrochloride, (RS)-{4'-[(4-Carbamimidoyl-benzylcarbamoyl)-ethoxymethyl]-3',5'-difluoro-biphenyl-3-yloxy}-acetic acid, (RS)-N-(4-Carbamimidoyl-benzyl)-2-(3'-carbamoylmethoxy-3,5-difluoro-biphenyl-4-yl)-2-ethoxy-acetamide hydrochloride, (RS)-N-(4-Carbamimidoyl-benzyl)-2-[3,5-difluoro-3'-(2-hydroxy-ethoxy)-biphenyl-4-yl]-2-ethoxy-acetamide hydrochloride, (RS)-N-(4-Carbamimidoyl-benzyl)-2-[3'-(3-dimethylamino-propoxy)-3,5-difluoro-biphenyl-4-yl]-2-ethoxy-acetamide hydrochloride, and (RS)-2-[2'-(2-Benzyloxy-ethoxy)-3,5-difluoro-biphenyl-4-yl]-N-(4-carbamimidoyl-benzyl)-2-ethoxy-acetamide hydrochloride, or a pharmaceutically acceptable salt thereof.

52. The compound according to claim 1, selected from the group consisting of (RS)-N-(4-Carbamimidoyl-benzyl)-2-[2'-(2-dimethylamino-ethoxy)-3,5-difluoro-biphenyl-4-yl]-2-ethoxy-acetamide hydrochloride, (RS)-N-(4-Carbamimidoyl-benzyl)-2-[3,5-difluoro-2'-(2-hydroxy-ethoxy)-biphenyl-4-yl]-2-ethoxy-acetamide hydrochloride, (RS)-{4'-[(4-Carbamimidoyl-benzylcarbamoyl)-ethoxymethyl]-3',5'-difluoro-biphenyl-2-yloxy}-acetic acid ethyl ester hydrochloride, (RS)-{4'-[(4-Carbamimidoyl-benzylcarbamoyl)-ethoxymethyl]-3',5'-difluoro-biphenyl-2-yloxy}-acetic acid, (RS)-2-(2'-Carbamoylmethoxy-3,5-difluoro-biphenyl-4-yl)-2-ethoxy-N-[4-(N-hydroxycarbamimidoyl)-benzyl]-acetamide, (RS)-N-(4-Carbamimidoyl-benzyl)-2-(2'-carbamoylmethoxy-3,5-difluoro-biphenyl-4-yl)-2-ethoxy-acetamide acetate, (RS)-N-(4-Carbamimidoyl-benzyl)-2-(2,6-difluoro-4-pyridin-4-yl-phenyl)-2-ethoxy-acetamide hydrochloride, (RS)-N-(4-Carbamimidoyl-benzyl)-2-(2,6-difluoro-4-pyrimidin-5-yl-phenyl)-2-ethoxy-acetamide hydrochloride, (RS)-N-(4-Carbamimidoyl-benzyl)-2-(2,6-difluoro-4-pyrimidin-2-yl-phenyl)-2-ethoxy-acetamide hydrochloride, and (RS)-N-(4-Carbamimidoyl-benzyl)-2-(2,6-difluoro-4-pyridin-2-yl-phenyl)-2-ethoxy-acetamide hydrochloride, or a pharmaceutically acceptable salt thereof.

53. The compound according to claim 1, selected from the group consisting of (RS)-2-[4-(2-Amino-pyrimidin-5-yl)-2,6-difluoro-phenyl]-N-(4-carbamimidoyl-benzyl)-2-ethoxy-acetamide hydrochloride, (RS)-N-(4-Carbamimidoyl-benzyl)-2-(2,6-difluoro-4-pyridin-3-yl-phenyl)-2-ethoxy-acetamide hydrochloride, (RS)-2-[4-(6-Amino-pyridin-2-yl)-2,6-difluoro-phenyl]-N-(4-carbamimidoyl-benzyl)-2-ethoxy-acetamide hydrochloride, (RS)-2-[4-(5-Amino-pyridin-2-yl)-2,6-difluoro-phenyl]-N-(4-carbamimidoyl-benzyl)-2-ethoxy-acetamide hydrochloride, (RS)-4'-[(4-Carbamimidoyl-benzylcarbamoyl)-ethoxymethyl]-3',5'-difluoro-biphenyl-3-carboxylic acid methyl ester hydrochloride, (RS)-(2-[4-(6-Amino-pyridin-3-yl)-2,6-difluoro-phenyl]-N-(4-carbamimidoyl-benzyl)-2-ethoxy-acetamide hydrochloride, (RS)-4'-[(4-Carbamimidoyl-benzylcarbamoyl)-ethoxymethyl]-3',5'-difluoro-biphenyl-3-carboxylic acid, (RS){Amino-[4-({2-[4-(6-amino-pyridin-3-yl)-2,6-difluoro-phenyl]-2-ethoxy-acetylamino}-methyl)-phenyl]-methylene}-carbamic acid ethyl ester, (RS)2-[4-(6-Amino-pyridin-3-yl)-2,6-difluoro-phenyl]-2-ethoxy-N-[4-(N-hydroxycarbamimidoyl)-benzyl]-acetamide, and (RS)-N-(4-Carbamidoyl-benzyl)-2-(3,5-difluoro-2'-hydroxymethyl-biphenyl-4-yl)-2-ethoxy-acetamide hydrochloride, or a pharmaceutically acceptable salt thereof.

54. The compound according to claim 1, selected from the group consisting of (RS)-N-(4-Carbamimidoyl-benzyl)-2-(2'-chloromethyl-3,5-difluoro-biphenyl-4-yl)-2-ethoxy-acetamide, (RS)-2-[3,5-Difluoro-2'-(hydroxyimino-methyl)-biphenyl-4-yl]-2-ethoxy-N-[4-(N-hydroxycarbamimidoyl)-benzyl]-acetamide, (RS)-2-(2'-Aminomethyl-3,5-difluoro-biphenyl-4-yl)-N-(4-carbamimidoyl-benzyl)-2-ethoxy-acetamide acetate, (RS)-N-(4-Carbamimidoyl-benzyl)-2-(2-fluoro-4-methoxy-3-phenoxy-phenyl)-2-methoxy-acetamide hydrochloride, (RS)-N-(4-carbamimidoyl-benzyl)-2-(2-ethynyl-6-fluoro-phenyl)-2-methoxy-acetamide hydrochlorideaccording, (RS)-N-(4-Carbamimidoyl-benzyl)-2-(2-ethyl-6-fluoro-phenyl)-2-methoxy-acetamide hydrochloride, (RS)-N-(4-Carbamimidoyl-benzyl)-2-[2-fluoro-6-(3-hydroxy-prop-1-ynyl)-phenyl]-2-methoxy-acetamide hydrochloride, (RS)-N-(4-Carbamimidoyl-benzyl)-2-[2-fluoro-6-(3-hydroxy-propyl)-phenyl]-2-methoxy-acetamide hydrochloride, (RS)-N-(4-Carbamimidoyl-benzyl)-2-(3-fluoro-biphenyl-2-yl)-2-methoxy-acetamide hydrochloride, and (RS)-2-(3'-Amino-3-fluoro-biphenyl-2-yl)-N-(4-carbamimidoyl-benzyl)-2-methoxy-acetamide hydrochloride, or a pharmaceutically acceptable salt thereof.

55. The compound according to claim 1, selected from the group consisting of (RS)-N-(4-Carbamimidoyl-benzyl)-2-(3-fluoro-3'-nitro-biphenyl-2-yl)-2-methoxy-acetamide hydrochloride, (RS)-2-[2-(6-Amino-pyridin-2-yl)-6-fluoro-phenyl]-N-(4-carbamimidoyl-benzyl)-2-methoxy-acetamide acetate, (RS)-{2-[(4-Carbamimidoyl-benzylcarbamoyl)-methoxy-methyl]-3-fluoro-phenoxy}-acetic acid methyl ester acetate, (RS)-{2-[(4-Carbamimidoyl-benzylcarbamoyl)-methoxy-methyl]-3-fluoro-phenoxy}-acetic acid, (RS)-N-(4-Carbamimidoyl-benzyl)-2-[2-(3-dimethylamino-propoxy)-6-fluoro-phenyl]-2-methoxy-acetamide hydrochloride, (RS)-N-(4-Carbamimidoyl-benzyl)-2-(2-fluoro-6-phenoxy-phenyl)-2-methoxy-acetamide hydrochloride, (RS)-N-(4-Carbamimidoyl-benzyl)-2-(2,6-difluoro-4-methoxy-phenyl)-2-ethoxy-acetamide hydrochloride, (RS)-2-(4-Benzyloxy-2,6-difluoro-phenyl)-N-(4-carbamimidoyl-benzyl)-2-ethoxy-acetamide hydrochloride, (RS)-N-(4-Carbamimidoyl-benzyl)-2-(2,6-difluoro-4-isopropoxy-phenyl)-2-ethoxy-acetamide hydrochloride, and (RS)-N-(4-Carbamimidoyl-benzyl)-2-[2,6-difluoro-4-(pyridin-2-ylmethoxy)-phenyl]-2-ethoxy-acetamide hydrochloride, or a pharmaceutically acceptable salt thereof.

56. The compound according to claim 1, selected from the group consisting of (RS)-2-[2,6-Difluoro-4-(pyridin-2-ylmethoxy)-phenyl]-2-ethoxy-N-[4-(N-hydroxycarbamimidoyl)-benzyl]-acetamide, (RS)-{Amino-[4-({2-[2,6-difluoro-4-(pyridin-2-ylmethoxy)-phenyl]-2-ethoxy-acetylamino}-methyl)-phenyl]-methylene}-carbamic acid ethyl ester, (RS)-N-(4-Carbamimidoyl-benzyl)-2-[2,6-difluoro-4-(pyridin-3-ylmethoxy)-phenyl]-2-ethoxy-acetamide hydrochloride, (RS)-N-(4-Carbamimidoyl-benzyl)-2-[2,6-difluoro-4-(pyridin-4-ylmethoxy)-phenyl]-2-ethoxy-acetamide hydrochloride, (RS)-N-(4-Carbamimidoyl-benzyl)-2-(2,6-difluoro-4-phenoxy-phenyl)-2-ethoxy-acetamide hydrochloride, (RS)-N-(4-Carbamimidoyl-benzyl)-2-[2,6-difluoro-4-(pyridin-3-yloxy)-phenyl]-2-ethoxy-acetamide hydrochloride, (RS)-N-(4-Carbamimidoyl-benzyl)-2-(2,6-difluoro-3-isopropoxy-phenyl)-2-ethoxy-acetamide hydrochloride, (RS)-N-(4-Carbamimidoyl-benzyl)-2-(3-carbamoyl-methoxy-2,6-difluoro-phenyl)-2-ethoxy-acetamide hydrochloride, (RS)-2-[3-(2-Benzyloxy-ethoxy)-2,6-difluoro-phenyl]-N-(4-carbamimidoyl-benzyl)-2-ethoxy-acetamide hydrochloride, and (RS)-N-(4-Carbamimidoyl-benzyl)-2-[2,6-difluoro-3-(2-hydroxy-ethoxy)-phenyl]-2-ethoxy-acetamide hydrochloride, or a pharmaceutically acceptable salt thereof.

57. The compound according to claim 1, selected from the group consisting of (RS)-N-(4-Carbamimidoyl-benzyl)-2-(2,6-difluoro-3-phenoxy-phenyl)-2-ethoxy-acetamide acetate, (RS)-N-(4-Carbamimidoyl-benzyl)-2-(2,4-difluoro-biphenyl-3-yl)-2-ethoxy-acetamide hydrochloride, (RS)-2-(2,6-Difluoro-3-phenylamino-phenyl)-N-[4-(N-hydroxycarbamimidoyl)-benzyl]-2-methoxy-acetamide, (RS)-N-(4-Carbamimidoyl-benzyl)-2-(2,6-difluoro-3-phenylamino-phenyl)-2-methoxy-acetamide acetate, (RS)-N-(4-Carbamimidoyl-benzyl)-2-(2,6-difluoro-3-isopropylamino-phenyl)-2-methoxy-acetamide acetate, (RS)-2-(3-Acetylamino-2,6-difluoro-phenyl)-N-(4-carbamimidoyl-benzyl)-2-methoxy-acetamide hydrochloride, (RS)-(4-Carbamimidoyl-benzyl)-2-(2,6-difluoro-3-phenylacetylamino-phenyl)-2-methoxy-acetamide hydrochloride, (RS)-N-(4-Carbamimidoyl-benzyl)-2-(2,6-difluoro-3-hydroxymethyl-phenyl)-2-ethoxy-acetamide hydrochloride, (RS)-2-[3-(Acetylamino-methyl)-2,6-difluoro-phenyl]-N-(4-carbamimidoyl-benzyl)-2-ethoxy-acetamide hydrochloride, and (RS)-2-(3-Aminomethyl-2,6-difluoro-phenyl)-N-(4-carbamimidoyl-benzyl)-2-ethoxy-acetamide acetic acid, or a pharmaceutically acceptable salt thereof.

58. The compound according to claim 1, selected from the group consisting of (RS)-(4-Carbamimidoyl-benzyl)-2-(2,6-difluoro-3-phenylaminomethyl-phenyl)-2-ethoxy-acetamide hydrochloride, (RS)-(4-Carbamimidoyl-benzyl)-2-(2,6-difluoro-3-morpholin-4-ylmethyl-phenyl)-2-ethoxy-acetamide hydrochloride, (RS)-(4-Carbamimidoyl-benzyl)-2-(2,6-difluoro-3-piperidin-1-ylmethyl-phenyl)-2-ethoxy-acetamide hydrochloride, (RS)-2-(3-Diethoxymethyl-2,6-difluoro-phenyl)-2-ethoxy-N-[4-(N-hydroxycarbamimidoyl)-benzyl]-acetamide, (RS)-(4-Carbamimidoyl-benzyl)-2-(2,6-difluoro-3-formyl-phenyl)-2-ethoxy-acetamide acetic acid (1:4), (RS)-N-(4-Carbamimidoyl-2,6-difluoro-benzyl)-2-(2,6-difluoro-4-methoxy-phenyl)-2-ethoxy-acetamide; hydrochloride, (RS)-N-(4-Carbamimidoyl-2,6-difluoro-benzyl)-2-ethoxy-2-(2-fluoro-4-methoxy-phenyl)-acetamide acetate, (RS)-N-(4-Carbamimidoyl-2,6-difluoro-benzyl)-2-(2,6-difluoro-4-methoxy-phenyl)-2-methoxy-acetamide acetate, and (RS)-N-(4-Carbamimidoyl-2,6-difluoro-benzyl)-2-(2-fluoro-4-methoxy-phenyl)-2-methoxy-acetamide acetate, or a pharamceutically acceptable salt thereof.

59. The compound according to claim 1, selected from the group consisting of (RS)-[4-Carbamimidoyl-2-(carbamoylmethyl-amino)-benzyl]-2-ethoxy-2-(2-fluoro-4-methoxy-phenyl)-acetamide hydrochloride, (RS)-N-(2-Benzylamino-4-carbamimidoyl-benzyl)-2-ethoxy-2-(2-fluoro-4-methoxy-phenyl)-acetamide acetate, (RS)-[4-Carbamimidoyl-2-(2-fluoro-benzylamino)-benzyl]-2-ethoxy-2-(2-fluoro-4-methoxy-phenyl)-acetamide hydrochloride, (RS)-{4-Carbamimidoyl-2-[(pyridin-2-ylmethyl)-amino]-benzyl}-2-ethoxy-2-(2-fluoro-4-methoxy-phenyl)-acetamide hydrochloride, (RS)-[4-Carbamimidoyl-2-(4-chloro-2-fluoro-benzylamino)-benzyl]-2-ethoxy-2-(2-fluoro-4-methoxy-phenyl)-acetamide hydrochloride, (RS)-(4-Carbamimidoyl-2-phenethylamino-benzyl)-2-ethoxy-2-(2-fluoro-4-methoxy-phenyl)-acetamide hydrochloride, (RS)-(5-Carbamimidoyl-2-{[2-ethoxy-2-(2-fluoro-4-methoxy-phenyl)-acetylamino]-methyl}-phenylamino)-acetic acid ethyl ester hydrochloride, (RS)-(5-Carbamimidoyl-2-[{2-ethoxy-2-(2-fluoro-4-methoxy-phenyl)-acetylamino]-methyl}-phenylamino)-acetic acid acetate, (RS)-(4-Carbamimidoyl-2-phenylmethanesulfonylamino-benzyl)-2-ethoxy-2-(2-fluoro-4-methoxy-phenyl)-acetamide hydrochloride, and (RS)-[2-(3-Benzyl-ureido)-4-carbamimidoyl-benzyl]-2-ethoxy-2-(2-fluoro-4-methoxy-phenyl)-acetamide acetate, or a pharmaceutically acceptable salt thereof.

60. The compound according to claim 1, selected from the group consisting of (RS)-(5-Carbamimidoyl-2-{[2-ethoxy-2-(2-fluoro-4-methoxy-phenyl)-acetylamino]-methyl}-phenyl)-carbamic acid benzyl ester hydrochloride, (RS)-(4-Carbamimidoyl-2-phenylamino-benzyl)-2-ethoxy-2-(2-fluoro-4-methoxy-phenyl)-acetamide hydrochloride, (RS)-2-[4-(6-Amino-pyridin-3-yl)-2,6-difluoro-phenyl]-N-(4-carbamimidoyl-2-carbamoylmethoxy-benzyl)-2-ethoxy-acetamide hydrochloride acetic acid (1:1:2), (RS)-(4-Carbamimidoyl-2-carbamoylmethoxy-benzyl)-2-[2,6-difluoro-4-(pyridin-2-ylmethoxy)-phenyl]-2-ethoxy-acetamide hydrochloride, (RS)-2-[4-(6-Amino-pyridin-3-yl)-2,6-difluoro-phenyl]-N-(4-carbamimidoyl-2,6-difluoro-benzyl)-2-ethoxy-acetamide acetate, (RS)-[(4-{[2-(2,6-Difluoro-4-methoxy-phenyl)-2-methoxy-acetylamino]-methyl}-phenyl)-imino-methyl]-carbamic acid tert-butyl ester, (S)-[(4-{[2-(2,6-Difluoro-4-methoxy-phenyl)-2-methoxy-acetylamino]-methyl}-phenyl)-imino-methyl]-carbamic acid tert-butyl ester, (R)-[(4-{[2-(2,6-Difluoro-4-methoxy-phenyl)-2-methoxy-acetylamino]-methyl}-phenyl)-imino-methyl]-carbamic acid tert-butyl ester, (S)-N-(4-Carbamimidoyl-benzyl)-2-(2,6-difluoro-4-methoxy-phenyl)-2-methoxy-acetamide formiate, and (R)-N-(4-Carbamimidoyl-benzyl)-2-(2,6-difluoro-4-methoxy-phenyl)-2-methoxy-acetamide formiate, or a pharmaceutically acceptable salt thereof.

61. The compound according to claim 1, selected from the group consisting of

[1-Amino-1-(4-{[(R)-2-ethoxy-2-(2-fluoro-4-methoxy-phenyl)-acetylamino]-methyl}-phenyl)-meth-(E)-ylidene]-carbamic acid benzyl ester, (R)-N-(4-Carbamimidoyl-benzyl)-2-ethoxy-2-(2-fluoro-4-methoxy-phenyl)-acetamide acetate, (RS)-[Amino-(4-{[2-ethoxy-2-(2-fluoro-4-methoxy-phenyl)-acetylamino]-methyl}-phenyl)-methylene]-carbamic acid benzyl ester, (RS)-[(4-{[2-(2,6-Difluoro-4-methoxy-phenyl)-2-methoxy-acetylamino]-methyl}-phenyl)-imino-methyl]-carbamic acid benzyl ester, (RS)-N-(4-Carbamimidoyl-benzyl)-2-[2,6-difluoro-4-(1-oxy-pyridin-4-yl)-phenyl]-2-methoxy-acetamide hydrochloride, (RS)-(4-Carbamimidoyl-benzyl)-2-[2,6-difluoro-4-(tetrahydro-pyran-4-yl)-phenyl]-2-ethoxy-acetamide acetate, and (RS)-(4-Carbamimidoyl-benzyl)-2-(4-cyclohexyl-2,6-difluoro-phenyl)-2-ethoxy-acetamide acetate, or a pharmaceutically acceptable salt thereof.

62. A process for the manufacture of compounds of formula (I) as defined in claim 1, which process comprises converting the nitrile group in a compound of formula (II)

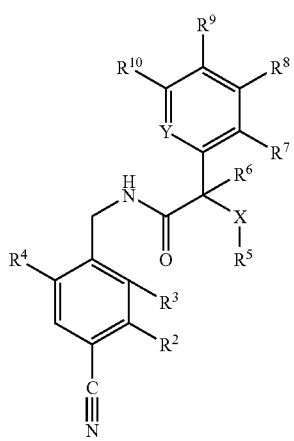
(II)

wherein $R^2$, $R^3$, $R^4$, $R^5$, $R^6$, $R^7$, $R^8$, $R^9$, $R^{10}$, X and Y are defined in claim 1, into a carbamimidoyl group, or into a N-hydroxy-carbamimidoyl group, or into a N-amino-carbamimidoyl group.

63. The process according to claim 62 in which further comprises converting the resulting compound into a pharmaceutically acceptable salt.

64. A pharmaceutical composition comprising a compound according to claim 1 and a pharmaceutically acceptable carrier or adjuvant.

* * * * *